US 7,015,001 B2

(12) United States Patent
Baltz et al.

(10) Patent No.: US 7,015,001 B2
(45) Date of Patent: Mar. 21, 2006

(54) DNA ENCODING SPNF OF THE SPINOSYN CLUSTER

(75) Inventors: Richard H. Baltz, Indianapolis, IN (US); M. Christine Broughton, Indianapolis, IN (US); Kathryn P. Crawford, Indianapolis, IN (US); Krishnamurthy Madduri, Woodlawn, OH (US); Donald J. Merlo, Carmel, IN (US); Patti J. Treadway, Greenwood, IN (US); Jan R. Turner, Carmel, IN (US); Clive Waldron, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 29 days.

(21) Appl. No.: 10/329,148

(22) Filed: Dec. 23, 2002

(65) Prior Publication Data

US 2004/0023343 A1    Feb. 5, 2004

Related U.S. Application Data

(62) Division of application No. 09/603,207, filed on Jun. 23, 2000, now Pat. No. 6,521,406, which is a division of application No. 09/370,700, filed on Aug. 9, 1999, now Pat. No. 6,274,350, which is a division of application No. 09/036,987, filed on Mar. 9, 1998, now Pat. No. 6,143,526.

(51) Int. Cl.
    *C12Q 1/68*    (2006.01)
(52) U.S. Cl. ................ 435/6; 435/320.1; 435/252.3; 435/254.11; 435/325; 435/419; 536/23.1; 536/23.2
(58) Field of Classification Search ............... 536/23.1, 536/23.2, 23.7; 435/320.1, 252.3, 254.11, 435/419, 325, 6
See application file for complete search history.

(56) References Cited

U.S. PATENT DOCUMENTS

| | | | |
|---|---|---|---|
| 4,874,748 A | 10/1989 | Katz et al. ............... 514/29 |
| 4,935,340 A | 6/1990 | Baltz et al. ............... 435/6 |
| 5,149,638 A | 9/1992 | Beckmann et al. ......... 435/76 |
| 5,252,474 A | 10/1993 | Gewain et al. .......... 435/172.3 |
| 5,362,634 A | 11/1994 | Boeck et al. ............. 435/76 |
| 5,614,619 A | 3/1997 | Pieperberg et al. |
| 5,672,491 A | 9/1997 | Khosla et al. ............. 435/148 |
| 5,672,497 A | 9/1997 | Cox et al. ............... 435/320.1 |
| 5,712,146 A | 1/1998 | Khosla et al. ......... 435/252.35 |
| 5,843,718 A | 12/1998 | Khosla et al. ............ 435/69.1 |
| 6,143,526 A * | 11/2000 | Baltz et al. ............. 435/76 |
| 6,274,350 B1 * | 8/2001 | Baltz et al. ............. 435/76 |
| 6,521,406 B1 * | 2/2003 | Baltz et al. ............. 435/6 |

FOREIGN PATENT DOCUMENTS

| | | |
|---|---|---|
| DE | 199 57 268 A1 | 3/2001 |
| EP | 0 791 655 A | 8/1997 |
| WO | WO87/03907 | 7/1987 |
| WO | WO93/06219 | 4/1993 |
| WO | WO93/13663 | 7/1993 |
| WO | WO 9946387 A1 * | 9/1999 |
| WO | WO 200116303 A2 * | 3/2001 |
| WO | WO 200279477 A2 * | 10/2002 |

OTHER PUBLICATIONS

Waldron et al. Cloning and analysis of the spinosad biosynthetic gene cluster of *Saccharopolyspora spinosa*. Chem Biol. 2001 May;8(5):487-99.*
Waldron et al. A cluster of genes for the biosynthesis of spinosyns, novel macrolide insect control agents produced by *Saccharopolyspora spinosa*. Antonie Van Leeuwenhoek. Dec. 2000;78(3-4):385-90.*
M. Inouye et al., "A gene encoding mycinamicin III O-methyltransferase from *Micromonospora griseorubida*," 1994, *Gene 141*: 121-124.
M. Geistlich et al., "Characterization of a novel regulatroy gene governing the expression of a polyketide syntase gene in *Streptomyces ambofaciens*," 1992, *Molecular Microbiology 6*: 2019-2029.
S. Donadio et al., "Modular Organization of Genes Required for Compley Polyketide Biosynthesis," 1991,*Science 252*: 675-679.
Donadio et al., "Organization of the enzymatic domains in the multifunctional polyketide synthase involved in erythromycin formation in *Saccharopolyspora erythraea*," 1992, *Gene 111*: 51-60.
Siggaard-Anderson, "Conserved residues in condensing enzyme domains of fatty acid syntases and related sequences," 1993, *Protein Seq Data Anal.* 5: 325-335.
Baltz et al., "Applications of transposition mutagenesis in antibiotic producing streptomycetes," 1997, Antonie van Leeuwenhoek 71: 179-187.
Donadio et al., "An erythromycin analog produced by reprogramming of polyketide synthesis," 1993, *Proc. Natl. Acad. Sci. USA 90*: 7119-7123.
Ruan et al., "Acyltransferase Domain Substitutions in Erythromycin Polyketide Synthase Yield Novel Erythromycin Derivatives," 1997, J. Bacteriol. 179: 6416-6425.
Matsushima P. et al.: "Conjugal transfer of cosmid DNA from *Escherichia coli* to *Saccharopolyspora spinosa*: effects of chromosomal insertions on macrolide A83543 production" GENE vol. 146, 1994, pp. 39-45.
Baltz R H et al.: "Molecular genetic methods for improving secondary-metabolite production in actinomycetes" Trends in Biotechnology, vol. 14, No. 7, Jul. 1, 1996, pp. 245-250.

* cited by examiner

*Primary Examiner*—Kathleen Kerr
(74) *Attorney, Agent, or Firm*—Donald Stuart

(57) ABSTRACT

Spinosyn biosynthetic genes from *Saccharopolyspora spinosa*, spinosyn producing microorganisms transformed with the biosynthetic genes, methods using the biosynthetic genes to increase production of spinosyn insecticidal macrolides, and methods using the genes or fragments thereof to change the products produced by spinosyn-producing microorganisms are provided.

6 Claims, 6 Drawing Sheets

Fig. 1C

SEQUENCE LISTING

<160> NUMBER OF SEQ ID NOS: 39

<210> SEQ ID NO 1
<211> LENGTH: 80161
<212> TYPE: DNA
<213> ORGANISM: Saccharopolyspora spinosa

<400> SEQUENCE: 1

```
gatctccatg aagctcaacg taggcacgga cggtcaggtg gactgggtga tcgcccgcga      60
cctgctggcc gacgggctga tcgccgaggc aggcgaaggc gatgtgcgga tcggccctcg     120
acggggtttt ccggggttgg tcgtgatcga gatgagctcg ccgtcggggc aggcctcctt     180
cgaggtgaat gctgaccagc ttgcggactt cttgaacgac acctacgacg tggtcgaacc     240
tggtgatgaa caccggtgga tgaacgtcga cgaggtgctg agccagctgc tctcgccaac     300
ctgtaatggc ccagctctcc cgaagcgccg cacgccaaag cgctggctgc gggacctggc     360
ggcgctgaac accgccacgc tgtgtctccg agctccagct ggaccacgtc ggtgccgtgc     420
gcccggctcg gtcaggccga aggtgctgat cttctccagg cgcgccatcg gcgcaggaag     480
cgctgcttct gctcccgccg cagtaccgtc gtgtcatggc cacggacagc ttcgattcct     540
cgaagctaca ggcggccgtg gcatcgagcg tcgcgtcgtg cgtctcggaa gtcagccgag     600
acgtctacac gcacctgatt accgaggctc cgcagttgcg agccgatgag atcgtcctca     660
gcattctacg gacgagtgtt gaggaaaata tcgccacatt gccgcacgtt ctcgaattcg     720
agattccgtt gggatattcg ccgggtcctg ctgcggtgtt ggagtatccg cgacgactgg     780
cgaaacattt ccatcaacgc gctgatcagg gccaaccgca tcgggcactt ccgcttcctg     840
tagtgatgcc tcgacgagat ccgccgccaa tgcgccgacg aggccgtatc cgcagcgacc     900
acgcaacgaa tgctcgcaac cagcttcggc tacatcgacc gcgtcacgga gcagatcgcc     960
gaaacctacc agctcgaacg ggaccgctgg ctcctggcga cgggacggcc gtgaggtctc    1020
tgcggcatcc gcatagcgtc ttctcccgct gaggcacatg aggtgttgcg cgcggtcgtt    1080
tccggcagtc gcacggcatt cgtcctagct gcgggcaatt gagggagcga agatttagag    1140
gagtgtggcc acgcggacca agccggcgag tgctcgggag cggctgtggg gcggccaggc    1200
gatgactgtc gtcacgtccg gcgcgtctag aaccggtacg gcggcgaggc cttcgagcag    1260
gttgacgcga ctggattcgg gcatgaccac ggtagtgcgg ccgagtgcga tcatttggaa    1320
cagttgcgtc tggttgcgta cttccacgcc ggggccatct ggatagacgc cgtcgggggcc    1380
```

-continued

```
gggccagcgc gcaagcggga gatccggcag tgagctgaca tccgccatcc gtacatgggg    1440
ctcgctggca agcggatgcg aggtcggaag aatggcgact tgttgctcgg tgttcagaat    1500
ttcgatgtcg agttcggccg tcgggtcgaa gggttgatgc aacagcgcca cgtcggcccg    1560
gccgtcatgc agcgttttct ggggctggga ttcgcagagc agcaggtcga cggccacggc    1620
tcccggctcg gcggcgtacg cgtcgagcaa cttcgccagc agctcaccgg aggcgccggc    1680
cttggcagcc aggactagcg agggctggct cgtcgcggca cgctgggtgc gtcgctcggc    1740
tgctgccagc gcgccgagga tcgcccggcc ttcggtcagc agcattgccc cggcttcggt    1800
gagcgagact ttgcggctgg tgcgttgcag caacacgact ccgagtcgtt gctcgagctg    1860
ggcgatcgtc cgcgacagcg gcggctgggc gatgcccagg cgctgggcgg cccggccgaa    1920
gtgcaactcc tcgcgactg caacgaagta ccgcaactcc cgcgtctcca tccgtcgagc    1980
ctaccgctga ttcatatcag ctgggtatcg gtgtgagacc tagatggtgt tggttccccg    2040
ccggtttcgg gccacgctag aaagcatgag cgaacgacg attgcactgg tcaccggcgc    2100
aaacaaggga atcggatacg agatcgcggc cgggctcggc gcgctggggt ggagcgtcgg    2160
aatcggggca cgggaccacc agcgcgggga ggatgccgtg gcgaaattgc gtgcggacgg    2220
cgtcgatgcg ttcgcggtat ccctggacgt gacagacgac gcgagcgtcg cggctgctgc    2280
ggctctgctc gaggagcgcg ccggccggct cgatgtgctg gttaataacg ccggcatcgc    2340
cggggcatgg ccggaggagc cctcgaccgt cacaccggcg agcctccggg cggtggtgga    2400
gaccaacgtg atcggcgtcg ttcgggttac caacgctatg ctgccgttgc tacgccgctc    2460
cgagcgcccg cggatcgtca accagtccag ccacgtcgct tccctgacct tgcaaaccac    2520
gccgggcgtc gacctcggcg ggatcagcgg agcctactca ccgtcgaaga cgttcctcaa    2580
cgcgatcacc atccagtacg ccaaggaact cagcgatacc aacatcaaaa tcaacaacgc    2640
ctgccccggc tacgtcgcga ccgaccttaa cggcttccac ggaaccagca cgccggcaga    2700
cggtgccagg atcgccattc ggctcgccac gctgccagac gacggcccga ccggaggcat    2760
gttcgacgac gccgggaatg tgccctggtg aggcgctcag tcggcgatgg tgcaatcgaa    2820
gtcggagagg ctcgctgcga ccgggtacgc cgaacaacac ctgttcctgt gggtacggat    2880
gtcggccttc gccgtctcgg tcattgacaa cctgtacttc gggcgccgtt accgccggtg    2940
cgccgcggtt gcctggcgac actgggccag ccgtggctca ccggcggctt aggtcaggcg    3000
tgggcggttg ccagcatggc gggtgcggct ttgcgtaggt cgggtaggcg catccggcgc    3060
gggagccggt cgagttcttc gccgatggcc ggtgctttgg ggctgctcag gagccgaaca    3120
cctcccagcc gcaggtgccg ggctgaaccg agtggttctc gtcggctcgg atcacaacgt    3180
ctgccggaac agctgcggcg aggtggtcgc agattcgagg cgggatcgtc ctcggcgacc    3240
ttgccgacga tcgcggctag ggcccagggc ttcgtcgacc tggttggcac ctagatcacg    3300
acggtcaaaa cttgccggca tcagagacga tcgaagtgat cccgggtcac gtcggcttat    3360
cggtcgagtg agtcccgggg cctgcccagc caggtcttgc gtcgttgttc cgggctcagt    3420
tgcggattcc gacgaacagg cctcggccgt tcggtgctcc aggaaggtat ccgcgcgga    3480
tccctgcgtc ttcgagcgcg gcggtgtact cgtcctcagt gaacagcgag aggatttcga    3540
actctgtgaa gtcccggatc ccggtgggtt cggcgactgt gtagcggacg gtcatccggc    3600
tcgtacggcc ctccaggacc gagtgcgata gccggctgat cacccgctcg ccgtggtgcg    3660
cgacggctcc ggtgacgaac ccgtcgatga acttgtcggg aaaccaccag ggttcgatga    3720
ccgcgactcc accaggggcc aggtgccggg ccatgttccg cgtcacgcgt cgcaggtcgt    3780
```

```
caacggtccg catgtaagcc gcggtaaagc acaggcaggt gatgacgtcg aatggctcgc      3840
cgaggtcgaa atcgcggatg tcaccgatgt gaatcggtac ctcagggact cgtctgatcg      3900
cgatctcccg catcgcatcg gacagttcaa gccccgcgac cttcgcgtat tcggcacgga      3960
atcgctctag gtgcgccccg gtcccacagg cgacgtcgag tagggactgt gcttcgggca      4020
gcctggtgcg tacgagctgg actacttccc cggcctcggc tgcccagtcc cggccacgcg      4080
cggagtggat cgcgtcgtag atgtcggcat gatctgggct gtataccgag gaggtttctg      4140
cgaatgtgtc gctcacgcgc gacatcctca ctttcggagt ggtgatcttt ggctgatgtg      4200
gtgttcgacg gccttctgga actcgtcagc caccgtgcgc acctcggcgt cgtcaaggct      4260
tgggtgcagt ggtagcagga gtgttctgcg gcaggcgtcc tccgcagaag gcagcttgca      4320
gtccgcgcgg tagatgggga ccttgtgcag gggcgggtag cggtagctcg tgtagatgcc      4380
gcgttccagc atttgctgcg ccacctggtc gcggatctcc ggagccagct ggacccagta      4440
gaagtagtgt gacgagacgt gcccatccgg tagcgtcggc ggtaggagga caccgggcac      4500
atcggaaagc aaccggtcgt actgcgtagc gatttctcta cgcctgttga tgaattctgg      4560
cagtttgcgc agctgcacgc tgccaagcgc tgccgtcatg tcgttcccga tcagccgctg      4620
gccgatgtct tcgacgcgaa tatcccacca gcggttggaa gacttggccg aatcgaatcc      4680
gctcatctgc tcaagaccgt ggtaggcgag tcgtcttgcg cggtgcgcca gctccggatc      4740
cgccgcgtag aacatgcccc catccccggt gaccaggatc ttcatcgcat cgaaactcca      4800
cgtggccagg tcaccaaagg ttccgcaagc ggtgccgtgc acggacgatg ccaccgcgca      4860
ggcggagtcc tcgatgagca tgaggcccctt ttcacggcag aaatcggcga tcgcggtgac      4920
ttctcccggc gatcctccat agtggagcag caatacggcc ttggtcgccg gcgtgatggc      4980
cctcgccaca tcatccagcg tggggttcaa cgtccggggg tcgacgtcgc agaacaccgg      5040
gcgggcaccg gaggatgcga tggcgttggc cgccgccacg aagcttatcg aaggaagtac      5100
cacgtcgtcg cctgggccga ggtcgagcac ctgcacggta aggaacagcg cggcagtccc      5160
cgagttgagg aacacgacct gttcgggatc cactcccagg tggtgggcga attcggcctc      5220
gaacgtccgg gtgcgcggcc cgagcccgat ccagttggag gcgaacacct ccgcgatcgc      5280
gtcgagttct tcggtgccga ggatcggctg gtgcaggttg atcacgttgc tgaaatcctc      5340
cgagatgccg ccatgctgga tgctaggaac tcttggccac gaattcagcg attgattcga      5400
cgacgtagtc gatcatttgg tccgttatgc ctgggtagac gccgacccag aaggttcggt      5460
cggtgacgat gtcgctgttg gtgagcgcgt cggcgatccg gtaccgcacc tgctcgaagg      5520
ccgggtgccg ggtgatgtta ccgccgaaca gcagtcgggt gccgatgttg cgggattcca      5580
ggaagttcac cagggcggca cgggtgaacc cggcgtccgc actgatggtg atcgcaaacc      5640
cgaaccagct cgggtcgctg tgcggtgtgg ctaccggcag cagcaggccc ggcaacccgg      5700 acagccttc gcgcaaccgt cgccagttac ggcggcgtgc cgacccgaat gcggaaatct      5760
tgctcaactg gctcagcgca agtgcggcct gcaggtcggt ggtcttgagg ttgtaaccga      5820
cgtgggagaa cgtgtacttg tggtcgtagc ccggtggaag ggtaccgagg tggtagtcga      5880
acctcttgcg gcaggtgttg tccacgccgg gctcgcacca gcaatcccgt ccccagtcac      5940
gcagcgactc gatgatgcga gccaattcca ggctgccggt caacacgcag ccaccctcgc      6000
cgctggtgat gtgatgggca ggatagaagc tgaccgttgt caggtcgccg aaggttccgg      6060
tcagccgtcc ccggtaggtg gatcccaccg catcacagtt gtcttcgacg aggaacagct      6120
```

```
cgtgttctttt tgcgatctcc gcgatttcgt cagcggcgaa gggggttgccc agggtgtgcg   6180
ccagcatgat ggctcgcgtc cgttccgtga cggcggcctt gatgcggtct ggcgttgcgt   6240
tgtaggtgcc cagttccacg tcgacgaata ccgggacgag tccgttttgg accgccggat   6300
tgatcgtcgt ggggaagccg accgccgcag tgatcacttc gtcgccgggc cgcagtcgtg   6360
cctcgccgag tttggggag gtaagcgaac tcagtgccag gagattggcc gacgaaccgg   6420
agttgacgag atgagcctyg cggaggccga agaagcgggc gaactcgctc tcgaatcgcc   6480
gtgcattccc gcccgcggcg atccggagct ccagcgcggc ttccaccagt gccacccggt   6540
cgtcctcgtc gagcacggcg cccgatggcc ggatcggcgt cgatccagcc acgaaggtcg   6600
gggattcctg ttcgcggtgg taatcgcgta cggatgccaa tatccggtcc ttggcatccg   6660
gcaccatctc agtagcggta gcgcaagtgt cgtcacacga agtcactctg gcgcgccctt   6720
tccccagcgc tctggttttc cggctctgca tgcaggcgac gatcagtctt cgcgccttgc   6780
cttcaggaga tgagcgatgc ccgtggcgaa tcgcgttatg acgtcccagc gggacagtgt   6840
gctgtctcgg cgccttacac cttcctgccc tggttcgatg cggtgcggga catcaggaca   6900
gcggagcaag gagaagcgct cattgactca gaaatcctcg atctaccggg cacacccgac   6960
tcggtagagc ccaggctagc gggaacgacc tgctcgcgct tgtcaagatc gctaccatca   7020
cctgaaggc ctaagatttg gcttgcgaaa gcggcgtttc ccggggggata tcagagattt   7080
ctgtgattct tggcatgctt cccgggtgtt caattgcgat cggagagttc atgcgtgtcc   7140
tgttcacccc gctgccggcg agttcgcact tcttcaacct ggtgccgttg gcgtgggcgt   7200
tgcgtgccgc ggggcacgag gtccgtgtcg ccatctgccc gaatatggtg tcgatggtca   7260
ccggagcagg actcaccgcg gttcccgtcg gcgacgagct cgacctcatc tccttggcgg   7320
ccaagaacga actcgttctc ggcagcgggg tctcgttcga cgagaagggg cggcatccgg   7380
aactcttcga cgagctgctg tcaatcaact ccggcagaga cacggacgcc gtggagcaac   7440
tccaccttgt ggatgaccga tcgctggacg atctcatggg gttcgccgag aaatggcagc   7500
ctgatctcgt tgtgtgggac gctatggtgt gttcggggcc agttgtggcg cgagcgctcg   7560
gcgcacgaca cgtgcggatg ctcgtcgccc tcgatgtgtc ggggtggctg cggtccggtt   7620
tcctcgaata ccaggaatcg aagccgcctg agcagcgcgt cgacccgctc gggacgtggc   7680
tgggagcgaa gctcgccaag ttcggagcca cgttcgatga agagatcgtg acgggccaag   7740
cgaccataga tccgattcca tcctggatgc gcctgcctgt ggacttggac tacatctcga   7800
tgcgtttcgt gccgtacaac ggtccggcgg tgttgccgga gtggttgcgc gaacgaccga   7860
cgaagccgcg cgtctgcatc acgcgcgggc tgaccaagcg gcggctgagc agggtgaccg   7920
aacagtacgg ggagcaaagt gaccaggaac aagcaatggt ggaaaggttg ttgcgcggcg   7980
cggccaggct cgacgtcgag gtgatcgcca ccttgtctga cgacgaagta cgggagatgg   8040
gggagttgcc ctcgaacgtc cggtccacg aatacgtacc gctcaacgaa ctgctggagt   8100
cgtgttcagt gatcatccat catggctcga cgacgacgca ggaaaccgcc acggtcaacg   8160
gcgtaccgca gttgattctc cctgggacct tctgggacga atctcgtagg gcggagctcc   8220
tagccgatcg gggagccggt ctggtcctcg accccgcgac gtttaccgaa gacgacgtgc   8280
gaggtcagct ggccccgcctg ctcgacgagc cgtcgttcgc tgccaacgcg gcgctgatcc   8340
gccgtgaaat cgaggaaagt cccagcccgc acgacatcgt tccacgtctg gaaaagctag   8400
ttgccgaacg tgaaccgcgc gcactgggcc agtctgatgg ccatccgtga gcaacgtgtg   8460
gccggaaaca tggacgccgg ggtttggcag gtgttcatcg ctgttgcgtc gactcggatt   8520
```

-continued

```
ccgccgtgac cgggacgatg ccaggcgagt cccgaagtca gattcttgtc cagaatcgtc    8580
caatggggtg ttgatctccc cagaggtttg cgctccaacc gatttccgac gaggatcgtg    8640
gcgcccgctg agcaacgact accgtgcggt cgagacatac cgctgtgcgc caggagcgaa    8700
ggtgggttgc ccgatcaccg tgctggtggt agatgccgag ccgaaggtca ccttggatga    8760
ggcggaagcc tggcgagagc acaccgaggc cgtggccgac gtccgtgtct tctccggcgg    8820
gcatttcttc atgaccgaac gccaggacga ggtgctcgcg gtccttacgg gcggatcgct    8880
tcgatgatcc tcgccaggcc gctggaccag accgcgacgc cctgggagc cggcgtgcac     8940 atcgtcacgg cagtgaggga ttgggcatga gcagttctgt cgaagctgag gcaagtgctg    9000
ctgcgccgct cggcagcaac aacacgcggc ggttcgtcga ctctgcgctg agcgcttgca    9060
atggcatgat tccgaccacg gagttccact gctggctcgc cgatcggctg ggcgagaaca    9120
gcttcgagac caatcgcatc ccgttcgacc gcctgtcgaa atggaaattc gatgccagca    9180
cggagaacct ggttcatgcc gacggtaggt tcttcacggt agaaggcctg caggtcgaga    9240
ccaactatgg cgcggcaccc agctggcacc agccgatcat caaccaggct gaagtaggta    9300
tcctcggcat tctcgtcaag gagatcgacg gcgtgctgca ctgcctcatg tcagcaaaga    9360
tggaaccggg caacgtcaac gtcctgcagc tctcgccgac ggttcaggca actcggagca    9420
actacacgca ggcacaccgt ggcagcgttc cgccctatgt ggactacttc ctcgggcggg    9480
gccgcggccg cgtgctggta gacgtgctcc agtctgaaca ggggtcctgg ttctaccgga    9540
agcgcaaccg gaacatggtg gtggaagtcc aggaggaagt gccagtcctg ccagacttct    9600
gctggttgac gctcggccag gtgctggctc tccttcgtca ggacaacatc gtcaacatgg    9660
acaccccgga cggtgctgtc tgcatcccgt tccacgattc cgccaccgga cccgaactag    9720
ccgcctcgga ggagcccttc cgacaggcgg tggccaggtc gctctcgcac ggcatcgatt    9780
cgtcgagtat ctccgaggcg gtcggttggt tcgaggaagc caaggcccgc taccgcttgc    9840
gggcaacgcg cgttccgctg agcagggtcg acaagtggta tcgcaccgat accgagatcg    9900
cccaccagga cggcaagtac ttcgcggtga tcgcggtgtc ggtgtccgcg accaatcgtg    9960
aggtcgccag ctggacgcag ccgatgatcg aaccgcgaga acaaggtgag atcgcactgt    10020
tggtcaagcg gatcggcgga gtgctgcacg gtttggtcca cgctcgggtg gaggctgggt    10080
ataagtggac tgcggaaatc gctcccacgg tccagtgcag tgtggccaac taccaaagca    10140
ccccgtcgaa cgactggccg ccgttcttgg acgacgtgct caccgccgat cccgaaaccg    10200
tgcggtacga atcgatcctg tccgaagaag gcggtcggtt ctaccaggcg cagaacaggt    10260
accggatcat cgaggtgcat gaggacttcg cggcacgacc tcccagcgac ttccggtgga    10320
tgactttggg acagttgggc gagctgctcc ggagcaccca cttcttgaac atccaggcgc    10380
gcagcttggt cgcctccctg catagcttgt gggcgttggg gcgatgacca gctcgatgcg    10440
aaagccggtg cgcatcggtg tgctcgggtg cgcttccttc gcgtggcgac ggatgctgcc    10500
cgcgatgtgc gacgtggccg aaacagaggt ggtggcggtg cgagccgtg atccggcgaa     10560 agccgaacgg ttcgcagcgc gattcgaatg cgaggcggtg ctgggttacc agcggctcct    10620
ggagcggccg gacatcgatg ccgtctacgt gccgttgccg cctggcatgc atgcagagtg    10680
gatcggcaag gcgcttgagg cagacaaaca cgtgcttgcg gagaaaccgc tgacgacgac    10740
ggcgtccgac accgctcgcc tggtcgggct ggccaggagg aagaacctgc tgctgcggga    10800
gaattacctg ttcctccacc acggccggca cgacgtggtc cgcgacctgc tgcaatccgg    10860
```

-continued

```
ggagatcggt gagctccggg agttcaccgc cgtgttcgga attccgccgc ttcccgacac    10920
ggacatccgc tatcgcaccg aactcggtgg cggagcgttg ctggacatcg gtgtctatcc    10980
cgcccgtgcc gctcggcact ttctcctcgg tccgctcacg gttctcggcg caagctcgca    11040
cgaggcccag gagtcgggcg tcgacttgtc gggcagcgtg ctgctccaat cggaaggtgg    11100
caccgttgcc cacctcggat acggtttcgt gcaccactac cgcagcgcgt acgagctgtg    11160
ggggagtcgt gggcgaatcg tcgtcgaccg ggcgttcacg ccgcccgccg agtggcaggc    11220
cgtgatccga atcgagcgga agggcgttgt cgacgagttg tccttgccag cggaagatca    11280
ggttcgcaag gcggtcaccg ccttcgcacg cgacatcaga gcaggacag gcgtggacga    11340
ccctgcggtg gccggagatt cgggcgaatc gatgatccag caggccgcgc tggtggaggc    11400
gatcggtcag gcccgtcggt gcgggtccac atagccgccc ggcatccgcg ggtagtagtt    11460
cgcctcgaag cctgaccggg catccggaag ccagcgggga agccgctgga gaggctcacc    11520
gccatccgct cacctggcat ctcgcggacc gctgatcgcg gacggctcgg agaagtgctc    11580
gtcgaaccac gagacgacca ctcgcgagct ggccagggcg cgggaaagt gagccaatcc    11640
ggagagcgga tgccaccgca ctggcgtacc cgccgcgcgg tagctgtccc ggagtcgctc    11700
gccgaatgcg aacggaacga tctcgtcgtc cgtgctgtgg tagacgagcg tggggaccac    11760
cggggccaccg ttcctacctg cgacgctttc ggccagtcgt gcgcgccatc gaggttgctc    11820
gaaaaggccg gaagtgtcga ggaagtcgct cagctcgcgg ccgaggaagc gggtgacgag    11880
ctccggtgca ccgagctcgc gcacttgatc aacggcggta cgacccgctt cggtgagaag    11940
ctcgtcgaat ggcagatcgg ggtaggcagc ggcatgcccg accaggccgg ccagcaccgg    12000
cccggtgaac accccgtcat ttcggtggat gatgtccagc agatcgatcg gcaccgcacc    12060
tgcggccgca gcgcggattc gcagttcagg tgcgtaggtg gggtgcagtt cgccggcgaa    12120
ggccgacgct tgcccaccct gcgcatagcc ccagatgccg accgggcagt cggtcgtcag    12180
gccggagccc ggtagccgtt gcgcagcgcg ggcggcatcg agcatggcgt gtccctgcgc    12240
cctgccgacg tgtaggtgt gggttccagg agtaccgagg ccttcgtagt cggtgatgac    12300
cacggcccac ccgcggtcga gggccacggc gatcagctcg gtctccggct cggttccggt    12360
tcgaagcagg tacgacgggg caacttggct accgaggccg tgggtgccca ctgcgaaagt    12420
gatgatgggg cgatcttcgc gcggccacgg gatgttcggc accagaacgg tgccggagac    12480
ggcgttcggc atgccaaggg cggagttgga ccggtagagg atttgccagg ccttggctgc    12540
gacgggttcg cccgtgccgc gcagtgccga cgggccgg gccctgagga gcgtgcccgg    12600
gacaccggc ggtagcggcg tcggcggtcg gtagaaggga tcatccgcgg gtgcccgcag    12660
atcgtcgccg accaggctgg cgtgctcgga ggccatcagg actgcttctt tcgagcctgc    12720
aggagcatga aacccatgct ttcctcgttt ctggcgtaat ccggatgttt ccggtattcc    12780
gcaaccgcg cgatcagctg tgctggtccc ggtccgtgct tcgccgcgat gtctcccaag    12840
tagcgttgct ggtaggtgcc gacagccgca ggctcgacgc cggcgagctc atcgagtttc    12900
cggagcaact cgtcgacgta ccaggagacc atgcacctgg tctgtgccgt gaggtcggtg    12960
acttcgagaa tctcgaaccc ggcttcgctg accagcgccg tgaagctgtt caaggtatgg    13020
gcggtcgtgc ccgtccaaac cgccgcgtac tcttccggga gtcgaacccg agtgatgatg    13080
tctccgagga cgaaccggcc gccgggttcc aggattcggt ggacctcgcg gatcgcggcg    13140
gcctggtcca cgatctgcac gacggactgc atcgcccatg cggcctgaaa gaaaccgtcc    13200
gggtagggca gctgggcgcc gtcgactaga tcgaactcaa gactgccggc cagtccggtc    13260
```

-continued

```
tcgttggcga gcctggtggc ggcggcgaga tgctgggcgt tcacggtgat tccggtgact    13320
cgaacgccgc tggcgcatgc cgcacggact acgggctgcc cattgccgca gcccaggtcg    13380
aacaggtgcg ctccgggacg gagcgcggcc ttgtcgatga acaggtcggt cagttggtcg    13440
gcagcatccg accacggtgt ggcaccggca tcctcccgat acccgcccgc ccagtaaccg    13500
tggtgcaggg gacgcccgtg cgccaacgca tcgaagatgg actccacctg atccgcggtc    13560
ggaaatgcct gtgtgttcgc ccctctgctg ttcactcgtc ctccgcgctg ttcacgtcgg    13620
ccaggtgcaa tatgtcgtcc agactccttg gcacccaagc aggaacgccg ccttcggcgt    13680
tgacgccttt ctccaggaac gcgatgttgt ggtaggtgtg gaggccgacc aaattgcgtt    13740
ccaggtagct cggctcgtac gagcccgcat gcggctgctc ctcgtgctga acgccttcca    13800
acaggttctt gagcaggctg accgtggtgc cgggtgcggc cgggcactgc gcctgcccgc    13860
cgaatccggg agcataggtc gtccacagat cctcgatcac gtatacgcca ccgctgcgca    13920
accgggggaa cagcgtttcc agggatgtgc gcacgtgtcc gttgatgtgg ctgccatcgt    13980
cgatgatgat gtcgaacggt ccgtacttgt cgtcaacggc ggccagctcc tcgggcttgc    14040
tctggtcggc gcggacggtg cagagcctct gctggtcgag aaggacttg tcgaaaacgt     14100
ccatcccgaa cacgaggccg cggtggaagt agcgcttcca catcttcagg gattcgccgc    14160
cgccaccgtc gaagttgtag ccaccgacac cgatctccag gatgcgcacc gggcgatcac    14220
ggaactcgcc gaggtgtcgc tcgtatagcg gggtgaacca gtgcaggccg ccccacttgt    14280
ccgtgcggta gtgggaggcg agcaagttga ggtcgggacg tcggtgcccg cagccggcga    14340
ccactgcgga gatggcctgg aagccatcgg acagttccga cggaccgggt atcgaaccgg    14400
atgtggtggt tcggaggaag ttggtgctcc gggcgccgac ggccctggga gctcctgggc    14460
cgaacaactc ggcgatgaga tcggtgagct cgtaaccgat ccgcagcggg acgtctccga    14520
ccggtcgttg ctcggccttg atcagctcac cggactgtag cgtcaggacg aagtcaacgg    14580
tctcgcctcg gtgggtgatc tggaccgcga cctcggtccg ttcgatgtcg ggggccggtt    14640
ccgcgcggaa gaggatctcg tcgatcagca cgggtgcgat cctggcgagt ccgagttcgg    14700
tggtcaggtc ggccaggctc gccgcactgg atccggcggc gaggatgatg cgttccacgg    14760
tttcgatctc gtgcgttgtg gacatcgtga tgagctcctc atggctgacc gggtgaaagc    14820
cgtgccggcg gtttgatcga caggccgtgc tggaagatgt tctgcggatc ccaccgcgct    14880
ttggcccgct gcagccgcgg gtagttgtct ttgtagtaca ggtcgtgcca ggcaacaccg    14940
gaggtgttcc acaatggatc ggccaagtcg gtgtccgggt agttgatgta ggagccgtcg    15000
acacgggtac ctggcaccgg aactccgccg gtttcggcgt acatctcgcg gtagaaaccg    15060
cgaatccagg tcagatgccg ctcgtcctcg gcgggctccg accagttcgt gacgaacagc    15120
gctttgagaa ccgagtcgcg ctgagcgagt cggtggccg acggagccac ggcattcgcc     15180
ataccgccgt aaccgagcag caacagcgcc gccgcagggt tgtcgtatcc gtagacggtc    15240
agccgccggt aaaccgtggc tagttgagct tcggacagcc cggtgcgcaa gtaggcggct    15300
ttgaccttgg tccgttgcat gcccggttcg ccgccttcgg cgatcgcccc ggccacctgg    15360
gtcgatcgca accacggcag ggtttcccgc agcccttcgg ctggagtcac gccgacctgg    15420
gcgttgatcg ccgacaggtg ttcggccagg gtgcgttccg cgttcggatc cgtgccgtcc    15480
aggtgaacgt tcagcgtgac gtagccagct gccggtgtg cgcagacgag cgtgctgaac      15540
aacccgagtt gcgtggattc aggcgcgctg tgctgctcgt accaattgcc gaagttctgt    15600
```

```
aggagcacgg cgaatgactg ctctgtcagt tcgtgccacg gccagtgaac gatcggagc    15660
agcactgtcg cgggcggccg tggcaggagc tctgcgcgt cggtgctgac cacgtccggc    15720
gttcggagcc aaaacctggt gacgatcccg aagttgccgc caccgccacc ggtgtgcgcc   15780
caccacaagt cgtgaccggc gcccgtggag ttccggtcgg cctcgacgat gtgcacttca   15840
ccggcctggt cgaccacgac gacctcgacg ccttgaaggt agtcgacgac cgaaccgaat   15900
cggcgcgaca gcgggccgta tcccccgccg aggatgtgcc cgcctgcgcc caccccggga   15960
catgcgccgg tcgggatcgt cacgccccag ttcttgaaca gggttcggta cacctgcccg   16020
agggcggcgc ccgcctcgat cgcgaatgcc ccgcgcgtgc tgtcgtagta cacgcggttg   16080
agctcggaga ggtcgacgag cactcggatc gccgggtccg caacgagatt ctcgaagcag   16140
tgcccgccgc tgcggacccc tacccgcctg ccggtgcgca cggcgtcggc gacggcgtgc   16200
acgacgtctt cggcggagct ggcgatgtgg atgcgttcgg gttttccggt gaacgggggg   16260
ttgtgcccga cgacgaggtc cggataacga ggatcgtcgg gctcgacggt gatctctgtt   16320
cctggggttc gacgattcat gggtgccggg tcatggaatt cgggcaccgc ccctcctttt   16380
ctgactggtc cactttgttc gcccgcagcc gagatcatct acgcgtccgg gtgattatct   16440
gtgtgtttca gctcatacgt gaaacccggt cgcctccgcc ggctctactt tgtggatcga   16500
tatcgcggtg cgcatggtgc cgtatgcgct ggaaccgaaa aggtgatgac ttaccatgag   16560
tgagatcgca gttgcccccct ggtcggtggt ggagcgtttg ctgctcgcgg cgggtgcggg   16620
cccggcgaag ctccaggaag cagtgcaggt ggccggactg gacgcggtgg ccgacgccat   16680
cgtcgacgaa ctcgtcgtac gctgcgatcc gctgtcgttg gacgagtcgg tgcgaatcgg   16740
cctggagatc acttctggcg ctcagctggt ccggagaacc gttgagctcg atcacgcagg   16800
cctgcggctc gcggcggtcg ccgaagcagc tgctgttctc cggttcgacg cggtggatct   16860
gctggaaggg ctcttcggcc cggttgacgg caggcggcac aacagccgtg aagtccgctg   16920
gtcggacagc atgacgcagt tctcgcccga ccagggcctc gccggcgcgc agcgcctgct   16980
ggcgttccgg aacaggggtgt ccaccgcggt gcacgccgtg ctggccgcag ccgccaccag   17040
gcgcgcggac ctcggtgcgc tggcagtccg ctacggatcc gacaaatggg cggacctgca   17100
ctggtacacc gaacactacg agcaccactt ctcccgattc caggatgccc cggtgcgagt   17160
gttggaaata ggaatcggtg gttatcacgc acccgaactc ggtggtgctt cgctgcgcat   17220
gtggcagcgg tacttccggc gaggtctcgt ttacgggctg gacattttcg agaaagccgg   17280
gaacgaaggg caccgagtgc gaaagctgcg aggtgaccag agcgatgcgg aattcctgga   17340
agacatggtg gcgaagatcg gcccgttcga cattgtcatc gacgacggca gccatgtcaa   17400
cgaccacgtc aagaaatcct tccaatccct gtttccgcac gtccgcccag gtggtttgta   17460
cgtcatcgag gatctccaga cggcgtactg gcccggctac ggcggtcgcg atggggaacc   17520
cgcggcccag cgcacctcga tcgacatgct caaagaactg atcgacgcc tgcattatca    17580
ggagcgcgaa tcgcggtgcg ggaccgagcc ctcctacacg gaacggaacg tggcggccct   17640
gcacttctac cacaacctgg tattcgtgga gaaagggctc aacgctgaga ctgccgcgcc   17700
ggggttcgtg ccccggcaag cgctcggcgt cgagggcggc tgagccgttc accagctgcg   17760
gcgccagtag gcgcccgtgc cgtcgatgtc gtggatgggt tccgtgatcc cgagttccgc   17820
gcggaacccc ttcaccgcgt cctggcagga cggcagaaaa tagtcgtcga tgatgacgaa   17880
tccgcccggc gagagcttcg ggtacaggtt ccgcaatgag tccattgtgg attcgtagag   17940
gtcgccgtcg agtcgtagca cggcgagttc ctggatgggg gcggtgggca aggtgtcccg   18000
```

-continued

```
gaaccagccg gggaggaacc tgacctgttc gtcgagcagc ccgtagcggg cgaagttctg    18060
ccggacggtc tcaagcgata cgccaagcac gtcgttgtac tcgtgcagcg ccatagcctg    18120
gtccgcttgg tggtcttgcg cagagctttc cggcattccc tggaaggaat ccactaccca    18180
gacggtacgt ccggtatctc cgaatgcctg agaaccgcg cgcatgaaga tgcatgcgcc    18240
gccccgccag acaccggtct cggcgaaatc cccgggaaca ccgtctgcga gcacggcttc    18300
cacgcagtgc tggaggttgt ccagccgctc cagaccgatc atcgtgtgcg cgacagttgg    18360
ccagtccgtg cctttggccc gagcggcctg cctgtagtcg gtgttgtcct gccaggcgtt    18420
cggatgcggc cgatcactgt aaatcgtgtt ggtgagtacc ttcttgagca ggtccaggta    18480
cagcgcgttc tgggagggca tcggttctcc ggatccagct gttctcgggt gactagttca    18540
tcaggcacgg atggccgcag tgttctccag tgtccgcacc agcgcggcgg gatgggcat    18600 ggccgtgatc tcgtcgctga gtttgattgc cgcagaagcg aagccggtgt cgccgagcac    18660
cgttgcgatt gagtcggtga actgttcgtg gtcggactgg gcctgctcat ccggcaagca    18720
gatgcccgcc ccggcagcgg cgaggttgcg cgcgtagtcg aactggtcga agtactgggg    18780
aagcacgagt tgcgggatgc cgagtcgggt cgcggtgaat gccgttcccg agccgcccgc    18840
gcagatgacc agctcgcagg tacgcaggaa caggttgagc gggaccgatt cggcgatccg    18900
ggcgttgtcg ggtaggtcgg tgagaagtgc ccggtgctcg ggggaacgg cgatcacggc    18960 ctcgacgccg ggcaactcgg tggcagccgc tactgcgcgc agcagcggag ccggcccggt    19020
ggcgttcagc accatgcggc ccatgcagat gcagacccgc cgtgctgagg tgcgcgccgc    19080
gccccatgcc gggaatgcgc cgcttccgtt gtacggcacg tactggaccg gtgcgccttg    19140
cggcgcgtcg cttgcttgca ggctcggcgg acagggatcg aggatgagct cgggagtggg    19200
caggccggtc agtccgtggt gccggcacac cgggtcaagc aactcgtggg ctcgatcgct    19260 gaagggcct gcgtggggt cgactccca gcggtgcagc acgaccggca ggtcgagcaa    19320
tccgccgagc acccggccga tcagcgcgca gacgtcgacc aacagcactg acggtcgcca    19380
ggcctcggcc agtcgaaggt attcggggag ctgatcgagc gagctttgcg cgacattgga    19440
cgcggtctgc tcccacagtt gccggcctgc ctcggtgtcg cgctgaccga acgccggatt    19500
gggaaagcgc agctgcgtgg ttccacccgt atcgccggtc ctgtcgttcc cgcggatccc    19560
ggccgtggtg agacctgcac catgcgcggt cgcctgcagc tctggtggtg cggcgatcag    19620
gacctcgtgc ccggatgctt gcagcgccca gcacagcggc accattgcca tgagatgcgt    19680 cggataggc aagggaacga cgagtacgcg catacttcgg accccagtct ctttccccg    19740 attagcgcag cagcccctac tcccattggc caggatttgg aaaatgcgct gcgtatgtcg    19800
atcgccgttg acgtccaacg gacttccggc ggcaacaata gtgtgtcacg gcaggaatgt    19860
cacgcgacca tcgaagatct ttgggtcgcc gcacctggtt tcacgcgaac gagtgaaatg    19920
cgcgagctcc gctcgatcgg ggtgggccgg acctgtacgg tgatcaccgt tggttctgcg    19980
gggattcatg gggaagattt gcgctggctg tttgcctcct ggccggatag ttatagtcgg    20040
taccgccgca tgcggcggta accgcgaatt aactgacggc tagtttgccg tcttttctct    20100
ctgtgtgttt cctgctcggt tccagaaaat tacgagaagg tgaacgttgc agagatcagg    20160
cataccggtg ttgccaggtg gcgcaccaac atcgcagcag gttgggcaga tgtatgacct    20220
ggtcacgccg ttgctgaact cggtcgcggg cggccctgc gccatccacc acggctactg    20280
ggagaacgac gggcgggctt cctggcagca ggccgccgac cggctcaccg accttgtcgc    20340
```

```
cgaacggacc gtgctcgatg gcggcgttcg actgctcgat gtggggtgcg gtaccggaca  20400
accagcgctg cgcgtcgcgc gcgacaacgc gatccagatc accggcatca ccgtcagcca  20460
ggtgcaagtg gccatcgccg ctgattgcgc acgcgaacgc ggactaagcc accgggtgga  20520
cttctcgtgc gtcgatgcca tgtccctgcc gtacccggac aatgctttcg acgccgcctg  20580
ggccatgcag tcgctgttgg agatgtccga accggaccgt gccatccggg aaatccttcg  20640
agtactcaaa cccggtggca tcctcggcgt caccgaggtc gtcaaacgag aagcgggcgg  20700
cgggatgccg gtgtccgggg acaggtggcc gaccggcctt cggatctgcc tggctgagca  20760
acttctggaa tcgctgcgtg cagcggggtt cgagatcctc gattgggagg acgtgtcgtc  20820
gaggacccgg tacttcatgc cgcagttcgc cgaagagctc gctgcgcacc agcacgggat  20880
cgcggacagg tacgggccgg ctgtcgccgg ctgggccgcc gcggtctgcg attatgagaa  20940
atatgcccac gacatgggct atgcgattct gacggcgcgg aagccggtcg gctgagggcg  21000
cgccgcaatt cgatgacgtt catgcgccgt gtcgagaat cgccggtggc ggcgccagca  21060
gaggctgaac ttactggtgg tgtgtccagg aatcggaggg gcagtaccga atgagcgaag  21120
ccgggaacct gatagccgtc atcggactgt cctgccgcct accccaggcg cctgacccgg  21180
cttccttctg gcggttgctg cgcaccggaa cggacgccat caccacggtc ccggaagggc  21240
ggtggggcga cccgttgcct ggtcgggatg cgcccaaggg cccggaatgg ggtggtttcc  21300
tggctgatgt cgactgcttc gatcccgagt tcttcgggat ctcgccgcga aagcggcaa  21360 ccgtggatcc ccagcagagg ctggctctgg agctcgcctg ggaggcactc gaagacgccg  21420
gtatccccgc cggcgagctg cgcggtactg ccgccggtgt gttcatgggg gcgatctctg  21480
acgactacgc cgccctgctg cgcgagagcc cgccggaagt ggctgcgcag taccgcctca  21540
ccggcaccca tcgaagcctg atcgccaacc gcgtgtccta tgtgctcggc ctgcgcgggc  21600
caagcctgac ggtggattca ggtcagtcct cgtccctggt cggcgtgcat ctcgccagcg  21660
agagcctgcg acggggtgag tgcacgatcg cactcgccgg cggcgtgaac ctcaacctgg  21720
ccgccgagag caacagcgct ctgatggact tcggcgcgct ctccccggac ggtcgctgct  21780
tcaccttcga tgtgcgggcg aacggttacg tccgtggtga gggcggcggc cttgtcgtgc  21840
tgaagaaggc cgatcaggcg cacgccgatg gcgaccggat ctactgcctc atccgcggca  21900
gcgcggtcaa caacgatggg ggcggtgccg ggctcaccgt tccggcggcg gacgcccagg  21960
cggagctgct gcgccaggca taccggaacg cgggcgtcga cccggccgcc gtgcagtatg  22020
tcgagctcca cggcagcgcg accagggtcg gggatcccgt cgaagcagca gccctcggag  22080
ctgtcctggg ggcggcgaga cggcccggcg acgagctgcg tgtggggtcg gcgaagacca  22140
acgtcggcca tctggaagca gcggcgggcg tcaccgggtt gctgaagacc gcactcagca  22200
tctggcaccg cgaactgccg ccgagtcttc atttcaccgc ccccaacccg gaaatcccgc  22260
tggacgaatt gaacctacgc gtccagcgtg atctgcggcc gtggccggag agcgagggggc  22320 cgctgctggc cggcgtcagc gccttcggaa tgggaggcac gaactgccac ctggtgctct  22380
ccggcacgtc ccggagtggag cgacggcgca gtggacccgc tgaggcgacc atgccgtggg  22440
tcttgtcggc cagaacaccg gtcgcattgc gtgcgcaggc ggcgcgcttg cacacgcacc  22500
tcaatacggc cggtcaaagt ccgttggacg tcgcctactc actggcgacc actcgatccg  22560
cgctaccgca ccgggccgcg ctggtcgcgg acgacgaacc gaaactgctc gccgggttga  22620
aggccctcgc tgacgcgac gacgcgccca cgctgtgcca cggcgcgact tccggcgagc  22680
gggcagcggt cttcgtctttt cccggacagg gcagccagtg gatcgggatg ggtaggcagc  22740
```

```
tgctcgaaac ctccgaggtt ttcgcggcgt cgatgtcgga ctgcgccgac gcattggcgc   22800
cacacctgga ttggtccctg ctggatgtgc tgcgcaacgc ggccggcgct gcgcaccttg   22860
accacgacga tgtcgtccag cccgcgctgt tcgccatcat ggtctcgctc gcggagctct   22920
ggcgttcgtg gggcgtgcgt ccggtggcgg tcgtcgggca ctcgcagggg gagatcgcgg   22980
cggcctgcgt cgccggggcc ctgtccgtcc gcgatgccgc cagggtggtg gcggtgcgca   23040
gcaggcttct gacggcgctg gccggcagtg gcgcgatggc ctcgttgcag catcccgccg   23100
aagaggtgcg gcaaatcctg ttgccctggc gcgatcggat cggcgtggcg ggggtgaacg   23160
gaccgtcgtc gaccctggtg tcaggggacc gggaggcgat ggcggaactg ctggccgagt   23220
gcgcagaccg agagctccgg atgcgccgga ttcccgttga atacgcctcc cattcgcctc   23280
acatcgaggt tgtccgggat gagctgctgg ggctgttggc gccggtcgaa cccaggacgg   23340
gaagcatccc gatctattcg acgacgaccg gggacctgct ggaccggccg atggacgccg   23400
actactggta ccgcaacctt cgtcaaccgg tgctgttcga agcggccgtc gaggccctgt   23460
tgaagcgggg gtacgacgca ttcatcgaga tcagcccaca cccggtgctg actgcgaaca   23520
tccaggaaac cgccgtgcga gcagggcggg aggtagtggc gctcgggaca ctccgccgcg   23580
gcgaaggtgg catgcggcag gcgctgacgt cgctggccag agcacacgta cacgagtgg    23640
ccgcggactg gcacgcggtc ttcgccggta ccggggcgca gcggtcgac ctgccgacgt     23700
acgcctttca gcgacagcgc tactggctgg acgcgaagct tcccgacgtc gccatgcccg   23760
agagcgacgt gtcgacggcg ttgcgggaaa agctgcggtc ttcgccgagg gcggacgtgg   23820
actcgacgac cctcacgatg atccgggcac aggcagccgt ggtcctcggc cactccgatc   23880
cgaaagaggt ggacccggat cggacgttca aggacctggg cttcgattcc tcgatggtgg   23940
tcgagctgtg cgaccgccta aacgccgcca caggtctgcg actcgcaccg agcgtcgttt   24000
tcgactgtcc tacgccggac aagctcgccc gccaggtacg gacgttgttg ttgggcgagc   24060
cggctcccat gacgtcacac cggccggact ccgatgcgga cgagcctatc gccgtgatcg   24120
ggatgggctg tcgttttccg ggtgggggtgt cctcgcccga ggagttgtgg cagttggtcg   24180
ccgctgggcg ggacgtcgtg tccgagttcc cggctgaccg aggttgggac ctggagcgtg   24240
cggggacatc gcacgtgcgc gccggcgggt tcttgcatgg cgccccggat tttgaccccg   24300
ggttcttccg gatttcgccg cgcgaggcgt tggcgatgga tccacagcag cggttgctgc   24360
tggaaatcgc ctgggaagca gtcgaacgag gcgggatcaa cccgcagcac ctgcacggaa   24420
gtcaaaccgg ggtcttcgtc ggcgcgacct ccctggacta cgggccacgc ctgcacgaag   24480
cgtccgagga ggcggccggg tacgtgctca ccggcagcac cacgagtgtg gcgtcgggtc   24540
gggttgcgta ttcgttcggg ttcgagggcc ctgcggtgac ggtggatacg gcgtgttcgt   24600
cgtcgttggt ggccctgcat ttggcgtgtc agtcgttgcg ttcgggtgag tgtgatctgg   24660
cgttggccgg tggtgtgacc gtgatggcca cgccggggat gttcgtggag ttttcgcggc   24720
agcgtggttt ggcgccggat gggcggtgca agtcgttcgc ggaggccgcc gacggcaccg   24780
gctggtccga gggtgctggc ctggttctac tggagcggtt gtcggatgcc cggcggaatg   24840
ggcatgaggt gctggcggtt gttcgtggta gtgcggtgaa tcaggacggt gcgtcgaatg   24900
gtttgaccgc gccgaatggt tcgtcgcagc agcgggtgat tgcccaggca ttggcgagtg   24960
cggggttgtc ggtgtccgat gtggatgctg tggaggcgca tgggacgggc acgcggcttg   25020
gtgatccgat cgaggcgcag gcgctgatcg ccacctacgg ccaggccgg cttccggaac     25080
```

```
ggccattgtg gttgggctcg atgaagtcga acatcggtca cgcgcaggca gctgcgggga   25140
tagccggcgt catgaagatg gtgatggcga tgcggcacgg gcagctaccg cgcacgttgc   25200
acgtggatga gccgacttct ggggtggatt ggtcggcggg gacggttcaa ctccttacgg   25260
agaacacgcc ctggcccggg agtggtcgtg ttcgtcgggt ggggtgtcg tcgttcggga   25320
tcagtggtac taacgcgcac gtcatcctcg aacagccccc gggagtgccg agtcagtctg   25380
cggggccggg ttcgggctct gtcgtggatg ttccggtggt gccgtggatg gtgtcgggca   25440
aaacacccga agcgctatcc gcgcaggcaa cggcgttgat gacctatctg gacgagcgac   25500
ctgatgtctc ctcgctggat gttgggtact cgctggcgtt gacacggtcg gcgctggatg   25560
agcgagcggt ggtgctgggg tcggaccgtg aaacgttgtt gtgcggtgtg aaagcgctgt   25620
ctgccggtca tgaggcttct gggttggtga ccggatctgt gggggctggg ggccgcatcg   25680
ggtttgtgtt ttccggtcag ggtggtcagt ggctggggat gggccggggg ctttaccggg   25740
cttttccggt gttcgctgct gcctttgacg aagcttgtgc cgagctggat gcgcatctgg   25800
gccaggaaat cggggttcgg gaggtggtgt ccggttcgga tgcgcagttg ctggatcgga   25860
cgttgtgggc gcagtcgggt ttgttcgcgt tgcaggtggg cttgctgaag ttgctggatt   25920
cgtgggggt tcggccgagt gtggtgttgg ggcattcggt gggcgagttg gcggcggcgt   25980
tcgcggcggg tgtggtgtcg ttgtcgggtg cggctcggtt ggtggcgggt cgtgcccggt   26040
tgatgcaggc gttgccgtct ggcggtggga tgctggcggt gcctgctggt gaggagctgt   26100
tgtggtcgtt gttggccgat cagggtgatc gtgtggggat cgccgcggtc aacgctgcgg   26160
ggtcggtggt gctctctggt gatcgggatg tgctcgatga ccttgccggt cggctggacg   26220
ggcaagggat ccggtcgagg tggttgcggg tgtcgcatgc gtttcattcg tatcggatgg   26280
atccgatgct ggcggagttc gccgaattgg cacgaaccgt ggattaccgg cgttgtgaag   26340
tgccgatcgt gtcgaccttg accggagacc tcgatgacgc tggcaggatg agcgggcccg   26400
actactgggt gcgtcaggtg cgagagccgg tccgcttcgc cgacggtgtc caggcgctgg   26460
tcgagcacga tgtggccacc gttgtcgagc tcggtccgga cggggcgttg tcggcgctga   26520
tccaggaatg tgtcgccgca tccgatcacg ccgggcggct gagcgcggtc ccggcgatgc   26580
gcaggaacca ggacgaggcg cagaaggtga tgacggccct ggcacacgtc cacgtacgtg   26640
gtggtgcggt ggactggcgg tcgttcttcg ccggtacaag ggcgaagcaa atcgagctgc   26700
ccacctacgc cttccaacga cagcggtact ggctgaacgc gctgcgtgaa tcttccgccg   26760
gcgacatggg caggcgtgtc gaagcgaagt tctgggggcgc cgtcgagcac gaagatgtgg   26820
aatcgcttgc acgcgtattg ggcattgtgg acgacggcgc tgctgtggat tccctgagaa   26880
gcgcccttcc ggtgttggcc ggttggcagc gaacccgcac caccgagtcc attatggatc   26940
agcggtgtta ccgaattggc tggcggcagg tagccggact cccgccgatg ggaactgttt   27000
tcggtacctg gctggtcttc gcgcctcatg gctggtccag cgaaccggag gtggtggact   27060
gcgttacggc actgcgggca cgtggtgcct cggtggtgtt ggtggaagct gatcccgacc   27120
cgacctcctt cggcgaccgg gtacgaaccc tgtgttcggg ccttccggat cttgttggcg   27180
tgttgtcaat gttgtgcttg gaagaatcgg tccttccggg attttctgcg gtgtcacggg   27240
gttttgcgtt gaccgtggag ttggtgcggg ttttgcgggc agctggtgcg actgcccggt   27300
tgtggttgct gacgtgtggt ggcgtgtcgg tgggagatgt accggttcgt ccagcgcagg   27360
ccctggcgtg ggggttgggg cgtgttgtgg ggttggagca tccggactgg tggggcggct   27420
tgatcgatat tccggtcttg ttcgacgaag acgctcaaga gcggttgtcg attgtgctgg   27480
```

-continued

```
caggtctcga tgaggacgag gtcgcgatcc gtcctgacgg catgttcgcg cgtcggttgg   27540
tacgccacac tgtctcagct gatgtgaaga aggcgtggcg ccccagggga tcggtgctgg   27600
tgacgggcgg cacgggtggt ttgggggcgc acgttgctcg ctggctggcc gacgccggag   27660
ccgaacatgt ggcgatggtg agtcgacgcg gcgagcaggc accgagtgct gagaagttgc   27720
ggacggaact ggaggatctg ggtacccggg tgtcgatcgt gtcatgcgat gtgaccgatc   27780
gcgaggcgct cgccgaagtg ctgaaagccc ttccggctga aaacccgttg accgcggtag   27840
tgcatgcggc aggcgtgatc gagactggtg atgcggcggc aatgagcctg gctgatttcg   27900
atcacgtgtt gtccgcaaag gtggccggtg ccgcgaatct ggatgccttg ttggccgatg   27960
tggaattgga cgcgttcgtc ttgttctcat cggtgtcagg agtttgggc gctgggggac    28020
acggggctta cgcagcggcg aatgcctatc tggatgcgct cgcggaacag cgtcggtcgc   28080
gagggctggt cgccgactgcg gtggcctggg ggccgtgggc cggcgagggc atggcctccg   28140
gagaaacagg agaccagctg cgccgatacg gcctttcccc aatggctccg cagcacgcca   28200
tcgccggaat ccggcaggcc gtggaacagg acgaaatttc cctggtagtg gccgatgtcg   28260
attgggcacg tttcagcgcg ggattgctgg cggctaggcc gcggccgctg ctgaacgaac   28320
tggccgaggt caaggaactc ctcgtcgatg cccagcccga ggcggagtc cttgccgacg     28380
cgtcgttgga atggcggcag cgattgtccg cggcaccgag gccgacacag gaacagctga   28440
tcctggagct ggtacgcggc gaaaccgctc tggtgctggg acaccccggg gcagcggccg   28500
ttgcatcgga acgagccttc aaggacagcg gattcgactc gcaggccgcg gtcgaactcc   28560
gcgttcggct caatcgagct accggcctcc agttgccatc gacaattatc ttcagccatc   28620
ccacgcctgc ggaactggct gcggagctgc gggcgaggct tcttcccgag tccgcaggag   28680
caggcattcc cgaggaggac gaggcgcgaa tcagagcggc actgacgtcg atcccgttcc   28740
cggccttgcg cgaggcaggc ttggtgagtc cgctgctcgc acttgccgga cacccggtcg   28800
actccggtat ctcctcggac gatgcggccg cgacctcgat cgatgcgatg gatgtagccg   28860
gcctcgtcga agcagcgctg ggcgaacgcg agtcctgaga ccgccgacct gggagatgac   28920
ggtgaccacc agttacgaag aagttgtcga ggcactgcga gcatcgctca aggagaacga   28980
acgcctccgg cgcggcaggg atcggttctc cgcggagaag gacgatccca tcgcgatcgt   29040
ggcgatgagt tgtcgttatc ccggtcaggt ctcctcgccg gaggacctgt ggcaactggc   29100
tgccggcggt gtggacgcga tctccgaagt tccgggggat cgcggatggg acctggatgg   29160
cgtgttcgtt ccggactccg atcgtcctgg cacgtcgtat gcctgcgcgg gcggttttct   29220
tcagggcgtg tcggagttcg acgcgggttt cttcgggatt tcgccgcgtg aggcgctggc   29280
gatggatccg cagcagcggt tgctgctgga agtcgcgtgg gaggtcttcg agcgggctgg   29340
gctggagcag cggtcgacac gcggttcccg cgttggcgtg ttcgtcggca ccaatggcca   29400
ggactacgcg tcgtggttgc ggacgccgcc gcctgcggtg gcaggtcatg tgctgacggg   29460
cggtgcggca gcggttcttt cgggccgggt tgcgtattcg ttcgggttcg agggtcctgc   29520
ggtgacggtg gatacggcgt gttcgtcgtc gttggtggcg ttgcacctgg cggggcaagc   29580
actgcgggcc ggtgagtgcg accttgccct tgccggtggc gtcacggtga tgtcgacgcc   29640
gaaggtgttc ctggagttct cccgccaacg gggtctcgcg ccggatgggc ggtgcaagtc   29700
gttcgcggcg ggtgcggatg gcactggatg gggtgagggt gccggactgt tgttgctgga   29760
gcggttgtcg gatgcccggc ggaatgggca tgaggtgctg gcggttgttc gtggtagtgc   29820
```

```
ggtgaatcag gacggtgcgt cgaatggttt gaccgcgccg aatggttcgt cgcagcagcg    29880
ggtgattacc caggcgttgg cgagtgcggg gttgtcggtg tccgatgtgg atgctgtgga    29940
ggcgcatggg acgggcacgc ggcttggtga tccgatcgag gcgcaggcgc tgatcgccac    30000
ctacggccgt gatcgtgatc ctggccggcc gttgtggttg gggtcggtca agtcgaacat    30060
cggtcatacg caagcggcgg cgggtgtggc tggtgtgatc aagatggtga tggcgatgcg    30120
gcacgggcag ctgccacgca cgttgcacgt ggaatcgccg tcgccggagg tggattggtc    30180
ggcggggacg gttcaactcc ttacggagaa cacgccctgg cccaggagtg gtcgtgttcg    30240
tcgggtgggg gtgtcgtcgt tcgggatcag tggtactaac gcgcacgtca tcctcgaaca    30300
gcccccggga gtgccgagtc agtctgcggg gccgggttcg ggttctgtcg tggatgttcc    30360
ggtggtgccg tggatggtgt cgggcaaaac acccgaagcg ctatccgcgc aggcaacggc    30420
gttgatgacc tatctggacg agcgacctga tgtctcctcg ctggatgttg ggtactcgct    30480
ggcgttgaca cggtcggcgc tggatgagcg agcggtggtg ctgggtcgg accgtgaaac    30540 gttgttgtgc ggtgtgaaag cgctgtctgc cggtcatgag gcttctgggt tggtgaccgg    30600
atctgtgggg gctgggggcc gcatcgggtt tgtgttttcc ggtcagggtg gtcagtggct    30660
ggggatgggc cggggggcttt accgggcttt tccggtgttc gctgctgcct ttgacgaagc    30720
ttgtgccgag ctggatgcac atctgggcca ggaaatcggg gttcgggagg tggtgtccgg    30780
ttcggatgcg cagttgctgg atcggacgtt gtgggcgcag tcgggtttgt tcgcgttgca    30840
ggtgggcttg ctgaagttgc tggattcgtg ggggttcgg ccgagtgtgg tgttggggca    30900
ttcggtgggc gagttggcgg cggcgttcgc ggcgggtgtg gtgtcgttgt cgggtgcggc    30960
tcggttggtg gcgggtcgtg cccggttgat gcaggcgttg ccgtctggcg gtgggatgct    31020
ggcggtgcct gctggtgagg agctgttgtg gtcgttgttg gccgatcagg gtgatcgtgt    31080
ggggatcgcc gcggtcaacg ctgcggggtc ggtggtgctc tctggtgatc gggatgtgct    31140 cgatgaccctt gccggtcggc tggacgggca agggatccgg tcgaggtggt tgcgggtgtc    31200 gcatgcgtttt cattcgtatc ggatggatcc gatgctggcg gagttcgccg aattggcacg    31260
aaccgtggat taccggcgtt gtgaagtgcc gatcgtgtcg accttgaccg gagacctcga    31320
tgacgctggc aggatgagcg ggcccgacta ctgggtgcgt caggtgcgag agccggtccg    31380
cttcgccgac ggtgtccagg cgctggtcga gcacgatgtg gccactgttg tcgagctcgg    31440
tccgacgggg gcgttgtcgg cgctgatcca ggaatgtgtc gccgcatccg atcacgccgg    31500
gcggctgagc gcggtcccgg cgatgcgcag gaaccaggac gaggcgcaga aggtgatgac    31560 ggcccctggca cacgtccacg tacgtggtgg tgcggtggac tggcggtcgt tcttcgccgg    31620
tacgggagcg aaacaaatcg agctgccacc ctacgccttc caacgacagc ggtactggct    31680
ggtgccatcg gattccggtg atgtgacagg tgccggtctg gccggggcgg agcatccgct    31740
gttgggtgct gtggtgccgg tcgcgggtgg tgacgaggtt ttgctgaccg gcaggatttc    31800
ggtgcggacg catccgtggc tggccgaaca ccgggtgctg ggtgaagtga tcgttgcggg    31860
caccgcgttg ctggagatcg ccttgcacgc ggggaacgt cttggttgtg aacgggtgga    31920
agagctcacc ctggaagcac cgctggtcct gccggagcgc ggggcgatcc aggttcagct    31980
gcgagtgggc gcgcccgaga attcggacg caggccgatg gcgctgtatt cacgcccga    32040 aggggcggcg gagcatgact ggacgcggca cgccacgggc cggttggcgc caggccgcgg    32100
cgaggcggct ggagacctgg ccgactggcc ggctcctggc gcgctgccgg tcgacctcga    32160
cgaattctat cgggaccctcg cagagcttgg gctggagtac ggcccgatct tccaagggct    32220
```

-continued

```
caaggcggcc tggcggcaag gggacgaggt gtacgccgaa gccgcgctgc cgggaacgga    32280
agattctggt ttcggggtgc atccggcact gctggacgcg gctctgcacg caacggctgt    32340
ccgagacatg gatgacgcac gcttgccgtt ccagtgggaa ggtgtgtccc tgcacgccaa    32400
ggccgcgccg gctttgcggg tccgcgtggt cccggctggt gacgatgcca agtccctgct    32460
ggtttgtgat ggcaccggtc gaccggtgat ctcggtggac cgactcgtat tgcggtcggc    32520
tgcggcccgg cggaccggtg cgcgccgaca ggcccatcaa gctcggttgt accggttgag    32580
ctggccaacg gttcaactgc cgacatccgc tcagccaccg tcctgcgtgc ttctcggcac    32640
ctcagaagtg tccgctgaca tacaggtgta tccggacctc cggtcgttga cggctgcgtt    32700
ggatgccggt gccgaaccac ccggcgtcgt catcgcaccc acgcccccg gcggtggacg     32760 aacagcggat gtccgggaga cgactcggca tgcactcgac ctggtacaag gctggctttc    32820
cgatcagcga ctcaacgaat cccgattgct cctggtgaca cagggagcag tggccgtgga    32880
gccgggcgaa cccgtgaccg atctggcgca ggccgcgctc tggggactgc tgcggtcgac    32940
gcagaccgaa caccctgatc gcttcgtcct cgtcgatgtg cctgagcccg cgcaactcct    33000
ccccgcgctg ccggggggtgc tggcctgcgg cgaacctcag ctcgcgttgc gacgtggcgg    33060
cgctcatgcg cccagactgg ctggactggg cagcgatgac gtcctgcccg tgccggacgg    33120
caccgggtgg cgattggagg ccacgcgccc gggaagcctg gatgggttgg cattggtgga    33180
cgaaccgacg gccacggcac cgctgggtga cggtgaggtc aggattgcga tgcgcgcggc    33240
cggggtgaac ttccgggatg cgctcatcgc gctcggtatg tatcccggtg tggcatcgct    33300
gggcagtgag ggcgccgggg tcgtggtgga gaccggcccc ggcgtcaccg gcctggcacc    33360
cggcgaccgc gtgatgggaa tgatcccgaa ggcgttcggg ccgctcgcgg tcgccgacca    33420
tcgcatggtg acgaggattc ccgctggttg gagcttcgcg cgggccgcat cggtgccgat    33480
cgtctttctc accgcctact acgcgctggt tgatctcgcc gggttgagac caggggagtc    33540
gttgctggtt cattcggccg ccggtggggt ggggatggcc gcgatccaac tcgccaggca    33600
cctcggtgca gaggtgtacg ccaccgctag cgaggacaag tggcaagccg tggagctgag    33660
ccgagaacac ctcgcttcgt cgcggacgtg cgatttcgag cagcagttcc tcggggcaac    33720
cggcggacgg ggcgtcgacg tcgtgctcaa ctccctcgcc ggggagttcg ccgatgcgtc    33780
tctgcgaatg ctgccgcgcg gtggccgttt cctggagttg gggaagacgg atgttcgtga    33840
ccccgtcgag gtcgccgatg cgcatccggg cgtgtcttac caggctttcg ataccgtaga    33900
ggcaggcccg cagcgaatcg gcgagatgct tcacgagctg gtggagttgt tcgagggacg    33960
cgtgctggag cccctgcctg tcacggcttg gacgttcgg caggcgcccg aggcgctacg    34020
gcacctgagc caagcgcggc atgtgggaaa gctggtgctc accatgcctc cggtgtggga    34080
cgccgcaggc acggttctgg ttaccggcgg aacgggagca cttggcgcag aggtcgcccg    34140
gcacctcgtg atcgagcgcg gggtgcgaaa cctggtcctc gtcagcaggc gcggtcccgc    34200
agccagtggc gctgctgagc tcgtggcgca actgacggcc tacggtgccg aggtttcctt    34260
gcaggcttgc gatgtcgccg atcgtgagac cttggcgaag gtgcttgcca gcatcccgga    34320
cgagcatccg ttgaccgccg tggtgcacgc ggctggtgtt ctcgacgacg gagtgtccga    34380
atcgctcacc gtggagcggc tggaccaggt tctgcgcccg aaggtcgatg gcgcgcggaa    34440
tctgctcgag ctgatcgacc cggacgtggc cctcgtgttg ttctcgtcgg tgtcgggtgt    34500
gctcggcagc ggtgggcagg gtaactacgc ggcggccaac tccttcctcg acgcattggc    34560
```

```
gcagcaaagg cagtcgcgcg gcctaccgac gagatcattg gcctgggggc cctgggcgga   34620
acatggcatg gccagcacct tgcgcgaagc cgagcaggat cgattggcgc gatctgggtt   34680
gctgccgatc tcgaccgagg aggggttgtc ccagttcgac gccgcgtgcg gcggcgcgca   34740
taccgtggtg gcgccggttc gattcagccg cttgtccgac gggaacgcga tcaagttctc   34800
cgtcctgcaa ggtttggtcg ggccgcatcg cgtcaacaaa gcggcgactg cggatgatgc   34860
cgagagcctc cggaaacggt tgggacgctt gccggatgca gaacaacatc ggattctgct   34920
ggacctcgtc cgcatgcatg tggcggcagt gctcggattc gccggttctc aggagatcac   34980
cgcggacggc acgttcaagg tgctgggctt cgactcgttg accgtggtcg agttgcgcaa   35040
ccggatcaac ggggcgacgg ggctgcgact gcccgccacc ctggtgttca actacccgac   35100
gccggatgcg ctcgccgcgc acctcgtcac cgcgctgtcc gcagaccgcc tggccggac   35160
attcgaggaa ctcgacaggt gggcggcgaa cctgcccacg ctggccaggg atgaggccac   35220
gcgggcgcag atcaccaccc ggctacaggc gatcttgcag agcctggcgg acgtgtccgg   35280
cggaaccggc ggcggctccg tgccggaccg gctcagatcg gccacggacg acgagctttt   35340
ccaactcctc gacaacgatc tcgaacttcc ctgatgcctc agccggagcc ttcgcaactt   35400
cctggaggga aacgccacat gtcgaatgaa gagaagctcc gggagtactt gcggcgtgcg   35460
ctcgtggatc tgcaccaggc gcgcgagcgg ctgcacgagg cggagtcggg agagcgggaa   35520
cccatcgcga tcgtggcgat gggctgccgg tacccgggtg gggtgcagga cccggaaggg   35580
ctgtggaaac tggtcgcctc cggtggcgac gccatcggtg aattccccgc tgatcgtggt   35640
tggcacctcg acgagctcta cgatcccgac ccggatcagc ccggaacctg ctacacccgg   35700
cacggcggct tcctccacga cgccggcgag ttcgacgcgg gattcttcga catcagcccc   35760
cgtgaggcgc tcgcgatgga cccgcagcag cggctgctgc tggaaatctc ctgggagacc   35820
gtcgaatccg ctgggatgga cccgaggtcc ttgcggggga ccgcaccgg ggtgttcgcg   35880
ggattgatgt acgagggcta tgacaccggc gcccaccggg caggagaagg tgtcgaaggc   35940
tatctcggaa ccggcaatgc gggaagcgtc gcctctggtc gggttgcgta tgcgttcggg   36000
ttcgagggcc cagcggtgac ggtagacacg gcgtgctcgt cgtcgttggt ggcgctgcat   36060
ttggcgtgtc agtcgttgcg gcagggcgag tgtgatctgg cgctggccgg tggagtgacg   36120
gtgatgtcga cgccggagag gttcgtggag ttctcccgtc agcgtggtct cgcaccggat   36180
gggcggtgta agtcgttcgc ggcggctgcg gatggaaccg gttggggtga gggtgccggt   36240
ttggtgttgc tggagcggct gtcagacgcc aggcggaacg ggcatcgggt actggcggtt   36300
gttcgtggta gcgcgtgaa tcaggacggt gcgtcgaacg gattgacggc cccgaacggg   36360
ctggcccagg agcgggtcat tcagcaggtg ctcacgagtg cggggctgtc ggcgtccgat   36420
gtggacgctg tggaggcgca tggaacgggt acgcggcttg gtgatccgat cgaggcgcag   36480
gctctgatag ccgcctatgg acaggatcgg gaccgggacc ggccgctgtg gttgggtcg   36540
gtcaagtcca acatcggtca tacgcaggcg gctgcgggcg tcgctggtgt gatcaagatg   36600
gtcatggcga tgcggcacgg ggagctgccg cgcacgttgc acgtggacga gccgaattcg   36660
cacgtggact ggtcggctgg tgcggtccga ctcctgaccg agaacatccg ctggccaggg   36720
acgggtacgc gccgcgctgg agtgtcgtcg ttcggggtaa gcggtaccaa cgcacacgtc   36780
atcctcgaac acgacccgct cgccgtgacc gagaacgagg aagcagcgca gtccccagca   36840
cctgggatcg tgcctgggc gttgtccggg cggtcgtcga cggcgctgcg ggcccaggcc   36900
gaacggctgc gcgagctgtg cgagcagacc gatcccgacc ccgtcgatgt cggtttctca   36960
```

```
ctggccgcca cgcgcacggc ttgggagcac cgagcggtgg tgcttggtcg ggacagcgct   37020
acgttgcgct ccgggcttgg cgttgttgcc agcggtgaac cagcggtcga tgtcgttgag   37080
gggagcgtcc tggacggcga ggtcgtcttc gtcttccccg gtcagggctg gcagtgggcc   37140
ggtatggcag tcgacctgct ggacgcttcg ccgacgttcg cgcgccacat ggacgagtgc   37200
gccaccgcgc tgcggaggta cgtggactgg tcgttggtcg acgtgctgcg cggagcggag   37260
aactccccac cgctggaccg ggtggacgtg ctccagcccg cgtccttcgc ggtgatggtg   37320
tcgctcgccg aggtgtggcg ttcctacggg gtgaggccgg cggccgtcgt cggccacagt   37380
caaggcgaaa tcgccgcggc ctgcgcagcc ggggtgctgc cgctggagga tgcggccagg   37440
cttgtcgcat tgcgcagcag agcgttgaag gactttcgg ggcggggtgg catggcgtcg   37500
ctggcctgcc ctgcggatga ggtcgcggca ttgttcgcgg gatcgggcgg ccgtctggaa   37560
gttgcggcga tcaacggccc gcgatcggtc gtggtgtccg gcgatctgga agcggtggac   37620
gaactgctgg cagagtgcgc tgaaaaggac atgcgtgcac gccgtatccc cgtcgactac   37680
gcctcgcatt cagcgcacgt ggaggtggtt cggagcccgg tgctggcggc cgccgccggg   37740
gtgcgacacc gggacggcca ggtgccgtgg tggtcgacgg tgatcggcga ctgggtggat   37800
ccggccaggc tggacggcga gtattggtat cggaacctcc ggcagccggt ccggttcgaa   37860
cacgccgtgc agggcctggt cgagcgggga ttcggcctgt tcatcgaaat gagtgcgcat   37920
ccggtgctga ccacggcggt cgaggaaacc ggtgcggagt cggagaccgc cgtggccgcg   37980
gtaggtacct tgcgacgtga ctcgggcggc ctccggaggt tgttgcattc gctggccgag   38040
gcgtacgtgc gcggcgccac cgtggactgg gccgtggcgt tcggggcgc gggccgacgg   38100 ctggacctgc cgacctaccc gttccagcgc cagcggtact ggctggacaa gggagctgcc   38160
tccgacgagg ctcgtgcggt ctcggacccg gcggcgggct ggttctggca gccgtggcg   38220 cgccaagacc tgaaaagcgt gtccgatgcc ctcgatctcg acgccgacgc accgctgagc   38280
gcaacacttc cagccctgtc cgtctggcac cgtcaggaac gagaaagggt cttggcagac   38340
ggttggcggt accgagtcga ctgggtacgg gtggccccgc agccggtccg gagaacgcgg   38400
gaaacctggc tcctggtcgt tcccccgggc ggcatcgagg aagcgctggt cgaacggctg   38460
acggatgcgt tgaacacgcg agggatcagc accctgcgcc tcgacgtgcc accggcggcc   38520
accagtggcg aactcgcaac cgaactccgc gccgcagccg acggtgaccc ggtgaaggca   38580
atcctgtcgc tcaccgcgtt ggacgagcga ccccacccc aatgcaagga cgtcccgagc   38640
gggattgcct tgctgctgaa cctggtcaag gcgctcggtg aagccgacct cagaattcct   38700
ctgtggacca tcacgcgtgg tgcggtcaag gcaggcccg cagatcggct gctgcgcccg   38760
atgcaggcgc aagcatgggg tctggggcga gtagccgcac tcgaacaccc cgagcgctgg   38820
ggtgggctga tcgacctgcc ggattcgctg acggcgacg tcctcacgag gctgggcgaa   38880
gcgctcacca acggcttggc ggaagaccaa ctggcgattc gccagtcggg cgtgctggcc   38940
cggcgactgg tacccgcccc ggcgaatcag cccgctggac gtaagtggcg ccccgaggg   39000 agcgcgctga tcacgggcgg actcggcgcg gtgggcgcac aggtggcgag gtggttggcc   39060
gaaatcggag ccgagcgaat cgtgctcacc agtcgacggg gcaaccaagc agcaggcgcc   39120
gccgagctgg aagccgaact ccgggccctt ggagcgcaag tgtccatcgt ggcttgcgac   39180
gtgaccgatc gtgccgagat gtccgcacta ctggccgagt tcgacgtcac cgcggtgttc   39240
cacgcggccg gagtcggtcg gctgctgccg ttggcggaga ccgaccagaa cggcctggcc   39300
```

```
gaaatatgcg cggcgaaggt ccgcggcgct caggtgctgg acgaactgtg cgacagcacc    39360
gatctcgatg ccttcgtcct gttctcctcg ggtgccgggg tatggggcgg gggcggtcag    39420
ggcgcttacg gcgcggcgaa cgcattcttg gacacactcg ccgaacaacg ccgagcacgc    39480
ggtctgccgg caacctcgat ctcctggggc agttgggccg gcggcggcat ggccgacggc    39540
gcggcgggcg aacacctgcg gcgacgcggg atacgtccga tgccggcggc gtcggccatc    39600
ctggctctgc aggaagtact tgaccaggat gagacgtgcg tgtcgatcgc tgatgtggac    39660
tgggaccgat tcgttcccac gttcgccgcg actcgcgcca cccggttgtt cgacgaagtg    39720
ccggcggcga gaaaggcgat gcccgcgaat gggccggcag aaccaggcgg ctcgccgttc    39780
gcccgcaatc tcgcggagct gccggaagcc caacgacgcc acgaactggt ggatctggtg    39840
tgcgcccagg tggcaaccgt gctcgggcac ggcagtcgcg aggaagtcca gcccgagcgg    39900
gcgttccgcg cgctcgggtt cgactccctc atggcggtgg atctgcgcaa tcgtttgacc    39960
accgccaccg ggttgcgcct gccgaccaca accgtcttcg                          40000
actacccgaa tccggccgcc ttggccgctc acctgctcga ggagctggtg ggtgatgtcg    40060
cgtcggctgc ggtgaccgct gccagcgcgc ccgcgagtga cgaaccgatc gcgatcgtcg    40120
cgatgagctg ccggtttccg ggtggcgcgc actcgccgga agacctgtgg cggctggtcg    40180
ccgccggcac ggaggtgatc ggcgagttcc cctccgaccg gggctgggat gcggaaggcc    40240
tttacgatcc ggatgcttcc aggcctggaa cgacgtatgc gcggatggcg ggattcctct    40300
acgacgccgg tgagttcgat gccgaccgt tcggcatcag cccacgtgag gcgttggcga    40360
tggatccgca gcagcggttg gtgctcgaaa tcgcctggga agccctcgaa cgggccggaa    40420
tcgatccgtt gtccttgaag ggcagtgggg tcggcacgta catcggcgct ggaagccgtg    40480
ggtacgcgac ggatgtgcgg cagtttcccg aggaggcgga gggctacctg ctgacgggta    40540
cctcggccag tgtgctgtcg ggtcgggtcg cgtattcgtt tggtttcgag ggtcctgcgg    40600
tgacggtgga tacggcttgt tcgtcgtcgt tggtggcgtt gcatctggcg tgccagtcgt    40660
tgcgttcggg cgagtgtgat ctggcgttgg ccggtggtgt gaccgtgatg tcgacgccgg    40720
agatgttcgt ggagttctcc cgtcagcgcg gtttggcgcc ggatgggcgg tgcaagtcgt    40780
tcgcggagag cgcggacggc accggctggg gcgaaggcgc gggcctgttg ttgctggagc    40840
ggttgtcgga cgcccaccgg aatgggcatc gggtgttggc ggtggttcgt gggtcagcgg    40900
tgaatcagga cggcgcctcg aacggactgg cggcgccgaa cggtccgtcg cagcagcggg    40960
tgatcaacca ggcactcgcg aatgcggctc tttcggcgtc cgatgtggat gcggtggagg    41020
cacatggcac cgggaccagg ctgggtgatc cgatcgaggc gcaggcattg atcgcaacgt    41080
atgggcaggc ccgggagcgg gatcggccct tgtggctggg gtcggtcaag tcgaacatcg    41140
gtcatacgca ggccgcggcg ggtgttgccg gtgtgatcaa gatggtgatg gccatgcggc    41200
acgggcagct gcccgcctcg ctgcacgcgg atgagcccac gtcggaggtc gattggtcgt    41260
cgggggcggt ccggctcctc gccgaacagg taccttggcc ggagtctgac cgtgttcgtc    41320
gggtgggggt ttcgtcgttc gggatcagcg gcaccaacgc acatgtgatc ctcgaacaag    41380
ctacgaatgc gccagatagt acagcggaga cggacaaaac agaatccgga tctactgtcg    41440
atattccggt cgttccctgg ttggtgtcgg gaaagacgac ggattccctg cggggacaag    41500
ccgaacgagt cttgtctcag gtcgagtccc ggccggagca gcgttcgctg gatgttgcct    41560
actcgcttgc ttctgccga gccgcgctgg atgaacgcgc tgtcgtgctg ggtgcggacc    41620
gcggtgagct ggttgctgga ctggcggcgt tggccgccgg tcaggaggct tctggggtga    41680
```

```
tcagcggaac tcgtgcttct gctcggttcg ggttcgtgtt ctcggggcag ggtggtcagt    41740
ggttggggat gggcagagcg ctctactcga agtttccggt gttcgctgct gcgtttgatg    41800
aggcttgcgc cgagttggag gcacatctgg gggaagaccg ccgggttcgg gatgtggtct    41860
tcggttccga tgcgcagctg ctggatcaga cgctgtgggc gcagtcgggt ctgttcgcgc    41920
tgcaagccgg cctcttgggg ctgctgggtt cgtgggcgt tcggccggat gtggtgatgg    41980
ggcattcggt cggggagttg gccgccgcgt ttgcggctgg cgtgttgtcg ttgcgggatg    42040
cggctcggtt ggtggccgcg cgcgcccggt tgatgcaagc cctgccctct gacggcgcga    42100
tgttggcggt ggctgctggt gaagaccttg ttcggccatt gctggccggt cgggaggagt    42160
ccgtgagcgt cgccgcgctc aatgcccccg gttcggtggt gttgtcgggc gatcgggagg    42220
tgctggccag catcgtcggc cggctgaccg agctccgagt ccggacgcgg cgcttgcggg    42280
tctcccatgc ttttcattcg caccggatgg acccgatgtt gggcgagttc gcccagatcg    42340
ccgagtctgc ggagttcggt aagccaacga caccgcttgt gtcgacgttg acgggtgagc    42400
tcgacagagc cgcggaaatg agcacaccag ggtattgggt gcgccaggcg cgtgaacccg    42460
tccgtttcgc cgacggtgtc caggccctgg cagcgcaggg cataggcacg gtcgtcgagc    42520
tcggcccgga cggaacgctg gcggcactgg ttcgggagtg tgcgaccgag tccgatcggg    42580
ttgggcggat ttcgtcgatc ccactgatgc gcagggagcg ggacgagacc cgttcggtga    42640
tgacagccct ggcgcatctc cacacccgtg gtggtgaggt ggactggcag gcgttttcg    42700 ccggtaccgg cgctaggcag ctcgagttgc caacgtatgc cttccaacga cagcactact    42760
ggatcgagtc cagtgcgcgg ccagcacgcg accgcgcaga catcggcgag gtggcggaac    42820
agttctggac cgcggttgac caaggcgatc tggcaacgtt ggtcgccgct ctggatcttg    42880
gggcggacga cgacacatgc gcatcgttga gcgatgtatt gccggcgttg tcctcctggc    42940
gaagcggact ccgcaaccgt tcgctcgtcg attcctgccg gtaccgaatc agttggcatt    43000
cctctcggga ggtgccggcc ccgaagattt ccggtacctg gctgttggtc gtgcccggtg    43060
ctgcggatga cggattggtc acggctttga cgagttcact ggtcggaggc ggcgccgagg    43120
tcgtccggat cggcctgtcc gaagaggacc cgcaccgcga ggacgtcgca cagcggctgg    43180
ccaatgcgct gacggatgcc ggtcaactcg gtggcgtgct ttcgctgttg gggctcgatg    43240
aatcgcctgc tccgggattc tcctgcttgc caactggttt cgcgctgact gtgcagcttc    43300
tgcgggcctt gcggaaggcc gacgtcgagg cgccttttg ggcggtgacg cgcggcggcg    43360
tcgcgttgga agatgtacgc gtgtctccgg agcaggccct ggtctggggg ctgctgcgtg    43420
tcgcgggact ggagcacccg gagttctggg gtggcttgat cgacctgcca tcggactggg    43480
acgaccgatt gggtgcccgg ttggcgggtg tgttggcgga tggtggcgag gatcaagtcg    43540
ccattcgccg tggtggtgtg ttcgtgcggc ggttggaacg cgctggtgcg tcgggtgccg    43600 gtcggtgtg gcgtcctcgg gggacggtgt tggtgacggg tggtacgggc ggtttggggg    43660
cgcatgttgc ccggtggttg gccggtgccg gggctgagca cgtggtgttg accagccgtc    43720
gaggagcgga cgctccgggc gctggggaat tgcgggcgga gctggaggcg ctgggtgctc    43780
gggtgtcgat tgtgccctgc gacgtggctg atcgtgacgc agtggctgga gtgttggcag    43840
ggatcggtgg ggagtgtccg ctgactgcgg tggtacacgc cgccggggtc ggcgaggcgg    43900
gcgacgtagt ggagatgggt ttggcggatt ttgcagcggt gtttgtcggcg aaggtgcgtg    43960 gtgcggcgaa tctggacgag ttgctggccg actcggagct ggatgcgttt gtgatgttct    44020
```

-continued

```
cctcggtgtc gggggtgtgg ggagccggcg gacagggtgc gtatgcggct gcgaacgcct    44080
acttggatgc gttggccgag cagcgtcggg cgaggggatt ggtcgggacc gcggttgcgt    44140
ggggaccgtg ggccggtgac ggcatggccg ccggcgaaac cggcgcacag ctgcaccgga    44200
tgggcctggc gtcgatggaa ccgagcgcgg cgctgctggc acttcagggt gcattggacc    44260
gcgatgagac ctccctcgtc gtggccgatg tcgattgggc acggttcgcc ccagccttca    44320
cctcggcacg tcgacgcccg ctgctggaca ccatcgacga ggcccgagcc gcattggaaa    44380
ccaccggcga acaagcgggc acaggcaaac ccgttgagct gacgcaacgc ctggccggac    44440
tgtcgcggaa ggaacgcgac gatgcggtat tggatctggt gcgggcggag acggcggctg    44500
tgctgggacg cgacgatgcc acggccctgg cgccatcgcg gccgttccag gaactcggat    44560
tcgactcctt gatggcggtg gagctgcgca accggctgaa caccgccacc gggatccagc    44620
tgcccgccag cacgattttc gactacccca atgccgagtc gctgtcgcgt cacctctgcg    44680
ccgagctttt cccaacggag actaccgtgg actcggccct tgccgagctc gatcgaatcg    44740
agcagcagct ctcgatgctc accggcgaag cgcgggcacg ggaccgaatc gcgacacgac    44800
tgcgagcccc ccacgagaag tggaacagcc agctgaagt accgaccgga gccgatgtcc    44860
tgagcacgct cgattcggcg acgcacgacg agatattcga gttcatcgac aacgagctcg    44920
acctgtcctg agcagttcct gcggaacttc aagcgccgaa atcgggtgga atcacaatg    44980
gccaatgaag aaaagctctt cggctatctg aagaaggtaa ctgcggacct gcatcagacc    45040
cggcagcgcc tgctcgcggc cgagagccgg agtcaggagc cgatcgcgat cgtctcggcg    45100
agctgccgac tgcccggcgg cgtcgactct cccgaagcgc tctggcaact cgtgcgcact    45160
ggcaccgacg ccatctcgga gttccccgcc gaccggggct gggatctcgg ccggttgtac    45220
gatcccgacc cgaaccacca gggaacgtcg tacacgcggg ccggcggttt cctcgcagga    45280
gcgggcgatt tcgaccccgc catgttcggg atttcgccgc gtgaggcgtt ggcgatggac    45340
ccgcagcaac ggttgttgct ggagctgtcc tgggaggccc tcgaacgggc gggcatagac    45400
ccgacatccc tgcgcggcag caagaccggt gtcttcggtg gtgtcacgcc ccaggagtac    45460
gggccgtcct tgcaggagat gagccgaaac gctgggggtt ttggactcac cgggcggatg    45520
gtgagtgtgg cgtcgggtcg ggttgcgtat tcgtttggtt ttgagggtcc tgcggtgacg    45580
gtggatacgg cgtgttcgtc gtcgttggtg gccctgcatt tggcgtgtca gtcgttgcgt    45640
tccggcgaat gcgatctcgc gctggccggc ggtgtgacgg tgatggcgac accggcgacg    45700
ttcgtggagt tctcccgtca gcgtggtttg gctccggacg ggcggtgcaa gtcgttcgcg    45760
gctgccgcgg atggcaccgg gtggggtgag ggtgccggtc tggtgttgct ggagcggttg    45820
tcggatgcgc ggcggaatgg gcacgaggtt ctggcggtgg tgcggggtag cgcggtgaac    45880
caggacggcg cgtcgaatgg tttgactgcg ccgaatggtc cgtcgcagca gcgggtgatc    45940
acccaggcgt tggcgagtgc ggggctgtcg gtttccgatg tggatgcggt cgaggcacat    46000
gggaccggga ccacgttggg tgatccgatc gaggcacagg ccctgatcgc cacgtacggg    46060
cagggccggg agaaggatcg gccgttgtgg ttggggtcgg tcaagtccaa catcggtcac    46120
acgcaggcgg ccgctggcgt tgccggcgtc atcaagatgg tcttggcgat gcggcacggg    46180
cagctgcccg ccacgttgca tgtggatgag cccacgtcgg cggtggactg gtcggcgggt    46240
tcggtccggc ttctcacgga gaacacgccc tggccggaca gtggtcgtcc ttgccgggtg    46300
ggggtgtcgt cgttcgggat cagcggcacc aacgcacatg tgattctcga acagtctcca    46360
gtcgagcagg gcgaaccggc cgggccggtc gaaggcgagc gggaaccgga tgtagccgtc    46420
```

```
cccgtggtgc cttgggtgct gtcgggtaag acaccggagg ctgcgcgggc gcaggccgaa   46480
cgggtgcatt cgcatatcga ggaccggccg gggctgtcgc cggtggatgt ggcgtattcg   46540
ctaggaatga cacgcgcggc gctggatgaa cgcgcagtgg tgttgggctc ggaccgtgcc   46600
gcgctcctga ccgggttgag ggcattcgcc gacggctgcg atgcgcccga agtggtttcg   46660
gggtctgtgg ggcttggtgg ccgcgtcggg ttcgtgttct cgggtcaggg tggtcagtgg   46720
ccggggatgg gccgggggct ctactcggtg tttccggtgt tcgccgacgc gttcgacgag   46780
gcttgcgcgg agttggatgc acacctgggc caggaactgc gggttcggga tgtggtgttc   46840
ggttcgcaag cgtggttgct ggatcggacg gtgtgggcgc agtcgggttt gttcgcgttg   46900
cagattggct tgctgcggct gctggggttc gtgggtgttc ggccggatgt ggtgttgggg   46960
cactcggtgg gtgagctggc tgcggtgcat gcggctggtg tgttgtcgtt gtcggaggcc   47020
gcgcggttgg tggcgggtcg cgcccggttg atgcaggcgt tgccttctgg tggtgccatg   47080
ctcgcggtcg ctacgggtga gtttcaggtc gatcctctgc tggatgggt gcgggaccgg   47140 atcggtatcg cggcggtgaa tggcccggaa tcggttgtgc tctctggtga ccgcgagctg   47200
ctcaccgaga tcgctgatcg gttgcacgat caggggtgcc ggacccggtg gttgcgggtg   47260
tcgcatgctt tccattcgcc ccatatggag ccgatgctgg aggagttcgc ccagatctcc   47320
cgaggccgcg aatatcacgc accggaactg ccgatcatct cgaccctgat cggtgagctg   47380
gacggtggtc gagtgatggg cactcccgag tactgggtgc gtcaggtgcg tgagcccgtc   47440
cgtttcgccg agggtgtcca ggcgcttgtc ggtcaggggtc tcggcacgat tgtcgaattg   47500
ggtccggacg gggcgttgtc gacgttggtc gaggagtgtg tggcggaatc cgggcgggtg   47560
gccgggatcc cgctgatgcg caaggaccgc gacgaggcgc gaaccgtgct ggcagctttg   47620
gcgcagatcc acacccgtgg tggtgaggtg gactggcggt cgttttcgc cggtaccggg   47680 gcgaagcaag tcgacctgcc cacctacgcc ttccagcggc agcggtactg gctggcatcc   47740
accgggcgtg cgggtgacgt gaccgccgcc ggattggccg aggcggacca tccgctgctc   47800
ggtgcggtgg ttgcgttggc agacggcgaa ggtgtggtgc tgaccggtcg gttgacagcg   47860
ggttcgcatc cgtggttgtc cgatcaccgg gtgctgggcg aaatcgtcgt ccccggcacc   47920
gcgatcgtcg agctggtgtg gcacgtcggc gagcgcctcg gttgtggccg ggtggaagaa   47980
ctggctttgg aagcgcccct gatcctgccg gatcatggag cggtccaggt tcaggtgctg   48040
gtgggaccgc ccggggaatc cggagcccgg tcggtggcgc tctactcctg tcctggcgag   48100
gcgatcgaac ccgagtggaa gaagcacgcg acgggcgtgc ttctcccacc cgtggccgcc   48160
gagaaccatg agctgaccgc atggcccccg gagaatgcga ccgaaatcga tgcagacggg   48220
gtctacgcat tccttgaagg gcacggtttc gcgtacggac cggcctttag atgtctgcgc   48280
ggtgcctggc gacgaggcgg ggaggtgttc gccgaagtcg cattgccgga tgacatgcag   48340
gcgggggtcg atcgattcgg cgtccacccc gcgttgctgg acgcggttct gcatgccgcc   48400
gcagccgaga cgtcggtggt ccagagcgaa gcgcgggtgc cgttctcgtg gcgtggggtg   48460
gaacttcgcg ccactgaaag cgcggtggtg cgggcgcgcc tctcgttgac ttcggatgac   48520
gaactgtcgt tggtcgcagt ggacccggct ggccgattcg tggccacggt tgattcgctg   48580
gtgacccgac cgatctcccg gcagcaggtg aggtctggcg cgatcggtga ttgcctgttc   48640
gaggtggagt ggcaccggaa ggcgttgttg ggaacaaccg ccggcgacga ccttgccatc   48700
gtcggtgacg gtcccagttg gccggaatcg gtgcgcgcaa ccgcacggtt cgcgaccctg   48760
```

```
gatgagttcc gtgcggccgt ggactcggac gttcctgccc cgggttcggt gttggtcgca   48820
gctatgtcgg ccgaagaggt cgagggtgga tccctgccgt cgcgcgccca agagtcgacc   48880
tccgatctgc tggctctcgt gcagtcgtgg cttgcggacg agcggttcgc cgaatcccag   48940
ctcgtggtcg tcacgcgtgc agcggtgtcg gccgactcgg attcggacgt cgcggacctg   49000
gtgggtgcgt cgtcgtgggg gttgttgagt tcagcccagt cggagaaccc gggtcgcttc   49060
gtgctggtgg acgtggacgg cacacctgag tcgtggcagg cgttgccggc cgccgtgcga   49120
gcaggagaac cgcagctggc acttcggcgc ggcgtggcgc tggtgcctcg gttggcgcga   49180
ctcacggtgc gcgaggaggg ctcctccccg caactcgaca cggacgggac cgtcctcatc   49240
acgggtggca ccggtgcgtt ggggggagtg gttgcccgtc acctggtgga ggagcacggg   49300
attcggcgtt tggtgttggc aggccggcgt ggctggaatg cgcctggagt ccacgagttg   49360
gtggatgagc tggcgcgcgc gggcgccgtg gttgaggtgg tggcttgcga tgtggctgac   49420
cgcaccgatc tggagcacgt gctggccgcc attccggtcg actggccgct gcgggggatc   49480
gtgcataccg ctggggtgct ggccgacgga gtgatcgggt ccttgtcggc ggcggatgtg   49540
ggcacggtgt ttgccccgaa ggtgacgggg gcatggcatc tgcacgagtt gacccgcgat   49600
ctggatctgt cgttcttcgt tcttttctct tccttctccg ggattgcggg tgccgcaggg   49660
caggccaact acgcggcggc gaacacgttc ctggatgcat tggcgcgtta tcgccgggcg   49720
cgtgggctgc ctgggttgtc gttggcgtgg ggactgtggg cgcaacccag cggtatgacg   49780
agtggcttgg acgcggcgtc ggtggagcgg ttggcgcgga cgggcatcgc agaactttcc   49840
acggaggatg gactccgcct gttcgatgcc gcgttcgcga aggaccgggc ttgcgtcgtt   49900
gccgctcgat tggacagggc gctgctggtc gggaacggac gatcgcacgc gattccggcg   49960
ctgttgagcg cgttggttcc tgttcgcggc ggtgtggcga ggaaaacagc caattctcag   50020
gccgcggatg aggacgcact gttgggtttg gtgcgggagc acgtttcggc cgtgctgggt   50080
tattcgggtg cggtcgaggt tgggggcgac cgtgctttcc gtgatctggg ttttgattcg   50140
ttgtctggcg tggagttgcg gaaccgcctt gccggggtgc tggggggtgcg gttgccggcg   50200 actgcggtgt tcgactatcc gacgccgcgg gcgctggcgc gtttcctgca tcaggaactg   50260
gcaggcgagg tcgcgtccac gtcgacgccg gtgaccaggg cagcgagtgc cgaagaggat   50320
cttgttgcga ttgtcgggat gggatgtcgt tttccgggtg gggtgtcgtc gccggaggag   50380
ctttggcggc tggtggccgg cggcgtggat gcggtggctg ggttcccaga cgatcgcggc   50440
tgggatctcg cggcgttgta cgatcctgat cccgatcgtc tcgggacctc gtatgtgtgt   50500
gagggcgggt ttctgcggga cgcggcggag ttcgatgctg acatgttcgg catcagcccg   50560
cgtgaggcgt tggcgatgga tccgcagcag cggttgctgc tggaggtcgc ctgggaaacc   50620
ttggagcggg ctgggatcga tccgttctcg ttgcacggca gccggaccgg tgtgttcgcg   50680
ggcttgatgt accacgacta tggggcccga ttcattacca gagcaccgga gggcttcgaa   50740
gggcacctcg ggacgggcaa tgcggggagc gtgctgtcgg gtcgggttgc gtattcgttt   50800
ggtttcgagg gtcctgcggt gacggtggat acggcgtgtt cgtcgtcgtt ggtggcgtta   50860
cacctggcgg gtcaagcact gcgggccggt gagtgcgaat tcgcccttgc cggtggcgtc   50920
acggtgatgt cgacgccgac gacgttcgtg gagttctccc gtcaacgggg tctggctccg   50980
gatgggcggt gcaagtcgtt cgcggcggcc gcggatggca ccgggtgggg cgagggtgcc   51040
ggtctggtgt tgctggagcg gttgtcggat gcccggcgca atgggcacga ggttctggcg   51100
gtggtgcggg gtagcgcggt gaaccaggac ggcgcgtcga atggcttgac tgcgccaaat   51160
```

```
ggtccgtcac agcaaagggt gatcacccag gcactcacga gtgccgggct gtccgtgtcc   51220
gacgtggatg ctgtggaggc gcatgggacg ggcacgcggc ttggtgatcc gatcgaggcg   51280
caggcgttga tcgctacgta cggccgggat cgtgatcccg gtcggccgtt gtggctgggg   51340
tcggtgaagt cgaatattgg tcacacccag gcggcggcgg tgtcgctgg tgtgatcaag    51400
atggtgatgg cgatgcggca gggggagctg ccgcgcacgt tgcacgtgga cgagccctcc   51460
gcgcaggtgg actggtctgc gggcacggtc caactcctca cggagaacac gccctggccc   51520
gacagcggtc gtcttcgccg gcgggcgtg tcatcgttcg ggatcagtgg caccaacgcg    51580
cacctgatcc ttgaacaacc tccgcgagag tcgcagcgct caacagagcc ggattcgggt   51640
tctgtccgcg attttccggt ggtgccgtgg atggtgtcgg gcaaaacacc gaagcgcta    51700
tccgcccagg cagatgcatt gatgtcctac ttgagcaatc gcgttgatgc ttccccgcga   51760
gatatcggtt attcgcttgc ggtgacccgt ccggcgttgg accaccgcgc tgtcgtgctg   51820
ggtgcggatc gtgccgcgtt gctgccgggc ttgaaagcgc tggccgttag taatgacgct   51880
gccgaggtga tcaccggcac tcgtgccgct gggccggtcg gattcgtgtt ctccggtcaa   51940
ggtggtcagt ggcccgggat gggaagcggg ctccactcgg cgtttccggt gttcgccgac   52000
gcgtttgacg aagcctgctg cgagctggat gcgcatctcg ggcagatggc ccggctacga   52060
gatgtgttgt ccggttcgga tacgcaactt ctggaccaga ccttgtgggc gcagccgggc   52120
ctgttcgcgt tgcaagtcgg actctgggag ttgttgggtt cgtggggtgt ccggcccgct   52180
gtggtgctgg gccactcgt cggtgagctg gcggcggcgt tcgcggctgg agtgttgtcg   52240
ttgcgggatg cggctcggct ggtggcgggc cgtgcccggt tgatgcaagc cctgccaact   52300
ggcggtgcca tgctcgctgc ggctgctgga gaggagcagc tgcgcccgtt gctggccgac   52360
tgcggtgatc gtgtggggat cgccgcggtc aacgctcccg ggtcggtggt gctctccggt   52420
gatcgggatg tgctcgatga cattgccggt cggctggacg ggcaagggat ccggtccagg   52480
tggttgcggg tttcgcatgc gtttcattcg catcggatgg atccgatgct ggcggagttc   52540
accgaaatcg cccggagcgt ggactaccgg tcgtcagggc tgccgatcgt gtcgacgttg   52600
acgggtgagc tcgatgaggt cggcatgccg gctacgccgg agtattgggt gcgccaggtg   52660
cgagaacccg tccgcttcgc cgacggtgtt gctgcgctcg cggctcacgg tgtgagcacc   52720
gtcgtcgagg tcggtccgga tggggtgttg tcggcgctgg tgcaggagtg cgcggccgga   52780
tccgatcagg gcggacgggt ggccgcggtt ccgctcatgc gcagcaatcg cgacgaggcg   52840
cacacggtga caacggcatt ggcgcagatc catgtgcgtg gtgctgaggt ggactggcgg   52900
tcgttttttcg ccggtaccgg ggcaaagcag gtcgagctgc ccacgtatgc cttccaacga   52960
cagcggtact ggcttgactc accatccgaa ccggtcgggc aatccgccga tcccgcgcgc   53020
cagtcgggct tctgggaact cgtcgagcag gaagatgtca gcgcgctcag cgccgctctg   53080
cacattaccg gcgatcacga cgtgcaggcg tccctggaat cggtggttcc ggtcctctcc   53140
tcctggcatc gccggatccg caacgaatcc ctggtcacc agtggcggta ccggatttcc    53200
tggcatgagc gggcagattt gccagacccc tcgttgtcgg ggacatggct cgtcgtcgtg   53260
ccggaggggt ggtcggcgag tcggcaagtt ctgcgtttca acgagatgtt cgaggaacgg   53320
ggttgcccgg cagttctgtt cgagctcgcc gggcacgacg aggaagccct ggcgcaacga   53380
ttccgctcgt tgcctgttgc gtcagggga ataagcggcg tgttgtcctt gctggcgctg    53440
gatgaatcgc cgtcctcgcc gaacgctgct ttgccgaatg cgcgcgctga actcgttggta  53500
```

-continued

```
ctgctgcgag ctctgcgggc cgcggatgtg tcggcgccat tgtggttggc gacgtgtggt    53560
ggtgtcgcgg tcggggatgt gccggtgaac ccggggcagg cgctggtgtg gggactgggt    53620
cgcgtcgtcg gtctggagca tccggcctgg tggggtggcc tggtcgacgt gccgtgcttg    53680
ctcgatgagg acgctcgaga acgcttgtcg gtcgtgttgg caggtcttgg cgaggacgag    53740
atcgcggtac gtcccggtgg tgtgttcgtg cggcggttgg aacgcgctgg tgcggcgtcg    53800
ggtgccgggt cggtgtggcg tcctcggggg acggtgttgg tgacgggtgg tacgggcggt    53860
ttggggcgc atgttgcccg gtggttggcg ggtgccgggg ctgagcatgt ggtgttgacc     53920
agccgtcgag gcgcggcggc tccgggcgct ggagatttgc gggcggagct ggaggcgctg    53980
ggcgctcggg tttcgatcac ggcctgcgac gtggccgatc gtgacgcttt ggccgaagtg    54040
ttggcgacca ttccggatga ttgcccgctg accgcggtga tgcatgcggc gggggtcgtt    54100
gaagtcggcg acgtggcgtc gatgtgtttg accgacttcg ttggggtgct gtcggcgaag    54160
gcaggtggtg cggcgaatct cgatgagttg ctcgccgatg tcgagctgga tgccttcgtg    54220
ctgttctcat ccgtctcggg tgtgtggggt gctggcgggc agggcgctta tgcggcggcg    54280
aatgcctact tggatgcgtt ggcgcagcag cgtcgggcaa gggggttggt ggggactgcg    54340
gttgcgtggg gcccgtgggc cggtgacgga atggccgcag gtgaaggcgg tgcacagctg    54400
cgccgggccg gcctggtgcc aatggctgcg gatcgggcgt tgctggcact tcagggcgca    54460
ttggatcgtg acgagacatc cctggtcgtg gccgatatgg cgtgggagag gttcgccccg    54520
gtgttcgcca tgtcccgtcg gcgtccgctg ctcgacgagc tgcccgaagc acagcaggcg    54580
ttggcggatg cggagaacac cactgatgct gcggactcgg ccgtcccgct accgcggctc    54640
gcgggcatgg cagccgccga acgccgccgc gcgatgctgg acctggtgct ggcggaggcc    54700
tcgattgtgt tgggacacaa cgggtctgac ccagttggtc ccgaccgggc gttccaggag    54760
ctcggatttg attcgctgat ggccgtcgaa ctgcgcaaca ggttgggcga ggcaacagga    54820
ttgagtctgc cggccacgtt gatcttcgat tatccgagcc catccgcgct ggctgagcag    54880
ctggtcggcg agctggtggg agcgcagccc gcgaccaccg tcgtggccgg ggccgatcca    54940
gtggatgatc cggttgtcgt ggtcgcgatg ggatgccggt atccgggcga cgtctgctcg    55000
cccgaggagc tgtggcagct ggtttctgcg ggacgtgatg cggtatcgac gttccccgtc    55060
gatcggggtt gggactgcaa cacgttgttc gacccggatc cggatcgggc aggcagtacc    55120
tatgtgcgag aaggtgcctt cctgaccggt gctgatcggt tcgacgccgg gttcttcggc    55180
atcagccctc gcgaggcgcg cgcaatggat ccgcagcaga ggttgttgct cgaagtggcg    55240
tgggaggttt tcgaacgagc aggaatcgct ccgctgtcgt tgcggggtag caggaccggt    55300
gtgttcgcgg ggaccaatgg gcaggaccac ggtgcgaaag tggctgccgc gccggaggcg    55360
gcgggtcacc tcctgaccgg aaacgccgcg agtgtcctgg ccggccggct ttcctacacg    55420
ttcggccttg aggggcctgc ggtggcggtg gataccgcgt gttcgtcgtc gttggtggcg    55480
ttgcatttgg cgtgccagtc gctgcgttcg ggtgagtgtg atatggcgtt ggcaggtggt    55540
gtgacggtga tgtcgacacc cctggctttc ctcgagttct ctcgtcagcg cggtttggcg    55600
ccagatggtc ggtgcaagtc gtttgcggcc gctgcggatg caccggggtg gggtgagggt    55660
gccggcctgc tgttgctgga gcggttgtcg gatgctcgtc ggaatggtca ccgggtgttg    55720
gccgtggttc gcgggtctgc ggtgaatcag gatggtgcgt cgaatggcct gactgcgccg    55780
aatggtccgt cgcagcagcg ggtgattcgg caggccctcg cgaatgcggg gctgtcggcg    55840
tccgatgtgg atgtcgtgga ggcgcacggg accggtaccg ggctcgggga tccgatcgag    55900
```

```
gcgcaggcgc tgatcgcgac atatgggcag gagcgggatc ctgagcgggc cctgtggctg    55960
gggtcgatca agtccaacat cggccacacg caggcggcgg ccggtgtggc ggggtcatc    56020 aagatggtgc aggccatgcg gcacgggag ttgcctgcga cgttgcacgt ggacaagccc    56080
actccacagg tggactggtc tgccggggcc gttcggctcc tcaccgggaa cacgccctgg    56140
cccgagagcg gccgtcctcg tcgagcgggg gtgtcgtcgt tcgggatcag cggcaccaac    56200
gcacacctca tcctcgaaca accaccgtcg gaaccagcgg agatcgacca atcggatcgg    56260
cgggtcactg cgcatccagc ggtgatcccg tggatgttgt cggctaggag tctcgcagcg    56320
ctgcaggccc aagcggctgc gctgcaggcc cggctggacc ggggtcctgg cgcttctccg    56380
ctggatttgg ggtattcact cgcgaccact cgttctgtgc tggacgaacg cgccgtcgtg    56440
tggggtgccg atcgggaggc actgctgtcc aggctggcag cgctcgccga tggccggacg    56500
gcgccggggg tgataacggg ctctgcgaat tccggtggcc gcatcggatt cgttttttcc    56560
ggtcagggca gtcagtggct ggggatggga aaggcgttgt gcgcggcttt ccggcgttc    56620 gcggacgcct tcgaggaagc ctgcgacgcg ctaagcgcac acctgggcgc ggacgttcgg    56680
ggtgtgctgt tcggtgctga tgagcagatg ctcgaccgga cgctgtgggc gcagtcgggg    56740
atcttcgcgg ttcaagtcgg cctcctggga ttgctgaggt cgtggggcgt gcggccggcc    56800
gcggtgctgg ggcactcggt cggcgagttg gctgcgcgcg acgcggctgg tgtgttgtcc    56860
ttgccggacg ctgcacggtt ggttgcggct cgggcccacc tgatgcaggc attgcccacc    56920
ggcggcgcaa tgctcgcggt cgccaccagc gaggcggcgg tcggaccgct gctttccggg    56980
gtgtgcgatc gggtcagcat cgctgcgatc aacggccccg agtcggtagt gctctccggc    57040
gaccgcgatg tgctcgtgga gctcgcaggc gaattcgatg cccagggct taggaccaaa    57100 tggttgcggg tctcccatgc tttccactcg caccggatgg aaccgattct ggacgagtac    57160
gcggaaaccg ccaggtgcgt cgagttcggt gaaccggtgg tgccgatcgt ctccgccgcg    57220
accggtgcgc tggacaccac cggactgatg tgcgcggccg actactggac gcgccaagtg    57280
cgtgatcctg tccgcttcgg agacggtgtc cgggcgctcg tcggccaagg cgtgacacg    57340 atcgtcgagt tcggcccgga cggggcgttg tcggccctgg tcgagcagtg cttggccggg    57400
tccgaccagg ctgggagggt ggcggcgatc ccgctgatgc gcagggaccg cgatgaggtc    57460
gagaccgcgg tggcggccct ggcgcacgtg cacgtccgcg gtggtgcggt ggactggtcg    57520
gcttgcttcg ccggcaccgg cgcccgcacc gtcgagttgc ccacctacgc cttccaacgc    57580
cagcggtact ggctggccgg gcaagcggac gggcgcggcg gcgatgtggt tgccgacccg    57640
gtcgacgcgc gcttctggga gttggtcgag cgcgccgatc cggaaccgtt ggtggatgaa    57700
ctctgcatcg accgggacca gcccttccgg gaggtgctgc ccgttctggc ttcctggcgc    57760
gagaaacaac gccaggaggc cctcgcggat tcctggcgct accaggtgcg ctggaggtcc    57820
gtcgaggtgc cgtccgcagc cgccctccgg ggcgtgtggc tggtggtgct tccagctgac    57880
gtgccccgag atcaaccggc ggtcgtcatc gacgcgctga tcgcgcgcgg cgccgaggtc    57940
gcggtcctgg aattgaccga gcaggacctc caacgcagtg cgcttgtgga caaggtgcgc    58000
gccgtcattg cggaccgcac cgaggtgacg ggtgtgttgt ctctgttggc gatgacggc    58060 atgccctgcg cggcgcatcc gcacctgtcc cgtggtgtcg ccgctaccgt gatcctgacg    58120
caggtgttgg gcgatgcggg tgtttccgcc ccgctgtggc tggccacgac cggtggcgtc    58180
gaggccggga ccgaggacgg tccggccgat ccggaccacg gcttgatctg ggggctcggc    58240
```

```
agggtcgtcg gccttgaaca tccgcagtgg tggggtggcc tgatcgacct tccggagaca    58300
ctggacgaga cgtcccggaa cgggttggtg gccgcactcg ccgggacggc ggccgaagat    58360
cagctcgccg tgcgttcatc cggggttgttc gttcgcagag tggtgcgcgc agcgcggaac   58420
ccccggtcag agacatggcg tagccgggga acggtcctca tcacgggcgg aacaggcgcg    58480
ctcggtgccg aggtcgcacg atggctggcc cggcggggag ctgagcacct ggtgttgatc    58540
agtcgccgcg gcccggaagc tcccggcgca gcggacctag gggccgagct gactgaactc    58600
ggcgtgaaag tcacagtctt ggcctgcgat gtgacggacc gcgacgagct ggcggcggtg    58660
ctggcggccg ttcccacgga gtatccgctg tcggcggtcg tgcacaccgc cggcgtcggg    58720
acgcctgcga acctggccga gacgaccttg gcgcagttcg ccgacgtgtt gtcggccaag    58780
gtcgtcggcc cggcgaacct ggaccggctg cttggcgggc aaccgttgga cgccttcgtg    58840
ctgttctcct cgatctcggg agtttgggga ccggcggcc aaggagccta ttcggccgcc     58900
aatgcgtatc tcgatgccct tgccgagcgc cgacgggctt gcgggcggcc ggcgacgtgc    58960
atcgcctggg gtccgtgggc gggtgcgggc atggccgttc aggaaggtaa cgaggcgcat    59020
ctccgccgaa ggggcctggt accgatgaa ccgcagtcgg ccctcttcgc gctgcaacag     59080
gccctgtccc aacgagaaac cgccatcacc gtcgcagatg tggactggga gcgattcgcc    59140
gcctctttca ccgcggcccg cccgcgacca ctgttggaag agatcgtgga tctacggccc    59200
gacaccgaga ccgaggagaa gcacggtgcc ggcgagctgg ggcagcagct ggccgcactg    59260
ccgcccgctg agcgcggaca cctgctgctg gaggtggtgc tggcggaaac cgccagcacc    59320
ctggggcacg attcggcgga ggctgtgcaa cccgatcgga ccttcgccga actgggcttc    59380
gattcgctga ccgcggtaga gctgcgcaac aggttgaacg cggtgaccgg gcttcgcctg    59440
ccgccgacgc tggttttcga ccacccgacg ccgctggcgt tgtccgaaca gttggttccg    59500
gccctggtcg cggagccgga caacggcatc gaatcgctgc tcgccgagct cgacaggctg    59560
gataccacgt tggcgcaagg gccttcgatc ccactggaag accaggccaa ggtggcggag    59620
cgcttgcacg cactcctcgc caagtgggac ggggcgcgtg acggcacggc cagagcgacg    59680
tcaccccaat cgctgacggc ggccacggac gacgaaatct tcgacctcat cgaccggaag    59740
ttccggcgct gaccgccctt tcctcgcctc agctcccctg attactggaa cggtgtattt    59800
cgatggccaa tgaagaaaag ctccgcgagt acctcaagcg tgtcgtcgtc gaactggaag    59860
aggcgcacga acgcctgcac gagttggagc gccaggagca cgaccccatc gcgatcgtgt    59920
cgatgggatg tcgttatccc ggtggcgtct ccactccgga ggagctgtgg cgactggtcg    59980 tcgacgagg agacgcgatc gcgaacttcc ccgaagaccg tggctggaat ctggacgagc     60040
tgttcgatcc tgatccgggc cgagccggga cctcctacgt ccgcgagggt ggtttcctgc    60100
gcggggtcgc ggacttcgat gccgggctct tcgggatcag tccgcgcgag gcacaggcga    60160
tggacccgca acagcggttg ctgctggaga tctcgtggga ggtgttcgag cgcgccggca    60220
ttgacccgtt ttcttgcgg ggtaccaaga ccggtgtgtt cgcgggcctg atctaccacg     60280
actacgcgtc gcggtttcgc aagaccccg cggagttcga gggttacttc gccaccggca     60340
acgcgggcag cgtcgcatcc ggccgggtgg cttacacctt cgggttagag ggcccggcgg    60400
tcaccgtgga caccgcctgc tcgtcgtccc tggtggcgct gcacctggcc tgccagtccc    60460
tgcggctggg cgaatgcgac ctggccctgg ccggtggcat ttcggtgatg gccacgccgg    60520
gagccttcgt cgagttcagc cggcaacgcg cactcgcctc ggatggccgg tgcaagccct    60580
tcgcggatgc cgccgacggc accggctggg gcgagggcgc cggaatgctg ctgctggaac    60640
```

```
ggctgtcgga cgcacgacga aacggccacc cggtgctggc ggcggtggtc ggttccgcga   60700
tcaaccagga cgggacgtcc aacggcctga ccgcgcccag cggtcccgca cagcagcgag   60760
tgatccgcca agccctggcg aacgccgggt tgtcgcccgc cgaggtcgat gtggtcgagg   60820
cgcacggcac gggcacggcc ttgggcgacc cgatcgaggc gcaggccctg atcgccacct   60880
acggggcgaa ccgtcggcg gatcatccgc tgctgctggg ttccctcaag tcgaacatcg   60940
gccacaccca ggctgccgcc ggtgtggccg gggtgatcaa gtcggtcctg gccatcaggc   61000
accgggagat gccccgcagc ctgcacatcg accagccatc gcagcacgtg gactggtcgg   61060
cgggcgcggt gcggctgctc acggacagcg ttgactggcc ggatctcggc aggccgcgcc   61120 gagcagggggt gtcctcgttc ggcatgagcg gtaccaacgc acacctgatc gtcgaggaag   61180
tatccgacga gccggtctcg ggcagtaccg agccgaccgg ggcatttccc tggccgctgt   61240
ccggcaagac ggagacggca ttgcgcgagc aggctgccga gttgctctcc gtagtgaccg   61300
agcacccgga gccgggactg ggggacgtcg ggtactcgct ggccaccggt cgcgctgcga   61360
tggagcaccg ggctgtcgtg gttgccgacg atcgggactc tttcgtcgcc ggactgacgg   61420
cgttggctgc gggcgttccg gcagccaacg tggtgcaggg cgcggccgac tgcaagggaa   61480
aggtcgcgtt cgtgttcccc ggccagggct cgcattggca ggggatggcg agggaactgt   61540
ccgaatcctc gccggtgttc cggcggaagc tggcggaatg cgccggcggct acggcccctt   61600 acgtggactg gtcgctgctc ggcgtccttc gcggtgatcc cgatgcaccc gcgctggatc   61660
gcgacgacgt gattcagctc gcgctgttcg ccatgatggt gtcgctggcc gaactgtggc   61720
gttcgtgcgg agtggagccc gccgcggtgg tcggtcattc ccaggggcgag atcgccgccg   61780 cccatgtggc aggcgctttg tccttgactg atgcggtgcg catcatcgct gcccgctgcg   61840
atgcggtgtc ggcgctgacc gggaagggag gcatgctcgc gattgccttg ccggaaagcg   61900
cggtggtgaa gcgaatcgca ggcctgccgg agctgaccgt tgcggcggtc aacgacccg   61960 gctccactgt cgtttccggc gaaccgtcgg ctctggagcg tctgcagacc gaactgaccg   62020
cggaaaacgt gcagacccgg cgggtgggaa ttgattacgc ctcgcattcg ccgcagatcg   62080
cgcaggtcca gggccggctt ctggaccggc tgggcgaagt cgggtccgaa cctgctgaga   62140
tcgctttcta ctcgacggtc accggcgagc ggacggacac cggccgactc gacgccgact   62200
actggtacca gaaccttcgg cagcccgtcc gcttccagca gaccgtcgcc cggatggcag   62260
atcagggcta tcggttcttc gtcgaggtga gcccgcaccc gctgctcacc gccggaatcc   62320
aggaaacgct ggaagccgcg gacgcgggcg gggtggtggt cggttcgctg cggcgtggcg   62380
agggcggctc ccgcgctgg ctgacttcgc tggccgagtg ccaggtgcgc ggactgccgg   62440
tgaattggga acaggtattc ctcaacaccg gagcccgacg cgtgccgctg ccgacctacc   62500
cgttccagcg gcagcggtac tggttggagt ccgccgagta cgacgcgggc gatctcggtt   62560
cggtgggctt gctctccgcc gagcatcccc tgctcggggc tgcggtgacg ctggccgatg   62620
cgggcgggtt cctgctgacc ggcaagctgt cggtcaagac ccagcccctgg ttggccgacc   62680 acgtggtcgg cggggcgatc ctgctgcccg gcaccgcgtt cgtggaaatg ctgatacgcg   62740
ccgcggacca ggtcgggtgc gatctgatcg aggagttgtc cctgacgact ccgctggttt   62800
tgcccgcgac cggtgcggtg caggtgcaga tcgcggttgg cggtccggac gaggccgggc   62860
gccgctcggt ccgcgtgcat tcctgtcgag acgacgccgt gccgcaggac tcgtggacct   62920
gccacgcgac cggcacgttg acctccagcg atcaccagga cgccggccag ggccccgatg   62980
```

```
ggatttggcc gcccaacgat gctgtcgcgg ttccgctgga cagcttctac gcccgcgcag  63040
ctgagcgggg cttcgatttc ggcccggcgt tccaggggtt gcaggcggct tggaagcgcg  63100
gagacgagat cttcgccgag gtcggcctgc ccaccgcaca ccgcgaagac gccggcaggt  63160
tcggaatcca ccctgctctg ctggatgcgg cactgcaggc gctgggcgca gccgaagagg  63220
atccggacga gggatggctc ccgttcgcgt ggcaaggtgt gtccctcaaa gcgacgggcg  63280
cactttccct tcgggtgcac ctcgttccgg cgggcgcgaa tgcggtgtcg gtgttcacga  63340
ccgacacgac tggccaagcc gtgctctcca tcgattcgct ggtgctgcgc cagatttcgg  63400
acaagcagtt ggcagcggcc cgtgcgatgg aacacgagtc cctgttccgg gtcgactgga  63460
agcgaatctc gcccggcgct gccaagccgg tctcctgggc agtgatcggc aatgacgaac  63520
tcgcccgagc ctgcggctcg gcacttggca cggaactcca ccccgacctg accgggttgg  63580
ctgacccgcc cccggacgtc gtggtggtgc catgcggtgc gtctcgccag gacttggacg  63640
ttgcttccga ggcacgtgcc gcgacacaac gcatgcttga cctgatccag gattggttgg  63700
cggcggcgcg attcgccgga tctcgcctgg tggttgtgac gtgtggtgcg cgtcgacag  63760
gtcccgccga gggtgtttcc gacctggtgc atgctgcgtc gtggggtttg ttgcgttcgg  63820
cgcagtcgga gaacccggac cgattcgtgt tggtcgatgt ggacggaacc gccgaatcat  63880
ggcgtgcgct cgcggcggcc gtgcgttccg gagaaccgca gctggcgttg cgcgccggtg  63940
aagtccgggt gcctcgcctg gcgcgatgtg ttgccgccga ggacagccgg atcccagtgc  64000
ccggtgcgga tgggacggtg ttgatttccg gcggtacggg cctgctgggc gggttggttg  64060
cccggcattt ggtggcggag cgcggtgtcc gccgcctggt gctcgcgggg cgacgcggct  64120
ggagcgcccc cggggtcacc gacctggtgg atgagttggt gggcctggga gctgcggtcg  64180
aggtggcgag ctgcgatgtc ggggatcggg cccagttgga ccggctgctg acgacgatct  64240
cggcagagtt cccgctgcgc ggagtggtgc atgcggccgg ggcacttgcc gacggggtcg  64300
tcgagtcgct gacaccagag cacgtggcaa aggtgttcgg cccgaaggcc gccggtgcgt  64360
ggcacctgca cgagttgact cttgatctgg atctctcgtt cttcgtgctc ttctcctcgt  64420
tctccggcgt ggcgggggct gcgggtcagg gaaactacgc ggcggcgaac gcgttcctgg  64480
acggcctggc tcagcaccgg cggacggcg ggctgcctgc ggtgtcgctg gcttggggct  64540
tgtgggagca gcccagcggg atgaccggag cgctcgatgc ggcgggccgt agccgcattg  64600
cgcgcaccaa tccgccgatg tccgcgccgg acgggttgcg gctgttcgag atggcgtttc  64660
gcgttccggg cgaatcgctt ctggttccgg tccacgtcga cctgaacgcc ctgcgcgctg  64720
atgcggccga cggcggtgtg cctgcgttgt tgcgcgacct ggtgccagcg cccgtgcggc  64780
ggagcgcggt caacgagtcg gcggacgtca acggtctggt tggtcggctg cggaggctgc  64840
cggacctgga tcaggaaacc cagctgttgg gtttggtgcg cgagcatgtt tcggcggtgc  64900
tggggcattc gggtgcggtc gaggtcgggg ccgatcgtgc tttccgggat ttgggttttg  64960
attcgttgtc cggtgtggag tttcggaacc ggcttggcgg ggtgctgggc gttcggttgc  65020
cggctactgc ggtgttcgac tatccgacac cgcgggcgtt ggttcggttc ttgctcgaca  65080
aactgattgg tggcgtggag gctccgactc ccgcaccggc ggctgtggcg cggtgactg  65140
ctgacgatcc cgttgtgatc gtggggatgg gctgtcgtta tccgggtggg gtgtcctcgc  65200
cggaggagct ttggcgtttg gtgccggggg gcttggatgc ggtggcggag ttcccggacg  65260
atcgtggctg ggatcaggcg gggttgttcg atccggatcc cgatcgtctt ggacctcgt  65320
atgtgtgtga gggtggcttc ctgcgagatg cggcagagtt cgatgccggt ttcttcggga  65380
```

```
tttccccgcg tgaggcgttg gcgatggatc cgcagcagcg gttgctgctg gaagtcgctt    65440
gggaaaccgt ggagcgggcg gggattgatc cgctttcgtt gcggggagc cggaccggcg     65500
tgttcgcggg gctgatgcac cacgactacg gcgcgcggtt catcacgagg gcgccggagg    65560
gtttcgaggg ttatctaggt aatggcagcg cgggaggcgt gttttcgggt cgggttgcgt    65620
attcgtttgg tttcgagggt cctgcggtga cggtggatac ggcgtgttcg tcgtcgttgg    65680
tggcgctgca cctggcgggt caagcactgc ggtctggtga gtgtgatctg gctcttgcgg    65740
gtggtgtgac ggtgatggcc acgccgggga tgttcgtgga gttttcgcgt caacggggct    65800
tggcggcgga tgggcggtgc aagtcgtttg cggcggctgc ggatggcacc ggttggggag    65860
aaggcgcggg cttggtgttg ttggagcggc gtgtcggatgc ccggcgcaac gggcacgcgg   65920
ttctggcggt cgtgcgggt agcgcggtga atcaggatgg tgcgtcgaat ggtttgacgg     65980
cgccgaatgg gccctcgcag cagcgggtga tcacgcaggc gttggcgagt gctggtttgt   66040
cggtgtctga tgtggacgcc gtggaggcgc atgggactgg aaccaggctt ggtgatccga   66100
ttgaggcgca ggctctgatt gccacttacg ggcaggggcg ggatagcgat cggccgttgt   66160
ggttggggtc ggtgaagtcg aatattggtc atacgcaggc ggcggcgggt gtcgctggtg   66220
tgatcaagat ggtgatggcg atgcggcacg ggcagctgcc cgcgacgttg catgtggatg   66280
aacctacgtc ggaagtggat tggtcggcgg gggatgtcca gctcctcacg gagaacaccc   66340
cctggcccgg caacagccat cctcggcggg tgggcgtgtc gtcgttcggg atcagcggca   66400
ccaacgcaca cgtcatcctc gaacaagcct cgaaaacacc agacgagact gcggacaaga   66460
gcggtcccga ttcggaatcg accgtggacc ttccagcggt cccgttgatc gtgtcgggga   66520
gaacaccggc agcgctcagc gctcaggcga gcgcattgtt gtcctatttg ggtgagcgtg   66580
gcgatatttc cacgctggat gcggcgttt cgttggcttc ctcccgggcc gcgttggagg    66640
agcgggcggt ggtgctggga gcggaccgcg aaacgttgtt gtccgggttg gaagcgctgg   66700
cttccggtcg cgaggcttct ggggtggtgt cgggatcccc ggtctctggc ggggttgggt   66760
tcgtgttcgc cggtcagggc ggacagtggt tggggatggg ccgggggctc tactcggttt   66820
ttccggtgtt cgctgacgcg tttgacgaag catgtgccgg actggacgcg catctggggc   66880
aggacgtggg ggtccgggat gtggtgtttg gttccgacgg gtccttgttg gatcggacgc   66940
tgtgggccca gtcgggtttg ttcgcgttgc aggttggttt gctgagcctg ctgggttcgt   67000
ggggtgtccg gccgggtgtg gtgctgggcc attcggtcgg cgagttcgcg gcggcggttg   67060
cggcgggagt gttgtcgttg ccggatgcgg ctcggatggt ggcgggtcgt gcccggttga   67120
tgcaggcgtt gccttctggc ggtgccatgt tggcggtggc tgctggtgag gagcagctgc   67180
ggccgttgtt ggccgatcgg gttgatggtg cgggtatcgc cgcggtcaac gctcctgagt   67240
cggtggtgct ctccggcgat cgggaggtgc ttgacgacat cgccgcgcg ctggatgggc    67300
aagggattcg gtggcggcgg ttgcgggttt cgcatgcgtt tcattcgtat cggatggacc   67360
cgatgttgca ggagttcgcc gaaatcgcac gcagcgtgga ctaccggcgt ggcgacctac   67420
cggtcgtgtc gacgttgacg ggtgagctcg acaccgcagg tgtgatggct acgccggagt   67480
attgggtgcg tcaggttcga gagcccgtcc gcttcgccga cggcgtccgg tgctcgcgc    67540
agcaaggggt cgccacgatc ttcgaactcg gccctgatgc gacgctgtcg gccctgattc   67600
ccgattgtca ttcgtgggct gatcaggcca tgccgattcc gatgctgcgt aaagaccgta   67660
cggaaaccga aactgtggtc gccgcggtgg cgcgggcgca cacgcgtggt gttccggtcg   67720
```

```
aatggtcggc gtatttcgcc ggcaccgggg cacggcgggt cgagttgccg acgtatgcct   67780
tccagcggca gcggtactgg ctggaaacat cggattacgg cgatgtgacg ggtatcggcc   67840
tggctgcggc ggagcatccg ttgctggggg ccgtggttgc gctggccgat ggtgatggga   67900
tggtgctgac cggccggttg tcggtgggga cgcatccgtg gctggcccag catcgcgtgc   67960
tgggcgaggt cgtcgtcccc ggcaccgcca tcctggagat ggccctgcac gcaggggcgc   68020
gtctcggctg tgaccgggtg aagagctca ccctggaaac accgctggtg gtccccgaac   68080
gcgcggcggg tgccggtagt cgtgggcctg cgggagggac cacagtttca attgaaactg   68140
cggaagaacg tgtgcggacg aacgacgcca tcgaaatcca gctgctggtg aacgcacccg   68200
acgaaggcgg tcggcgaagg gtgtcgctgt attcccgccc ggccggtggg tcgagaggtg   68260
ggggttggac gcgccacgcc accggcgaac tcgtcgtcgg caccaccggt ggtagggcgg   68320
ttcctgattg gtcggctgag ggtgccgagt cgattgctct cgatgagttc tacgtcgctc   68380
tggccggaaa cggttcgag tacggccgt tgttccaggg gcttcaggcg gcatggcgtc   68440
gtggtgacga ggttctcgcc gaaatcgccc cgccggccga ggccgatgcg atggcgtcgg   68500
gatacctgct cgacccagcg ttgctggatg ccgcgctgca ggcgtccgcg ctcggcgacc   68560
gcccggagca aggcggcgcg tggctgccgt tctcattcac cggcgtcgaa ctttccgctc   68620
cggcagggac gatcagcagg gtgcggctgg agaccaggcg acccgacgcg atatcggtgg   68680
ccgtgatgga tgagagtggg cggttgctcg cctcgatcga ttctctcagg ctacgaagcg   68740
tgtcgtcggg acagctggcg aatcgggacg ctgtccgcga cgcgctgttc gaggtgacct   68800
gggagccggt ggcgacgcag tcgacggaac cgggtcgctg ggccctgctt ggtgatactg   68860 cctgcgtaa agacgatctc atcaaactcg caacggattc cgccgaccgc tgcgcggatc   68920
tggcggcgct agccgagaaa cttgattcca gcgcgctggt tcctgatgtc gtggtctact   68980
gcgccggaga acaggcggat cccggcaccg gcgcagccgc acttgcggag acccagcaga   69040
cgttggctct gctccaagcg tggttggctg agccgcggtt ggccgaggca cgtctggtgg   69100
tggtgacgtg tgcagcggtg acgacggctc cgagtgacgg tgcatcagag ctggcacatg   69160
cgccgttgtg ggggttgttg cgtgccgcgc aggtggagaa cccggggcag tttgtgctgg   69220
cggacgtcga cggaaccgcc gaatcgtggc gtgcgttgcc gagtgcgttg ggctcgatgg   69280
aaccgcagtt ggccctgcgg aagggcgcgg tgcgagcgcc ccgcttggct tcggtcgccg   69340
ggcagatcga cgtgcccgcg gttgtggcgg atcccgaccg aaccgtgctg atttcgggcg   69400
gcacgggcct gttgggggc gcggttgccc gccacctggt gaccgaacgc ggtgtccgcc   69460
gattggtgtt gacgggccgt cgtggctggg atgctcctgg aatcaccgag ttggtgggtg   69520
agctgaacgg cctcggtgcc gtggtcgacg tggtggcgtg cgacgtcgcg gatcgtgctg   69580
atctggagtc gttgctggcg gcggtcccgg cggaatttcc gttgtgcggc gtggtgcatg   69640
ccgcgggggc gctggccgac ggggtgatcg agtcgttgtc accggacgac gtgggagcgg   69700
tgttcggccc gaaggcggcg ggggcgtgga atctgcacga gctgactcgt gatacggacc   69760
tgtcgttctt cgcgttgttc tcctcgcttt ccggtgttgc cggcgctcct ggtcagggca   69820
attatgcggc ggcgaacgcg ttcctggacg cattggcgca ttaccggcgg tcacagggac   69880
tgcctgcggt gtcgctggcc tggggcctgt gggagcagcc gagcgggatg acggagacgc   69940
tcagcgaggt cgaccggagc aggatcgcgc gcgccaaccc gccgttgtcc accaaggagg   70000
gattgcggct gttcgatgcc gggctggcgc tggaccgggc agcggtagtt ccggcgaagt   70060
tggacaggac tttcctggcc gagcaggcgc ggtcgggctc gctgcccgca ttgttgacgg   70120
```

-continued

```
cactggtacc ccccatccgt cgtaataggc gggctagcgg aaccgagctc gcggacgagg   70180
gcaccctgct cggggtggtg cgggagcatg ccgcggccgt gctgggtat tcgagcgcgg    70240 ctgacgtcgg ggtcgagcgc gctttccggg atctgggttt tgattcgttg tctggtgtgg   70300
agttgcggaa ccgccttgcc ggggtgctgg gggtgcggtt gccggcgact gcggtgttcg   70360
actatccgac gccgagggcg ctggcccggt tcctgcacca ggaactggca gacgagatcg   70420
ctacgacgcc agcgccggtg acgacgacca gggcaccggt cgccgaagac gatctcgtcg   70480
cgatagtcgg gatgggatgc cgttttcccg gtcaggtgtc ctcgccggag gagctctggc   70540
gtttggtggc cgggggcgtg gatgcggtcg cggacttccc agccgatcgc ggctgggatc   70600
tggcaggctt gttcgatccg gacccggaac gggctgggaa gacctacgtg cgggaagggg   70660
ccttcctcac cgacgccgat cggttcgatg cgggtttctt cgggatttcc ccgcgtgagg   70720
cgttggcgat ggatccgcag caacggctgt tgctggagct gtcctgggag gccattgaac   70780
gggcagggat cgatccgggt tcgctgaggg ggagtcggac cggtgtgttc gcggggctga   70840
tgtaccacga ctatgcgcc cggttcgcca gccgagcccc ggaaggtttc gaggggtatc    70900
tcggcaatgg cagtgctggg agtgtcgcgt cgggccggat tgcgtactcg tttggtttcg   70960
agggtcctgc ggtgacggtg gatactgcgt gttcgtcgtc gttggtggcg ttgcatttgg   71020
cgggtcagtc gttgcgttcc ggcgaatgcg atctcgccct tgccggtggt gtgacggtga   71080
tgtcgacgcc cggacgtttt gtggaattct cccgtcagcg gggcctggca ccggacgggc   71140
ggtgcaagtc gttcgcggag agcgcggacg gtaccggttg gggtgagggt gctggttttgg  71200 tgttgttgga gcggttgtcg gatgctcggc ggaatgggca tcgggtgttg gcggtggttc   71260
gtgggtcggc ggtgaatcag gatggtgcgt cgaatggctt gaccgcgccg aatggtccct   71320
cgcagcagcg ggtcatccag caggcgttgg cgagtgcggg tctgtcggtg tccgatgtgg   71380
atgccgtgga ggcgcatggg accgggacca ggttgggtga tccgattgag gcgcaggctc   71440
tgattgctac gtatgggcgc gatcgtgatc ccggtcggcc gttgtggttg ggtcggtga    71500 agtccaacat cggtcatacg caggcggcgg cgggtgttgc cggtgtgatc aagatggtga   71560
tggcgatgcg gcacgggcaa cttccgcgca cgctgcacgt ggatgcaccc tcctcgcagg   71620
tggattggtc ggcggggagg gtccagctcc tgacggagaa cacgccctgg cccgacagtg   71680
gtcgcccctg tcgggtgggg gtgtcgtcgt tcgggatcag cggcaccaac gcgcacgtca   71740
tcctggaaca gtccacgggg cagatggatc aggcagcgga gccggattcg agtcctgttc   71800
tggatgttcc ggtggtgccg tgggtggtgt cgggcaaaac acccgaagcg ctatccgccc   71860
aggcggcaac gttggcgacc tatttggacc aaaatgttga tgtctcccct ctggacgttg   71920
ggatttcgct tgcggtgacc cgttcggcgc tggatgagcg ggcggtggtg ctggggtcgg   71980
atcgtgacac gttgttgtct ggcctgaatg cgctggctgc cggtcatgag gctgctggcg   72040
tggttacggg acctgtcggg attggtggcc ggaccgggtt tgtgttcgcc ggtcaaggcg   72100
gtcagtggtt gggatgggc cgccggttgt actcggagtt tccggcgttc gccggtgctt    72160
tcgacgaagc atgcgccgag ctcgatgcga acctggggag ggaagtcggg gttcgggatg   72220
tggtgttcgg ctccgacgag tccttgctgg atcggacttt gtgggcgcag tcgggttttgt  72280 tcgcgttgca ggtcggtctc tgggaattgt tgggtacgtg gggtgttcgg cccagcgtag   72340
tgctggggca ttcggtcggg gagctagccg cggcgttcgc cgcaggtgtg ctgtcgatgg   72400
cggaggcggc tcggctggtg gcgggtcgtg cgcggttgat gcaggcgttg ccttctggcg   72460
```

```
gtgccatgct ggcggtgtcc gcgaccgagg cccgagtcgg cccgctgctc gatggggtgc    72520
gggatcgtgt tggtgtcgca gcggttaacg ctccggggtc ggtggtgctt tccggtgacc    72580
gggatgtgct cgatggcatt gccggtcggc tggacgggca aggtatccgg tcgaggtggt    72640
tgcgggtttc gcacgcgttt cattcgcatc ggatggatcc gatgctggcg gagttcgccg    72700
agctcgcacg gagcgtggac taccggtctc cacggctgcc gattgtctcg acgctgaccg    72760
gaaacctcga tgacgtgggc gtgatggcta cgccggagta ttgggtgcgc caggtgcgag    72820
agcccgtccg cttcgccgac ggtgtccagg cgcttgtgga ccaaggcgtc gacacgattg    72880
tggaactcgg tccggacggg gcgttgtcga gcttggttca agagtgtgtg gcggagtccg    72940
ggcgggcgac ggggattccg ttggtgcgga gagaccgtga tgaggtccga acggtgctgg    73000
acgctttggc gcagacccac actcgtggtg gcgcggtgga ctgggggtca tttttcgctg    73060
gtacgagggc aacgcaagtc gaccttccca cgtatgcctt ccaacgacag cggtactggc    73120
tggagccatc ggattccggt gatgtgaccg gtgttggcct gaccggggcg gagcatccgc    73180
tgttgggtgc cgtggtgccg gtcgcgggcg gcgatgaggt gctgctgacc ggcaggctgt    73240
cggtggggac gcatccgtgg ctggcggaac accgcgtgct gggcgaagtc gtcgtccccg    73300
gcaccgcgtt gctggagatg gcgtggcggg ccggtagcca ggtcggttgt gaacgtgtgg    73360
aggagctcac cttggaggca ccgctggtcc tgccggagcg gggcgctgcg gcggtgcagt    73420
tggcggtggg ggctccggat gaggccggcc ggcgcagttt gcagctctat tcccgaggcg    73480
ctgatgaaga cggcgactgg cggcggattg cctccgggct gttggcccag gccaatgcgg    73540
tgccgccggc ggattcgacg gcatggccgc cggacggcgc cgggcaggtc gatctggcgg    73600
agttctacga gcgcctcgcc gagcgcggct tgacctacgg tccggtattc caagggctcc    73660
gcgccgcatg gcggcacggc gacgatatct tcgccgaatt ggccgggtca ccagacgcct    73720
cgggtttcgg catccacccg gcgctgctgg acgctgcact gcacgcgatg gcgcttggtg    73780
cttcgcccga ctcggaagcg cgtctgccgt tttcctggcg tggcgcccag ctgtaccgcg    73840
ctgaaggagc agcgcttcgg gtacggctct cgccgctggg ctccggtgca gtctcattga    73900
cgttggtgga tgccacaggg cgacgagtcg ctgcggtgga atcgctttcg acgcgaccgg    73960
tctccaccga ccagatcggt gccggtcgcg gcgatcaaga gcggctgctg cacgtcgagt    74020
gggtaaggtc ggctgaatct gcggggatgt ctctgacctc ctgcgcggtg gtcggttttgg    74080 gcgaaccgga gtggcacgct gcgctgaaga ccactggtgt ccaagtcgag tcccatgcgg    74140
accttgcttc gttggccacc gaggttgcca agcggggttc agctcctggt gcggtcatcg    74200
tcccgtgccc gcgaccccga gcgatgcagg agctgccgac cgccgcgcga agggcgacgc    74260
aacaggcgat ggcgatgctg cagcaatggc ttgccgatga ccggttcgtc agtacgcgcc    74320
tgatcctgct gacgcatcgg gcggtctccg cagttgctgg agaagacgtg ctcgacctgg    74380
tacacgcgcc gctgtgggc ttggtccgca gcgcgcaagc ggagcacccg gaccgattcg    74440
ccttgatcga tatggacgac gagcgagcat cgcagacggc actcgccgaa gcgctgactg    74500
cgggagaagc gcagctcgcg gtgcggtcgg gagttgtgct ggcgcccgc ctcggccagg    74560 tgaaggtgag tggaggtgaa gcgttcaggt gggatgaagg caccgtgctg gtcaccggcg    74620
gaaccggcgg gctcggggcc ctgctcgcac gccatctggt cagcgcccac ggtgtgcggc    74680
acctgttgct cgcaagtcgc cgtggtctgg cggcgcccgg agcggatgag ctggtggccg    74740
agctggagca ggccggcgcc gacgtcgcgg tcgtcgcgtg cgactcggca gatcgggact    74800
cgcttgcgcg gctggtggcg tcggtgcctg cggaaaaccc gttgcgggtg gtggtgcacg    74860
```

```
ccgccggtgt gctggatgac ggtgtgctga tgtcgatgtc gccggagcgc ttggacgcgg      74920
tgttgcggcc caaagtggat gccgcgtggt acctgcacga gctgactcgg gaactcggtc      74980
tgtcggcgtt cgtgttgttc tcctcggtcg cgggcctgtt cggcggtgcg gggcagagca      75040
attacgctgc cggcaacgct ttcctggatg ccttggcgca ttgccggcag gcccaggggc      75100
tgcccgcgct gtcgctggcc tccgggctgt gggcgagtat cgatggaatg gcgggcgacc      75160
tcgctgcggc agatgtggag cggctgtcgc gggcaggcat tggcccgctt tcggcaccgg      75220
gagggctggc cttgttcgac gctgccgttg gctcggacga accgttgctg gcaccggtgc      75280
gactggatgt cgaagcactg cgtgtgcagg cccgatccgt gcagacccgg attccggaaa      75340
tgctgcatgg catggcaatg gggccaagcc gccgcactcc gttcacttcc agggttgagc      75400
cgttgcacga acggctggcc ggattgtcgg agggcgaacg tcggcagcaa gtgctccagc      75460
gcgtccgcgc cgatatcgcg gtggtactgg ggcacggcag gtcgagcgat gtggacatcg      75520
agaagccttt ggccgagctg ggtttcgact cgctgacggc catcgaactc cgcaaccgtc      75580
tcgctaccgc caccggactg cggcttcccg cgacgctggc cttcgaccac ggcactgcgg      75640
cggcactcgc ccagcacgtg tgcgcgcagc taggcaccgc gaccgcgccg gcaccgaggc      75700
gaaccgacga caacgacgcc acggagcccg tgaggtcgct cttccaacag gcgtatgcgg      75760
ctggccggat acttgacggg atggatttgg tgaaggtcgc tgcccagttg cgaccggtgt      75820
tcggttcgcc tggcgagctg gaatccctgc cgaaacccgt ccagctttcc cgtggtcccg      75880
aagagcttgc cttggtgtgc atgccggcgc tgatcgggat gccgcccgca cagcagtacg      75940
cgcggatcgc cgccgggttc cgcgatgtgc gggacgtttc ggtgatcccg atgcctggat      76000
tcattgcggg agaaccgctg ccgtccgcca tcgaggtggc ggttcggacg caggcggagg      76060
cggtgctgca ggaattcgcc gggggctcgt tcgtactggt cgggcattcc tccgggggct      76120
ggctggcgca cgaggtagcc ggtgagctgg agcgtcgcgg ggtcgtcccg gccggggtcg      76180
tactgctgga cacctacatc cccggtgaga tcacgccgag gttctccgtg gcgatggccc      76240 accgacgta tgagaagctc gcgactttca cggacatgca ggatgtcggt atcaccgcga      76300
tgggcgggta cttccggatg ttcaccgagt ggactccgac gccgatcggt gctccgacgc      76360
tgttcgtgcg gaccgaagat tgcgtcgcag accctgaagg gcggccgtgg acagatgact      76420
cctggcggcc agggtggact ctcgcggatg ccacggtcca ggtgccgggc gaccacttct      76480
cgatgatgga cgagcacgcc gggtccaccg cacaggcagt cgcgagttgg cttgacaaac      76540
tcaaccagcg caccgctcgg caacgctgac gggcgtcctt ttaggacctt ctgggcggca      76600
ccggccaccc cggcggtgcc gccttccgtg gtccaggctc gccgatcttg acggcgcacg      76660
atgcgcggca cgcgcgctga tcgtgattcc gctgccgctc gtggccatcg gcctggcgaa      76720
tcatgtcctt tcgggcaacg tcaaacgaat tcgtccgagc ccgcattccg aggtgagggg      76780
cacccttggg tggctgagcc gctcaaggt gccctcacc tcgaaattcg tccgatttgg      76840
gcggtggacg caaccccggt gggcgtggtg cgtctttctt gttgacagag cggtgagaag      76900
ccgctgacac acctgagagg aaaaggggag catgatgctc aagcgccacc gtttgacgac      76960
cgccatcacc ggccttctgg ggggagtact gctggtcagc ggctgcggaa ccgccgccgc      77020
acttcagtcc tcgccggcgc ccgggcatga cgcgcgcaat gttggtatgg cctcgggcgg      77080
gggcggcggg gacatcggca cgtcgaactg ctcggaggcc gatttcctcg ccaccgcgac      77140
accggtgaaa ggcgaccccg gcagtttcat cgtggcgtac gggaaccggt cggacaagac      77200
```

```
ctgcacgatc aacggcggcg tgccgaacct caagggcgtg gacatgagca actcgccgat    77260
cgaggacctg ccggtcgagg acgtgcggct tcccgacgcg cccaaggaat tcaccctcca    77320
gcccggtcag agcgcgtacg ccggcattgg catggtcctg gccgacagcg gcgacccgaa    77380
cgcccatgtc ctcaccgggt tccagtcctc gctgccggac atgtccgagg cccagccggt    77440
caacgttctc ggcgacggca acgtgaagtt cgccgcgaag tacctgcgag tcagctcgct    77500
ggtgtctacc gcagacgagc tgcgctaaaa cccatgtgag tcccgcagat tcgacctcgc    77560
cgtgcggcgc ctccggcgaa gcgtccgtac gtttgtcgtt gtgaccagcg ttgttcacgt    77620
ccgggcgcag cgctggtaca tactcaggcg tctcgggcgc ctccaacggg gcctggcatc    77680
cggggccgtc gagtgcggcg gcgctgacgc gttctctgtc gggcgttgtc acgccgccgg    77740
cctcgaaccg gtcccgcccc gtcggagccg gtggtccagc gcggtgtggc ggcggccgga    77800
gccgacggtg cgcaccgcct gcccgagggc cttttcgaa ccgacgagga ccacgacctt    77860
cttgccccgg gtgaccgccg tgtagagcag gttgcgctgc agcatcatcc aggcgcttgt    77920
ggtcaagggg atcaccacgc acgggtattc gcttccctgc gaacgatgga tggtcaccgc    77980
gtaggcgtgg accagttcgt cgagttctgt gaagtcgtag tcgatgtcct cgtcctcgtc    78040
ggttcgcacg gtcatggtct gtgcttcgtt gtcgagggcg gacacgacgc cctgcgtgcc    78100
gttgaacacg ccgttggcgc ccttgtcgta gttgttgcgg atctgcgtga ccttgtcgcc    78160
gacgcggaag atccgtccgc cgaaccgccg ctctggcagg ccctccctgg ccggggtgat    78220
cgcttcctgc aacagctggt tcagcgcgcc tgcacctgcg gggcctcgat gcatcggggc    78280
gaggacctgc acgtcggtgc gcgggttgaa ccggaacttc gcgggatcc ggcgggcgac    78340 gacgtcgacg gtgagctcgg cggtcggttc gctttcctct acgtggaaca ggaagaagtc    78400
ggtcagcccg tgtgtcagcg gatagtcccc ggcgttgatt cggtgcgcgt tggtcaccac    78460
cccggactcg gcggcctgcc ggaacacctc gttgagccgc acgtgtggaa tcggggtgcc    78520
aggggcgagc agatcgcgca gtacctcacc ggctccgacc gacgggagct ggtcgacgtc    78580
gccgaccagc agcaggtgcg cgccgggcgc gatcgccttg gccagtttgt tggctaacag    78640
caggtcgagc atggacgcct cgtcgaccac gacgaggtcg gcgtccagcg ggttgtcccg    78700
gtcgtaggcg gcgtccccgc ccggctggag ttggagcagg cggtgcacgg tcgccgcgtc    78760
gtgtccggtg agctcggtca gccgcttcgc cgctcgtccc gtcggcgcgg cgaggatcac    78820
cttggccttt ttcgcctgag ctaatgcgat gatcgaccgc acggtgaagc tcttgccgca    78880
gcctggacct ccggtgagca cggcgacctt ctcggtcagg gccagcttga cggcgcgctc    78940
ctgcgcctcg gcgagttcgg caccggtagc gcggcgcaac cagtcgaggg ccttgtgcca    79000
atcgacgtcg gcgaagacgg gcatccggtc cgcgctggtg ttcagcagcc gggacagctg    79060
gttggccagg gcgacttcgg cgcggtggaa gggcacgagg tagatcgcga ccgtcggcac    79120
ctcgtcgtca tcggtgggga tctcctcgcg gaccacacct tcctcggtga cgagttcggc    79180
gaggcattcg atcaccagcc cggtgtcgac ggcgaggatc ttcaccgcct cggcgatcag    79240
ctcgttctcc ggcaggtagc agttgccgtc gccggtggac tccgacagcg tgaactgaag    79300
gcccgccttt acccgctgcg gggagtcgtg cgggattccc accgctttgg cgatggtgtc    79360
ggcggtcttg aaaccgattc cccacacgtc gcctgccagc cggtatggct cttccttgac    79420
ggtccggatc gcgtcgtcgt ggtactgctt gtagatcttc accgccagcg aggtcgagac    79480
gccgacgcct tgcaggaaga tcatcacctc cttgatcgcc ttctgctcct cccacgcgtc    79540
ggcgatcagc ttcgtccgct tcgggccgag cttggggacc tcgatcagcc gcgcgggttc    79600
```

```
ctgctcgatg acgtcgagcg cggcgacgcc gaagtggtcg acgatcttct cggcgagttt    79660
ggggccgatg cccttgatca ggccagaccc caggtagcgg cggataccct tgcacggtcgc   79720 aggcagcacg tcgtgtagt cgtcgacgtg aactgccgc ccgtactggg ggtgcgaccc      79780
ccaccggccg cgcatgcgca acgcctcgcc gggctgcgcg cccagcagcg cgccgacgac    79840
cgtcaccagg tcaccgcccc ggccggtgtc gatccgcgcg acggtgtagc cgctctcctc    79900
gttggcgaac gtgatccgct ccagcgtgcc ctccagcacc gcagtccacg tggccgactc    79960
ccgtcctttt tccaccgaca acacgtatca cgaacggctg tcaagcaaac cggcggtcac    80020
cacatgcagc ggcatctccc gaacgcctcg ggctccggcg tcagcgggtg ggcgttcgcg    80080
atgccttggt gcggccggtg ggagttgtag atttttttcgt cctcgcgcag ggcctggagt   80140
aggtgccgct ggctccagat c                                              80161
```

<210> SEQ ID NO 2
<211> LENGTH: 2595
<212> TYPE: PRT
<213> ORGANISM: Saccharopolyspora spinosa

<400> SEQUENCE: 2

```
Met Ser Glu Ala Gly Asn Leu Ile Ala Val Ile Gly Leu Ser Cys Arg
 1               5                  10                  15

Leu Pro Gln Ala Pro Asp Pro Ala Ser Phe Trp Arg Leu Leu Arg Thr
            20                  25                  30

Gly Thr Asp Ala Ile Thr Thr Val Pro Glu Gly Arg Trp Gly Asp Pro
        35                  40                  45

Leu Pro Gly Arg Asp Ala Pro Lys Gly Pro Glu Trp Gly Gly Phe Leu
    50                  55                  60

Ala Asp Val Asp Cys Phe Asp Pro Glu Phe Phe Gly Ile Ser Pro Arg
65                  70                  75                  80

Glu Ala Ala Thr Val Asp Pro Gln Gln Arg Leu Ala Leu Glu Leu Ala
                85                  90                  95

Trp Glu Ala Leu Glu Asp Ala Gly Ile Pro Ala Gly Glu Leu Arg Gly
            100                 105                 110

Thr Ala Ala Gly Val Phe Met Gly Ala Ile Ser Asp Asp Tyr Ala Ala
        115                 120                 125

Leu Leu Arg Glu Ser Pro Pro Glu Val Ala Ala Gln Tyr Arg Leu Thr
    130                 135                 140

Gly Thr His Arg Ser Leu Ile Ala Asn Arg Val Ser Tyr Val Leu Gly
145                 150                 155                 160

Leu Arg Gly Pro Ser Leu Thr Val Asp Ser Gly Gln Ser Ser Ser Leu
                165                 170                 175

Val Gly Val His Leu Ala Ser Glu Ser Leu Arg Arg Gly Glu Cys Thr
            180                 185                 190

Ile Ala Leu Ala Gly Gly Val Asn Leu Asn Leu Ala Ala Glu Ser Asn
        195                 200                 205

Ser Ala Leu Met Asp Phe Gly Ala Leu Ser Pro Asp Gly Arg Cys Phe
    210                 215                 220

Thr Phe Asp Val Arg Ala Asn Gly Tyr Val Arg Gly Glu Gly Gly Gly
225                 230                 235                 240

Leu Val Val Leu Lys Lys Ala Asp Gln Ala His Ala Asp Gly Asp Arg
                245                 250                 255

Ile Tyr Cys Leu Ile Arg Gly Ser Ala Val Asn Asn Asp Gly Gly Gly
            260                 265                 270
```

```
Ala Gly Leu Thr Val Pro Ala Ala Asp Ala Gln Ala Glu Leu Leu Arg
        275                 280                 285

Gln Ala Tyr Arg Asn Ala Gly Val Asp Pro Ala Ala Val Gln Tyr Val
    290                 295                 300

Glu Leu His Gly Ser Ala Thr Arg Val Gly Asp Pro Val Glu Ala Ala
305                 310                 315                 320

Ala Leu Gly Ala Val Leu Gly Ala Ala Arg Arg Pro Gly Asp Glu Leu
                325                 330                 335

Arg Val Gly Ser Ala Lys Thr Asn Val Gly His Leu Glu Ala Ala Ala
            340                 345                 350

Gly Val Thr Gly Leu Leu Lys Thr Ala Leu Ser Ile Trp His Arg Glu
        355                 360                 365

Leu Pro Pro Ser Leu His Phe Thr Ala Pro Asn Pro Glu Ile Pro Leu
    370                 375                 380

Asp Glu Leu Asn Leu Arg Val Gln Arg Asp Leu Arg Pro Trp Pro Glu
385                 390                 395                 400

Ser Glu Gly Pro Leu Leu Ala Gly Val Ser Ala Phe Gly Met Gly Gly
                405                 410                 415

Thr Asn Cys His Leu Val Leu Ser Gly Thr Ser Arg Val Glu Arg Arg
            420                 425                 430

Arg Ser Gly Pro Ala Glu Ala Thr Met Pro Trp Val Leu Ser Ala Arg
        435                 440                 445

Thr Pro Val Ala Leu Arg Ala Gln Ala Ala Arg Leu His Thr His Leu
    450                 455                 460

Asn Thr Ala Gly Gln Ser Pro Leu Asp Val Ala Tyr Ser Leu Ala Thr
465                 470                 475                 480

Thr Arg Ser Ala Leu Pro His Arg Ala Ala Leu Val Ala Asp Asp Glu
                485                 490                 495

Pro Lys Leu Leu Ala Gly Leu Lys Ala Leu Ala Asp Gly Asp Asp Ala
            500                 505                 510

Pro Thr Leu Cys His Gly Ala Thr Ser Gly Glu Arg Ala Ala Val Phe
        515                 520                 525

Val Phe Pro Gly Gln Gly Ser Gln Trp Ile Gly Met Gly Arg Gln Leu
    530                 535                 540

Leu Glu Thr Ser Glu Val Phe Ala Ala Ser Met Ser Asp Cys Ala Asp
545                 550                 555                 560

Ala Leu Ala Pro His Leu Asp Trp Ser Leu Leu Asp Val Leu Arg Asn
                565                 570                 575

Ala Ala Gly Ala Ala His Leu Asp His Asp Val Val Gln Pro Ala
            580                 585                 590

Leu Phe Ala Ile Met Val Ser Leu Ala Glu Leu Trp Arg Ser Trp Gly
        595                 600                 605

Val Arg Pro Val Ala Val Gly His Ser Gln Gly Glu Ile Ala Ala
    610                 615                 620

Ala Cys Val Ala Gly Ala Leu Ser Val Arg Asp Ala Ala Arg Val Val
625                 630                 635                 640

Ala Val Arg Ser Arg Leu Leu Thr Ala Leu Ala Gly Ser Gly Ala Met
                645                 650                 655

Ala Ser Leu Gln His Pro Ala Glu Glu Val Arg Gln Ile Leu Leu Pro
            660                 665                 670

Trp Arg Asp Arg Ile Gly Val Ala Gly Val Asn Gly Pro Ser Ser Thr
        675                 680                 685
```

-continued

| | | | | | | | | | | | | |
|---|---|---|---|---|---|---|---|---|---|---|---|---|
|Leu|Val|Ser|Gly|Asp|Arg|Glu|Ala|Met|Ala|Glu|Leu|Ala|Glu|Cys|

Leu Val Ser Gly Asp Arg Glu Ala Met Ala Glu Leu Ala Glu Cys
    690             695             700

Ala Asp Arg Glu Leu Arg Met Arg Ile Pro Val Glu Tyr Ala Ser
705             710             715             720

His Ser Pro His Ile Glu Val Val Arg Asp Leu Leu Gly Leu Leu
            725             730             735

Ala Pro Val Glu Pro Arg Thr Gly Ser Ile Pro Ile Tyr Ser Thr Thr
            740             745             750

Thr Gly Asp Leu Leu Asp Arg Pro Met Asp Ala Asp Tyr Trp Tyr Arg
    755             760             765

Asn Leu Arg Gln Pro Val Leu Phe Glu Ala Ala Val Glu Ala Leu Leu
770             775             780

Lys Arg Gly Tyr Asp Ala Phe Ile Glu Ile Ser Pro His Pro Val Leu
785             790             795             800

Thr Ala Asn Ile Gln Glu Thr Ala Val Arg Ala Gly Arg Glu Val Val
            805             810             815

Ala Leu Gly Thr Leu Arg Arg Gly Glu Gly Met Arg Gln Ala Leu
            820             825             830

Thr Ser Leu Ala Arg Ala His Val His Gly Val Ala Ala Asp Trp His
    835             840             845

Ala Val Phe Ala Gly Thr Gly Ala Gln Arg Val Asp Leu Pro Thr Tyr
850             855             860

Ala Phe Gln Arg Gln Arg Tyr Trp Leu Asp Ala Lys Leu Pro Asp Val
865             870             875             880

Ala Met Pro Glu Ser Asp Val Ser Thr Ala Leu Arg Glu Lys Leu Arg
            885             890             895

Ser Ser Pro Arg Ala Asp Val Asp Ser Thr Thr Leu Thr Met Ile Arg
            900             905             910

Ala Gln Ala Ala Val Leu Gly His Ser Asp Pro Lys Glu Val Asp
    915             920             925

Pro Asp Arg Thr Phe Lys Asp Leu Gly Phe Asp Ser Ser Met Val Val
930             935             940

Glu Leu Cys Asp Arg Leu Asn Ala Ala Thr Gly Leu Arg Leu Ala Pro
945             950             955             960

Ser Val Val Phe Asp Cys Pro Thr Pro Asp Lys Leu Ala Arg Gln Val
            965             970             975

Arg Thr Leu Leu Leu Gly Glu Pro Ala Pro Met Thr Ser His Arg Pro
    980             985             990

Asp Ser Asp Ala Asp Glu Pro Ile Ala Val Ile Gly Met Gly Cys Arg
    995             1000            1005

Phe Pro Gly Gly Val Ser Ser Pro Glu Glu Leu Trp Gln Leu Val Ala
    1010            1015            1020

Ala Gly Arg Asp Val Val Ser Glu Phe Pro Ala Asp Arg Gly Trp Asp
1025            1030            1035            1040

Leu Glu Arg Ala Gly Thr Ser His Val Arg Ala Gly Gly Phe Leu His
            1045            1050            1055

Gly Ala Pro Asp Phe Asp Pro Gly Phe Phe Arg Ile Ser Pro Arg Glu
            1060            1065            1070

Ala Leu Ala Met Asp Pro Gln Gln Arg Leu Leu Leu Glu Ile Ala Trp
    1075            1080            1085

Glu Ala Val Glu Arg Gly Gly Ile Asn Pro Gln His Leu His Gly Ser
    1090            1095            1100

Gln Thr Gly Val Phe Val Gly Ala Thr Ser Leu Asp Tyr Gly Pro Arg

-continued

```
             1105                1110                1115                1120
Leu His Glu Ala Ser Glu Glu Ala Ala Gly Tyr Val Leu Thr Gly Ser
                    1125                1130                1135
Thr Thr Ser Val Ala Ser Gly Arg Val Ala Tyr Ser Phe Gly Phe Glu
                1140                1145                1150
Gly Pro Ala Val Thr Val Asp Thr Ala Cys Ser Ser Leu Val Ala
            1155                1160                1165
Leu His Leu Ala Cys Gln Ser Leu Arg Ser Gly Glu Cys Asp Leu Ala
        1170                1175                1180
Leu Ala Gly Gly Val Thr Val Met Ala Thr Pro Gly Met Phe Val Glu
1185                1190                1195                1200
Phe Ser Arg Gln Arg Gly Leu Ala Pro Asp Gly Arg Cys Lys Ser Phe
                    1205                1210                1215
Ala Glu Ala Ala Asp Gly Thr Gly Trp Ser Glu Gly Ala Gly Leu Val
                1220                1225                1230
Leu Leu Glu Arg Leu Ser Asp Ala Arg Arg Asn Gly His Glu Val Leu
            1235                1240                1245
Ala Val Val Arg Gly Ser Ala Val Asn Gln Asp Gly Ala Ser Asn Gly
        1250                1255                1260
Leu Thr Ala Pro Asn Gly Ser Ser Gln Gln Arg Val Ile Ala Gln Ala
1265                1270                1275                1280
Leu Ala Ser Ala Gly Leu Ser Val Ser Asp Val Asp Ala Val Glu Ala
                    1285                1290                1295
His Gly Thr Gly Thr Arg Leu Gly Asp Pro Ile Glu Ala Gln Ala Leu
                1300                1305                1310
Ile Ala Thr Tyr Gly Gln Gly Arg Leu Pro Glu Arg Pro Leu Trp Leu
            1315                1320                1325
Gly Ser Met Lys Ser Asn Ile Gly His Ala Gln Ala Ala Ala Gly Ile
        1330                1335                1340
Ala Gly Val Met Lys Met Val Met Ala Met Arg His Gly Gln Leu Pro
1345                1350                1355                1360
Arg Thr Leu His Val Asp Glu Pro Thr Ser Gly Val Asp Trp Ser Ala
                    1365                1370                1375
Gly Thr Val Gln Leu Leu Thr Glu Asn Thr Pro Trp Pro Gly Ser Gly
                1380                1385                1390
Arg Val Arg Arg Val Gly Val Ser Ser Phe Gly Ile Ser Gly Thr Asn
            1395                1400                1405
Ala His Val Ile Leu Glu Gln Pro Pro Gly Val Pro Ser Gln Ser Ala
        1410                1415                1420
Gly Pro Gly Ser Gly Ser Val Val Asp Val Pro Val Pro Trp Met
1425                1430                1435                1440
Val Ser Gly Lys Thr Pro Glu Ala Leu Ser Ala Gln Ala Thr Ala Leu
                    1445                1450                1455
Met Thr Tyr Leu Asp Glu Arg Pro Asp Val Ser Ser Leu Asp Val Gly
                1460                1465                1470
Tyr Ser Leu Ala Leu Thr Arg Ser Ala Leu Asp Glu Arg Ala Val Val
            1475                1480                1485
Leu Gly Ser Asp Arg Glu Thr Leu Leu Cys Gly Val Lys Ala Leu Ser
        1490                1495                1500
Ala Gly His Glu Ala Ser Gly Leu Val Thr Gly Ser Val Gly Ala Gly
1505                1510                1515                1520
Gly Arg Ile Gly Phe Val Phe Ser Gly Gln Gly Gly Gln Trp Leu Gly
                    1525                1530                1535
```

```
                                  -continued

Met Gly Arg Gly Leu Tyr Arg Ala Phe Pro Val Phe Ala Ala Phe
        1540                1545                1550

Asp Glu Ala Cys Ala Glu Leu Asp Ala His Leu Gly Gln Glu Ile Gly
    1555                1560                1565

Val Arg Glu Val Val Ser Gly Ser Asp Ala Gln Leu Leu Asp Arg Thr
1570                1575                1580

Leu Trp Ala Gln Ser Gly Leu Phe Ala Leu Gln Val Gly Leu Leu Lys
1585                1590                1595                1600

Leu Leu Asp Ser Trp Gly Val Arg Pro Ser Val Val Leu Gly His Ser
                1605                1610                1615

Val Gly Glu Leu Ala Ala Ala Phe Ala Ala Gly Val Val Ser Leu Ser
            1620                1625                1630

Gly Ala Ala Arg Leu Val Ala Gly Arg Ala Arg Leu Met Gln Ala Leu
        1635                1640                1645

Pro Ser Gly Gly Gly Met Leu Ala Val Pro Ala Gly Glu Glu Leu Leu
    1650                1655                1660

Trp Ser Leu Leu Ala Asp Gln Gly Asp Arg Val Gly Ile Ala Ala Val
1665                1670                1675                1680

Asn Ala Ala Gly Ser Val Val Leu Ser Gly Asp Arg Asp Val Leu Asp
                1685                1690                1695

Asp Leu Ala Gly Arg Leu Asp Gly Gln Gly Ile Arg Ser Arg Trp Leu
            1700                1705                1710

Arg Val Ser His Ala Phe His Ser Tyr Arg Met Asp Pro Met Leu Ala
        1715                1720                1725

Glu Phe Ala Glu Leu Ala Arg Thr Val Asp Tyr Arg Arg Cys Glu Val
    1730                1735                1740

Pro Ile Val Ser Thr Leu Thr Gly Asp Leu Asp Asp Ala Gly Arg Met
1745                1750                1755                1760

Ser Gly Pro Asp Tyr Trp Val Arg Gln Val Arg Glu Pro Val Arg Phe
                1765                1770                1775

Ala Asp Gly Val Gln Ala Leu Val Glu His Asp Val Ala Thr Val Val
            1780                1785                1790

Glu Leu Gly Pro Asp Gly Ala Leu Ser Ala Leu Ile Gln Glu Cys Val
        1795                1800                1805

Ala Ala Ser Asp His Ala Gly Arg Leu Ser Ala Val Pro Ala Met Arg
    1810                1815                1820

Arg Asn Gln Asp Glu Ala Gln Lys Val Met Thr Ala Leu Ala His Val
1825                1830                1835                1840

His Val Arg Gly Gly Ala Val Asp Trp Arg Ser Phe Phe Ala Gly Thr
                1845                1850                1855

Arg Ala Lys Gln Ile Glu Leu Pro Thr Tyr Ala Phe Gln Arg Gln Arg
            1860                1865                1870

Tyr Trp Leu Asn Ala Leu Arg Glu Ser Ser Ala Gly Asp Met Gly Arg
        1875                1880                1885

Arg Val Glu Ala Lys Phe Trp Gly Ala Val Glu His Glu Asp Val Glu
    1890                1895                1900

Ser Leu Ala Arg Val Leu Gly Ile Val Asp Asp Gly Ala Ala Val Asp
1905                1910                1915                1920

Ser Leu Arg Ser Ala Leu Pro Val Leu Ala Gly Trp Gln Arg Thr Arg
                1925                1930                1935

Thr Thr Glu Ser Ile Met Asp Pro Arg Cys Tyr Arg Ile Gly Trp Arg
            1940                1945                1950
```

```
Gln Val Ala Gly Leu Pro Pro Met Gly Thr Val Phe Gly Thr Trp Leu
    1955                1960                1965

Val Phe Ala Pro His Gly Trp Ser Ser Glu Pro Glu Val Val Asp Cys
    1970                1975                1980

Val Thr Ala Leu Arg Ala Arg Gly Ala Ser Val Val Leu Val Glu Ala
1985                1990                1995                2000

Asp Pro Asp Pro Thr Ser Phe Gly Asp Arg Val Arg Thr Leu Cys Ser
                2005                2010                2015

Gly Leu Pro Asp Leu Val Gly Val Leu Ser Met Leu Cys Leu Glu Glu
            2020                2025                2030

Ser Val Leu Pro Gly Phe Ser Ala Val Ser Arg Gly Phe Ala Leu Thr
            2035                2040                2045

Val Glu Leu Val Arg Val Leu Arg Ala Ala Gly Ala Thr Ala Arg Leu
    2050                2055                2060

Trp Leu Leu Thr Cys Gly Gly Val Ser Val Gly Asp Val Pro Val Arg
2065                2070                2075                2080

Pro Ala Gln Ala Leu Ala Trp Gly Leu Gly Arg Val Val Gly Leu Glu
                2085                2090                2095

His Pro Asp Trp Trp Gly Gly Leu Ile Asp Ile Pro Val Leu Phe Asp
            2100                2105                2110

Glu Asp Ala Gln Glu Arg Leu Ser Ile Val Leu Ala Gly Leu Asp Glu
            2115                2120                2125

Asp Glu Val Ala Ile Arg Pro Asp Gly Met Phe Ala Arg Arg Leu Val
    2130                2135                2140

Arg His Thr Val Ser Ala Asp Val Lys Lys Ala Trp Arg Pro Arg Gly
2145                2150                2155                2160

Ser Val Leu Val Thr Gly Gly Thr Gly Gly Leu Gly Ala His Val Ala
                2165                2170                2175

Arg Trp Leu Ala Asp Ala Gly Ala Glu His Val Ala Met Val Ser Arg
            2180                2185                2190

Arg Gly Glu Gln Ala Pro Ser Ala Glu Lys Leu Arg Thr Glu Leu Glu
            2195                2200                2205

Asp Leu Gly Thr Arg Val Ser Ile Val Ser Cys Asp Val Thr Asp Arg
    2210                2215                2220

Glu Ala Leu Ala Glu Val Leu Lys Ala Leu Pro Ala Glu Asn Pro Leu
2225                2230                2235                2240

Thr Ala Val Val His Ala Ala Gly Val Ile Glu Thr Gly Asp Ala Ala
                2245                2250                2255

Ala Met Ser Leu Ala Asp Phe Asp His Val Leu Ser Ala Lys Val Ala
            2260                2265                2270

Gly Ala Ala Asn Leu Asp Ala Leu Leu Ala Asp Val Glu Leu Asp Ala
            2275                2280                2285

Phe Val Leu Phe Ser Ser Val Ser Gly Val Trp Gly Ala Gly Gly His
    2290                2295                2300

Gly Ala Tyr Ala Ala Ala Asn Ala Tyr Leu Asp Ala Leu Ala Glu Gln
2305                2310                2315                2320

Arg Arg Ser Arg Gly Leu Val Ala Thr Ala Val Ala Trp Gly Pro Trp
                2325                2330                2335

Ala Gly Glu Gly Met Ala Ser Gly Glu Thr Gly Asp Gln Leu Arg Arg
            2340                2345                2350

Tyr Gly Leu Ser Pro Met Ala Pro Gln His Ala Ile Ala Gly Ile Arg
            2355                2360                2365

Gln Ala Val Glu Gln Asp Glu Ile Ser Leu Val Val Ala Asp Val Asp
```

```
                2370              2375              2380
Trp Ala Arg Phe Ser Ala Gly Leu Leu Ala Ala Arg Pro Arg Pro Leu
2385                2390              2395              2400
Leu Asn Glu Leu Ala Glu Val Lys Glu Leu Leu Val Asp Ala Gln Pro
                2405              2410              2415
Glu Ala Gly Val Leu Ala Asp Ala Ser Leu Glu Trp Arg Gln Arg Leu
                2420              2425              2430
Ser Ala Ala Pro Arg Pro Thr Gln Glu Gln Leu Ile Leu Glu Leu Val
        2435              2440              2445
Arg Gly Glu Thr Ala Leu Val Leu Gly His Pro Gly Ala Ala Ala Val
        2450              2455              2460
Ala Ser Glu Arg Ala Phe Lys Asp Ser Gly Phe Asp Ser Gln Ala Ala
2465                2470              2475              2480
Val Glu Leu Arg Val Arg Leu Asn Arg Ala Thr Gly Leu Gln Leu Pro
                2485              2490              2495
Ser Thr Ile Ile Phe Ser His Pro Thr Pro Ala Glu Leu Ala Ala Glu
                2500              2505              2510
Leu Arg Ala Arg Leu Leu Pro Glu Ser Ala Gly Ala Gly Ile Pro Glu
        2515              2520              2525
Glu Asp Glu Ala Arg Ile Arg Ala Ala Leu Thr Ser Ile Pro Phe Pro
        2530              2535              2540
Ala Leu Arg Glu Ala Gly Leu Val Ser Pro Leu Leu Ala Leu Ala Gly
2545                2550              2555              2560
His Pro Val Asp Ser Gly Ile Ser Ser Asp Ala Ala Ala Thr Ser
                2565              2570              2575
Ile Asp Ala Met Asp Val Ala Gly Leu Val Glu Ala Ala Leu Gly Glu
        2580              2585              2590
Arg Glu Ser
        2595

<210> SEQ ID NO 3
<211> LENGTH: 2152
<212> TYPE: PRT
<213> ORGANISM: Saccharopolyspora spinosa

<400> SEQUENCE: 3

Met Thr Val Thr Thr Ser Tyr Glu Glu Val Val Glu Ala Leu Arg Ala
 1               5                  10                  15
Ser Leu Lys Glu Asn Glu Arg Leu Arg Arg Gly Arg Asp Arg Phe Ser
            20                  25                  30
Ala Glu Lys Asp Asp Pro Ile Ala Ile Val Ala Met Ser Cys Arg Tyr
        35                  40                  45
Pro Gly Gln Val Ser Ser Pro Glu Asp Leu Trp Gln Leu Ala Ala Gly
    50                  55                  60
Gly Val Asp Ala Ile Ser Glu Val Pro Gly Asp Arg Gly Trp Asp Leu
65                  70                  75                  80
Asp Gly Val Phe Val Pro Asp Ser Asp Arg Pro Gly Thr Ser Tyr Ala
                85                  90                  95
Cys Ala Gly Gly Phe Leu Gln Gly Val Ser Glu Phe Asp Ala Gly Phe
            100                 105                 110
Phe Gly Ile Ser Pro Arg Glu Ala Leu Ala Met Asp Pro Gln Gln Arg
        115                 120                 125
Leu Leu Leu Glu Val Ala Trp Glu Val Phe Glu Arg Ala Gly Leu Glu
    130                 135                 140
```

-continued

```
Gln Arg Ser Thr Arg Gly Ser Arg Val Gly Val Phe Val Gly Thr Asn
145                 150                 155                 160

Gly Gln Asp Tyr Ala Ser Trp Leu Arg Thr Pro Pro Ala Val Ala
            165                 170                 175

Gly His Val Leu Thr Gly Gly Ala Ala Val Leu Ser Gly Arg Val
        180                 185                 190

Ala Tyr Ser Phe Gly Phe Glu Gly Pro Ala Val Thr Val Asp Thr Ala
    195                 200                 205

Cys Ser Ser Ser Leu Val Ala Leu His Leu Ala Gly Gln Ala Leu Arg
210                 215                 220

Ala Gly Glu Cys Asp Leu Ala Leu Ala Gly Gly Val Thr Val Met Ser
225                 230                 235                 240

Thr Pro Lys Val Phe Leu Glu Phe Ser Arg Gln Arg Gly Leu Ala Pro
                245                 250                 255

Asp Gly Arg Cys Lys Ser Phe Ala Ala Gly Ala Asp Gly Thr Gly Trp
            260                 265                 270

Gly Glu Gly Ala Gly Leu Leu Leu Leu Glu Arg Leu Ser Asp Ala Arg
        275                 280                 285

Arg Asn Gly His Glu Val Leu Ala Val Val Arg Gly Ser Ala Val Asn
    290                 295                 300

Gln Asp Gly Ala Ser Asn Gly Leu Thr Ala Pro Asn Gly Ser Ser Gln
305                 310                 315                 320

Gln Arg Val Ile Thr Gln Ala Leu Ala Ser Ala Gly Leu Ser Val Ser
                325                 330                 335

Asp Val Asp Ala Val Glu Ala His Gly Thr Gly Thr Arg Leu Gly Asp
            340                 345                 350

Pro Ile Glu Ala Gln Ala Leu Ile Ala Thr Tyr Gly Arg Asp Arg Asp
        355                 360                 365

Pro Gly Arg Pro Leu Trp Leu Gly Ser Val Lys Ser Asn Ile Gly His
    370                 375                 380

Thr Gln Ala Ala Ala Gly Val Ala Gly Val Ile Lys Met Val Met Ala
385                 390                 395                 400

Met Arg His Gly Gln Leu Pro Arg Thr Leu His Val Glu Ser Pro Ser
                405                 410                 415

Pro Glu Val Asp Trp Ser Ala Gly Thr Val Gln Leu Leu Thr Glu Asn
            420                 425                 430

Thr Pro Trp Pro Arg Ser Gly Arg Val Arg Arg Val Gly Val Ser Ser
        435                 440                 445

Phe Gly Ile Ser Gly Thr Asn Ala His Val Ile Leu Glu Gln Pro Pro
    450                 455                 460

Gly Val Pro Ser Gln Ser Ala Gly Pro Gly Ser Gly Val Val Asp
465                 470                 475                 480

Val Pro Val Val Pro Trp Met Val Ser Gly Lys Thr Pro Glu Ala Leu
                485                 490                 495

Ser Ala Gln Ala Thr Ala Leu Met Thr Tyr Leu Asp Glu Arg Pro Asp
            500                 505                 510

Val Ser Ser Leu Asp Val Gly Tyr Ser Leu Ala Leu Thr Arg Ser Ala
        515                 520                 525

Leu Asp Glu Arg Ala Val Val Leu Gly Ser Asp Arg Glu Thr Leu Leu
    530                 535                 540

Cys Gly Val Lys Ala Leu Ser Ala Gly His Glu Ala Ser Gly Leu Val
545                 550                 555                 560

Thr Gly Ser Val Gly Ala Gly Gly Arg Ile Gly Phe Val Phe Ser Gly
```

-continued

```
            565                 570                 575
Gln Gly Gly Gln Trp Leu Gly Met Gly Arg Gly Leu Tyr Arg Ala Phe
            580                 585                 590
Pro Val Phe Ala Ala Ala Phe Asp Glu Ala Cys Ala Glu Leu Asp Ala
            595                 600                 605
His Leu Gly Gln Glu Ile Gly Val Arg Glu Val Val Ser Gly Ser Asp
            610                 615                 620
Ala Gln Leu Leu Asp Arg Thr Leu Trp Ala Gln Ser Gly Leu Phe Ala
625                 630                 635                 640
Leu Gln Val Gly Leu Leu Lys Leu Leu Asp Ser Trp Gly Val Arg Pro
            645                 650                 655
Ser Val Val Leu Gly His Ser Val Gly Glu Leu Ala Ala Ala Phe Ala
            660                 665                 670
Ala Gly Val Val Ser Leu Ser Gly Ala Ala Arg Leu Val Ala Gly Arg
            675                 680                 685
Ala Arg Leu Met Gln Ala Leu Pro Ser Gly Gly Met Leu Ala Val
            690                 695                 700
Pro Ala Gly Glu Glu Leu Leu Trp Ser Leu Leu Ala Asp Gln Gly Asp
705                 710                 715                 720
Arg Val Gly Ile Ala Ala Val Asn Ala Ala Gly Ser Val Val Leu Ser
            725                 730                 735
Gly Asp Arg Asp Val Leu Asp Asp Leu Ala Gly Arg Leu Asp Gly Gln
            740                 745                 750
Gly Ile Arg Ser Arg Trp Leu Arg Val Ser His Ala Phe His Ser Tyr
            755                 760                 765
Arg Met Asp Pro Met Leu Ala Glu Phe Ala Glu Leu Ala Arg Thr Val
            770                 775                 780
Asp Tyr Arg Arg Cys Glu Val Pro Ile Val Ser Thr Leu Thr Gly Asp
785                 790                 795                 800
Leu Asp Asp Ala Gly Arg Met Ser Gly Pro Asp Tyr Trp Val Arg Gln
            805                 810                 815
Val Arg Glu Pro Val Arg Phe Ala Asp Gly Val Gln Ala Leu Val Glu
            820                 825                 830
His Asp Val Ala Thr Val Glu Leu Gly Pro Asp Gly Ala Leu Ser
            835                 840                 845
Ala Leu Ile Gln Glu Cys Val Ala Ser Asp His Ala Gly Arg Leu
            850                 855                 860
Ser Ala Val Pro Ala Met Arg Arg Asn Gln Asp Glu Ala Gln Lys Val
865                 870                 875                 880
Met Thr Ala Leu Ala His Val His Val Arg Gly Gly Ala Val Asp Trp
            885                 890                 895
Arg Ser Phe Phe Ala Gly Thr Gly Ala Lys Gln Ile Glu Leu Pro Thr
            900                 905                 910
Tyr Ala Phe Gln Arg Gln Arg Tyr Trp Leu Val Pro Ser Asp Ser Gly
            915                 920                 925
Asp Val Thr Gly Ala Gly Leu Ala Gly Ala Glu His Pro Leu Leu Gly
            930                 935                 940
Ala Val Val Pro Val Ala Gly Asp Glu Val Leu Leu Thr Gly Arg
945                 950                 955                 960
Ile Ser Val Arg Thr His Pro Trp Leu Ala Glu His Arg Val Leu Gly
            965                 970                 975
Glu Val Ile Val Ala Gly Thr Ala Leu Leu Glu Ile Ala Leu His Ala
            980                 985                 990
```

-continued

Gly Glu Arg Leu Gly Cys Glu Arg Val Glu Leu Thr Leu Glu Ala
         995                1000                1005

Pro Leu Val Leu Pro Glu Arg Gly Ala Ile Gln Val Gln Leu Arg Val
    1010                1015                1020

Gly Ala Pro Glu Asn Ser Gly Arg Arg Pro Met Ala Leu Tyr Ser Arg
1025                1030                1035                1040

Pro Glu Gly Ala Ala Glu His Asp Trp Thr Arg His Ala Thr Gly Arg
             1045                1050                1055

Leu Ala Pro Gly Arg Gly Glu Ala Ala Gly Asp Leu Ala Asp Trp Pro
         1060                1065                1070

Ala Pro Gly Ala Leu Pro Val Asp Leu Asp Glu Phe Tyr Arg Asp Leu
    1075                1080                1085

Ala Glu Leu Gly Leu Glu Tyr Gly Pro Ile Phe Gln Gly Leu Lys Ala
    1090                1095                1100

Ala Trp Arg Gln Gly Asp Glu Val Tyr Ala Glu Ala Leu Pro Gly
1105                1110                1115                1120

Thr Glu Asp Ser Gly Phe Gly Val His Pro Ala Leu Leu Asp Ala Ala
             1125                1130                1135

Leu His Ala Thr Ala Val Arg Asp Met Asp Asp Ala Arg Leu Pro Phe
             1140                1145                1150

Gln Trp Glu Gly Val Ser Leu His Ala Lys Ala Ala Pro Ala Leu Arg
         1155                1160                1165

Val Arg Val Val Pro Ala Gly Asp Ala Lys Ser Leu Leu Val Cys
    1170                1175                1180

Asp Gly Thr Gly Arg Pro Val Ile Ser Val Asp Arg Leu Val Leu Arg
1185                1190                1195                1200

Ser Ala Ala Ala Arg Arg Thr Gly Ala Arg Arg Gln Ala His Gln Ala
             1205                1210                1215

Arg Leu Tyr Arg Leu Ser Trp Pro Thr Val Gln Leu Pro Thr Ser Ala
         1220                1225                1230

Gln Pro Pro Ser Cys Val Leu Leu Gly Thr Ser Glu Val Ser Ala Asp
         1235                1240                1245

Ile Gln Val Tyr Pro Asp Leu Arg Ser Leu Thr Ala Ala Leu Asp Ala
    1250                1255                1260

Gly Ala Glu Pro Pro Gly Val Val Ile Ala Pro Thr Pro Pro Gly Gly
1265                1270                1275                1280

Gly Arg Thr Ala Asp Val Arg Glu Thr Thr Arg His Ala Leu Asp Leu
             1285                1290                1295

Val Gln Gly Trp Leu Ser Asp Gln Arg Leu Asn Glu Ser Arg Leu Leu
         1300                1305                1310

Leu Val Thr Gln Gly Ala Val Ala Val Glu Pro Gly Glu Pro Val Thr
    1315                1320                1325

Asp Leu Ala Gln Ala Ala Leu Trp Gly Leu Leu Arg Ser Thr Gln Thr
    1330                1335                1340

Glu His Pro Asp Arg Phe Val Leu Val Asp Val Pro Glu Pro Ala Gln
1345                1350                1355                1360

Leu Leu Pro Ala Leu Pro Gly Val Leu Ala Cys Gly Glu Pro Gln Leu
             1365                1370                1375

Ala Leu Arg Arg Gly Gly Ala His Ala Pro Arg Leu Ala Gly Leu Gly
         1380                1385                1390

Ser Asp Asp Val Leu Pro Val Pro Asp Gly Thr Gly Trp Arg Leu Glu
    1395                1400                1405

-continued

```
Ala Thr Arg Pro Gly Ser Leu Asp Gly Leu Ala Leu Val Asp Glu Pro
    1410                1415                1420

Thr Ala Thr Ala Pro Leu Gly Asp Gly Glu Val Arg Ile Ala Met Arg
1425                1430                1435                1440

Ala Ala Gly Val Asn Phe Arg Asp Ala Leu Ile Ala Leu Gly Met Tyr
            1445                1450                1455

Pro Gly Val Ala Ser Leu Gly Ser Glu Gly Ala Gly Val Val Val Glu
            1460                1465                1470

Thr Gly Pro Gly Val Thr Gly Leu Ala Pro Gly Asp Arg Val Met Gly
    1475                1480                1485

Met Ile Pro Lys Ala Phe Gly Pro Leu Ala Val Ala Asp His Arg Met
    1490                1495                1500

Val Thr Arg Ile Pro Ala Gly Trp Ser Phe Ala Arg Ala Ala Ser Val
1505                1510                1515                1520

Pro Ile Val Phe Leu Thr Ala Tyr Tyr Ala Leu Val Asp Leu Ala Gly
            1525                1530                1535

Leu Arg Pro Gly Glu Ser Leu Leu Val His Ser Ala Ala Gly Gly Val
            1540                1545                1550

Gly Met Ala Ala Ile Gln Leu Ala Arg His Leu Gly Ala Glu Val Tyr
        1555                1560                1565

Ala Thr Ala Ser Glu Asp Lys Trp Gln Ala Val Glu Leu Ser Arg Glu
    1570                1575                1580

His Leu Ala Ser Ser Arg Thr Cys Asp Phe Glu Gln Gln Phe Leu Gly
1585                1590                1595                1600

Ala Thr Gly Gly Arg Gly Val Asp Val Val Leu Asn Ser Leu Ala Gly
            1605                1610                1615

Glu Phe Ala Asp Ala Ser Leu Arg Met Leu Pro Arg Gly Gly Arg Phe
            1620                1625                1630

Leu Glu Leu Gly Lys Thr Asp Val Arg Asp Pro Val Glu Val Ala Asp
        1635                1640                1645

Ala His Pro Gly Val Ser Tyr Gln Ala Phe Asp Thr Val Glu Ala Gly
    1650                1655                1660

Pro Gln Arg Ile Gly Glu Met Leu His Glu Leu Val Glu Leu Phe Glu
1665                1670                1675                1680

Gly Arg Val Leu Glu Pro Leu Pro Val Thr Ala Trp Asp Val Arg Gln
            1685                1690                1695

Ala Pro Glu Ala Leu Arg His Leu Ser Gln Ala Arg His Val Gly Lys
            1700                1705                1710

Leu Val Leu Thr Met Pro Pro Val Trp Asp Ala Ala Gly Thr Val Leu
        1715                1720                1725

Val Thr Gly Gly Thr Gly Ala Leu Gly Ala Glu Val Ala Arg His Leu
    1730                1735                1740

Val Ile Glu Arg Gly Val Arg Asn Leu Val Leu Val Ser Arg Arg Gly
1745                1750                1755                1760

Pro Ala Ala Ser Gly Ala Ala Glu Leu Val Ala Gln Leu Thr Ala Tyr
            1765                1770                1775

Gly Ala Glu Val Ser Leu Gln Ala Cys Asp Val Ala Asp Arg Glu Thr
            1780                1785                1790

Leu Ala Lys Val Leu Ala Ser Ile Pro Asp Glu His Pro Leu Thr Ala
        1795                1800                1805

Val Val His Ala Ala Gly Val Leu Asp Asp Gly Val Ser Glu Ser Leu
    1810                1815                1820

Thr Val Glu Arg Leu Asp Gln Val Leu Arg Pro Lys Val Asp Gly Ala
```

-continued

```
              1825                1830                1835                1840

Arg Asn Leu Leu Glu Leu Ile Asp Pro Asp Val Ala Leu Val Leu Phe
            1845                1850                1855

Ser Ser Val Ser Gly Val Leu Gly Ser Gly Gly Gln Gly Asn Tyr Ala
            1860                1865                1870

Ala Ala Asn Ser Phe Leu Asp Ala Leu Ala Gln Gln Arg Gln Ser Arg
            1875                1880                1885

Gly Leu Pro Thr Arg Ser Leu Ala Trp Gly Pro Trp Ala Glu His Gly
            1890                1895                1900

Met Ala Ser Thr Leu Arg Glu Ala Glu Gln Asp Arg Leu Ala Arg Ser
1905                1910                1915                1920

Gly Leu Leu Pro Ile Ser Thr Glu Glu Gly Leu Ser Gln Phe Asp Ala
            1925                1930                1935

Ala Cys Gly Gly Ala His Thr Val Val Ala Pro Val Arg Phe Ser Arg
            1940                1945                1950

Leu Ser Asp Gly Asn Ala Ile Lys Phe Ser Val Leu Gln Gly Leu Val
            1955                1960                1965

Gly Pro His Arg Val Asn Lys Ala Ala Thr Ala Asp Asp Ala Glu Ser
            1970                1975                1980

Leu Arg Lys Arg Leu Gly Arg Leu Pro Asp Ala Glu Gln His Arg Ile
1985                1990                1995                2000

Leu Leu Asp Leu Val Arg Met His Val Ala Ala Val Leu Gly Phe Ala
            2005                2010                2015

Gly Ser Gln Glu Ile Thr Ala Asp Gly Thr Phe Lys Val Leu Gly Phe
            2020                2025                2030

Asp Ser Leu Thr Val Val Glu Leu Arg Asn Arg Ile Asn Gly Ala Thr
            2035                2040                2045

Gly Leu Arg Leu Pro Ala Thr Leu Val Phe Asn Tyr Pro Thr Pro Asp
            2050                2055                2060

Ala Leu Ala Ala His Leu Val Thr Ala Leu Ser Ala Asp Arg Leu Ala
2065                2070                2075                2080

Gly Thr Phe Glu Glu Leu Asp Arg Trp Ala Ala Asn Leu Pro Thr Leu
            2085                2090                2095

Ala Arg Asp Glu Ala Thr Arg Ala Gln Ile Thr Thr Arg Leu Gln Ala
            2100                2105                2110

Ile Leu Gln Ser Leu Ala Asp Val Ser Gly Gly Thr Gly Gly Gly Ser
            2115                2120                2125

Val Pro Asp Arg Leu Arg Ser Ala Thr Asp Glu Leu Phe Gln Leu
    2130                2135                2140

Leu Asp Asn Asp Leu Glu Leu Pro
2145                2150

<210> SEQ ID NO 4
<211> LENGTH: 3170
<212> TYPE: PRT
<213> ORGANISM: Saccharopolyspora spinosa

<400> SEQUENCE: 4

Met Ser Asn Glu Glu Lys Leu Arg Glu Tyr Leu Arg Arg Ala Leu Val
  1               5                  10                  15

Asp Leu His Gln Ala Arg Glu Arg Leu His Glu Ala Glu Ser Gly Glu
             20                  25                  30

Arg Glu Pro Ile Ala Ile Val Ala Met Gly Cys Arg Tyr Pro Gly Gly
         35                  40                  45
```

-continued

```
Val Gln Asp Pro Glu Gly Leu Trp Lys Leu Val Ala Ser Gly Gly Asp
 50                  55                  60

Ala Ile Gly Glu Phe Pro Ala Asp Arg Gly Trp His Leu Asp Glu Leu
 65                  70                  75                  80

Tyr Asp Pro Asp Pro Asp Gln Pro Gly Thr Cys Tyr Thr Arg His Gly
                 85                  90                  95

Gly Phe Leu His Asp Ala Gly Glu Phe Asp Ala Gly Phe Phe Asp Ile
                100                 105                 110

Ser Pro Arg Glu Ala Leu Ala Met Asp Pro Gln Gln Arg Leu Leu Leu
            115                 120                 125

Glu Ile Ser Trp Glu Thr Val Glu Ser Ala Gly Met Asp Pro Arg Ser
130                 135                 140

Leu Arg Gly Ser Arg Thr Gly Val Phe Ala Gly Leu Met Tyr Glu Gly
145                 150                 155                 160

Tyr Asp Thr Gly Ala His Arg Ala Gly Glu Gly Val Glu Gly Tyr Leu
                165                 170                 175

Gly Thr Gly Asn Ala Gly Ser Val Ala Ser Gly Arg Val Ala Tyr Ala
            180                 185                 190

Phe Gly Phe Glu Gly Pro Ala Val Thr Val Asp Thr Ala Cys Ser Ser
        195                 200                 205

Ser Leu Val Ala Leu His Leu Ala Cys Gln Ser Leu Arg Gln Gly Glu
210                 215                 220

Cys Asp Leu Ala Leu Ala Gly Gly Val Thr Val Met Ser Thr Pro Glu
225                 230                 235                 240

Arg Phe Val Glu Phe Ser Arg Gln Arg Gly Leu Ala Pro Asp Gly Arg
                245                 250                 255

Cys Lys Ser Phe Ala Ala Ala Asp Gly Thr Gly Trp Gly Glu Gly
            260                 265                 270

Ala Gly Leu Val Leu Leu Glu Arg Leu Ser Asp Ala Arg Arg Asn Gly
        275                 280                 285

His Arg Val Leu Ala Val Val Arg Gly Ser Ala Val Asn Gln Asp Gly
290                 295                 300

Ala Ser Asn Gly Leu Thr Ala Pro Asn Gly Leu Ala Gln Glu Arg Val
305                 310                 315                 320

Ile Gln Gln Val Leu Thr Ser Ala Gly Leu Ser Ala Ser Asp Val Asp
                325                 330                 335

Ala Val Glu Ala His Gly Thr Gly Thr Arg Leu Gly Asp Pro Ile Glu
            340                 345                 350

Ala Gln Ala Leu Ile Ala Ala Tyr Gly Gln Asp Arg Asp Arg Asp Arg
        355                 360                 365

Pro Leu Trp Leu Gly Ser Val Lys Ser Asn Ile Gly His Thr Gln Ala
370                 375                 380

Ala Ala Gly Val Ala Gly Val Ile Lys Met Val Met Ala Met Arg His
385                 390                 395                 400

Gly Glu Leu Pro Arg Thr Leu His Val Asp Glu Pro Asn Ser His Val
                405                 410                 415

Asp Trp Ser Ala Gly Ala Val Arg Leu Leu Thr Glu Asn Ile Arg Trp
            420                 425                 430

Pro Gly Thr Gly Thr Arg Arg Ala Gly Val Ser Ser Phe Gly Val Ser
        435                 440                 445

Gly Thr Asn Ala His Val Ile Leu Glu His Asp Pro Leu Ala Val Thr
450                 455                 460

Glu Asn Glu Glu Ala Ala Gln Ser Pro Ala Pro Gly Ile Val Pro Trp
```

-continued

```
            465                 470                 475                 480
        Ala Leu Ser Gly Arg Ser Ser Thr Ala Leu Arg Ala Gln Ala Glu Arg
                        485                 490                 495
        Leu Arg Glu Leu Cys Glu Gln Thr Asp Pro Asp Pro Val Asp Val Gly
                    500                 505                 510
        Phe Ser Leu Ala Ala Thr Arg Thr Ala Trp Glu His Arg Ala Val Val
                    515                 520                 525
        Leu Gly Arg Asp Ser Ala Thr Leu Arg Ser Gly Leu Gly Val Val Ala
                    530                 535                 540
        Ser Gly Glu Pro Ala Val Asp Val Glu Gly Ser Val Leu Asp Gly
        545                 550                 555                 560
        Glu Val Val Phe Val Phe Pro Gly Gln Gly Trp Gln Trp Ala Gly Met
                            565                 570                 575
        Ala Val Asp Leu Leu Asp Ala Ser Pro Thr Phe Ala Arg His Met Asp
                        580                 585                 590
        Glu Cys Ala Thr Ala Leu Arg Arg Tyr Val Asp Trp Ser Leu Val Asp
                    595                 600                 605
        Val Leu Arg Gly Ala Glu Asn Ser Pro Pro Leu Asp Arg Val Asp Val
                610                 615                 620
        Leu Gln Pro Ala Ser Phe Ala Val Met Val Ser Leu Ala Glu Val Trp
        625                 630                 635                 640
        Arg Ser Tyr Gly Val Arg Pro Ala Ala Val Gly His Ser Gln Gly
                            645                 650                 655
        Glu Ile Ala Ala Ala Cys Ala Ala Gly Val Leu Pro Leu Glu Asp Ala
                        660                 665                 670
        Ala Arg Leu Val Ala Leu Arg Ser Arg Ala Leu Lys Gly Leu Ser Gly
                        675                 680                 685
        Arg Gly Gly Met Ala Ser Leu Ala Cys Pro Ala Asp Glu Val Ala Ala
                    690                 695                 700
        Leu Phe Ala Gly Ser Gly Arg Leu Glu Val Ala Ala Ile Asn Gly
        705                 710                 715                 720
        Pro Arg Ser Val Val Ser Gly Asp Leu Glu Ala Val Asp Glu Leu
                        725                 730                 735
        Leu Ala Glu Cys Ala Glu Lys Asp Met Arg Ala Arg Arg Ile Pro Val
                    740                 745                 750
        Asp Tyr Ala Ser His Ser Ala His Val Glu Val Val Arg Ser Pro Val
                    755                 760                 765
        Leu Ala Ala Ala Ala Gly Val Arg His Arg Asp Gly Gln Val Pro Trp
                    770                 775                 780
        Trp Ser Thr Val Ile Gly Asp Trp Val Asp Pro Ala Arg Leu Asp Gly
        785                 790                 795                 800
        Glu Tyr Trp Tyr Arg Asn Leu Arg Gln Pro Val Arg Phe Glu His Ala
                        805                 810                 815
        Val Gln Gly Leu Val Glu Arg Gly Phe Gly Leu Phe Ile Glu Met Ser
                        820                 825                 830
        Ala His Pro Val Leu Thr Thr Ala Val Glu Glu Thr Gly Ala Glu Ser
                    835                 840                 845
        Glu Thr Ala Val Ala Ala Val Gly Thr Leu Arg Arg Asp Ser Gly Gly
                    850                 855                 860
        Leu Arg Arg Leu Leu His Ser Leu Ala Glu Ala Tyr Val Arg Gly Ala
        865                 870                 875                 880
        Thr Val Asp Trp Ala Val Ala Phe Gly Gly Ala Gly Arg Arg Leu Asp
                            885                 890                 895
```

-continued

```
Leu Pro Thr Tyr Pro Phe Gln Arg Gln Arg Tyr Trp Leu Asp Lys Gly
            900                 905                 910
Ala Ala Ser Asp Glu Ala Arg Ala Val Ser Asp Pro Ala Ala Gly Trp
            915                 920                 925
Phe Trp Gln Ala Val Ala Arg Gln Asp Leu Lys Ser Val Ser Asp Ala
            930                 935                 940
Leu Asp Leu Asp Ala Asp Ala Pro Leu Ser Ala Thr Leu Pro Ala Leu
945                 950                 955                 960
Ser Val Trp His Arg Gln Glu Arg Glu Arg Val Leu Ala Asp Gly Trp
                965                 970                 975
Arg Tyr Arg Val Asp Trp Val Arg Val Ala Pro Gln Pro Val Arg Arg
            980                 985                 990
Thr Arg Glu Thr Trp Leu Leu Val Pro Pro Gly Gly Ile Glu Glu
            995                 1000                1005
Ala Leu Val Glu Arg Leu Thr Asp Ala Leu Asn Thr Arg Gly Ile Ser
        1010                1015                1020
Thr Leu Arg Leu Asp Val Pro Pro Ala Ala Thr Ser Gly Glu Leu Ala
1025                1030                1035                1040
Thr Glu Leu Arg Ala Ala Ala Asp Gly Asp Pro Val Lys Ala Ile Leu
                1045                1050                1055
Ser Leu Thr Ala Leu Asp Glu Arg Pro His Pro Glu Cys Lys Asp Val
            1060                1065                1070
Pro Ser Gly Ile Ala Leu Leu Leu Asn Leu Val Lys Ala Leu Gly Glu
        1075                1080                1085
Ala Asp Leu Arg Ile Pro Leu Trp Thr Ile Thr Arg Gly Ala Val Lys
1090                1095                1100
Ala Gly Pro Ala Asp Arg Leu Leu Arg Pro Met Gln Ala Gln Ala Trp
1105                1110                1115                1120
Gly Leu Gly Arg Val Ala Ala Leu Glu His Pro Glu Arg Trp Gly Gly
            1125                1130                1135
Leu Ile Asp Leu Pro Asp Ser Leu Asp Gly Asp Val Leu Thr Arg Leu
        1140                1145                1150
Gly Glu Ala Leu Thr Asn Gly Leu Ala Glu Asp Gln Leu Ala Ile Arg
        1155                1160                1165
Gln Ser Gly Val Leu Ala Arg Arg Leu Val Pro Ala Pro Ala Asn Gln
    1170                1175                1180
Pro Ala Gly Arg Lys Trp Arg Pro Arg Gly Ser Ala Leu Ile Thr Gly
1185                1190                1195                1200
Gly Leu Gly Ala Val Gly Ala Gln Val Ala Arg Trp Leu Ala Glu Ile
            1205                1210                1215
Gly Ala Glu Arg Ile Val Leu Thr Ser Arg Arg Gly Asn Gln Ala Ala
            1220                1225                1230
Gly Ala Ala Glu Leu Glu Ala Glu Leu Arg Ala Leu Gly Ala Gln Val
        1235                1240                1245
Ser Ile Val Ala Cys Asp Val Thr Asp Arg Ala Glu Met Ser Ala Leu
1250                1255                1260
Leu Ala Glu Phe Asp Val Thr Ala Val Phe His Ala Ala Gly Val Gly
1265                1270                1275                1280
Arg Leu Leu Pro Leu Ala Glu Thr Asp Gln Asn Gly Leu Ala Glu Ile
            1285                1290                1295
Cys Ala Ala Lys Val Arg Gly Ala Gln Val Leu Asp Glu Leu Cys Asp
            1300                1305                1310
```

-continued

```
Ser Thr Asp Leu Asp Ala Phe Val Leu Phe Ser Ser Gly Ala Gly Val
    1315                1320                1325

Trp Gly Gly Gly Gly Gln Gly Ala Tyr Gly Ala Ala Asn Ala Phe Leu
            1330                1335                1340

Asp Thr Leu Ala Glu Gln Arg Arg Ala Arg Gly Leu Pro Ala Thr Ser
1345                1350                1355                1360

Ile Ser Trp Gly Ser Trp Ala Gly Gly Gly Met Ala Asp Gly Ala Ala
                1365                1370                1375

Gly Glu His Leu Arg Arg Arg Gly Ile Arg Pro Met Pro Ala Ala Ser
            1380                1385                1390

Ala Ile Leu Ala Leu Gln Glu Val Leu Asp Gln Asp Glu Thr Cys Val
        1395                1400                1405

Ser Ile Ala Asp Val Asp Trp Asp Arg Phe Val Pro Thr Phe Ala Ala
    1410                1415                1420

Thr Arg Ala Thr Arg Leu Phe Asp Glu Val Pro Ala Ala Arg Lys Ala
1425                1430                1435                1440

Met Pro Ala Asn Gly Pro Ala Glu Pro Gly Gly Ser Pro Phe Ala Arg
                1445                1450                1455

Asn Leu Ala Glu Leu Pro Glu Ala Gln Arg Arg His Glu Leu Val Asp
            1460                1465                1470

Leu Val Cys Ala Gln Val Ala Thr Val Leu Gly His Gly Ser Arg Glu
        1475                1480                1485

Glu Val Gln Pro Glu Arg Ala Phe Arg Ala Leu Gly Phe Asp Ser Leu
    1490                1495                1500

Met Ala Val Asp Leu Arg Asn Arg Leu Thr Thr Ala Thr Gly Leu Arg
1505                1510                1515                1520

Leu Pro Thr Thr Thr Val Phe Asp Tyr Pro Asn Pro Ala Ala Leu Ala
                1525                1530                1535

Ala His Leu Leu Glu Glu Leu Val Gly Asp Val Ala Ser Ala Ala Val
            1540                1545                1550

Thr Ala Ala Ser Ala Pro Ala Ser Asp Glu Pro Ile Ala Ile Val Ala
        1555                1560                1565

Met Ser Cys Arg Phe Pro Gly Gly Ala His Ser Pro Glu Asp Leu Trp
    1570                1575                1580

Arg Leu Val Ala Ala Gly Thr Glu Val Ile Gly Glu Phe Pro Ser Asp
1585                1590                1595                1600

Arg Gly Trp Asp Ala Glu Gly Leu Tyr Asp Pro Asp Ala Ser Arg Pro
                1605                1610                1615

Gly Thr Thr Tyr Ala Arg Met Ala Gly Phe Leu Tyr Asp Ala Gly Glu
            1620                1625                1630

Phe Asp Ala Asp Leu Phe Gly Ile Ser Pro Arg Glu Ala Leu Ala Met
        1635                1640                1645

Asp Pro Gln Gln Arg Leu Val Leu Glu Ile Ala Trp Glu Ala Leu Glu
    1650                1655                1660

Arg Ala Gly Ile Asp Pro Leu Ser Leu Lys Gly Ser Gly Val Gly Thr
1665                1670                1675                1680

Tyr Ile Gly Ala Gly Ser Arg Gly Tyr Ala Thr Asp Val Arg Gln Phe
                1685                1690                1695

Pro Glu Glu Ala Glu Gly Tyr Leu Leu Thr Gly Thr Ser Ala Ser Val
            1700                1705                1710

Leu Ser Gly Arg Val Ala Tyr Ser Phe Gly Phe Glu Gly Pro Ala Val
        1715                1720                1725

Thr Val Asp Thr Ala Cys Ser Ser Ser Leu Val Ala Leu His Leu Ala
```

```
                    1730           1735           1740
Cys Gln Ser Leu Arg Ser Gly Glu Cys Asp Leu Ala Leu Ala Gly Gly
            1745           1750           1755           1760
Val Thr Val Met Ser Thr Pro Glu Met Phe Val Glu Phe Ser Arg Gln
                    1765           1770           1775
Arg Gly Leu Ala Pro Asp Gly Arg Cys Lys Ser Phe Ala Glu Ser Ala
            1780           1785           1790
Asp Gly Thr Gly Trp Gly Glu Gly Ala Gly Leu Leu Leu Glu Arg
        1795           1800           1805
Leu Ser Asp Ala His Arg Asn Gly His Arg Val Leu Ala Val Val Arg
    1810           1815           1820
Gly Ser Ala Val Asn Gln Asp Gly Ala Ser Asn Gly Leu Ala Ala Pro
1825           1830           1835           1840
Asn Gly Pro Ser Gln Gln Arg Val Ile Asn Gln Ala Leu Ala Asn Ala
            1845           1850           1855
Ala Leu Ser Ala Ser Asp Val Asp Ala Val Glu Ala His Gly Thr Gly
                    1860           1865           1870
Thr Arg Leu Gly Asp Pro Ile Glu Ala Gln Ala Leu Ile Ala Thr Tyr
            1875           1880           1885
Gly Gln Ala Arg Glu Arg Asp Arg Pro Leu Trp Leu Gly Ser Val Lys
        1890           1895           1900
Ser Asn Ile Gly His Thr Gln Ala Ala Ala Gly Val Ala Gly Val Ile
1905           1910           1915           1920
Lys Met Val Met Ala Met Arg His Gly Gln Leu Pro Ala Ser Leu His
            1925           1930           1935
Ala Asp Glu Pro Thr Ser Glu Val Asp Trp Ser Ser Gly Ala Val Arg
        1940           1945           1950
Leu Leu Ala Glu Gln Val Pro Trp Pro Glu Ser Asp Arg Val Arg Arg
        1955           1960           1965
Val Gly Val Ser Ser Phe Gly Ile Ser Gly Thr Asn Ala His Val Ile
    1970           1975           1980
Leu Glu Gln Ala Thr Asn Ala Pro Asp Ser Thr Ala Glu Thr Asp Lys
1985           1990           1995           2000
Thr Glu Ser Gly Ser Thr Val Asp Ile Pro Val Val Pro Trp Leu Val
            2005           2010           2015
Ser Gly Lys Thr Thr Asp Ser Leu Arg Gly Gln Ala Glu Arg Val Leu
            2020           2025           2030
Ser Gln Val Glu Ser Arg Pro Glu Gln Arg Ser Leu Asp Val Ala Tyr
        2035           2040           2045
Ser Leu Ala Ser Gly Arg Ala Ala Leu Asp Glu Arg Ala Val Val Leu
    2050           2055           2060
Gly Ala Asp Arg Gly Glu Leu Val Ala Gly Leu Ala Ala Leu Ala Ala
2065           2070           2075           2080
Gly Gln Glu Ala Ser Gly Val Ile Ser Gly Thr Arg Ala Ser Ala Arg
            2085           2090           2095
Phe Gly Phe Val Phe Ser Gly Gln Gly Gly Gln Trp Leu Gly Met Gly
            2100           2105           2110
Arg Ala Leu Tyr Ser Lys Phe Pro Val Phe Ala Ala Ala Phe Asp Glu
        2115           2120           2125
Ala Cys Ala Glu Leu Glu Ala His Leu Gly Glu Asp Arg Arg Val Arg
    2130           2135           2140
Asp Val Val Phe Gly Ser Asp Ala Gln Leu Leu Asp Gln Thr Leu Trp
2145           2150           2155           2160
```

-continued

Ala Gln Ser Gly Leu Phe Ala Leu Gln Ala Gly Leu Gly Leu Leu
                2165                2170                2175

Gly Ser Trp Gly Val Arg Pro Asp Val Val Met Gly His Ser Val Gly
            2180                2185                2190

Glu Leu Ala Ala Ala Phe Ala Ala Gly Val Leu Ser Leu Arg Asp Ala
            2195                2200                2205

Ala Arg Leu Val Ala Ala Arg Ala Arg Leu Met Gln Ala Leu Pro Ser
    2210                2215                2220

Asp Gly Ala Met Leu Ala Val Ala Ala Gly Glu Asp Leu Val Arg Pro
2225                2230                2235                2240

Leu Leu Ala Gly Arg Glu Glu Ser Val Ser Val Ala Ala Leu Asn Ala
                2245                2250                2255

Pro Gly Ser Val Val Leu Ser Gly Asp Arg Glu Val Leu Ala Ser Ile
            2260                2265                2270

Val Gly Arg Leu Thr Glu Leu Arg Val Arg Thr Arg Arg Leu Arg Val
        2275                2280                2285

Ser His Ala Phe His Ser His Arg Met Asp Pro Met Leu Gly Glu Phe
    2290                2295                2300

Ala Gln Ile Ala Glu Ser Ala Glu Phe Gly Lys Pro Thr Thr Pro Leu
2305                2310                2315                2320

Val Ser Thr Leu Thr Gly Glu Leu Asp Arg Ala Ala Glu Met Ser Thr
            2325                2330                2335

Pro Gly Tyr Trp Val Arg Gln Ala Arg Glu Pro Val Arg Phe Ala Asp
        2340                2345                2350

Gly Val Gln Ala Leu Ala Ala Gln Gly Ile Gly Thr Val Val Glu Leu
    2355                2360                2365

Gly Pro Asp Gly Thr Leu Ala Ala Leu Val Arg Glu Cys Ala Thr Glu
    2370                2375                2380

Ser Asp Arg Val Gly Arg Ile Ser Ser Ile Pro Leu Met Arg Arg Glu
2385                2390                2395                2400

Arg Asp Glu Thr Arg Ser Val Met Thr Ala Leu Ala His Leu His Thr
            2405                2410                2415

Arg Gly Gly Glu Val Asp Trp Gln Ala Phe Phe Ala Gly Thr Gly Ala
        2420                2425                2430

Arg Gln Leu Glu Leu Pro Thr Tyr Ala Phe Gln Arg Gln His Tyr Trp
    2435                2440                2445

Ile Glu Ser Ser Ala Arg Pro Ala Arg Asp Arg Ala Asp Ile Gly Glu
    2450                2455                2460

Val Ala Glu Gln Phe Trp Thr Ala Val Asp Gln Gly Asp Leu Ala Thr
2465                2470                2475                2480

Leu Val Ala Ala Leu Asp Leu Gly Ala Asp Asp Thr Cys Ala Ser
            2485                2490                2495

Leu Ser Asp Val Leu Pro Ala Leu Ser Ser Trp Arg Ser Gly Leu Arg
        2500                2505                2510

Asn Arg Ser Leu Val Asp Ser Cys Arg Tyr Arg Ile Ser Trp His Ser
    2515                2520                2525

Ser Arg Glu Val Pro Ala Pro Lys Ile Ser Gly Thr Trp Leu Leu Val
    2530                2535                2540

Val Pro Gly Ala Ala Asp Asp Gly Leu Val Thr Ala Leu Thr Ser Ser
2545                2550                2555                2560

Leu Val Gly Gly Gly Ala Glu Val Val Arg Ile Gly Leu Ser Glu Glu
            2565                2570                2575

-continued

```
Asp Pro His Arg Glu Asp Val Ala Gln Arg Leu Ala Asn Ala Leu Thr
            2580                2585                2590

Asp Ala Gly Gln Leu Gly Gly Val Leu Ser Leu Leu Gly Leu Asp Glu
        2595                2600                2605

Ser Pro Ala Pro Gly Phe Ser Cys Leu Pro Thr Gly Phe Ala Leu Thr
    2610                2615                2620

Val Gln Leu Leu Arg Ala Leu Arg Lys Ala Asp Val Glu Ala Pro Phe
2625                2630                2635                2640

Trp Ala Val Thr Arg Gly Gly Val Ala Leu Glu Asp Val Arg Val Ser
            2645                2650                2655

Pro Glu Gln Ala Leu Val Trp Gly Leu Leu Arg Val Ala Gly Leu Glu
        2660                2665                2670

His Pro Glu Phe Trp Gly Gly Leu Ile Asp Leu Pro Ser Asp Trp Asp
    2675                2680                2685

Asp Arg Leu Gly Ala Arg Leu Ala Gly Val Leu Ala Asp Gly Gly Glu
    2690                2695                2700

Asp Gln Val Ala Ile Arg Arg Gly Gly Val Phe Val Arg Arg Leu Glu
2705                2710                2715                2720

Arg Ala Gly Ala Ser Gly Ala Gly Ser Val Trp Arg Pro Arg Gly Thr
            2725                2730                2735

Val Leu Val Thr Gly Gly Thr Gly Gly Leu Gly Ala His Val Ala Arg
        2740                2745                2750

Trp Leu Ala Gly Ala Gly Ala Glu His Val Val Leu Thr Ser Arg Arg
    2755                2760                2765

Gly Ala Asp Ala Pro Gly Ala Gly Glu Leu Arg Ala Glu Leu Glu Ala
    2770                2775                2780

Leu Gly Ala Arg Val Ser Ile Val Pro Cys Asp Val Ala Asp Arg Asp
2785                2790                2795                2800

Ala Val Ala Gly Val Leu Ala Gly Ile Gly Gly Glu Cys Pro Leu Thr
            2805                2810                2815

Ala Val Val His Ala Ala Gly Val Gly Glu Ala Gly Asp Val Val Glu
        2820                2825                2830

Met Gly Leu Ala Asp Phe Ala Ala Val Leu Ser Ala Lys Val Arg Gly
    2835                2840                2845

Ala Ala Asn Leu Asp Glu Leu Leu Ala Asp Ser Glu Leu Asp Ala Phe
    2850                2855                2860

Val Met Phe Ser Ser Val Ser Gly Val Trp Gly Ala Gly Gly Gln Gly
2865                2870                2875                2880

Ala Tyr Ala Ala Ala Asn Ala Tyr Leu Asp Ala Leu Ala Glu Gln Arg
            2885                2890                2895

Arg Ala Arg Gly Leu Val Gly Thr Ala Val Ala Trp Gly Pro Trp Ala
        2900                2905                2910

Gly Asp Gly Met Ala Ala Gly Glu Thr Gly Ala Gln Leu His Arg Met
    2915                2920                2925

Gly Leu Ala Ser Met Glu Pro Ser Ala Ala Leu Leu Ala Leu Gln Gly
    2930                2935                2940

Ala Leu Asp Arg Asp Glu Thr Ser Leu Val Val Ala Asp Val Asp Trp
2945                2950                2955                2960

Ala Arg Phe Ala Pro Ala Phe Thr Ser Ala Arg Arg Pro Leu Leu
            2965                2970                2975

Asp Thr Ile Asp Glu Ala Arg Ala Ala Leu Glu Thr Thr Gly Glu Gln
        2980                2985                2990

Ala Gly Thr Gly Lys Pro Val Glu Leu Thr Gln Arg Leu Ala Gly Leu
```

```
            2995                3000                3005
Ser Arg Lys Glu Arg Asp Asp Ala Val Leu Asp Leu Val Arg Ala Glu
     3010                3015                3020

Thr Ala Ala Val Leu Gly Arg Asp Asp Ala Thr Ala Leu Ala Pro Ser
3025                3030                3035                3040

Arg Pro Phe Gln Glu Leu Gly Phe Asp Ser Leu Met Ala Val Glu Leu
              3045                3050                3055

Arg Asn Arg Leu Asn Thr Ala Thr Gly Ile Gln Leu Pro Ala Ser Thr
         3060                3065                3070

Ile Phe Asp Tyr Pro Asn Ala Glu Ser Leu Ser Arg His Leu Cys Ala
     3075                3080                3085

Glu Leu Phe Pro Thr Glu Thr Thr Val Asp Ser Ala Leu Ala Glu Leu
     3090                3095                3100

Asp Arg Ile Glu Gln Gln Leu Ser Met Leu Thr Gly Glu Ala Arg Ala
3105                3110                3115                3120

Arg Asp Arg Ile Ala Thr Arg Leu Arg Ala Leu His Glu Lys Trp Asn
              3125                3130                3135

Ser Ala Ala Glu Val Pro Thr Gly Ala Asp Val Leu Ser Thr Leu Asp
         3140                3145                3150

Ser Ala Thr His Asp Glu Ile Phe Glu Phe Ile Asp Asn Glu Leu Asp
         3155                3160                3165

Leu Ser
   3170

<210> SEQ ID NO 5
<211> LENGTH: 4928
<212> TYPE: PRT
<213> ORGANISM: Saccharopolyspora spinosa

<400> SEQUENCE: 5

Val Glu Ile Thr Met Ala Asn Glu Glu Lys Leu Phe Gly Tyr Leu Lys
 1               5                  10                  15

Lys Val Thr Ala Asp Leu His Gln Thr Arg Gln Arg Leu Leu Ala Ala
             20                  25                  30

Glu Ser Arg Ser Gln Glu Pro Ile Ala Ile Val Ser Ala Ser Cys Arg
         35                  40                  45

Leu Pro Gly Gly Val Asp Ser Pro Glu Ala Leu Trp Gln Leu Val Arg
     50                  55                  60

Thr Gly Thr Asp Ala Ile Ser Glu Phe Pro Ala Asp Arg Gly Trp Asp
 65                  70                  75                  80

Leu Gly Arg Leu Tyr Asp Pro Asp Pro Asn His Gln Gly Thr Ser Tyr
                 85                  90                  95

Thr Arg Ala Gly Gly Phe Leu Ala Gly Ala Gly Asp Phe Asp Pro Ala
            100                 105                 110

Met Phe Gly Ile Ser Pro Arg Glu Ala Leu Ala Met Asp Pro Gln Gln
        115                 120                 125

Arg Leu Leu Leu Glu Leu Ser Trp Glu Ala Leu Glu Arg Ala Gly Ile
    130                 135                 140

Asp Pro Thr Ser Leu Arg Gly Ser Lys Thr Gly Val Phe Gly Gly Val
145                 150                 155                 160

Thr Pro Gln Glu Tyr Gly Pro Ser Leu Gln Glu Met Ser Arg Asn Ala
                165                 170                 175

Gly Gly Phe Gly Leu Thr Gly Arg Met Val Ser Val Ala Ser Gly Arg
            180                 185                 190
```

-continued

```
Val Ala Tyr Ser Phe Gly Phe Glu Gly Pro Ala Val Thr Val Asp Thr
            195                 200                 205

Ala Cys Ser Ser Ser Leu Val Ala Leu His Leu Ala Cys Gln Ser Leu
            210                 215                 220

Arg Ser Gly Glu Cys Asp Leu Ala Leu Ala Gly Gly Val Thr Val Met
225                 230                 235                 240

Ala Thr Pro Ala Thr Phe Val Glu Phe Ser Arg Gln Arg Gly Leu Ala
                245                 250                 255

Pro Asp Gly Arg Cys Lys Ser Phe Ala Ala Ala Asp Gly Thr Gly
                260                 265                 270

Trp Gly Glu Gly Ala Gly Leu Val Leu Leu Glu Arg Leu Ser Asp Ala
            275                 280                 285

Arg Arg Asn Gly His Glu Val Leu Ala Val Val Arg Gly Ser Ala Val
            290                 295                 300

Asn Gln Asp Gly Ala Ser Asn Gly Leu Thr Ala Pro Asn Gly Pro Ser
305                 310                 315                 320

Gln Gln Arg Val Ile Thr Gln Ala Leu Ala Ser Ala Gly Leu Ser Val
                325                 330                 335

Ser Asp Val Asp Ala Val Glu Ala His Gly Thr Gly Thr Thr Leu Gly
            340                 345                 350

Asp Pro Ile Glu Ala Gln Ala Leu Ile Ala Thr Tyr Gly Gln Gly Arg
            355                 360                 365

Glu Lys Asp Arg Pro Leu Trp Leu Gly Ser Val Lys Ser Asn Ile Gly
370                 375                 380

His Thr Gln Ala Ala Ala Gly Val Ala Gly Val Ile Lys Met Val Leu
385                 390                 395                 400

Ala Met Arg His Gly Gln Leu Pro Ala Thr Leu His Val Asp Glu Pro
                405                 410                 415

Thr Ser Ala Val Asp Trp Ser Ala Gly Ser Val Arg Leu Leu Thr Glu
            420                 425                 430

Asn Thr Pro Trp Pro Asp Ser Gly Arg Pro Cys Arg Val Gly Val Ser
            435                 440                 445

Ser Phe Gly Ile Ser Gly Thr Asn Ala His Val Ile Leu Glu Gln Ser
            450                 455                 460

Pro Val Glu Gln Gly Glu Pro Ala Gly Pro Val Glu Gly Glu Arg Glu
465                 470                 475                 480

Pro Asp Val Ala Val Pro Val Pro Trp Val Leu Ser Gly Lys Thr
                485                 490                 495

Pro Glu Ala Ala Arg Ala Gln Ala Glu Arg Val His Ser His Ile Glu
            500                 505                 510

Asp Arg Pro Gly Leu Ser Pro Val Asp Val Ala Tyr Ser Leu Gly Met
            515                 520                 525

Thr Arg Ala Ala Leu Asp Glu Arg Ala Val Val Leu Gly Ser Asp Arg
            530                 535                 540

Ala Ala Leu Leu Thr Gly Leu Arg Ala Phe Ala Asp Gly Cys Asp Ala
545                 550                 555                 560

Pro Glu Val Val Ser Gly Ser Val Gly Leu Gly Gly Arg Val Gly Phe
                565                 570                 575

Val Phe Ser Gly Gln Gly Gly Gln Trp Pro Gly Met Gly Arg Gly Leu
            580                 585                 590

Tyr Ser Val Phe Pro Val Phe Ala Asp Ala Phe Asp Glu Ala Cys Ala
            595                 600                 605

Glu Leu Asp Ala His Leu Gly Gln Glu Leu Arg Val Arg Asp Val Val
```

```
                610             615             620
Phe Gly Ser Gln Ala Trp Leu Leu Asp Arg Thr Val Trp Ala Gln Ser
625                 630                 635                 640

Gly Leu Phe Ala Leu Gln Ile Gly Leu Leu Arg Leu Leu Gly Ser Trp
                645                 650                 655

Gly Val Arg Pro Asp Val Val Leu Gly His Ser Val Gly Glu Leu Ala
                660                 665                 670

Ala Val His Ala Ala Gly Val Leu Ser Leu Ser Glu Ala Ala Arg Leu
                675                 680                 685

Val Ala Gly Arg Ala Arg Leu Met Gln Ala Leu Pro Ser Gly Gly Ala
690                 695                 700

Met Leu Ala Val Ala Thr Gly Glu Phe Gln Val Asp Pro Leu Leu Asp
705                 710                 715                 720

Gly Val Arg Asp Arg Ile Gly Ile Ala Ala Val Asn Gly Pro Glu Ser
                725                 730                 735

Val Val Leu Ser Gly Asp Arg Glu Leu Leu Thr Glu Ile Ala Asp Arg
                740                 745                 750

Leu His Asp Gln Gly Cys Arg Thr Arg Trp Leu Arg Val Ser His Ala
                755                 760                 765

Phe His Ser Pro His Met Glu Pro Met Leu Glu Glu Phe Ala Gln Ile
                770                 775                 780

Ser Arg Gly Arg Glu Tyr His Ala Pro Glu Leu Pro Ile Ile Ser Thr
785                 790                 795                 800

Leu Ile Gly Glu Leu Asp Gly Gly Arg Val Met Gly Thr Pro Glu Tyr
                805                 810                 815

Trp Val Arg Gln Val Arg Glu Pro Val Arg Phe Ala Glu Gly Val Gln
                820                 825                 830

Ala Leu Val Gly Gln Gly Val Gly Thr Ile Val Glu Leu Gly Pro Asp
                835                 840                 845

Gly Ala Leu Ser Thr Leu Val Glu Glu Cys Val Ala Glu Ser Gly Arg
                850                 855                 860

Val Ala Gly Ile Pro Leu Met Arg Lys Asp Arg Asp Glu Ala Arg Thr
865                 870                 875                 880

Val Leu Ala Ala Leu Ala Gln Ile His Thr Arg Gly Gly Glu Val Asp
                885                 890                 895

Trp Arg Ser Phe Phe Ala Gly Thr Gly Ala Lys Gln Val Asp Leu Pro
                900                 905                 910

Thr Tyr Ala Phe Gln Arg Gln Arg Tyr Trp Leu Ala Ser Thr Gly Arg
                915                 920                 925

Ala Gly Asp Val Thr Ala Gly Leu Ala Glu Ala Asp His Pro Leu
                930                 935                 940

Leu Gly Ala Val Val Ala Leu Ala Asp Gly Glu Gly Val Val Leu Thr
945                 950                 955                 960

Gly Arg Leu Thr Ala Gly Ser His Pro Trp Leu Ser Asp His Arg Val
                965                 970                 975

Leu Gly Glu Ile Val Val Pro Gly Thr Ala Ile Val Glu Leu Val Trp
                980                 985                 990

His Val Gly Glu Arg Leu Gly Cys Gly Arg Val Glu Glu Leu Ala Leu
                995                 1000                1005

Glu Ala Pro Leu Ile Leu Pro Asp His Gly Ala Val Gln Val Gln Val
    1010                1015                1020

Leu Val Gly Pro Pro Gly Glu Ser Gly Ala Arg Ser Val Ala Leu Tyr
1025                1030                1035                1040
```

```
Ser Cys Pro Gly Glu Ala Ile Glu Pro Glu Trp Lys Lys His Ala Thr
            1045                1050                1055

Gly Val Leu Leu Pro Pro Val Ala Ala Glu Asn His Glu Leu Thr Ala
        1060                1065                1070

Trp Pro Pro Glu Asn Ala Thr Glu Ile Asp Ala Asp Gly Val Tyr Ala
    1075                1080                1085

Phe Leu Glu Gly His Gly Phe Ala Tyr Gly Pro Ala Phe Arg Cys Leu
1090                1095                1100

Arg Gly Ala Trp Arg Arg Gly Glu Val Phe Ala Glu Val Ala Leu
1105                1110                1115                1120

Pro Asp Asp Met Gln Ala Gly Val Asp Arg Phe Gly Val His Pro Ala
                1125                1130                1135

Leu Leu Asp Ala Val Leu His Ala Ala Ala Glu Thr Ser Val Val
            1140                1145                1150

Gln Ser Glu Ala Arg Val Pro Phe Ser Trp Arg Gly Val Glu Leu Arg
    1155                1160                1165

Ala Thr Glu Ser Ala Val Val Arg Ala Arg Leu Ser Leu Thr Ser Asp
    1170                1175                1180

Asp Glu Leu Ser Leu Val Ala Val Asp Pro Ala Gly Arg Phe Val Ala
1185                1190                1195                1200

Thr Val Asp Ser Leu Val Thr Arg Pro Ile Ser Arg Gln Gln Val Arg
            1205                1210                1215

Ser Gly Ala Ile Gly Asp Cys Leu Phe Glu Val Glu Trp His Arg Lys
        1220                1225                1230

Ala Leu Leu Gly Thr Thr Ala Gly Asp Asp Leu Ala Ile Val Gly Asp
    1235                1240                1245

Gly Pro Ser Trp Pro Glu Ser Val Arg Ala Thr Ala Arg Phe Ala Thr
    1250                1255                1260

Leu Asp Glu Phe Arg Ala Ala Val Asp Ser Asp Val Pro Ala Pro Gly
1265                1270                1275                1280

Ser Val Leu Val Ala Ala Met Ser Ala Glu Glu Val Glu Gly Gly Ser
            1285                1290                1295

Leu Pro Ser Arg Ala Gln Glu Ser Thr Ser Asp Leu Leu Ala Leu Val
        1300                1305                1310

Gln Ser Trp Leu Ala Asp Glu Arg Phe Ala Glu Ser Gln Leu Val Val
    1315                1320                1325

Val Thr Arg Ala Ala Val Ser Ala Asp Ser Asp Ser Asp Val Ala Asp
    1330                1335                1340

Leu Val Gly Ala Ser Ser Trp Gly Leu Leu Ser Ser Ala Gln Ser Glu
1345                1350                1355                1360

Asn Pro Gly Arg Phe Val Leu Val Asp Val Asp Gly Thr Pro Glu Ser
        1365                1370                1375

Trp Gln Ala Leu Pro Ala Ala Val Arg Ala Gly Glu Pro Gln Leu Ala
        1380                1385                1390

Leu Arg Arg Gly Val Ala Leu Val Pro Arg Leu Ala Arg Leu Thr Val
        1395                1400                1405

Arg Glu Glu Gly Ser Ser Pro Gln Leu Asp Thr Asp Gly Thr Val Leu
    1410                1415                1420

Ile Thr Gly Gly Thr Gly Ala Leu Gly Gly Val Val Ala Arg His Leu
1425                1430                1435                1440

Val Glu Glu His Gly Ile Arg Arg Leu Val Leu Ala Gly Arg Arg Gly
            1445                1450                1455
```

-continued

```
Trp Asn Ala Pro Gly Val His Glu Leu Val Asp Glu Leu Ala Arg Ala
        1460                1465                1470

Gly Ala Val Val Glu Val Val Ala Cys Asp Val Ala Asp Arg Thr Asp
        1475                1480                1485

Leu Glu His Val Leu Ala Ala Ile Pro Val Asp Trp Pro Leu Arg Gly
        1490                1495                1500

Ile Val His Thr Ala Gly Val Leu Ala Asp Gly Val Ile Gly Ser Leu
1505                1510                1515                1520

Ser Ala Ala Asp Val Gly Thr Val Phe Ala Pro Lys Val Thr Gly Ala
            1525                1530                1535

Trp His Leu His Glu Leu Thr Arg Asp Leu Asp Leu Ser Phe Val
        1540                1545                1550

Leu Phe Ser Ser Phe Ser Gly Ile Ala Gly Ala Ala Gly Gln Ala Asn
        1555                1560                1565

Tyr Ala Ala Ala Asn Thr Phe Leu Asp Ala Leu Ala Arg Tyr Arg Arg
        1570                1575                1580

Ala Arg Gly Leu Pro Gly Leu Ser Leu Ala Trp Gly Leu Trp Ala Gln
1585                1590                1595                1600

Pro Ser Gly Met Thr Ser Gly Leu Asp Ala Ala Ser Val Glu Arg Leu
            1605                1610                1615

Ala Arg Thr Gly Ile Ala Glu Leu Ser Thr Glu Asp Gly Leu Arg Leu
        1620                1625                1630

Phe Asp Ala Ala Phe Ala Lys Asp Arg Ala Cys Val Val Ala Ala Arg
        1635                1640                1645

Leu Asp Arg Ala Leu Leu Val Gly Asn Gly Arg Ser His Ala Ile Pro
        1650                1655                1660

Ala Leu Leu Ser Ala Leu Val Pro Val Arg Gly Gly Val Ala Arg Lys
1665                1670                1675                1680

Thr Ala Asn Ser Gln Ala Ala Asp Glu Asp Ala Leu Leu Gly Leu Val
            1685                1690                1695

Arg Glu His Val Ser Ala Val Leu Gly Tyr Ser Gly Ala Val Glu Val
        1700                1705                1710

Gly Gly Asp Arg Ala Phe Arg Asp Leu Gly Phe Asp Ser Leu Ser Gly
        1715                1720                1725

Val Glu Leu Arg Asn Arg Leu Ala Gly Val Leu Gly Val Arg Leu Pro
        1730                1735                1740

Ala Thr Ala Val Phe Asp Tyr Pro Thr Pro Arg Ala Leu Ala Arg Phe
1745                1750                1755                1760

Leu His Gln Glu Leu Ala Gly Glu Val Ala Ser Thr Ser Thr Pro Val
            1765                1770                1775

Thr Arg Ala Ala Ser Ala Glu Glu Asp Leu Val Ala Ile Val Gly Met
        1780                1785                1790

Gly Cys Arg Phe Pro Gly Gly Val Ser Ser Pro Glu Glu Leu Trp Arg
        1795                1800                1805

Leu Val Ala Gly Gly Val Asp Ala Val Ala Gly Phe Pro Asp Asp Arg
        1810                1815                1820

Gly Trp Asp Leu Ala Ala Leu Tyr Asp Pro Asp Pro Asp Arg Leu Gly
1825                1830                1835                1840

Thr Ser Tyr Val Cys Glu Gly Gly Phe Leu Arg Asp Ala Ala Glu Phe
            1845                1850                1855

Asp Ala Asp Met Phe Gly Ile Ser Pro Arg Glu Ala Leu Ala Met Asp
        1860                1865                1870

Pro Gln Gln Arg Leu Leu Leu Glu Val Ala Trp Glu Thr Leu Glu Arg
```

-continued

```
            1875                1880                1885
Ala Gly Ile Asp Pro Phe Ser Leu His Gly Ser Arg Thr Gly Val Phe
            1890                1895                1900
Ala Gly Leu Met Tyr His Asp Tyr Gly Ala Arg Phe Ile Thr Arg Ala
1905                1910                1915                1920
Pro Glu Gly Phe Glu Gly His Leu Gly Thr Gly Asn Ala Gly Ser Val
                    1925                1930                1935
Leu Ser Gly Arg Val Ala Tyr Ser Phe Gly Phe Gly Pro Ala Val
                1940                1945                1950
Thr Val Asp Thr Ala Cys Ser Ser Leu Val Ala Leu His Leu Ala
        1955                1960                1965
Gly Gln Ala Leu Arg Ala Gly Glu Cys Glu Phe Ala Leu Ala Gly Gly
    1970                1975                1980
Val Thr Val Met Ser Thr Pro Thr Thr Phe Val Glu Phe Ser Arg Gln
1985                1990                1995                2000
Arg Gly Leu Ala Pro Asp Gly Arg Cys Lys Ser Phe Ala Ala Ala Ala
                    2005                2010                2015
Asp Gly Thr Gly Trp Gly Glu Gly Ala Gly Leu Val Leu Leu Glu Arg
            2020                2025                2030
Leu Ser Asp Ala Arg Arg Asn Gly His Glu Val Leu Ala Val Val Arg
        2035                2040                2045
Gly Ser Ala Val Asn Gln Asp Gly Ala Ser Asn Gly Leu Thr Ala Pro
2050                2055                2060
Asn Gly Pro Ser Gln Gln Arg Val Ile Thr Gln Ala Leu Thr Ser Ala
2065                2070                2075                2080
Gly Leu Ser Val Ser Asp Val Asp Ala Val Glu Ala His Gly Thr Gly
            2085                2090                2095
Thr Arg Leu Gly Asp Pro Ile Glu Ala Gln Ala Leu Ile Ala Thr Tyr
            2100                2105                2110
Gly Arg Asp Arg Asp Pro Gly Arg Pro Leu Trp Leu Gly Ser Val Lys
        2115                2120                2125
Ser Asn Ile Gly His Thr Gln Ala Ala Ala Gly Val Ala Gly Val Ile
    2130                2135                2140
Lys Met Val Met Ala Met Arg Gln Gly Glu Leu Pro Arg Thr Leu His
2145                2150                2155                2160
Val Asp Glu Pro Ser Ala Gln Val Asp Trp Ser Ala Gly Thr Val Gln
            2165                2170                2175
Leu Leu Thr Glu Asn Thr Pro Trp Pro Asp Ser Gly Arg Leu Arg Arg
            2180                2185                2190
Ala Gly Val Ser Ser Phe Gly Ile Ser Gly Thr Asn Ala His Leu Ile
        2195                2200                2205
Leu Glu Gln Pro Pro Arg Glu Ser Gln Arg Ser Thr Glu Pro Asp Ser
    2210                2215                2220
Gly Ser Val Arg Asp Phe Pro Val Val Pro Trp Met Val Ser Gly Lys
2225                2230                2235                2240
Thr Pro Glu Ala Leu Ser Ala Gln Ala Asp Ala Leu Met Ser Tyr Leu
            2245                2250                2255
Ser Asn Arg Val Asp Ala Ser Pro Arg Asp Ile Gly Tyr Ser Leu Ala
            2260                2265                2270
Val Thr Arg Pro Ala Leu Asp His Arg Ala Val Val Leu Gly Ala Asp
        2275                2280                2285
Arg Ala Ala Leu Leu Pro Gly Leu Lys Ala Leu Ala Val Ser Asn Asp
    2290                2295                2300
```

```
Ala Ala Glu Val Ile Thr Gly Thr Arg Ala Ala Gly Pro Val Gly Phe
2305                2310                2315                2320

Val Phe Ser Gly Gln Gly Gly Gln Trp Pro Gly Met Gly Ser Gly Leu
            2325                2330                2335

His Ser Ala Phe Pro Val Phe Ala Asp Ala Phe Asp Glu Ala Cys Cys
        2340                2345                2350

Glu Leu Asp Ala His Leu Gly Gln Met Ala Arg Leu Arg Asp Val Leu
    2355                2360                2365

Ser Gly Ser Asp Thr Gln Leu Leu Asp Gln Thr Leu Trp Ala Gln Pro
2370                2375                2380

Gly Leu Phe Ala Leu Gln Val Gly Leu Trp Glu Leu Leu Gly Ser Trp
2385                2390                2395                2400

Gly Val Arg Pro Ala Val Val Leu Gly His Ser Val Gly Glu Leu Ala
            2405                2410                2415

Ala Ala Phe Ala Ala Gly Val Leu Ser Leu Arg Asp Ala Ala Arg Leu
        2420                2425                2430

Val Ala Gly Arg Ala Arg Leu Met Gln Ala Leu Pro Thr Gly Gly Ala
    2435                2440                2445

Met Leu Ala Ala Ala Ala Gly Glu Glu Gln Leu Arg Pro Leu Leu Ala
2450                2455                2460

Asp Cys Gly Asp Arg Val Gly Ile Ala Ala Val Asn Ala Pro Gly Ser
2465                2470                2475                2480

Val Val Leu Ser Gly Asp Arg Asp Val Leu Asp Asp Ile Ala Gly Arg
            2485                2490                2495

Leu Asp Gly Gln Gly Ile Arg Ser Arg Trp Leu Arg Val Ser His Ala
        2500                2505                2510

Phe His Ser His Arg Met Asp Pro Met Leu Ala Glu Phe Thr Glu Ile
    2515                2520                2525

Ala Arg Ser Val Asp Tyr Arg Ser Ser Gly Leu Pro Ile Val Ser Thr
2530                2535                2540

Leu Thr Gly Glu Leu Asp Glu Val Gly Met Pro Ala Thr Pro Glu Tyr
2545                2550                2555                2560

Trp Val Arg Gln Val Arg Glu Pro Val Arg Phe Ala Asp Gly Val Ala
            2565                2570                2575

Ala Leu Ala Ala His Gly Val Ser Thr Val Glu Val Gly Pro Asp
        2580                2585                2590

Gly Val Leu Ser Ala Leu Val Gln Glu Cys Ala Ala Gly Ser Asp Gln
    2595                2600                2605

Gly Gly Arg Val Ala Ala Val Pro Leu Met Arg Ser Asn Arg Asp Glu
2610                2615                2620

Ala His Thr Val Thr Thr Ala Leu Ala Gln Ile His Val Arg Gly Ala
2625                2630                2635                2640

Glu Val Asp Trp Arg Ser Phe Phe Ala Gly Thr Gly Ala Lys Gln Val
            2645                2650                2655

Glu Leu Pro Thr Tyr Ala Phe Gln Arg Gln Arg Tyr Trp Leu Asp Ser
        2660                2665                2670

Pro Ser Glu Pro Val Gly Gln Ser Ala Asp Pro Ala Arg Gln Ser Gly
    2675                2680                2685

Phe Trp Glu Leu Val Glu Gln Glu Asp Val Ser Ala Leu Ser Ala Ala
2690                2695                2700

Leu His Ile Thr Gly Asp His Asp Val Gln Ala Ser Leu Glu Ser Val
2705                2710                2715                2720
```

-continued

Val Pro Val Leu Ser Ser Trp His Arg Arg Ile Arg Asn Glu Ser Leu
            2725                2730                2735

Val His Gln Trp Arg Tyr Arg Ile Ser Trp His Glu Arg Ala Asp Leu
        2740                2745                2750

Pro Asp Pro Ser Leu Ser Gly Thr Trp Leu Val Val Pro Glu Gly
        2755                2760            2765

Trp Ser Ala Ser Arg Gln Val Leu Arg Phe Asn Glu Met Phe Glu Glu
        2770                2775                2780

Arg Gly Cys Pro Ala Val Leu Phe Glu Leu Ala Gly His Asp Glu Glu
2785                2790                2795                2800

Ala Leu Ala Gln Arg Phe Arg Ser Leu Pro Val Ala Ser Gly Gly Ile
            2805                2810                2815

Ser Gly Val Leu Ser Leu Leu Ala Leu Asp Glu Ser Pro Ser Ser Pro
            2820                2825                2830

Asn Ala Ala Leu Pro Asn Gly Ala Leu Asn Ser Leu Val Leu Leu Arg
            2835                2840                2845

Ala Leu Arg Ala Ala Asp Val Ser Ala Pro Leu Trp Leu Ala Thr Cys
            2850                2855            2860

Gly Gly Val Ala Val Gly Asp Val Pro Val Asn Pro Gly Gln Ala Leu
2865                2870                2875                2880

Val Trp Gly Leu Gly Arg Val Val Gly Leu Glu His Pro Ala Trp Trp
            2885                2890                2895

Gly Gly Leu Val Asp Val Pro Cys Leu Leu Asp Glu Asp Ala Arg Glu
                2900            2905                2910

Arg Leu Ser Val Val Leu Ala Gly Leu Gly Glu Asp Glu Ile Ala Val
            2915                2920                2925

Arg Pro Gly Gly Val Phe Val Arg Arg Leu Glu Arg Ala Gly Ala Ala
            2930                2935            2940

Ser Gly Ala Gly Ser Val Trp Arg Pro Arg Gly Thr Val Leu Val Thr
2945                2950                2955                2960

Gly Gly Thr Gly Gly Leu Gly Ala His Val Ala Arg Trp Leu Ala Gly
                2965            2970                2975

Ala Gly Ala Glu His Val Val Leu Thr Ser Arg Arg Gly Ala Ala Ala
            2980                2985                2990

Pro Gly Ala Gly Asp Leu Arg Ala Glu Leu Glu Ala Leu Gly Ala Arg
            2995                3000                3005

Val Ser Ile Thr Ala Cys Asp Val Ala Asp Arg Asp Ala Leu Ala Glu
        3010                3015                3020

Val Leu Ala Thr Ile Pro Asp Asp Cys Pro Leu Thr Ala Val Met His
3025                3030                3035                3040

Ala Ala Gly Val Val Glu Val Gly Asp Val Ala Ser Met Cys Leu Thr
            3045                3050                3055

Asp Phe Val Gly Val Leu Ser Ala Lys Ala Gly Gly Ala Ala Asn Leu
            3060                3065                3070

Asp Glu Leu Leu Ala Asp Val Glu Leu Asp Ala Phe Val Leu Phe Ser
        3075                3080                3085

Ser Val Ser Gly Val Trp Gly Ala Gly Gly Gln Gly Ala Tyr Ala Ala
        3090                3095                3100

Ala Asn Ala Tyr Leu Asp Ala Leu Ala Gln Gln Arg Arg Ala Arg Gly
3105                3110                3115                3120

Leu Val Gly Thr Ala Val Ala Trp Gly Pro Trp Ala Gly Asp Gly Met
            3125                3130                3135

Ala Ala Gly Glu Gly Gly Ala Gln Leu Arg Arg Ala Gly Leu Val Pro

-continued

```
                3140                3145                3150
Met Ala Ala Asp Arg Ala Leu Leu Ala Leu Gln Gly Ala Leu Asp Arg
        3155                3160                3165
Asp Glu Thr Ser Leu Val Val Ala Asp Met Ala Trp Glu Arg Phe Ala
    3170                3175                3180
Pro Val Phe Ala Met Ser Arg Arg Pro Leu Leu Asp Glu Leu Pro
3185                3190                3195                3200
Glu Ala Gln Gln Ala Leu Ala Asp Ala Glu Asn Thr Thr Asp Ala Ala
            3205                3210                3215
Asp Ser Ala Val Pro Leu Pro Arg Leu Ala Gly Met Ala Ala Ala Glu
        3220                3225                3230
Arg Arg Arg Ala Met Leu Asp Leu Val Leu Ala Glu Ala Ser Ile Val
        3235                3240                3245
Leu Gly His Asn Gly Ser Asp Pro Val Gly Pro Asp Arg Ala Phe Gln
        3250                3255                3260
Glu Leu Gly Phe Asp Ser Leu Met Ala Val Glu Leu Arg Asn Arg Leu
3265                3270                3275                3280
Gly Glu Ala Thr Gly Leu Ser Leu Pro Ala Thr Leu Ile Phe Asp Tyr
            3285                3290                3295
Pro Ser Pro Ser Ala Leu Ala Glu Gln Leu Val Gly Glu Leu Val Gly
        3300                3305                3310
Ala Gln Pro Ala Thr Thr Val Val Ala Gly Ala Asp Pro Val Asp Asp
        3315                3320                3325
Pro Val Val Val Ala Met Gly Cys Arg Tyr Pro Gly Asp Val Cys
    3330                3335                3340
Ser Pro Glu Glu Leu Trp Gln Leu Val Ser Ala Gly Arg Asp Ala Val
3345                3350                3355                3360
Ser Thr Phe Pro Val Asp Arg Gly Trp Asp Cys Asn Thr Leu Phe Asp
            3365                3370                3375
Pro Asp Pro Asp Arg Ala Gly Ser Thr Tyr Val Arg Glu Gly Ala Phe
            3380                3385                3390
Leu Thr Gly Ala Asp Arg Phe Asp Ala Gly Phe Phe Gly Ile Ser Pro
        3395                3400                3405
Arg Glu Ala Arg Ala Met Asp Pro Gln Gln Arg Leu Leu Leu Glu Val
    3410                3415                3420
Ala Trp Glu Val Phe Glu Arg Ala Gly Ile Ala Pro Leu Ser Leu Arg
3425                3430                3435                3440
Gly Ser Arg Thr Gly Val Phe Ala Gly Thr Asn Gly Gln Asp His Gly
            3445                3450                3455
Ala Lys Val Ala Ala Ala Pro Glu Ala Ala Gly His Leu Leu Thr Gly
            3460                3465                3470
Asn Ala Ala Ser Val Leu Ala Gly Arg Leu Ser Tyr Thr Phe Gly Leu
        3475                3480                3485
Glu Gly Pro Ala Val Ala Val Asp Thr Ala Cys Ser Ser Ser Leu Val
        3490                3495                3500
Ala Leu His Leu Ala Cys Gln Ser Leu Arg Ser Gly Glu Cys Asp Met
3505                3510                3515                3520
Ala Leu Ala Gly Gly Val Thr Val Met Ser Thr Pro Leu Ala Phe Leu
            3525                3530                3535
Glu Phe Ser Arg Gln Arg Gly Leu Ala Pro Asp Gly Arg Cys Lys Ser
            3540                3545                3550
Phe Ala Ala Ala Ala Asp Gly Thr Gly Trp Gly Glu Gly Ala Gly Leu
        3555                3560                3565
```

-continued

Val Leu Leu Glu Arg Leu Ser Asp Ala Arg Arg Asn Gly His Arg Val
    3570                3575                3580

Leu Ala Val Val Arg Gly Ser Ala Val Asn Gln Asp Gly Ala Ser Asn
3585                3590                3595                3600

Gly Leu Thr Ala Pro Asn Gly Pro Ser Gln Gln Arg Val Ile Arg Gln
            3605                3610                3615

Ala Leu Ala Asn Ala Gly Leu Ser Ala Ser Asp Val Asp Val Val Glu
            3620                3625                3630

Ala His Gly Thr Gly Thr Gly Leu Gly Asp Pro Ile Glu Ala Gln Ala
            3635                3640                3645

Leu Ile Ala Thr Tyr Gly Gln Glu Arg Asp Pro Glu Arg Ala Leu Trp
    3650                3655                3660

Leu Gly Ser Ile Lys Ser Asn Ile Gly His Thr Gln Ala Ala Ala Gly
3665                3670                3675                3680

Val Ala Gly Val Ile Lys Met Val Gln Ala Met Arg His Gly Glu Leu
            3685                3690                3695

Pro Ala Thr Leu His Val Asp Lys Pro Thr Pro Gln Val Asp Trp Ser
            3700                3705                3710

Ala Gly Ala Val Arg Leu Leu Thr Gly Asn Thr Pro Trp Pro Glu Ser
    3715                3720                3725

Gly Arg Pro Arg Arg Ala Gly Val Ser Ser Phe Gly Ile Ser Gly Thr
    3730                3735                3740

Asn Ala His Leu Ile Leu Glu Gln Pro Pro Ser Glu Pro Ala Glu Ile
3745                3750                3755                3760

Asp Gln Ser Asp Arg Arg Val Thr Ala His Pro Ala Val Ile Pro Trp
            3765                3770                3775

Met Leu Ser Ala Arg Ser Leu Ala Ala Leu Gln Ala Gln Ala Ala Ala
            3780                3785                3790

Leu Gln Ala Arg Leu Asp Arg Gly Pro Gly Ala Ser Pro Leu Asp Leu
    3795                3800                3805

Gly Tyr Ser Leu Ala Thr Thr Arg Ser Val Leu Asp Glu Arg Ala Val
    3810                3815                3820

Val Trp Gly Ala Asp Arg Glu Ala Leu Leu Ser Arg Leu Ala Ala Leu
3825                3830                3835                3840

Ala Asp Gly Arg Thr Ala Pro Gly Val Ile Thr Gly Ser Ala Asn Ser
            3845                3850                3855

Gly Gly Arg Ile Gly Phe Val Phe Ser Gly Gln Gly Ser Gln Trp Leu
    3860                3865                3870

Gly Met Gly Lys Ala Leu Cys Ala Ala Phe Pro Ala Phe Ala Asp Ala
    3875                3880                3885

Phe Glu Glu Ala Cys Asp Ala Leu Ser Ala His Leu Gly Ala Asp Val
    3890                3895                3900

Arg Gly Val Leu Phe Gly Ala Asp Glu Gln Met Leu Asp Arg Thr Leu
3905                3910                3915                3920

Trp Ala Gln Ser Gly Ile Phe Ala Val Gln Val Gly Leu Leu Gly Leu
            3925                3930                3935

Leu Arg Ser Trp Gly Val Arg Pro Ala Ala Val Leu Gly His Ser Val
            3940                3945                3950

Gly Glu Leu Ala Ala Ala His Ala Ala Gly Val Leu Ser Leu Pro Asp
    3955                3960                3965

Ala Ala Arg Leu Val Ala Ala Arg Ala His Leu Met Gln Ala Leu Pro
3970                3975                3980

-continued

```
Thr Gly Gly Ala Met Leu Ala Val Ala Thr Ser Glu Ala Ala Val Gly
3985                3990                3995                4000

Pro Leu Leu Ser Gly Val Cys Asp Arg Val Ser Ile Ala Ala Ile Asn
            4005                4010                4015

Gly Pro Glu Ser Val Val Leu Ser Gly Asp Arg Asp Val Leu Val Glu
        4020                4025                4030

Leu Ala Gly Glu Phe Asp Ala Arg Gly Leu Arg Thr Lys Trp Leu Arg
    4035                4040                4045

Val Ser His Ala Phe His Ser His Arg Met Glu Pro Ile Leu Asp Glu
    4050                4055                4060

Tyr Ala Glu Thr Ala Arg Cys Val Glu Phe Gly Glu Pro Val Val Pro
4065                4070                4075                4080

Ile Val Ser Ala Ala Thr Gly Ala Leu Asp Thr Thr Gly Leu Met Cys
            4085                4090                4095

Ala Ala Asp Tyr Trp Thr Arg Gln Val Arg Asp Pro Val Arg Phe Gly
        4100                4105                4110

Asp Gly Val Arg Ala Leu Val Gly Gln Gly Val Asp Thr Ile Val Glu
        4115                4120                4125

Phe Gly Pro Asp Gly Ala Leu Ser Ala Leu Val Glu Gln Cys Leu Ala
    4130                4135                4140

Gly Ser Asp Gln Ala Gly Arg Val Ala Ala Ile Pro Leu Met Arg Arg
4145                4150                4155                4160

Asp Arg Asp Glu Val Glu Thr Ala Val Ala Ala Leu Ala His Val His
            4165                4170                4175

Val Arg Gly Gly Ala Val Asp Trp Ser Ala Cys Phe Ala Gly Thr Gly
        4180                4185                4190

Ala Arg Thr Val Glu Leu Pro Thr Tyr Ala Phe Gln Arg Gln Arg Tyr
    4195                4200                4205

Trp Leu Ala Gly Gln Ala Asp Gly Arg Gly Gly Asp Val Val Ala Asp
    4210                4215                4220

Pro Val Asp Ala Arg Phe Trp Glu Leu Val Glu Arg Ala Asp Pro Glu
4225                4230                4235                4240

Pro Leu Val Asp Glu Leu Cys Ile Asp Arg Asp Gln Pro Phe Arg Glu
            4245                4250                4255

Val Leu Pro Val Leu Ala Ser Trp Arg Glu Lys Gln Arg Gln Glu Ala
        4260                4265                4270

Leu Ala Asp Ser Trp Arg Tyr Gln Val Arg Trp Arg Ser Val Glu Val
    4275                4280                4285

Pro Ser Ala Ala Ala Leu Arg Gly Val Trp Leu Val Val Leu Pro Ala
    4290                4295                4300

Asp Val Pro Arg Asp Gln Pro Ala Val Ile Asp Ala Leu Ile Ala
4305                4310                4315                4320

Arg Gly Ala Glu Val Ala Val Leu Glu Leu Thr Glu Gln Asp Leu Gln
            4325                4330                4335

Arg Ser Ala Leu Val Asp Lys Val Arg Ala Val Ile Ala Asp Arg Thr
        4340                4345                4350

Glu Val Thr Gly Val Leu Ser Leu Leu Ala Met Asp Gly Met Pro Cys
    4355                4360                4365

Ala Ala His Pro His Leu Ser Arg Gly Val Ala Ala Thr Val Ile Leu
    4370                4375                4380

Thr Gln Val Leu Gly Asp Ala Gly Val Ser Ala Pro Leu Trp Leu Ala
4385                4390                4395                4400

Thr Thr Gly Gly Val Glu Ala Gly Thr Glu Asp Gly Pro Ala Asp Pro
```

```
                        4405                4410                4415
Asp His Gly Leu Ile Trp Gly Leu Gly Arg Val Val Gly Leu Glu His
            4420                4425                4430
Pro Gln Trp Trp Gly Gly Leu Ile Asp Leu Pro Glu Thr Leu Asp Glu
        4435                4440                4445
Thr Ser Arg Asn Gly Leu Val Ala Ala Leu Ala Gly Thr Ala Ala Glu
    4450                4455                4460
Asp Gln Leu Ala Val Arg Ser Ser Gly Leu Phe Val Arg Arg Val Val
4465                4470                4475                4480
Arg Ala Ala Arg Asn Pro Arg Ser Glu Thr Trp Arg Ser Arg Gly Thr
            4485                4490                4495
Val Leu Ile Thr Gly Gly Thr Gly Ala Leu Gly Ala Glu Val Ala Arg
        4500                4505                4510
Trp Leu Ala Arg Arg Gly Ala Glu His Leu Val Leu Ile Ser Arg Arg
        4515                4520                4525
Gly Pro Glu Ala Pro Gly Ala Ala Asp Leu Gly Ala Glu Leu Thr Glu
        4530                4535                4540
Leu Gly Val Lys Val Thr Val Leu Ala Cys Asp Val Thr Asp Arg Asp
4545                4550                4555                4560
Glu Leu Ala Ala Val Leu Ala Ala Val Pro Thr Glu Tyr Pro Leu Ser
            4565                4570                4575
Ala Val Val His Thr Ala Gly Val Gly Thr Pro Ala Asn Leu Ala Glu
        4580                4585                4590
Thr Thr Leu Ala Gln Phe Ala Asp Val Leu Ser Ala Lys Val Val Gly
        4595                4600                4605
Ala Ala Asn Leu Asp Arg Leu Leu Gly Gly Gln Pro Leu Asp Ala Phe
    4610                4615                4620
Val Leu Phe Ser Ser Ile Ser Gly Val Trp Gly Ala Gly Gly Gln Gly
4625                4630                4635                4640
Ala Tyr Ser Ala Ala Asn Ala Tyr Leu Asp Ala Leu Ala Glu Arg Arg
            4645                4650                4655
Arg Ala Cys Gly Arg Pro Ala Thr Cys Ile Ala Trp Gly Pro Trp Ala
        4660                4665                4670
Gly Ala Gly Met Ala Val Gln Glu Gly Asn Glu Ala His Leu Arg Arg
        4675                4680                4685
Arg Gly Leu Val Pro Met Glu Pro Gln Ser Ala Leu Phe Ala Leu Gln
    4690                4695                4700
Gln Ala Leu Ser Gln Arg Glu Thr Ala Ile Thr Val Ala Asp Val Asp
4705                4710                4715                4720
Trp Glu Arg Phe Ala Ala Ser Phe Thr Ala Ala Arg Pro Arg Pro Leu
            4725                4730                4735
Leu Glu Glu Ile Val Asp Leu Arg Pro Asp Thr Glu Thr Glu Glu Lys
            4740                4745                4750
His Gly Ala Gly Glu Leu Gly Gln Gln Leu Ala Ala Leu Pro Pro Ala
        4755                4760                4765
Glu Arg Gly His Leu Leu Leu Glu Val Val Leu Ala Glu Thr Ala Ser
4770                4775                4780
Thr Leu Gly His Asp Ser Ala Glu Ala Val Gln Pro Asp Arg Thr Phe
4785                4790                4795                4800
Ala Glu Leu Gly Phe Asp Ser Leu Thr Ala Val Glu Leu Arg Asn Arg
            4805                4810                4815
Leu Asn Ala Val Thr Gly Leu Arg Leu Pro Pro Thr Leu Val Phe Asp
        4820                4825                4830
```

-continued

```
His Pro Thr Pro Leu Ala Leu Ser Glu Gln Leu Val Pro Ala Leu Val
        4835                4840                4845

Ala Glu Pro Asp Asn Gly Ile Glu Ser Leu Leu Ala Glu Leu Asp Arg
    4850                4855                4860

Leu Asp Thr Thr Leu Ala Gln Gly Pro Ser Ile Pro Leu Glu Asp Gln
4865                4870                4875                4880

Ala Lys Val Ala Glu Arg Leu His Ala Leu Leu Ala Lys Trp Asp Gly
                4885                4890                4895

Ala Arg Asp Gly Thr Ala Arg Ala Thr Ser Pro Gln Ser Leu Thr Ala
            4900                4905                4910

Ala Thr Asp Asp Glu Ile Phe Asp Leu Ile Asp Arg Lys Phe Arg Arg
        4915                4920                4925

<210> SEQ ID NO 6
<211> LENGTH: 5588
<212> TYPE: PRT
<213> ORGANISM: Saccharopolyspora spinosa

<400> SEQUENCE: 6

Met Ala Asn Glu Glu Lys Leu Arg Glu Tyr Leu Lys Arg Val Val Val
 1               5                  10                  15

Glu Leu Glu Glu Ala His Glu Arg Leu His Glu Leu Glu Arg Gln Glu
             20                  25                  30

His Asp Pro Ile Ala Ile Val Ser Met Gly Cys Arg Tyr Pro Gly Gly
         35                  40                  45

Val Ser Thr Pro Glu Glu Leu Trp Arg Leu Val Asp Gly Gly Asp
     50                  55                  60

Ala Ile Ala Asn Phe Pro Glu Asp Arg Gly Trp Asn Leu Asp Glu Leu
65                  70                  75                  80

Phe Asp Pro Asp Pro Gly Arg Ala Gly Thr Ser Tyr Val Arg Glu Gly
                 85                  90                  95

Gly Phe Leu Arg Gly Val Ala Asp Phe Asp Ala Gly Leu Phe Gly Ile
                100                 105                 110

Ser Pro Arg Glu Ala Gln Ala Met Asp Pro Gln Gln Arg Leu Leu Leu
            115                 120                 125

Glu Ile Ser Trp Glu Val Phe Glu Arg Ala Gly Ile Asp Pro Phe Ser
        130                 135                 140

Leu Arg Gly Thr Lys Thr Gly Val Phe Ala Gly Leu Ile Tyr His Asp
145                 150                 155                 160

Tyr Ala Ser Arg Phe Arg Lys Thr Pro Ala Glu Phe Glu Gly Tyr Phe
                165                 170                 175

Ala Thr Gly Asn Ala Gly Ser Val Ala Ser Gly Arg Val Ala Tyr Thr
            180                 185                 190

Phe Gly Leu Glu Gly Pro Ala Val Thr Val Asp Thr Ala Cys Ser Ser
        195                 200                 205

Ser Leu Val Ala Leu His Leu Ala Cys Gln Ser Leu Arg Leu Gly Glu
    210                 215                 220

Cys Asp Leu Ala Leu Ala Gly Gly Ile Ser Val Met Ala Thr Pro Gly
225                 230                 235                 240

Ala Phe Val Glu Phe Ser Arg Gln Arg Ala Leu Ala Ser Asp Gly Arg
                245                 250                 255

Cys Lys Pro Phe Ala Asp Ala Asp Gly Thr Gly Trp Gly Glu Gly
            260                 265                 270

Ala Gly Met Leu Leu Leu Glu Arg Leu Ser Asp Ala Arg Arg Asn Gly
```

```
                275                 280                 285
His Pro Val Leu Ala Ala Val Val Gly Ser Ala Ile Asn Gln Asp Gly
            290                 295                 300

Thr Ser Asn Gly Leu Thr Ala Pro Ser Gly Pro Ala Gln Gln Arg Val
305                 310                 315                 320

Ile Arg Gln Ala Leu Ala Asn Ala Gly Leu Ser Pro Ala Glu Val Asp
            325                 330                 335

Val Val Glu Ala His Gly Thr Gly Thr Ala Leu Gly Asp Pro Ile Glu
            340                 345                 350

Ala Gln Ala Leu Ile Ala Thr Tyr Gly Ala Asn Arg Ser Ala Asp His
            355                 360                 365

Pro Leu Leu Leu Gly Ser Leu Lys Ser Asn Ile Gly His Thr Gln Ala
            370                 375                 380

Ala Ala Gly Val Ala Gly Val Ile Lys Ser Val Leu Ala Ile Arg His
385                 390                 395                 400

Arg Glu Met Pro Arg Ser Leu His Ile Asp Gln Pro Ser Gln His Val
            405                 410                 415

Asp Trp Ser Ala Gly Ala Val Arg Leu Leu Thr Asp Ser Val Asp Trp
            420                 425                 430

Pro Asp Leu Gly Arg Pro Arg Arg Ala Gly Val Ser Ser Phe Gly Met
            435                 440                 445

Ser Gly Thr Asn Ala His Leu Ile Val Glu Glu Val Ser Asp Glu Pro
            450                 455                 460

Val Ser Gly Ser Thr Glu Pro Thr Gly Ala Phe Pro Trp Pro Leu Ser
465                 470                 475                 480

Gly Lys Thr Glu Thr Ala Leu Arg Glu Gln Ala Ala Glu Leu Leu Ser
            485                 490                 495

Val Val Thr Glu His Pro Glu Pro Gly Leu Gly Asp Val Gly Tyr Ser
            500                 505                 510

Leu Ala Thr Gly Arg Ala Ala Met Glu His Arg Ala Val Val Val Ala
            515                 520                 525

Asp Asp Arg Asp Ser Phe Val Ala Gly Leu Thr Ala Leu Ala Ala Gly
            530                 535                 540

Val Pro Ala Ala Asn Val Val Gln Gly Ala Ala Asp Cys Lys Gly Lys
545                 550                 555                 560

Val Ala Phe Val Phe Pro Gly Gln Gly Ser His Trp Gln Gly Met Ala
            565                 570                 575

Arg Glu Leu Ser Glu Ser Ser Pro Val Phe Arg Arg Lys Leu Ala Glu
            580                 585                 590

Cys Ala Ala Thr Ala Pro Tyr Val Asp Trp Ser Leu Leu Gly Val
            595                 600                 605

Leu Arg Gly Asp Pro Asp Ala Pro Leu Asp Arg Asp Val Ile
            610                 615                 620

Gln Leu Ala Leu Phe Ala Met Met Val Ser Leu Ala Glu Leu Trp Arg
625                 630                 635                 640

Ser Cys Gly Val Glu Pro Ala Ala Val Gly His Ser Gln Gly Glu
            645                 650                 655

Ile Ala Ala Ala His Val Ala Gly Ala Leu Ser Leu Thr Asp Ala Val
            660                 665                 670

Arg Ile Ile Ala Ala Arg Cys Asp Ala Val Ser Ala Leu Thr Gly Lys
            675                 680                 685

Gly Gly Met Leu Ala Ile Ala Leu Pro Glu Ser Ala Val Val Lys Arg
            690                 695                 700
```

-continued

```
Ile Ala Gly Leu Pro Glu Leu Thr Val Ala Ala Val Asn Gly Pro Gly
705                 710                 715                 720

Ser Thr Val Val Ser Gly Glu Pro Ser Ala Leu Glu Arg Leu Gln Thr
            725                 730                 735

Glu Leu Thr Ala Glu Asn Val Gln Thr Arg Arg Val Gly Ile Asp Tyr
        740                 745                 750

Ala Ser His Ser Pro Gln Ile Ala Gln Val Gln Gly Arg Leu Leu Asp
    755                 760                 765

Arg Leu Gly Glu Val Gly Ser Glu Pro Ala Glu Ile Ala Phe Tyr Ser
770                 775                 780

Thr Val Thr Gly Glu Arg Thr Asp Thr Gly Arg Leu Asp Ala Asp Tyr
785                 790                 795                 800

Trp Tyr Gln Asn Leu Arg Gln Pro Val Arg Phe Gln Gln Thr Val Ala
                805                 810                 815

Arg Met Ala Asp Gln Gly Tyr Arg Phe Phe Val Glu Val Ser Pro His
            820                 825                 830

Pro Leu Leu Thr Ala Gly Ile Gln Glu Thr Leu Glu Ala Ala Asp Ala
        835                 840                 845

Gly Gly Val Val Gly Ser Leu Arg Arg Gly Glu Gly Gly Ser Arg
    850                 855                 860

Arg Trp Leu Thr Ser Leu Ala Glu Cys Gln Val Arg Gly Leu Pro Val
865                 870                 875                 880

Asn Trp Glu Gln Val Phe Leu Asn Thr Gly Ala Arg Arg Val Pro Leu
                885                 890                 895

Pro Thr Tyr Pro Phe Gln Arg Gln Arg Tyr Trp Leu Glu Ser Ala Glu
            900                 905                 910

Tyr Asp Ala Gly Asp Leu Gly Ser Val Gly Leu Leu Ser Ala Glu His
        915                 920                 925

Pro Leu Leu Gly Ala Ala Val Thr Leu Ala Asp Ala Gly Gly Phe Leu
    930                 935                 940

Leu Thr Gly Lys Leu Ser Val Lys Thr Gln Pro Trp Leu Ala Asp His
945                 950                 955                 960

Val Val Gly Gly Ala Ile Leu Pro Gly Thr Ala Phe Val Glu Met
                965                 970                 975

Leu Ile Arg Ala Ala Asp Gln Val Gly Cys Asp Leu Ile Glu Glu Leu
            980                 985                 990

Ser Leu Thr Thr Pro Leu Val Leu Pro Ala Thr Gly Ala Val Gln Val
        995                 1000                1005

Gln Ile Ala Val Gly Gly Pro Asp Glu Ala Gly Arg Arg Ser Val Arg
    1010                1015                1020

Val His Ser Cys Arg Asp Asp Ala Val Pro Gln Asp Ser Trp Thr Cys
1025                1030                1035                1040

His Ala Thr Gly Thr Leu Thr Ser Ser Asp His Gln Asp Ala Gly Gln
                1045                1050                1055

Gly Pro Asp Gly Ile Trp Pro Pro Asn Asp Ala Val Ala Val Pro Leu
            1060                1065                1070

Asp Ser Phe Tyr Ala Arg Ala Ala Glu Arg Gly Phe Asp Phe Gly Pro
        1075                1080                1085

Ala Phe Gln Gly Leu Gln Ala Ala Trp Lys Arg Gly Asp Glu Ile Phe
    1090                1095                1100

Ala Glu Val Gly Leu Pro Thr Ala His Arg Glu Asp Ala Gly Arg Phe
1105                1110                1115                1120
```

-continued

Gly Ile His Pro Ala Leu Leu Asp Ala Ala Leu Gln Ala Leu Gly Ala
               1125                1130                1135

Ala Glu Glu Asp Pro Asp Glu Gly Trp Leu Pro Phe Ala Trp Gln Gly
       1140                1145                1150

Val Ser Leu Lys Ala Thr Gly Ala Leu Ser Leu Arg Val His Leu Val
   1155                1160                1165

Pro Ala Gly Ala Asn Ala Val Ser Val Phe Thr Thr Asp Thr Thr Gly
1170                1175                1180

Gln Ala Val Leu Ser Ile Asp Ser Leu Val Leu Arg Gln Ile Ser Asp
1185                1190                1195                1200

Lys Gln Leu Ala Ala Ala Arg Ala Met Glu His Glu Ser Leu Phe Arg
       1205                1210                1215

Val Asp Trp Lys Arg Ile Ser Pro Gly Ala Ala Lys Pro Val Ser Trp
       1220                1225                1230

Ala Val Ile Gly Asn Asp Glu Leu Ala Arg Ala Cys Gly Ser Ala Leu
       1235                1240                1245

Gly Thr Glu Leu His Pro Asp Leu Thr Gly Leu Ala Asp Pro Pro Pro
       1250                1255                1260

Asp Val Val Val Pro Cys Gly Ala Ser Arg Gln Asp Leu Asp Val
1265                1270                1275                1280

Ala Ser Glu Ala Arg Ala Ala Thr Gln Arg Met Leu Asp Leu Ile Gln
       1285                1290                1295

Asp Trp Leu Ala Ala Ala Arg Phe Ala Gly Ser Arg Leu Val Val Val
       1300                1305                1310

Thr Cys Gly Ala Ala Ser Thr Gly Pro Ala Glu Gly Val Ser Asp Leu
       1315                1320                1325

Val His Ala Ala Ser Trp Gly Leu Leu Arg Ser Ala Gln Ser Glu Asn
   1330                1335                1340

Pro Asp Arg Phe Val Leu Val Asp Val Asp Gly Thr Ala Glu Ser Trp
1345                1350                1355                1360

Arg Ala Leu Ala Ala Ala Val Arg Ser Gly Glu Pro Gln Leu Ala Leu
       1365                1370                1375

Arg Ala Gly Glu Val Arg Val Pro Arg Leu Ala Arg Cys Val Ala Ala
       1380                1385                1390

Glu Asp Ser Arg Ile Pro Val Pro Gly Ala Asp Gly Thr Val Leu Ile
       1395                1400                1405

Ser Gly Gly Thr Gly Leu Leu Gly Gly Leu Val Ala Arg His Leu Val
   1410                1415                1420

Ala Glu Arg Gly Val Arg Arg Leu Val Leu Ala Gly Arg Arg Gly Trp
1425                1430                1435                1440

Ser Ala Pro Gly Val Thr Asp Leu Val Asp Glu Leu Val Gly Leu Gly
       1445                1450                1455

Ala Ala Val Glu Val Ala Ser Cys Asp Val Gly Asp Arg Ala Gln Leu
       1460                1465                1470

Asp Arg Leu Leu Thr Thr Ile Ser Ala Glu Phe Pro Leu Arg Gly Val
       1475                1480                1485

Val His Ala Ala Gly Ala Leu Ala Asp Gly Val Val Glu Ser Leu Thr
       1490                1495                1500

Pro Glu His Val Ala Lys Val Phe Gly Pro Lys Ala Ala Gly Ala Trp
1505                1510                1515                1520

His Leu His Glu Leu Thr Leu Asp Leu Asp Leu Ser Phe Phe Val Leu
       1525                1530                1535

Phe Ser Ser Phe Ser Gly Val Ala Gly Ala Ala Gly Gln Gly Asn Tyr

-continued

```
                1540                1545                1550
Ala Ala Ala Asn Ala Phe Leu Asp Gly Leu Ala Gln His Arg Arg Thr
    1555                1560                1565

Ala Gly Leu Pro Ala Val Ser Leu Ala Trp Gly Leu Trp Glu Gln Pro
    1570                1575                1580

Ser Gly Met Thr Gly Ala Leu Asp Ala Ala Gly Arg Ser Arg Ile Ala
1585                1590                1595                1600

Arg Thr Asn Pro Pro Met Ser Ala Pro Asp Gly Leu Arg Leu Phe Glu
                1605                1610                1615

Met Ala Phe Arg Val Pro Gly Glu Ser Leu Leu Val Pro Val His Val
            1620                1625                1630

Asp Leu Asn Ala Leu Arg Ala Asp Ala Ala Asp Gly Gly Val Pro Ala
        1635                1640                1645

Leu Leu Arg Asp Leu Val Pro Ala Pro Val Arg Arg Ser Ala Val Asn
    1650                1655                1660

Glu Ser Ala Asp Val Asn Gly Leu Val Gly Arg Leu Arg Arg Leu Pro
1665                1670                1675                1680

Asp Leu Asp Gln Glu Thr Gln Leu Leu Gly Leu Val Arg Glu His Val
                1685                1690                1695

Ser Ala Val Leu Gly His Ser Gly Ala Val Glu Val Gly Ala Asp Arg
            1700                1705                1710

Ala Phe Arg Asp Leu Gly Phe Asp Ser Leu Ser Gly Val Glu Phe Arg
        1715                1720                1725

Asn Arg Leu Gly Gly Val Leu Gly Val Arg Leu Pro Ala Thr Ala Val
    1730                1735                1740

Phe Asp Tyr Pro Thr Pro Arg Ala Leu Val Arg Phe Leu Leu Asp Lys
1745                1750                1755                1760

Leu Ile Gly Gly Val Glu Ala Pro Thr Pro Ala Pro Ala Ala Val Ala
                1765                1770                1775

Ala Val Thr Ala Asp Asp Pro Val Val Ile Val Gly Met Gly Cys Arg
            1780                1785                1790

Tyr Pro Gly Gly Val Ser Ser Pro Glu Glu Leu Trp Arg Leu Val Ala
        1795                1800                1805

Gly Gly Leu Asp Ala Val Ala Glu Phe Pro Asp Asp Arg Gly Trp Asp
    1810                1815                1820

Gln Ala Gly Leu Phe Asp Pro Asp Pro Asp Arg Leu Gly Thr Ser Tyr
1825                1830                1835                1840

Val Cys Glu Gly Gly Phe Leu Arg Asp Ala Ala Glu Phe Asp Ala Gly
                1845                1850                1855

Phe Phe Gly Ile Ser Pro Arg Glu Ala Leu Ala Met Asp Pro Gln Gln
            1860                1865                1870

Arg Leu Leu Leu Glu Val Ala Trp Glu Thr Val Glu Arg Ala Gly Ile
        1875                1880                1885

Asp Pro Leu Ser Leu Arg Gly Ser Arg Thr Gly Val Phe Ala Gly Leu
    1890                1895                1900

Met His His Asp Tyr Gly Ala Arg Phe Ile Thr Arg Ala Pro Glu Gly
1905                1910                1915                1920

Phe Glu Gly Tyr Leu Gly Asn Gly Ser Ala Gly Gly Val Phe Ser Gly
                1925                1930                1935

Arg Val Ala Tyr Ser Phe Gly Phe Glu Gly Pro Ala Val Thr Val Asp
            1940                1945                1950

Thr Ala Cys Ser Ser Ser Leu Val Ala Leu His Leu Ala Gly Gln Ala
        1955                1960                1965
```

-continued

Leu Arg Ser Gly Glu Cys Asp Leu Ala Leu Ala Gly Gly Val Thr Val
1970                1975                1980

Met Ala Thr Pro Gly Met Phe Val Glu Phe Ser Arg Gln Arg Gly Leu
1985                1990                1995                2000

Ala Ala Asp Gly Arg Cys Lys Ser Phe Ala Ala Ala Asp Gly Thr
        2005                2010                2015

Gly Trp Gly Glu Gly Ala Gly Leu Val Leu Glu Arg Leu Ser Asp
        2020                2025                2030

Ala Arg Arg Asn Gly His Ala Val Leu Ala Val Val Arg Gly Ser Ala
        2035                2040                2045

Val Asn Gln Asp Gly Ala Ser Asn Gly Leu Thr Ala Pro Asn Gly Pro
    2050                2055                2060

Ser Gln Gln Arg Val Ile Thr Gln Ala Leu Ala Ser Ala Gly Leu Ser
2065                2070                2075                2080

Val Ser Asp Val Asp Ala Val Glu Ala His Gly Thr Gly Thr Arg Leu
            2085                2090                2095

Gly Asp Pro Ile Glu Ala Gln Ala Leu Ile Ala Thr Tyr Gly Gln Gly
        2100                2105                2110

Arg Asp Ser Asp Arg Pro Leu Trp Leu Gly Ser Val Lys Ser Asn Ile
        2115                2120                2125

Gly His Thr Gln Ala Ala Ala Gly Val Ala Gly Val Ile Lys Met Val
    2130                2135                2140

Met Ala Met Arg His Gly Gln Leu Pro Ala Thr Leu His Val Asp Glu
2145                2150                2155                2160

Pro Thr Ser Glu Val Asp Trp Ser Ala Gly Asp Val Gln Leu Leu Thr
            2165                2170                2175

Glu Asn Thr Pro Trp Pro Gly Asn Ser His Pro Arg Arg Val Gly Val
        2180                2185                2190

Ser Ser Phe Gly Ile Ser Gly Thr Asn Ala His Val Ile Leu Glu Gln
        2195                2200                2205

Ala Ser Lys Thr Pro Asp Glu Thr Ala Asp Lys Ser Gly Pro Asp Ser
    2210                2215                2220

Glu Ser Thr Val Asp Leu Pro Ala Val Pro Leu Ile Val Ser Gly Arg
2225                2230                2235                2240

Thr Pro Ala Ala Leu Ser Ala Gln Ala Ser Ala Leu Leu Ser Tyr Leu
            2245                2250                2255

Gly Glu Arg Gly Asp Ile Ser Thr Leu Asp Ala Ala Phe Ser Leu Ala
        2260                2265                2270

Ser Ser Arg Ala Ala Leu Glu Glu Arg Ala Val Val Leu Gly Ala Asp
        2275                2280                2285

Arg Glu Thr Leu Leu Ser Gly Leu Glu Ala Leu Ala Ser Gly Arg Glu
    2290                2295                2300

Ala Ser Gly Val Val Ser Gly Ser Pro Val Ser Gly Val Gly Phe
2305                2310                2315                2320

Val Phe Ala Gly Gln Gly Gly Gln Trp Leu Gly Met Gly Arg Gly Leu
            2325                2330                2335

Tyr Ser Val Phe Pro Val Phe Ala Asp Ala Phe Asp Glu Ala Cys Ala
        2340                2345                2350

Gly Leu Asp Ala His Leu Gly Gln Asp Val Gly Val Arg Asp Val Val
        2355                2360                2365

Phe Gly Ser Asp Gly Ser Leu Leu Asp Arg Thr Leu Trp Ala Gln Ser
    2370                2375                2380

```
-continued

Gly Leu Phe Ala Leu Gln Val Gly Leu Leu Ser Leu Gly Ser Trp
        2385            2390            2395            2400

Gly Val Arg Pro Gly Val Val Leu Gly His Ser Val Gly Glu Phe Ala
            2405            2410            2415

Ala Ala Val Ala Ala Gly Val Leu Ser Leu Pro Asp Ala Ala Arg Met
            2420            2425            2430

Val Ala Gly Arg Ala Arg Leu Met Gln Ala Leu Pro Ser Gly Gly Ala
            2435            2440            2445

Met Leu Ala Val Ala Ala Gly Glu Glu Gln Leu Arg Pro Leu Leu Ala
            2450            2455            2460

Asp Arg Val Asp Gly Ala Gly Ile Ala Ala Val Asn Ala Pro Glu Ser
2465            2470            2475            2480

Val Val Leu Ser Gly Asp Arg Glu Val Leu Asp Asp Ile Ala Gly Ala
            2485            2490            2495

Leu Asp Gly Gln Gly Ile Arg Trp Arg Arg Leu Arg Val Ser His Ala
            2500            2505            2510

Phe His Ser Tyr Arg Met Asp Pro Met Leu Gln Glu Phe Ala Glu Ile
            2515            2520            2525

Ala Arg Ser Val Asp Tyr Arg Arg Gly Asp Leu Pro Val Val Ser Thr
            2530            2535            2540

Leu Thr Gly Glu Leu Asp Thr Ala Gly Val Met Ala Thr Pro Glu Tyr
2545            2550            2555            2560

Trp Val Arg Gln Val Arg Glu Pro Val Arg Phe Ala Asp Gly Val Arg
            2565            2570            2575

Val Leu Ala Gln Gln Gly Val Ala Thr Ile Phe Glu Leu Gly Pro Asp
            2580            2585            2590

Ala Thr Leu Ser Ala Leu Ile Pro Asp Cys His Ser Trp Ala Asp Gln
            2595            2600            2605

Ala Met Pro Ile Pro Met Leu Arg Lys Asp Arg Thr Glu Thr Glu Thr
            2610            2615            2620

Val Val Ala Ala Val Ala Arg Ala His Thr Arg Gly Val Pro Val Glu
2625            2630            2635            2640

Trp Ser Ala Tyr Phe Ala Gly Thr Gly Ala Arg Arg Val Glu Leu Pro
            2645            2650            2655

Thr Tyr Ala Phe Gln Arg Gln Arg Tyr Trp Leu Glu Thr Ser Asp Tyr
            2660            2665            2670

Gly Asp Val Thr Gly Ile Gly Leu Ala Ala Ala Glu His Pro Leu Leu
            2675            2680            2685

Gly Ala Val Val Ala Leu Ala Asp Gly Asp Gly Met Val Leu Thr Gly
            2690            2695            2700

Arg Leu Ser Val Gly Thr His Pro Trp Leu Ala Gln His Arg Val Leu
2705            2710            2715            2720

Gly Glu Val Val Val Pro Gly Thr Ala Ile Leu Glu Met Ala Leu His
            2725            2730            2735

Ala Gly Ala Arg Leu Gly Cys Asp Arg Val Glu Glu Leu Thr Leu Glu
            2740            2745            2750

Thr Pro Leu Val Val Pro Glu Arg Ala Ala Gly Ala Gly Ser Arg Gly
            2755            2760            2765

Pro Ala Gly Gly Thr Thr Val Ser Ile Glu Thr Ala Glu Glu Arg Val
            2770            2775            2780

Arg Thr Asn Asp Ala Ile Glu Ile Gln Leu Leu Val Asn Ala Pro Asp
2785            2790            2795            2800

Glu Gly Gly Arg Arg Arg Val Ser Leu Tyr Ser Arg Pro Ala Gly Gly
```

-continued

```
                2805                2810                2815
Ser Arg Gly Gly Gly Trp Thr Arg His Ala Thr Gly Glu Leu Val Val
            2820                2825                2830
Gly Thr Thr Gly Gly Arg Ala Val Pro Asp Trp Ser Ala Glu Gly Ala
            2835                2840                2845
Glu Ser Ile Ala Leu Asp Glu Phe Tyr Val Ala Leu Ala Gly Asn Gly
            2850                2855                2860
Phe Glu Tyr Gly Pro Leu Phe Gln Gly Leu Gln Ala Ala Trp Arg Arg
2865                2870                2875                2880
Gly Asp Glu Val Leu Ala Glu Ile Ala Pro Pro Ala Glu Ala Asp Ala
            2885                2890                2895
Met Ala Ser Gly Tyr Leu Leu Asp Pro Ala Leu Leu Asp Ala Ala Leu
            2900                2905                2910
Gln Ala Ser Ala Leu Gly Asp Arg Pro Glu Gln Gly Gly Ala Trp Leu
            2915                2920                2925
Pro Phe Ser Phe Thr Gly Val Glu Leu Ser Ala Pro Ala Gly Thr Ile
            2930                2935                2940
Ser Arg Val Arg Leu Glu Thr Arg Arg Pro Asp Ala Ile Ser Val Ala
2945                2950                2955                2960
Val Met Asp Glu Ser Gly Arg Leu Leu Ala Ser Ile Asp Ser Leu Arg
            2965                2970                2975
Leu Arg Ser Val Ser Ser Gly Gln Leu Ala Asn Arg Asp Ala Val Arg
            2980                2985                2990
Asp Ala Leu Phe Glu Val Thr Trp Glu Pro Val Ala Thr Gln Ser Thr
            2995                3000                3005
Glu Pro Gly Arg Trp Ala Leu Leu Gly Asp Thr Ala Cys Gly Lys Asp
            3010                3015                3020
Asp Leu Ile Lys Leu Ala Thr Asp Ser Ala Asp Arg Cys Ala Asp Leu
3025                3030                3035                3040
Ala Ala Leu Ala Glu Lys Leu Asp Ser Ser Ala Leu Val Pro Asp Val
            3045                3050                3055
Val Val Tyr Cys Ala Gly Glu Gln Ala Asp Pro Gly Thr Gly Ala Ala
            3060                3065                3070
Ala Leu Ala Glu Thr Gln Gln Thr Leu Ala Leu Leu Gln Ala Trp Leu
            3075                3080                3085
Ala Glu Pro Arg Leu Ala Glu Ala Arg Leu Val Val Val Thr Cys Ala
            3090                3095                3100
Ala Val Thr Thr Ala Pro Ser Asp Gly Ala Ser Glu Leu Ala His Ala
3105                3110                3115                3120
Pro Leu Trp Gly Leu Leu Arg Ala Ala Gln Val Glu Asn Pro Gly Gln
            3125                3130                3135
Phe Val Leu Ala Asp Val Asp Gly Thr Ala Glu Ser Trp Arg Ala Leu
            3140                3145                3150
Pro Ser Ala Leu Gly Ser Met Glu Pro Gln Leu Ala Leu Arg Lys Gly
            3155                3160                3165
Ala Val Arg Ala Pro Arg Leu Ala Ser Val Ala Gly Gln Ile Asp Val
            3170                3175                3180
Pro Ala Val Val Ala Asp Pro Asp Arg Thr Val Leu Ile Ser Gly Gly
            3185                3190                3195                3200
Thr Gly Leu Leu Gly Gly Ala Val Ala Arg His Leu Val Thr Glu Arg
            3205                3210                3215
Gly Val Arg Arg Leu Val Leu Thr Gly Arg Arg Gly Trp Asp Ala Pro
            3220                3225                3230
```

-continued

```
Gly Ile Thr Glu Leu Val Gly Glu Leu Asn Gly Leu Gly Ala Val Val
        3235                3240                3245

Asp Val Val Ala Cys Asp Val Ala Asp Arg Ala Asp Leu Glu Ser Leu
    3250                3255                3260

Leu Ala Ala Val Pro Ala Glu Phe Pro Leu Cys Gly Val Val His Ala
3265                3270                3275                3280

Ala Gly Ala Leu Ala Asp Gly Val Ile Glu Ser Leu Ser Pro Asp Asp
        3285                3290                3295

Val Gly Ala Val Phe Gly Pro Lys Ala Ala Gly Ala Trp Asn Leu His
            3300                3305                3310

Glu Leu Thr Arg Asp Thr Asp Leu Ser Phe Phe Ala Leu Phe Ser Ser
        3315                3320                3325

Leu Ser Gly Val Ala Gly Ala Pro Gly Gln Gly Asn Tyr Ala Ala Ala
        3330                3335                3340

Asn Ala Phe Leu Asp Ala Leu Ala His Tyr Arg Arg Ser Gln Gly Leu
3345                3350                3355                3360

Pro Ala Val Ser Leu Ala Trp Gly Leu Trp Glu Gln Pro Ser Gly Met
        3365                3370                3375

Thr Glu Thr Leu Ser Glu Val Asp Arg Ser Arg Ile Ala Arg Ala Asn
        3380                3385                3390

Pro Pro Leu Ser Thr Lys Glu Gly Leu Arg Leu Phe Asp Ala Gly Leu
            3395                3400                3405

Ala Leu Asp Arg Ala Ala Val Val Pro Ala Lys Leu Asp Arg Thr Phe
        3410                3415                3420

Leu Ala Glu Gln Ala Arg Ser Gly Ser Leu Pro Ala Leu Leu Thr Ala
3425                3430                3435                3440

Leu Val Pro Pro Ile Arg Arg Asn Arg Arg Ala Ser Gly Thr Glu Leu
        3445                3450                3455

Ala Asp Glu Gly Thr Leu Leu Gly Val Val Arg Glu His Ala Ala Ala
            3460                3465                3470

Val Leu Gly Tyr Ser Ser Ala Ala Asp Val Gly Val Glu Arg Ala Phe
        3475                3480                3485

Arg Asp Leu Gly Phe Asp Ser Leu Ser Gly Val Glu Leu Arg Asn Arg
        3490                3495                3500

Leu Ala Gly Val Leu Gly Val Arg Leu Pro Ala Thr Ala Val Phe Asp
3505                3510                3515                3520

Tyr Pro Thr Pro Arg Ala Leu Ala Arg Phe Leu His Gln Glu Leu Ala
        3525                3530                3535

Asp Glu Ile Ala Thr Thr Pro Ala Pro Val Thr Thr Thr Arg Ala Pro
            3540                3545                3550

Val Ala Glu Asp Asp Leu Val Ala Ile Val Gly Met Gly Cys Arg Phe
        3555                3560                3565

Pro Gly Gln Val Ser Ser Pro Glu Glu Leu Trp Arg Leu Val Ala Gly
        3570                3575                3580

Gly Val Asp Ala Val Ala Asp Phe Pro Ala Asp Arg Gly Trp Asp Leu
3585                3590                3595                3600

Ala Gly Leu Phe Asp Pro Asp Pro Glu Arg Ala Gly Lys Thr Tyr Val
            3605                3610                3615

Arg Glu Gly Ala Phe Leu Thr Asp Ala Asp Arg Phe Asp Ala Gly Phe
        3620                3625                3630

Phe Gly Ile Ser Pro Arg Glu Ala Leu Ala Met Asp Pro Gln Gln Arg
        3635                3640                3645
```

-continued

```
Leu Leu Leu Glu Leu Ser Trp Glu Ala Ile Glu Arg Ala Gly Ile Asp
    3650                3655                3660
Pro Gly Ser Leu Arg Gly Ser Arg Thr Gly Val Phe Ala Gly Leu Met
3665                3670                3675                3680
Tyr His Asp Tyr Gly Ala Arg Phe Ala Ser Arg Ala Pro Glu Gly Phe
        3685                3690                3695
Glu Gly Tyr Leu Gly Asn Gly Ser Ala Gly Ser Val Ala Ser Gly Arg
    3700                3705                3710
Ile Ala Tyr Ser Phe Gly Phe Glu Gly Pro Ala Val Thr Val Asp Thr
        3715                3720                3725
Ala Cys Ser Ser Ser Leu Val Ala Leu His Leu Ala Gly Gln Ser Leu
    3730                3735                3740
Arg Ser Gly Glu Cys Asp Leu Ala Leu Ala Gly Gly Val Thr Val Met
3745                3750                3755                3760
Ser Thr Pro Gly Thr Phe Val Glu Phe Ser Arg Gln Arg Gly Leu Ala
        3765                3770                3775
Pro Asp Gly Arg Cys Lys Ser Phe Ala Glu Ser Ala Asp Gly Thr Gly
    3780                3785                3790
Trp Gly Glu Gly Ala Gly Leu Val Leu Leu Glu Arg Leu Ser Asp Ala
    3795                3800                3805
Arg Arg Asn Gly His Arg Val Leu Ala Val Val Arg Gly Ser Ala Val
    3810                3815                3820
Asn Gln Asp Gly Ala Ser Asn Gly Leu Thr Ala Pro Asn Gly Pro Ser
3825                3830                3835                3840
Gln Gln Arg Val Ile Gln Gln Ala Leu Ala Ser Ala Gly Leu Ser Val
        3845                3850                3855
Ser Asp Val Asp Ala Val Glu Ala His Gly Thr Gly Thr Arg Leu Gly
    3860                3865                3870
Asp Pro Ile Glu Ala Gln Ala Leu Ile Ala Thr Tyr Gly Arg Asp Arg
    3875                3880                3885
Asp Pro Gly Arg Pro Leu Trp Leu Gly Ser Val Lys Ser Asn Ile Gly
    3890                3895                3900
His Thr Gln Ala Ala Ala Gly Val Ala Gly Val Ile Lys Met Val Met
3905                3910                3915                3920
Ala Met Arg His Gly Gln Leu Pro Arg Thr Leu His Val Asp Ala Pro
        3925                3930                3935
Ser Ser Gln Val Asp Trp Ser Ala Gly Arg Val Gln Leu Leu Thr Glu
    3940                3945                3950
Asn Thr Pro Trp Pro Asp Ser Gly Arg Pro Cys Arg Val Gly Val Ser
    3955                3960                3965
Ser Phe Gly Ile Ser Gly Thr Asn Ala His Val Ile Leu Glu Gln Ser
    3970                3975                3980
Thr Gly Gln Met Asp Gln Ala Ala Glu Pro Asp Ser Ser Pro Val Leu
3985                3990                3995                4000
Asp Val Pro Val Val Pro Trp Val Val Ser Gly Lys Thr Pro Glu Ala
        4005                4010                4015
Leu Ser Ala Gln Ala Ala Thr Leu Ala Thr Tyr Leu Asp Gln Asn Val
        4020                4025                4030
Asp Val Ser Pro Leu Asp Val Gly Ile Ser Leu Ala Val Thr Arg Ser
        4035                4040                4045
Ala Leu Asp Glu Arg Ala Val Val Leu Gly Ser Asp Arg Asp Thr Leu
    4050                4055                4060
Leu Ser Gly Leu Asn Ala Leu Ala Ala Gly His Glu Ala Ala Gly Val
```

-continued

```
            4065                4070                4075                4080
      Val Thr Gly Pro Val Gly Ile Gly Gly Arg Thr Gly Phe Val Phe Ala
                      4085                4090                4095
      Gly Gln Gly Gly Gln Trp Leu Gly Met Gly Arg Arg Leu Tyr Ser Glu
                      4100                4105                4110
      Phe Pro Ala Phe Ala Gly Ala Phe Asp Glu Ala Cys Ala Glu Leu Asp
                      4115                4120                4125
      Ala Asn Leu Gly Arg Glu Val Gly Val Arg Asp Val Val Phe Gly Ser
                      4130                4135                4140
      Asp Glu Ser Leu Leu Asp Arg Thr Leu Trp Ala Gln Ser Gly Leu Phe
      4145                4150                4155                4160
      Ala Leu Gln Val Gly Leu Trp Glu Leu Leu Gly Thr Trp Gly Val Arg
                      4165                4170                4175
      Pro Ser Val Val Leu Gly His Ser Val Gly Glu Leu Ala Ala Ala Phe
                      4180                4185                4190
      Ala Ala Gly Val Leu Ser Met Ala Glu Ala Ala Arg Leu Val Ala Gly
                      4195                4200                4205
      Arg Ala Arg Leu Met Gln Ala Leu Pro Ser Gly Gly Ala Met Leu Ala
                      4210                4215                4220
      Val Ser Ala Thr Glu Ala Arg Val Gly Pro Leu Leu Asp Gly Val Arg
      4225                4230                4235                4240
      Asp Arg Val Gly Val Ala Ala Val Asn Ala Pro Gly Ser Val Val Leu
                      4245                4250                4255
      Ser Gly Asp Arg Asp Val Leu Asp Gly Ile Ala Gly Arg Leu Asp Gly
                      4260                4265                4270
      Gln Gly Ile Arg Ser Arg Trp Leu Arg Val Ser His Ala Phe His Ser
                      4275                4280                4285
      His Arg Met Asp Pro Met Leu Ala Glu Phe Ala Glu Leu Ala Arg Ser
                      4290                4295                4300
      Val Asp Tyr Arg Ser Pro Arg Leu Pro Ile Val Ser Thr Leu Thr Gly
      4305                4310                4315                4320
      Asn Leu Asp Asp Val Gly Val Met Ala Thr Pro Glu Tyr Trp Val Arg
                      4325                4330                4335
      Gln Val Arg Glu Pro Val Arg Phe Ala Asp Gly Val Gln Ala Leu Val
                      4340                4345                4350
      Asp Gln Gly Val Asp Thr Ile Val Glu Leu Gly Pro Asp Gly Ala Leu
                      4355                4360                4365
      Ser Ser Leu Val Gln Glu Cys Val Ala Glu Ser Gly Arg Ala Thr Gly
                      4370                4375                4380
      Ile Pro Leu Val Arg Arg Asp Arg Asp Glu Val Arg Thr Val Leu Asp
      4385                4390                4395                4400
      Ala Leu Ala Gln Thr His Thr Arg Gly Gly Ala Val Asp Trp Gly Ser
                      4405                4410                4415
      Phe Phe Ala Gly Thr Arg Ala Thr Gln Val Asp Leu Pro Thr Tyr Ala
                      4420                4425                4430
      Phe Gln Arg Gln Arg Tyr Trp Leu Glu Pro Ser Asp Ser Gly Asp Val
                      4435                4440                4445
      Thr Gly Val Gly Leu Thr Gly Ala Glu His Pro Leu Leu Gly Ala Val
                      4450                4455                4460
      Val Pro Val Ala Gly Gly Asp Glu Val Leu Leu Thr Gly Arg Leu Ser
      4465                4470                4475                4480
      Val Gly Thr His Pro Trp Leu Ala Glu His Arg Val Leu Gly Glu Val
                      4485                4490                4495
```

-continued

```
Val Val Pro Gly Thr Ala Leu Leu Glu Met Ala Trp Arg Ala Gly Ser
        4500                4505                4510

Gln Val Gly Cys Glu Arg Val Glu Glu Leu Thr Leu Glu Ala Pro Leu
        4515                4520                4525

Val Leu Pro Glu Arg Gly Ala Ala Val Gln Leu Ala Val Gly Ala
        4530                4535            4540

Pro Asp Glu Ala Gly Arg Arg Ser Leu Gln Leu Tyr Ser Arg Gly Ala
4545                4550                4555                4560

Asp Glu Asp Gly Asp Trp Arg Arg Ile Ala Ser Gly Leu Leu Ala Gln
            4565                4570                4575

Ala Asn Ala Val Pro Pro Ala Asp Ser Thr Ala Trp Pro Pro Asp Gly
            4580                4585                4590

Ala Gly Gln Val Asp Leu Ala Glu Phe Tyr Glu Arg Leu Ala Glu Arg
            4595                4600                4605

Gly Leu Thr Tyr Gly Pro Val Phe Gln Gly Leu Arg Ala Ala Trp Arg
        4610                4615                4620

His Gly Asp Asp Ile Phe Ala Glu Leu Ala Gly Ser Pro Asp Ala Ser
4625                4630                4635                4640

Gly Phe Gly Ile His Pro Ala Leu Leu Asp Ala Ala Leu His Ala Met
            4645                4650                4655

Ala Leu Gly Ala Ser Pro Asp Ser Glu Ala Arg Leu Pro Phe Ser Trp
        4660                4665                4670

Arg Gly Ala Gln Leu Tyr Arg Ala Glu Gly Ala Ala Leu Arg Val Arg
        4675                4680                4685

Leu Ser Pro Leu Gly Ser Gly Ala Val Ser Leu Thr Leu Val Asp Ala
        4690                4695                4700

Thr Gly Arg Arg Val Ala Ala Val Glu Ser Leu Ser Thr Arg Pro Val
4705                4710                4715                4720

Ser Thr Asp Gln Ile Gly Ala Gly Arg Gly Asp Gln Glu Arg Leu Leu
            4725                4730                4735

His Val Glu Trp Val Arg Ser Ala Glu Ser Ala Gly Met Ser Leu Thr
            4740                4745                4750

Ser Cys Ala Val Val Gly Leu Gly Glu Pro Glu Trp His Ala Ala Leu
        4755                4760                4765

Lys Thr Thr Gly Val Gln Val Glu Ser His Ala Asp Leu Ala Ser Leu
        4770                4775                4780

Ala Thr Glu Val Ala Lys Arg Gly Ser Ala Pro Gly Ala Val Ile Val
4785                4790                4795                4800

Pro Cys Pro Arg Pro Arg Ala Met Gln Glu Leu Pro Thr Ala Ala Arg
            4805                4810                4815

Arg Ala Thr Gln Gln Ala Met Ala Met Leu Gln Gln Trp Leu Ala Asp
            4820                4825                4830

Asp Arg Phe Val Ser Thr Arg Leu Ile Leu Leu Thr His Arg Ala Val
        4835                4840                4845

Ser Ala Val Ala Gly Glu Asp Val Leu Asp Leu Val His Ala Pro Leu
        4850                4855                4860

Trp Gly Leu Val Arg Ser Ala Gln Ala Glu His Pro Asp Arg Phe Ala
4865                4870                4875                4880

Leu Ile Asp Met Asp Asp Glu Arg Ala Ser Gln Thr Ala Leu Ala Glu
            4885                4890                4895

Ala Leu Thr Ala Gly Glu Ala Gln Leu Ala Val Arg Ser Gly Val Val
            4900                4905                4910
```

```
Leu Ala Pro Arg Leu Gly Gln Val Lys Val Ser Gly Gly Glu Ala Phe
        4915                4920                4925

Arg Trp Asp Glu Gly Thr Val Leu Val Thr Gly Gly Thr Gly Gly Leu
        4930                4935                4940

Gly Ala Leu Leu Ala Arg His Leu Val Ser Ala His Gly Val Arg His
4945                4950                4955                4960

Leu Leu Leu Ala Ser Arg Arg Gly Leu Ala Ala Pro Gly Ala Asp Glu
        4965                4970                4975

Leu Val Ala Glu Leu Glu Gln Ala Gly Ala Asp Val Ala Val Val Ala
        4980                4985                4990

Cys Asp Ser Ala Asp Arg Asp Ser Leu Ala Arg Leu Val Ala Ser Val
        4995                5000                5005

Pro Ala Glu Asn Pro Leu Arg Val Val His Ala Ala Gly Val Leu
        5010                5015                5020

Asp Asp Gly Val Leu Met Ser Met Ser Pro Glu Arg Leu Asp Ala Val
5025                5030                5035                5040

Leu Arg Pro Lys Val Asp Ala Ala Trp Tyr Leu His Glu Leu Thr Arg
        5045                5050                5055

Glu Leu Gly Leu Ser Ala Phe Val Leu Phe Ser Ser Val Ala Gly Leu
        5060                5065                5070

Phe Gly Gly Ala Gly Gln Ser Asn Tyr Ala Ala Gly Asn Ala Phe Leu
        5075                5080                5085

Asp Ala Leu Ala His Cys Arg Gln Ala Gln Gly Leu Pro Ala Leu Ser
        5090                5095                5100

Leu Ala Ser Gly Leu Trp Ala Ser Ile Asp Gly Met Ala Gly Asp Leu
5105                5110                5115                5120

Ala Ala Ala Asp Val Glu Arg Leu Ser Arg Ala Gly Ile Gly Pro Leu
        5125                5130                5135

Ser Ala Pro Gly Gly Leu Ala Leu Phe Asp Ala Ala Val Gly Ser Asp
        5140                5145                5150

Glu Pro Leu Leu Ala Pro Val Arg Leu Asp Val Glu Ala Leu Arg Val
        5155                5160                5165

Gln Ala Arg Ser Val Gln Thr Arg Ile Pro Glu Met Leu His Gly Met
        5170                5175                5180

Ala Met Gly Pro Ser Arg Arg Thr Pro Phe Thr Ser Arg Val Glu Pro
5185                5190                5195                5200

Leu His Glu Arg Leu Ala Gly Leu Ser Glu Gly Glu Arg Arg Gln Gln
        5205                5210                5215

Val Leu Gln Arg Val Arg Ala Asp Ile Ala Val Val Leu Gly His Gly
        5220                5225                5230

Arg Ser Ser Asp Val Asp Ile Glu Lys Pro Leu Ala Glu Leu Gly Phe
        5235                5240                5245

Asp Ser Leu Thr Ala Ile Glu Leu Arg Asn Arg Leu Ala Thr Ala Thr
        5250                5255                5260

Gly Leu Arg Leu Pro Ala Thr Leu Ala Phe Asp His Gly Thr Ala Ala
5265                5270                5275                5280

Ala Leu Ala Gln His Val Cys Ala Gln Leu Gly Thr Ala Thr Ala Pro
        5285                5290                5295

Ala Pro Arg Arg Thr Asp Asp Asn Asp Ala Thr Glu Pro Val Arg Ser
        5300                5305                5310

Leu Phe Gln Gln Ala Tyr Ala Ala Gly Arg Ile Leu Asp Gly Met Asp
        5315                5320                5325

Leu Val Lys Val Ala Ala Gln Leu Arg Pro Val Phe Gly Ser Pro Gly
```

```
        5330              5335              5340
Glu Leu Glu Ser Leu Pro Lys Pro Val Gln Leu Ser Arg Gly Pro Glu
5345              5350              5355              5360

Glu Leu Ala Leu Val Cys Met Pro Ala Leu Ile Gly Met Pro Pro Ala
        5365              5370              5375

Gln Gln Tyr Ala Arg Ile Ala Ala Gly Phe Arg Asp Val Arg Asp Val
            5380              5385              5390

Ser Val Ile Pro Met Pro Gly Phe Ile Ala Gly Glu Pro Leu Pro Ser
        5395              5400              5405

Ala Ile Glu Val Ala Val Arg Thr Gln Ala Glu Ala Val Leu Gln Glu
    5410              5415              5420

Phe Ala Gly Gly Ser Phe Val Leu Val Gly His Ser Ser Gly Gly Trp
5425              5430              5435              5440

Leu Ala His Glu Val Ala Gly Glu Leu Glu Arg Arg Gly Val Val Pro
            5445              5450              5455

Ala Gly Val Val Leu Leu Asp Thr Tyr Ile Pro Gly Glu Ile Thr Pro
        5460              5465              5470

Arg Phe Ser Val Ala Met Ala His Arg Thr Tyr Glu Lys Leu Ala Thr
    5475              5480              5485

Phe Thr Asp Met Gln Asp Val Gly Ile Thr Ala Met Gly Gly Tyr Phe
    5490              5495              5500

Arg Met Phe Thr Glu Trp Thr Pro Thr Pro Ile Gly Ala Pro Thr Leu
5505              5510              5515              5520

Phe Val Arg Thr Glu Asp Cys Val Ala Asp Pro Glu Gly Arg Pro Trp
            5525              5530              5535

Thr Asp Asp Ser Trp Arg Pro Gly Trp Thr Leu Ala Asp Ala Thr Val
            5540              5545              5550

Gln Val Pro Gly Asp His Phe Ser Met Met Asp Glu His Ala Gly Ser
        5555              5560              5565

Thr Ala Gln Ala Val Ala Ser Trp Leu Asp Lys Leu Asn Gln Arg Thr
    5570              5575              5580

Ala Arg Gln Arg
5585

<210> SEQ ID NO 7
<211> LENGTH: 275
<212> TYPE: PRT
<213> ORGANISM: Saccharopolyspora spinosa

<400> SEQUENCE: 7

Val Leu Pro Gly Gly Ala Pro Thr Ser Gln Gln Val Gly Gln Met Tyr
 1               5                  10                  15

Asp Leu Val Thr Pro Leu Leu Asn Ser Val Ala Gly Gly Pro Cys Ala
                20                  25                  30

Ile His His Gly Tyr Trp Glu Asn Asp Gly Arg Ala Ser Trp Gln Gln
            35                  40                  45

Ala Ala Asp Arg Leu Thr Asp Leu Val Ala Glu Arg Thr Val Leu Asp
        50                  55                  60

Gly Gly Val Arg Leu Leu Asp Val Gly Cys Gly Thr Gly Gln Pro Ala
65                  70                  75                  80

Leu Arg Val Ala Arg Asp Asn Ala Ile Gln Ile Thr Gly Ile Thr Val
                85                  90                  95

Ser Gln Val Gln Val Ala Ile Ala Ala Asp Cys Ala Arg Glu Arg Gly
            100                 105                 110
```

-continued

```
Leu Ser His Arg Val Asp Phe Ser Cys Val Asp Ala Met Ser Leu Pro
        115                 120                 125
Tyr Pro Asp Asn Ala Phe Asp Ala Ala Trp Ala Met Gln Ser Leu Leu
    130                 135                 140
Glu Met Ser Glu Pro Asp Arg Ala Ile Arg Glu Ile Leu Arg Val Leu
145                 150                 155                 160
Lys Pro Gly Gly Ile Leu Gly Val Thr Glu Val Val Lys Arg Glu Ala
                165                 170                 175
Gly Gly Gly Met Pro Val Ser Gly Asp Arg Trp Pro Thr Gly Leu Arg
            180                 185                 190
Ile Cys Leu Ala Glu Gln Leu Leu Glu Ser Leu Arg Ala Ala Gly Phe
        195                 200                 205
Glu Ile Leu Asp Trp Glu Asp Val Ser Ser Arg Thr Arg Tyr Phe Met
    210                 215                 220
Pro Gln Phe Ala Glu Glu Leu Ala Ala His Gln His Gly Ile Ala Asp
225                 230                 235                 240
Arg Tyr Gly Pro Ala Val Ala Gly Trp Ala Ala Ala Val Cys Asp Tyr
                245                 250                 255
Glu Lys Tyr Ala His Asp Met Gly Tyr Ala Ile Leu Thr Ala Arg Lys
            260                 265                 270
Pro Val Gly
        275

<210> SEQ ID NO 8
<211> LENGTH: 390
<212> TYPE: PRT
<213> ORGANISM: Saccharopolyspora spinosa

<400> SEQUENCE: 8

Met Arg Val Leu Val Pro Leu Pro Tyr Pro Thr His Leu Met Ala
  1               5                  10                  15
Met Val Pro Leu Cys Trp Ala Leu Gln Ala Ser Gly His Glu Val Leu
                 20                  25                  30
Ile Ala Ala Pro Pro Glu Leu Gln Ala Thr Ala His Gly Ala Gly Leu
             35                  40                  45
Thr Thr Ala Gly Ile Arg Gly Asn Asp Arg Thr Gly Asp Thr Gly Gly
         50                  55                  60
Thr Thr Gln Leu Arg Phe Pro Asn Pro Ala Phe Gly Gln Arg Asp Thr
 65                  70                  75                  80
Glu Ala Gly Arg Gln Leu Trp Glu Gln Thr Ala Ser Asn Val Ala Gln
                 85                  90                  95
Ser Ser Leu Asp Gln Leu Pro Glu Tyr Leu Arg Leu Ala Glu Ala Trp
                100                 105                 110
Arg Pro Ser Val Leu Leu Val Asp Val Cys Ala Leu Ile Gly Arg Val
            115                 120                 125
Leu Gly Gly Leu Leu Asp Leu Pro Val Val Leu His Arg Trp Gly Val
        130                 135                 140
Asp Pro Thr Ala Gly Pro Phe Ser Asp Arg Ala His Glu Leu Leu Asp
145                 150                 155                 160
Pro Val Cys Arg His His Gly Leu Thr Gly Leu Pro Thr Pro Glu Leu
                165                 170                 175
Ile Leu Asp Pro Cys Pro Pro Ser Leu Gln Ala Ser Asp Ala Pro Gln
            180                 185                 190
Gly Ala Pro Val Gln Tyr Val Pro Tyr Asn Gly Ser Gly Ala Phe Pro
        195                 200                 205
```

```
Ala Trp Gly Ala Ala Arg Thr Ser Ala Arg Val Cys Ile Cys Met
    210                 215                 220

Gly Arg Met Val Leu Asn Ala Thr Gly Pro Ala Pro Leu Leu Arg Ala
225                 230                 235                 240

Val Ala Ala Ala Thr Glu Leu Pro Gly Val Glu Ala Val Ile Ala Val
                245                 250                 255

Pro Pro Glu His Arg Ala Leu Leu Thr Asp Leu Pro Asp Asn Ala Arg
            260                 265                 270

Ile Ala Glu Ser Val Pro Leu Asn Leu Phe Leu Arg Thr Cys Glu Leu
        275                 280                 285

Val Ile Cys Ala Gly Gly Ser Gly Thr Ala Phe Thr Ala Thr Arg Leu
    290                 295                 300

Gly Ile Pro Gln Leu Val Leu Pro Gln Tyr Phe Asp Gln Phe Asp Tyr
305                 310                 315                 320

Ala Arg Asn Leu Ala Ala Gly Ala Gly Ile Cys Leu Pro Asp Glu
                325                 330                 335

Gln Ala Gln Ser Asp His Glu Gln Phe Thr Asp Ser Ile Ala Thr Val
            340                 345                 350

Leu Gly Asp Thr Gly Phe Ala Ser Ala Ala Ile Lys Leu Ser Asp Glu
        355                 360                 365

Ile Thr Ala Met Pro His Pro Ala Ala Leu Val Arg Thr Leu Glu Asn
    370                 375                 380

Thr Ala Ala Ile Arg Ala
385                 390

<210> SEQ ID NO 9
<211> LENGTH: 250
<212> TYPE: PRT
<213> ORGANISM: Saccharopolyspora spinosa

<400> SEQUENCE: 9

Met Pro Ser Gln Asn Ala Leu Tyr Leu Asp Leu Leu Lys Lys Val Leu
  1               5                  10                  15

Thr Asn Thr Ile Tyr Ser Asp Arg Pro His Pro Asn Ala Trp Gln Asp
            20                  25                  30

Asn Thr Asp Tyr Arg Gln Ala Ala Arg Ala Lys Gly Thr Asp Trp Pro
        35                  40                  45

Thr Val Ala His Thr Met Ile Gly Leu Glu Arg Leu Asp Asn Leu Gln
    50                  55                  60

His Cys Val Glu Ala Val Leu Ala Asp Gly Val Pro Gly Asp Phe Ala
 65                  70                  75                  80

Glu Thr Gly Val Trp Arg Gly Gly Ala Cys Ile Phe Met Arg Ala Val
                85                  90                  95

Leu Gln Ala Phe Gly Asp Thr Gly Arg Thr Val Trp Val Val Asp Ser
            100                 105                 110

Phe Gln Gly Met Pro Glu Ser Ser Ala Gln Asp His Gln Ala Asp Gln
        115                 120                 125

Ala Met Ala Leu His Glu Tyr Asn Asp Val Leu Gly Val Ser Leu Glu
    130                 135                 140

Thr Val Arg Gln Asn Phe Ala Arg Tyr Gly Leu Leu Asp Glu Gln Val
145                 150                 155                 160

Arg Phe Leu Pro Gly Trp Phe Arg Asp Thr Leu Pro Thr Ala Pro Ile
                165                 170                 175

Gln Glu Leu Ala Val Leu Arg Leu Asp Gly Asp Leu Tyr Glu Ser Thr
```

-continued

```
                180              185              190
Met Asp Ser Leu Arg Asn Leu Tyr Pro Lys Leu Ser Pro Gly Gly Phe
            195                  200              205

Val Ile Ile Asp Asp Tyr Phe Leu Pro Ser Cys Gln Asp Ala Val Lys
        210                  215              220

Gly Phe Arg Ala Glu Leu Gly Ile Thr Glu Pro Ile His Asp Ile Asp
225                 230              235                  240

Gly Thr Gly Ala Tyr Trp Arg Arg Ser Trp
                245              250

<210> SEQ ID NO 10
<211> LENGTH: 395
<212> TYPE: PRT
<213> ORGANISM: Saccharopolyspora spinosa

<400> SEQUENCE: 10

Met Ser Glu Ile Ala Val Ala Pro Trp Ser Val Glu Arg Leu Leu
  1               5                  10                  15

Leu Ala Ala Gly Ala Gly Pro Ala Lys Leu Gln Glu Ala Val Gln Val
             20                  25                  30

Ala Gly Leu Asp Ala Val Ala Asp Ala Ile Val Asp Glu Leu Val Val
         35                  40                  45

Arg Cys Asp Pro Leu Ser Leu Asp Glu Ser Val Arg Ile Gly Leu Glu
     50                  55                  60

Ile Thr Ser Gly Ala Gln Leu Val Arg Arg Thr Val Glu Leu Asp His
 65                  70                  75                  80

Ala Gly Leu Arg Leu Ala Ala Val Ala Glu Ala Ala Val Leu Arg
                 85                  90                  95

Phe Asp Ala Val Asp Leu Leu Glu Gly Leu Phe Gly Pro Val Asp Gly
                100                 105                 110

Arg Arg His Asn Ser Arg Glu Val Arg Trp Ser Asp Ser Met Thr Gln
            115                 120                 125

Phe Ser Pro Asp Gln Gly Leu Ala Gly Ala Gln Arg Leu Leu Ala Phe
        130                 135                 140

Arg Asn Arg Val Ser Thr Ala Val His Ala Val Leu Ala Ala Ala Ala
145                 150                 155                 160

Thr Arg Arg Ala Asp Leu Gly Ala Leu Ala Val Arg Tyr Gly Ser Asp
                165                 170                 175

Lys Trp Ala Asp Leu His Trp Tyr Thr Glu His Tyr Glu His His Phe
            180                 185                 190

Ser Arg Phe Gln Asp Ala Pro Val Arg Val Leu Glu Ile Gly Ile Gly
        195                 200                 205

Gly Tyr His Ala Pro Glu Leu Gly Gly Ala Ser Leu Arg Met Trp Gln
    210                 215                 220

Arg Tyr Phe Arg Arg Gly Leu Val Tyr Gly Leu Asp Ile Phe Glu Lys
225                 230                 235                 240

Ala Gly Asn Glu Gly His Arg Val Arg Lys Leu Arg Gly Asp Gln Ser
                245                 250                 255

Asp Ala Glu Phe Leu Glu Asp Met Val Ala Lys Ile Gly Pro Phe Asp
            260                 265                 270

Ile Val Ile Asp Asp Gly Ser His Val Asn Asp His Val Lys Lys Ser
        275                 280                 285

Phe Gln Ser Leu Phe Pro His Val Arg Pro Gly Gly Leu Tyr Val Ile
    290                 295                 300
```

```
Glu Asp Leu Gln Thr Ala Tyr Trp Pro Gly Tyr Gly Arg Asp Gly
305                 310                 315                 320

Glu Pro Ala Ala Gln Arg Thr Ser Ile Asp Met Leu Lys Glu Leu Ile
                325                 330                 335

Asp Gly Leu His Tyr Gln Glu Arg Glu Ser Arg Cys Gly Thr Glu Pro
                340                 345                 350

Ser Tyr Thr Glu Arg Asn Val Ala Ala Leu His Phe Tyr His Asn Leu
            355                 360                 365

Val Phe Val Glu Lys Gly Leu Asn Ala Glu Thr Ala Ala Pro Gly Phe
        370                 375                 380

Val Pro Arg Gln Ala Leu Gly Val Glu Gly Gly
385                 390                 395

<210> SEQ ID NO 11
<211> LENGTH: 539
<212> TYPE: PRT
<213> ORGANISM: Saccharopolyspora spinosa

<400> SEQUENCE: 11

Met Ile Ser Ala Ala Gly Glu Gln Ser Gly Pro Val Arg Lys Gly Gly
1               5                   10                  15

Ala Val Pro Glu Phe His Asp Pro Ala Pro Met Asn Arg Arg Thr Pro
                20                  25                  30

Gly Thr Glu Ile Thr Val Glu Pro Asp Asp Pro Arg Tyr Pro Asp Leu
            35                  40                  45

Val Val Gly His Asn Pro Arg Phe Thr Gly Lys Pro Glu Arg Ile His
        50                  55                  60

Ile Ala Ser Ser Ala Glu Asp Val Val His Ala Val Ala Asp Ala Val
65                  70                  75                  80

Arg Thr Gly Arg Arg Val Gly Val Arg Ser Gly Gly His Cys Phe Glu
                85                  90                  95

Asn Leu Val Ala Asp Pro Ala Ile Arg Val Leu Val Asp Leu Ser Glu
                100                 105                 110

Leu Asn Arg Val Tyr Tyr Asp Ser Thr Arg Gly Ala Phe Ala Ile Glu
            115                 120                 125

Ala Gly Ala Ala Leu Gly Gln Val Tyr Arg Thr Leu Phe Lys Asn Trp
        130                 135                 140

Gly Val Thr Ile Pro Thr Gly Ala Cys Pro Gly Val Gly Ala Gly Gly
145                 150                 155                 160

His Ile Leu Gly Gly Gly Tyr Gly Pro Leu Ser Arg Arg Phe Gly Ser
                165                 170                 175

Val Val Asp Tyr Leu Gln Gly Val Glu Val Val Val Asp Gln Ala
            180                 185                 190

Gly Glu Val His Ile Val Glu Ala Asp Arg Asn Ser Thr Gly Ala Gly
        195                 200                 205

His Asp Leu Trp Trp Ala His Thr Gly Gly Gly Gly Asn Phe Gly
    210                 215                 220

Ile Val Thr Arg Phe Trp Leu Arg Thr Pro Asp Val Val Ser Thr Asp
225                 230                 235                 240

Ala Ala Glu Leu Leu Pro Arg Pro Pro Ala Thr Val Leu Leu Arg Ser
                245                 250                 255

Phe His Trp Pro Trp His Glu Leu Thr Glu Gln Ser Phe Ala Val Leu
            260                 265                 270

Leu Gln Asn Phe Gly Asn Trp Tyr Glu Gln His Ser Ala Pro Glu Ser
        275                 280                 285
```

```
Thr Gln Leu Gly Leu Phe Ser Thr Leu Val Cys Ala His Arg Gln Ala
        290                 295                 300

Gly Tyr Val Thr Leu Asn Val His Leu Asp Gly Thr Asp Pro Asn Ala
305                 310                 315                 320

Glu Arg Thr Leu Ala Glu His Leu Ser Ala Ile Asn Ala Gln Val Gly
                325                 330                 335

Val Thr Pro Ala Glu Gly Leu Arg Glu Thr Leu Pro Trp Leu Arg Ser
            340                 345                 350

Thr Gln Val Ala Gly Ala Ile Ala Glu Gly Gly Glu Pro Gly Met Gln
        355                 360                 365

Arg Thr Lys Val Lys Ala Ala Tyr Leu Arg Thr Gly Leu Ser Glu Ala
370                 375                 380

Gln Leu Ala Thr Val Tyr Arg Arg Leu Thr Val Tyr Gly Tyr Asp Asn
385                 390                 395                 400

Pro Ala Ala Leu Leu Leu Gly Tyr Gly Gly Met Ala Asn Ala
                405                 410                 415

Val Ala Pro Ser Ala Thr Ala Leu Ala Gln Arg Asp Ser Val Leu Lys
            420                 425                 430

Ala Leu Phe Val Thr Asn Trp Ser Glu Pro Ala Glu Asp Glu Arg His
        435                 440                 445

Leu Thr Trp Ile Arg Gly Phe Tyr Arg Glu Met Tyr Ala Glu Thr Gly
    450                 455                 460

Gly Val Pro Val Pro Gly Thr Arg Val Asp Gly Ser Tyr Ile Asn Tyr
465                 470                 475                 480

Pro Asp Thr Asp Leu Ala Asp Pro Leu Trp Asn Thr Ser Gly Val Ala
                485                 490                 495

Trp His Asp Leu Tyr Tyr Lys Asp Asn Tyr Pro Arg Leu Gln Arg Ala
            500                 505                 510

Lys Ala Arg Trp Asp Pro Gln Asn Ile Phe Gln His Gly Leu Ser Ile
        515                 520                 525

Lys Pro Pro Ala Arg Leu Ser Pro Gly Gln Pro
    530                 535

<210> SEQ ID NO 12
<211> LENGTH: 397
<212> TYPE: PRT
<213> ORGANISM: Saccharopolyspora spinosa

<400> SEQUENCE: 12

Met Ser Thr Thr His Glu Ile Glu Thr Val Glu Arg Ile Ile Leu Ala
  1               5                  10                  15

Ala Gly Ser Ser Ala Ala Ser Leu Ala Asp Leu Thr Thr Glu Leu Gly
                20                  25                  30

Leu Ala Arg Ile Ala Pro Val Leu Ile Asp Glu Ile Leu Phe Arg Ala
            35                  40                  45

Glu Pro Ala Pro Asp Ile Glu Arg Thr Glu Val Ala Val Gln Ile Thr
        50                  55                  60

His Arg Gly Glu Thr Val Asp Phe Val Leu Thr Leu Gln Ser Gly Glu
 65                  70                  75                  80

Leu Ile Lys Ala Glu Gln Arg Pro Val Gly Asp Val Pro Leu Arg Ile
                85                  90                  95

Gly Tyr Glu Leu Thr Asp Leu Ile Ala Glu Leu Phe Gly Pro Gly Ala
                100                 105                 110

Pro Arg Ala Val Gly Ala Arg Ser Thr Asn Phe Leu Arg Thr Thr Thr
```

```
                115                 120                 125
Ser Gly Ser Ile Pro Gly Pro Ser Glu Leu Ser Asp Gly Phe Gln Ala
    130                 135                 140

Ile Ser Ala Val Val Ala Gly Cys Gly His Arg Arg Pro Asp Leu Asn
145                 150                 155                 160

Leu Leu Ala Ser His Tyr Arg Thr Asp Lys Trp Gly Leu His Trp
                165                 170                 175

Phe Thr Pro Leu Tyr Glu Arg His Leu Gly Glu Phe Arg Asp Arg Pro
            180                 185                 190

Val Arg Ile Leu Glu Ile Gly Val Gly Tyr Asn Phe Asp Gly Gly
        195                 200                 205

Gly Gly Glu Ser Leu Lys Met Trp Lys Arg Tyr Phe His Arg Gly Leu
    210                 215                 220

Val Phe Gly Met Asp Val Phe Asp Lys Ser Phe Leu Asp Gln Gln Arg
225                 230                 235                 240

Leu Cys Thr Val Arg Ala Asp Gln Ser Lys Pro Glu Glu Leu Ala Ala
                245                 250                 255

Val Asp Asp Lys Tyr Gly Pro Phe Asp Ile Ile Asp Asp Gly Ser
            260                 265                 270

His Ile Asn Gly His Val Arg Thr Ser Leu Glu Thr Leu Phe Pro Arg
        275                 280                 285

Leu Arg Ser Gly Gly Val Tyr Val Ile Glu Asp Leu Trp Thr Thr Tyr
    290                 295                 300

Ala Pro Gly Phe Gly Gly Gln Ala Gln Cys Pro Ala Ala Pro Gly Thr
305                 310                 315                 320

Thr Val Ser Leu Leu Lys Asn Leu Leu Glu Gly Val Gln His Glu Glu
                325                 330                 335

Gln Pro His Ala Gly Ser Tyr Glu Pro Ser Tyr Leu Glu Arg Asn Leu
            340                 345                 350

Val Gly Leu His Thr Tyr His Asn Ile Ala Phe Leu Glu Lys Gly Val
        355                 360                 365

Asn Ala Glu Gly Gly Val Pro Ala Trp Val Pro Arg Ser Leu Asp Asp
370                 375                 380

Ile Leu His Leu Ala Asp Val Asn Ser Ala Glu Asp Glu
385                 390                 395

<210> SEQ ID NO 13
<211> LENGTH: 283
<212> TYPE: PRT
<213> ORGANISM: Saccharopolyspora spinosa

<400> SEQUENCE: 13

Val Glu Ser Ile Phe Asp Ala Leu Ala His Gly Arg Pro Leu His His
  1               5                  10                  15

Gly Tyr Trp Ala Gly Gly Tyr Arg Glu Asp Ala Gly Ala Thr Pro Trp
                 20                  25                  30

Ser Asp Ala Ala Asp Gln Leu Thr Asp Leu Phe Ile Asp Lys Ala Ala
             35                  40                  45

Leu Arg Pro Gly Ala His Leu Phe Asp Leu Gly Cys Gly Asn Gly Gln
         50                  55                  60

Pro Val Val Arg Ala Ala Cys Ala Ser Gly Val Arg Val Thr Gly Ile
 65                  70                  75                  80

Thr Val Asn Ala Gln His Leu Ala Ala Ala Thr Arg Leu Ala Asn Glu
                 85                  90                  95
```

-continued

```
Thr Gly Leu Ala Gly Ser Leu Glu Phe Asp Leu Val Asp Gly Ala Gln
            100                 105                 110

Leu Pro Tyr Pro Asp Gly Phe Phe Gln Ala Ala Trp Ala Met Gln Ser
        115                 120                 125

Val Val Gln Ile Val Asp Gln Ala Ala Ile Arg Glu Val His Arg
    130                 135                 140

Ile Leu Glu Pro Gly Gly Arg Phe Val Leu Gly Asp Ile Ile Thr Arg
145                 150                 155                 160

Val Arg Leu Pro Glu Glu Tyr Ala Ala Val Trp Thr Gly Thr Thr Ala
                165                 170                 175

His Thr Leu Asn Ser Phe Thr Ala Leu Val Ser Glu Ala Gly Phe Glu
            180                 185                 190

Ile Leu Glu Val Thr Asp Leu Thr Ala Gln Thr Arg Cys Met Val Ser
        195                 200                 205

Trp Tyr Val Asp Glu Leu Leu Arg Lys Leu Asp Glu Leu Ala Gly Val
    210                 215                 220

Glu Pro Ala Ala Val Gly Thr Tyr Gln Gln Arg Tyr Leu Gly Asp Ile
225                 230                 235                 240

Ala Ala Lys His Gly Pro Gly Pro Ala Gln Leu Ile Ala Ala Val Ala
                245                 250                 255

Glu Tyr Arg Lys His Pro Asp Tyr Ala Arg Asn Glu Glu Ser Met Gly
            260                 265                 270

Phe Met Leu Leu Gln Ala Arg Lys Lys Gln Ser
        275                 280

<210> SEQ ID NO 14
<211> LENGTH: 320
<212> TYPE: PRT
<213> ORGANISM: Saccharopolyspora spinosa

<400> SEQUENCE: 14

Met Pro Asn Ala Val Ser Gly Thr Val Leu Val Pro Asn Ile Pro Trp
  1               5                  10                  15

Pro Arg Glu Asp Arg Pro Ile Ile Thr Phe Ala Val Gly Thr His Gly
             20                  25                  30

Leu Gly Ser Gln Val Ala Pro Ser Tyr Leu Leu Arg Thr Gly Thr Glu
         35                  40                  45

Pro Glu Thr Glu Leu Ile Ala Val Ala Leu Asp Arg Gly Trp Ala Val
     50                  55                  60

Val Ile Thr Asp Tyr Glu Gly Leu Gly Thr Pro Gly Thr His Thr Tyr
 65                  70                  75                  80

Thr Val Gly Arg Ala Gln Gly His Ala Met Leu Asp Ala Ala Arg Ala
                 85                  90                  95

Ala Gln Arg Leu Pro Gly Ser Gly Leu Thr Thr Asp Cys Pro Val Gly
            100                 105                 110

Ile Trp Gly Tyr Ala Gln Gly Gly Gln Ala Ser Ala Phe Ala Gly Glu
        115                 120                 125

Leu His Pro Thr Tyr Ala Pro Glu Leu Arg Ile Arg Ala Ala Ala Ala
    130                 135                 140

Gly Ala Val Pro Ile Asp Leu Leu Asp Ile Ile His Arg Asn Asp Gly
145                 150                 155                 160

Val Phe Thr Gly Pro Val Leu Ala Gly Leu Val Gly His Ala Ala Ala
                165                 170                 175

Tyr Pro Asp Leu Pro Phe Asp Glu Leu Leu Thr Glu Ala Gly Arg Thr
            180                 185                 190
```

```
Ala Val Asp Gln Val Arg Glu Leu Gly Ala Pro Glu Leu Val Thr Arg
            195                 200                 205

Phe Leu Gly Arg Glu Leu Ser Asp Phe Leu Asp Thr Ser Gly Leu Phe
    210                 215                 220

Glu Gln Pro Arg Trp Arg Ala Arg Leu Ala Glu Ser Val Ala Gly Arg
225                 230                 235                 240

Asn Gly Gly Pro Val Val Pro Thr Leu Val Tyr His Ser Thr Asp Asp
                245                 250                 255

Glu Ile Val Pro Phe Ala Phe Gly Glu Arg Leu Arg Asp Ser Tyr Arg
                260                 265                 270

Ala Ala Gly Thr Pro Val Arg Trp His Pro Leu Ser Gly Leu Ala His
            275                 280                 285

Phe Pro Ala Ala Leu Ala Ser Ser Arg Val Val Ser Trp Phe Asp
    290                 295                 300

Glu His Phe Ser Glu Pro Ser Ala Ile Ser Gly Pro Arg Asp Ala Arg
305                 310                 315                 320

<210> SEQ ID NO 15
<211> LENGTH: 332
<212> TYPE: PRT
<213> ORGANISM: Saccharopolyspora spinosa

<400> SEQUENCE: 15

Met Arg Lys Pro Val Arg Ile Gly Val Leu Gly Cys Ala Ser Phe Ala
1               5                   10                  15

Trp Arg Arg Met Leu Pro Ala Met Cys Asp Val Ala Glu Thr Glu Val
                20                  25                  30

Val Ala Val Ala Ser Arg Asp Pro Ala Lys Ala Glu Arg Phe Ala Ala
            35                  40                  45

Arg Phe Glu Cys Glu Ala Val Leu Gly Tyr Gln Arg Leu Leu Glu Arg
        50                  55                  60

Pro Asp Ile Asp Ala Val Tyr Val Pro Leu Pro Gly Met His Ala
65                  70                  75                  80

Glu Trp Ile Gly Lys Ala Leu Glu Ala Asp Lys His Val Leu Ala Glu
                85                  90                  95

Lys Pro Leu Thr Thr Ala Ser Asp Thr Ala Arg Leu Val Gly Leu
            100                 105                 110

Ala Arg Arg Lys Asn Leu Leu Arg Glu Asn Tyr Leu Phe Leu His
        115                 120                 125

His Gly Arg His Asp Val Val Arg Asp Leu Leu Gln Ser Gly Glu Ile
    130                 135                 140

Gly Glu Leu Arg Glu Phe Thr Ala Val Phe Gly Ile Pro Pro Leu Pro
145                 150                 155                 160

Asp Thr Asp Ile Arg Tyr Arg Thr Glu Leu Gly Gly Ala Leu Leu
                165                 170                 175

Asp Ile Gly Val Tyr Pro Ala Arg Ala Ala Arg His Phe Leu Leu Gly
            180                 185                 190

Pro Leu Thr Val Leu Gly Ala Ser Ser His Glu Ala Gln Glu Ser Gly
        195                 200                 205

Val Asp Leu Ser Gly Ser Val Leu Leu Gln Ser Glu Gly Gly Thr Val
    210                 215                 220

Ala His Leu Gly Tyr Gly Phe Val His Tyr Arg Ser Ala Tyr Glu
225                 230                 235                 240

Leu Trp Gly Ser Arg Gly Arg Ile Val Val Asp Arg Ala Phe Thr Pro
```

```
                            245                 250                 255
Pro Ala Glu Trp Gln Ala Val Ile Arg Ile Glu Arg Lys Gly Val Val
            260                 265                 270
Asp Glu Leu Ser Leu Pro Ala Glu Asp Gln Val Arg Lys Ala Val Thr
        275                 280                 285
Ala Phe Ala Arg Asp Ile Arg Ala Gly Thr Gly Val Asp Asp Pro Ala
    290                 295                 300
Val Ala Gly Asp Ser Gly Glu Ser Met Ile Gln Gln Ala Ala Leu Val
305                 310                 315                 320
Glu Ala Ile Gly Gln Ala Arg Arg Cys Gly Ser Thr
                325                 330

<210> SEQ ID NO 16
<211> LENGTH: 486
<212> TYPE: PRT
<213> ORGANISM: Saccharopolyspora spinosa

<400> SEQUENCE: 16

Met Ser Ser Ser Val Glu Ala Glu Ala Ser Ala Ala Ala Pro Leu Gly
  1               5                  10                  15
Ser Asn Asn Thr Arg Arg Phe Val Asp Ser Ala Leu Ser Ala Cys Asn
             20                  25                  30
Gly Met Ile Pro Thr Thr Glu Phe His Cys Trp Leu Ala Asp Arg Leu
         35                  40                  45
Gly Glu Asn Ser Phe Glu Thr Asn Arg Ile Pro Phe Asp Arg Leu Ser
     50                  55                  60
Lys Trp Lys Phe Asp Ala Ser Thr Glu Asn Leu Val His Ala Asp Gly
 65                  70                  75                  80
Arg Phe Phe Thr Val Glu Gly Leu Gln Val Glu Thr Asn Tyr Gly Ala
                 85                  90                  95
Ala Pro Ser Trp His Gln Pro Ile Ile Asn Gln Ala Glu Val Gly Ile
            100                 105                 110
Leu Gly Ile Leu Val Lys Glu Ile Asp Gly Val Leu His Cys Leu Met
        115                 120                 125
Ser Ala Lys Met Glu Pro Gly Asn Val Asn Val Leu Gln Leu Ser Pro
    130                 135                 140
Thr Val Gln Ala Thr Arg Ser Asn Tyr Thr Gln Ala His Arg Gly Ser
145                 150                 155                 160
Val Pro Pro Tyr Val Asp Tyr Phe Leu Gly Arg Gly Arg Gly Arg Val
                165                 170                 175
Leu Val Asp Val Leu Gln Ser Glu Gln Gly Ser Trp Phe Tyr Arg Lys
            180                 185                 190
Arg Asn Arg Asn Met Val Val Glu Val Gln Glu Val Pro Val Leu
        195                 200                 205
Pro Asp Phe Cys Trp Leu Thr Leu Gly Gln Val Leu Ala Leu Leu Arg
    210                 215                 220
Gln Asp Asn Ile Val Asn Met Asp Thr Arg Thr Val Leu Ser Cys Ile
225                 230                 235                 240
Pro Phe His Asp Ser Ala Thr Gly Pro Glu Leu Ala Ala Ser Glu Glu
                245                 250                 255
Pro Phe Arg Gln Ala Val Ala Arg Ser Leu Ser His Gly Ile Asp Ser
            260                 265                 270
Ser Ser Ile Ser Glu Ala Val Gly Trp Phe Glu Glu Ala Lys Ala Arg
        275                 280                 285
```

```
Tyr Arg Leu Arg Ala Thr Arg Val Pro Leu Ser Arg Val Asp Lys Trp
        290                 295                 300

Tyr Arg Thr Asp Thr Glu Ile Ala His Gln Asp Gly Lys Tyr Phe Ala
305                 310                 315                 320

Val Ile Ala Val Ser Val Ser Ala Thr Asn Arg Glu Val Ala Ser Trp
                325                 330                 335

Thr Gln Pro Met Ile Glu Pro Arg Glu Gln Gly Glu Ile Ala Leu Leu
            340                 345                 350

Val Lys Arg Ile Gly Gly Val Leu His Gly Leu Val His Ala Arg Val
        355                 360                 365

Glu Ala Gly Tyr Lys Trp Thr Ala Glu Ile Ala Pro Thr Val Gln Cys
    370                 375                 380

Ser Val Ala Asn Tyr Gln Ser Thr Pro Ser Asn Asp Trp Pro Pro Phe
385                 390                 395                 400

Leu Asp Asp Val Leu Thr Ala Asp Pro Glu Thr Val Arg Tyr Glu Ser
                405                 410                 415

Ile Leu Ser Glu Gly Gly Arg Phe Tyr Gln Ala Gln Asn Arg Tyr
            420                 425                 430

Arg Ile Ile Glu Val His Glu Asp Phe Ala Ala Arg Pro Pro Ser Asp
        435                 440                 445

Phe Arg Trp Met Thr Leu Gly Gln Leu Gly Glu Leu Leu Arg Ser Thr
    450                 455                 460

His Phe Leu Asn Ile Gln Ala Arg Ser Leu Val Ala Ser Leu His Ser
465                 470                 475                 480

Leu Trp Ala Leu Gly Arg
                485

<210> SEQ ID NO 17
<211> LENGTH: 455
<212> TYPE: PRT
<213> ORGANISM: Saccharopolyspora spinosa

<400> SEQUENCE: 17

Val Ile Leu Gly Met Leu Pro Gly Cys Ser Ile Ala Ile Gly Glu Phe
1               5                   10                  15

Met Arg Val Leu Phe Thr Pro Leu Pro Ala Ser Ser His Phe Phe Asn
            20                  25                  30

Leu Val Pro Leu Ala Trp Ala Leu Arg Ala Ala Gly His Glu Val Arg
        35                  40                  45

Val Ala Ile Cys Pro Asn Met Val Ser Met Val Thr Gly Ala Gly Leu
    50                  55                  60

Thr Ala Val Pro Val Gly Asp Glu Leu Asp Leu Ile Ser Leu Ala Ala
65                  70                  75                  80

Lys Asn Glu Leu Val Leu Gly Ser Gly Val Ser Phe Asp Glu Lys Gly
                85                  90                  95

Arg His Pro Glu Leu Phe Asp Glu Leu Leu Ser Ile Asn Ser Gly Arg
            100                 105                 110

Asp Thr Asp Ala Val Glu Gln Leu His Leu Val Asp Asp Arg Ser Leu
        115                 120                 125

Asp Asp Leu Met Gly Phe Ala Glu Lys Trp Gln Pro Asp Leu Val Val
    130                 135                 140

Trp Asp Ala Met Val Cys Ser Gly Pro Val Val Ala Arg Ala Leu Gly
145                 150                 155                 160

Ala Arg His Val Arg Met Leu Val Ala Leu Asp Val Ser Gly Trp Leu
                165                 170                 175
```

```
Arg Ser Gly Phe Leu Glu Tyr Gln Glu Ser Lys Pro Pro Glu Gln Arg
            180                 185                 190

Val Asp Pro Leu Gly Thr Trp Leu Gly Ala Lys Leu Ala Lys Phe Gly
            195                 200                 205

Ala Thr Phe Asp Glu Glu Ile Val Thr Gly Gln Ala Thr Ile Asp Pro
            210                 215                 220

Ile Pro Ser Trp Met Arg Leu Pro Val Asp Leu Asp Tyr Ile Ser Met
225                 230                 235                 240

Arg Phe Val Pro Tyr Asn Gly Pro Ala Val Leu Pro Glu Trp Leu Arg
            245                 250                 255

Glu Arg Pro Thr Lys Pro Arg Val Cys Ile Thr Arg Gly Leu Thr Lys
            260                 265                 270

Arg Leu Ser Arg Val Thr Glu Gln Tyr Gly Glu Gln Ser Asp Gln
            275                 280                 285

Glu Gln Ala Met Val Glu Arg Leu Leu Arg Gly Ala Ala Arg Leu Asp
            290                 295                 300

Val Glu Val Ile Ala Thr Leu Ser Asp Asp Glu Val Arg Glu Met Gly
305                 310                 315                 320

Glu Leu Pro Ser Asn Val Arg Val His Glu Tyr Val Pro Leu Asn Glu
            325                 330                 335

Leu Leu Glu Ser Cys Ser Val Ile Ile His His Gly Ser Thr Thr Thr
            340                 345                 350

Gln Glu Thr Ala Thr Val Asn Gly Val Pro Gln Leu Ile Leu Pro Gly
            355                 360                 365

Thr Phe Trp Asp Glu Ser Arg Arg Ala Glu Leu Leu Ala Asp Arg Gly
            370                 375                 380

Ala Gly Leu Val Leu Asp Pro Ala Thr Phe Thr Glu Asp Asp Val Arg
385                 390                 395                 400

Gly Gln Leu Ala Arg Leu Leu Asp Glu Pro Ser Phe Ala Ala Asn Ala
            405                 410                 415

Ala Leu Ile Arg Arg Glu Ile Glu Glu Ser Pro Ser Pro His Asp Ile
            420                 425                 430

Val Pro Arg Leu Glu Lys Leu Val Ala Glu Arg Glu Asn Arg Arg Thr
            435                 440                 445

Gly Gln Ser Asp Gly His Pro
            450                 455

<210> SEQ ID NO 18
<211> LENGTH: 462
<212> TYPE: PRT
<213> ORGANISM: Saccharopolyspora spinosa

<400> SEQUENCE: 18

Met Gln Ser Arg Lys Thr Arg Ala Leu Gly Lys Gly Arg Ala Arg Val
1               5                   10                  15

Thr Ser Cys Asp Asp Thr Cys Ala Thr Ala Thr Glu Met Val Pro Asp
                20                  25                  30

Ala Lys Asp Arg Ile Leu Ala Ser Val Arg Asp Tyr His Arg Glu Gln
            35                  40                  45

Glu Ser Pro Thr Phe Val Ala Gly Ser Thr Pro Ile Arg Pro Ser Gly
        50                  55                  60

Ala Val Leu Asp Glu Asp Asp Arg Val Ala Leu Val Glu Ala Ala Leu
65                  70                  75                  80

Glu Leu Arg Ile Ala Ala Gly Gly Asn Ala Arg Arg Phe Glu Ser Glu
```

```
                      85                  90                  95
Phe Ala Arg Phe Phe Gly Leu Arg Lys Ala His Leu Val Asn Ser Gly
                100                 105                 110
Ser Ser Ala Asn Leu Leu Ala Leu Ser Ser Leu Thr Ser Pro Lys Leu
            115                 120                 125
Gly Glu Ala Arg Leu Arg Pro Gly Asp Glu Val Ile Thr Ala Ala Val
        130                 135                 140
Gly Phe Pro Thr Thr Ile Asn Pro Ala Val Gln Asn Gly Leu Val Pro
145                 150                 155                 160
Val Phe Val Asp Val Glu Leu Gly Thr Tyr Asn Ala Thr Pro Asp Arg
                165                 170                 175
Ile Lys Ala Ala Val Thr Glu Arg Thr Arg Ala Ile Met Leu Ala His
                180                 185                 190
Thr Leu Gly Asn Pro Phe Ala Ala Asp Glu Ile Ala Glu Ile Ala Lys
            195                 200                 205
Glu His Glu Leu Phe Leu Val Glu Asp Asn Cys Asp Ala Val Gly Ser
        210                 215                 220
Thr Tyr Arg Gly Arg Leu Thr Gly Thr Phe Gly Asp Leu Thr Thr Val
225                 230                 235                 240
Ser Phe Tyr Pro Ala His His Ile Thr Ser Gly Glu Gly Gly Cys Val
                245                 250                 255
Leu Thr Gly Ser Leu Glu Leu Ala Arg Ile Ile Glu Ser Leu Arg Asp
                260                 265                 270
Trp Gly Arg Asp Cys Trp Cys Glu Pro Gly Val Asp Asn Thr Cys Arg
            275                 280                 285
Lys Arg Phe Asp Tyr His Leu Gly Thr Leu Pro Pro Gly Tyr Asp His
        290                 295                 300
Lys Tyr Thr Phe Ser His Val Gly Tyr Asn Leu Lys Thr Thr Asp Leu
305                 310                 315                 320
Gln Ala Ala Leu Ala Leu Ser Gln Leu Ser Lys Ile Ser Ala Phe Gly
                325                 330                 335
Ser Ala Arg Arg Arg Asn Trp Arg Arg Leu Arg Glu Gly Leu Ser Gly
            340                 345                 350
Leu Pro Gly Leu Leu Leu Pro Val Ala Thr Pro His Ser Asp Pro Ser
        355                 360                 365
Trp Phe Gly Phe Ala Ile Thr Ile Ser Ala Asp Ala Gly Phe Thr Arg
370                 375                 380
Ala Ala Leu Val Asn Phe Leu Glu Ser Arg Asn Ile Gly Thr Arg Leu
385                 390                 395                 400
Leu Phe Gly Gly Asn Ile Thr Arg His Pro Ala Phe Glu Gln Val Arg
                405                 410                 415
Tyr Arg Ile Ala Asp Ala Leu Thr Asn Ser Asp Ile Val Thr Asp Arg
                420                 425                 430
Thr Phe Trp Val Gly Val Tyr Pro Gly Ile Thr Asp Gln Met Ile Asp
            435                 440                 445
Tyr Val Val Glu Ser Ile Ala Glu Phe Val Ala Lys Ser Ser
450                 455                 460

<210> SEQ ID NO 19
<211> LENGTH: 385
<212> TYPE: PRT
<213> ORGANISM: Saccharopolyspora spinosa

<400> SEQUENCE: 19
```

```
Val Ile Asn Leu His Gln Pro Ile Leu Gly Thr Glu Leu Asp Ala
 1               5                  10                 15

Ile Ala Glu Val Phe Ala Ser Asn Trp Ile Gly Leu Gly Pro Arg Thr
                 20                  25                  30

Arg Thr Phe Glu Ala Glu Phe Ala His His Leu Gly Val Asp Pro Glu
             35                  40                  45

Gln Val Val Phe Leu Asn Ser Gly Thr Ala Ala Leu Phe Leu Thr Val
     50                  55                  60

Gln Val Leu Asp Leu Gly Pro Gly Asp Asp Val Val Leu Pro Ser Ile
 65                  70                  75                  80

Ser Phe Val Ala Ala Asn Ala Ile Ala Ser Ser Gly Ala Arg Pro
                 85                  90                  95

Val Phe Cys Asp Val Asp Pro Arg Thr Leu Asn Pro Thr Leu Asp Asp
                100                 105                 110

Val Ala Arg Ala Ile Thr Pro Ala Thr Lys Ala Val Leu Leu Leu His
                115                 120                 125

Tyr Gly Gly Ser Pro Gly Glu Val Thr Ala Ile Ala Asp Phe Cys Arg
    130                 135                 140

Glu Lys Gly Leu Met Leu Ile Glu Asp Ser Ala Cys Ala Val Ala Ser
145                 150                 155                 160

Ser Val His Gly Thr Ala Cys Gly Thr Phe Gly Asp Leu Ala Thr Trp
                165                 170                 175

Ser Phe Asp Ala Met Lys Ile Leu Val Thr Gly Asp Gly Met Phe
                180                 185                 190

Tyr Ala Ala Asp Pro Glu Leu Ala His Arg Ala Arg Leu Ala Tyr
        195                 200                 205

His Gly Leu Glu Gln Met Ser Gly Phe Asp Ser Ala Lys Ser Ser Asn
    210                 215                 220

Arg Trp Trp Asp Ile Arg Val Glu Asp Ile Gly Gln Arg Leu Ile Gly
225                 230                 235                 240

Asn Asp Met Thr Ala Ala Leu Gly Ser Val Gln Leu Arg Lys Leu Pro
                245                 250                 255

Glu Phe Ile Asn Arg Arg Arg Glu Ile Ala Thr Gln Tyr Asp Arg Leu
                260                 265                 270

Leu Ser Asp Val Pro Gly Val Leu Leu Pro Pro Thr Leu Pro Asp Gly
        275                 280                 285

His Val Ser Ser His Tyr Phe Tyr Trp Val Gln Leu Ala Pro Glu Ile
    290                 295                 300

Arg Asp Gln Val Ala Gln Gln Met Leu Glu Arg Gly Ile Tyr Thr Ser
305                 310                 315                 320

Tyr Arg Tyr Pro Pro Leu His Lys Val Pro Ile Tyr Arg Ala Asp Cys
                325                 330                 335

Lys Leu Pro Ser Ala Glu Asp Ala Cys Arg Arg Thr Leu Leu Leu Pro
                340                 345                 350

Leu His Pro Ser Leu Asp Asp Ala Glu Val Arg Thr Val Ala Asp Glu
        355                 360                 365

Phe Gln Lys Ala Val Glu His His Ile Ser Gln Arg Ser Pro Leu Arg
370                 375                 380

Lys
385

<210> SEQ ID NO 20
<211> LENGTH: 249
<212> TYPE: PRT
```

<213> ORGANISM: Saccharopolyspora spinosa

<400> SEQUENCE: 20

```
Met Ser Arg Val Ser Asp Thr Phe Ala Glu Thr Ser Val Tyr Ser
 1               5                  10                  15

Pro Asp His Ala Asp Ile Tyr Asp Ala Ile His Ser Ala Arg Gly Arg
                 20                  25                  30

Asp Trp Ala Ala Glu Ala Gly Glu Val Val Gln Leu Val Arg Thr Arg
             35                  40                  45

Leu Pro Glu Ala Gln Ser Leu Leu Asp Val Ala Cys Gly Thr Gly Ala
 50                  55                  60

His Leu Glu Arg Phe Arg Ala Glu Tyr Ala Lys Val Ala Gly Leu Glu
 65                  70                  75                  80

Leu Ser Asp Ala Met Arg Glu Ile Ala Ile Arg Arg Val Pro Glu Val
                 85                  90                  95

Pro Ile His Ile Gly Asp Ile Arg Asp Phe Asp Leu Gly Glu Pro Phe
            100                 105                 110

Asp Val Ile Thr Cys Leu Cys Phe Thr Ala Ala Tyr Met Arg Thr Val
            115                 120                 125

Asp Asp Leu Arg Arg Val Thr Arg Asn Met Ala Arg His Leu Ala Pro
130                 135                 140

Gly Gly Val Ala Val Ile Glu Pro Trp Trp Phe Pro Asp Lys Phe Ile
145                 150                 155                 160

Asp Gly Phe Val Thr Gly Ala Val Ala His His Gly Glu Arg Val Ile
                165                 170                 175

Ser Arg Leu Ser His Ser Val Leu Glu Gly Arg Thr Ser Arg Met Thr
            180                 185                 190

Val Arg Tyr Thr Val Ala Glu Pro Thr Gly Ile Arg Asp Phe Thr Glu
        195                 200                 205

Phe Glu Ile Leu Ser Leu Phe Thr Glu Asp Tyr Thr Ala Ala Leu
    210                 215                 220

Glu Asp Ala Gly Ile Arg Ala Glu Tyr Leu Pro Gly Ala Pro Asn Gly
225                 230                 235                 240

Arg Gly Leu Phe Val Gly Ile Arg Asn
                245
```

<210> SEQ ID NO 21
<211> LENGTH: 255
<212> TYPE: PRT
<213> ORGANISM: Saccharopolyspora spinosa

<400> SEQUENCE: 21

```
Met Val Leu Val Pro Arg Arg Phe Arg Ala Thr Leu Glu Ser Met Ser
 1               5                  10                  15

Glu Gln Thr Ile Ala Leu Val Thr Gly Ala Asn Lys Gly Ile Gly Tyr
                 20                  25                  30

Glu Ile Ala Ala Gly Leu Gly Ala Leu Gly Trp Ser Val Gly Ile Gly
             35                  40                  45

Ala Arg Asp His Gln Arg Gly Glu Asp Ala Val Ala Lys Leu Arg Ala
 50                  55                  60

Asp Gly Val Asp Ala Phe Ala Val Ser Leu Asp Val Thr Asp Asp Ala
 65                  70                  75                  80

Ser Val Ala Ala Ala Ala Leu Leu Glu Glu Arg Ala Gly Arg Leu
                 85                  90                  95

Asp Val Leu Val Asn Asn Ala Gly Ile Ala Gly Ala Trp Pro Glu Glu
```

-continued

```
                100                 105                 110
Pro Ser Thr Val Thr Pro Ala Ser Leu Arg Ala Val Glu Thr Asn
            115                 120                 125
Val Ile Gly Val Val Arg Val Thr Asn Ala Met Leu Pro Leu Leu Arg
    130                 135                 140
Arg Ser Glu Arg Pro Arg Ile Val Asn Gln Ser Ser His Val Ala Ser
145                 150                 155                 160
Leu Thr Leu Gln Thr Thr Pro Gly Val Asp Leu Gly Gly Ile Ser Gly
                165                 170                 175
Ala Tyr Ser Pro Ser Lys Thr Phe Leu Asn Ala Ile Thr Ile Gln Tyr
            180                 185                 190
Ala Lys Glu Leu Ser Asp Thr Asn Ile Lys Ile Asn Asn Ala Cys Pro
        195                 200                 205
Gly Tyr Val Ala Thr Asp Leu Asn Gly Phe His Gly Thr Ser Thr Pro
    210                 215                 220
Ala Asp Gly Ala Arg Ile Ala Ile Arg Leu Ala Thr Leu Pro Asp Asp
225                 230                 235                 240
Gly Pro Thr Gly Gly Met Phe Asp Asp Ala Gly Asn Val Pro Trp
                245                 250                 255

<210> SEQ ID NO 22
<211> LENGTH: 278
<212> TYPE: PRT
<213> ORGANISM: Saccharopolyspora spinosa

<400> SEQUENCE: 22

Met Glu Thr Arg Glu Leu Arg Tyr Phe Val Ala Val Ala Glu Glu Leu
 1               5                  10                  15
His Phe Gly Arg Ala Ala Gln Arg Leu Gly Ile Ala Gln Pro Pro Leu
                20                  25                  30
Ser Arg Thr Ile Ala Gln Leu Glu Gln Arg Leu Gly Val Val Leu Leu
            35                  40                  45
Gln Arg Thr Ser Arg Lys Val Ser Leu Thr Glu Ala Gly Ala Met Leu
        50                  55                  60
Leu Thr Glu Gly Arg Ala Ile Leu Gly Ala Leu Ala Ala Glu Arg
 65                 70                  75                  80
Arg Thr Gln Arg Ala Ala Thr Ser Gln Pro Ser Leu Val Leu Ala Ala
                85                  90                  95
Lys Ala Gly Ala Ser Gly Glu Leu Leu Ala Lys Leu Leu Asp Ala Tyr
            100                 105                 110
Ala Ala Glu Pro Gly Ala Val Ala Val Asp Leu Leu Leu Cys Glu Ser
        115                 120                 125
Gln Pro Gln Lys Thr Leu His Asp Gly Arg Ala Asp Val Ala Leu Leu
    130                 135                 140
His Gln Pro Phe Asp Pro Thr Ala Glu Leu Asp Ile Glu Ile Leu Asn
145                 150                 155                 160
Thr Glu Gln Gln Val Ala Ile Leu Pro Thr Ser His Pro Leu Ala Ser
                165                 170                 175
Glu Pro His Val Arg Met Ala Asp Val Ser Ser Leu Pro Asp Leu Pro
            180                 185                 190
Leu Ala Arg Trp Pro Gly Pro Asp Gly Val Tyr Pro Asp Gly Pro Gly
        195                 200                 205
Val Glu Val Arg Asn Gln Thr Gln Leu Phe Gln Met Ile Ala Leu Gly
    210                 215                 220
```

```
Arg Thr Thr Val Val Met Pro Glu Ser Ser Arg Val Asn Leu Leu Glu
225                 230                 235                 240

Gly Leu Ala Ala Val Pro Val Leu Asp Ala Pro Asp Val Thr Thr Val
                245                 250                 255

Ile Ala Trp Pro Pro His Ser Arg Ser Arg Ala Leu Ala Gly Leu Val
                260                 265                 270

Arg Val Ala Thr Leu Leu
        275
```

<210> SEQ ID NO 23
<211> LENGTH: 198
<212> TYPE: PRT
<213> ORGANISM: Saccharopolyspora spinosa

<400> SEQUENCE: 23

```
Met Met Leu Lys Arg His Arg Leu Thr Thr Ala Ile Thr Gly Leu Leu
1               5                   10                  15

Gly Gly Val Leu Leu Val Ser Gly Cys Gly Thr Ala Ala Ala Leu Gln
            20                  25                  30

Ser Ser Pro Ala Pro Gly His Asp Ala Arg Asn Val Gly Met Ala Ser
        35                  40                  45

Gly Gly Gly Gly Gly Asp Ile Gly Thr Ser Asn Cys Ser Glu Ala Asp
    50                  55                  60

Phe Leu Ala Thr Ala Thr Pro Val Lys Gly Asp Pro Gly Ser Phe Ile
65                  70                  75                  80

Val Ala Tyr Gly Asn Arg Ser Asp Lys Thr Cys Thr Ile Asn Gly Gly
                85                  90                  95

Val Pro Asn Leu Lys Gly Val Asp Met Ser Asn Ser Pro Ile Glu Asp
            100                 105                 110

Leu Pro Val Glu Asp Val Arg Leu Pro Asp Ala Pro Lys Glu Phe Thr
        115                 120                 125

Leu Gln Pro Gly Gln Ser Ala Tyr Ala Gly Ile Gly Met Val Leu Ala
    130                 135                 140

Asp Ser Gly Asp Pro Asn Ala His Val Leu Thr Gly Phe Gln Ser Ser
145                 150                 155                 160

Leu Pro Asp Met Ser Glu Ala Gln Pro Val Asn Val Leu Gly Asp Gly
                165                 170                 175

Asn Val Lys Phe Ala Ala Lys Tyr Leu Arg Val Ser Ser Leu Val Ser
            180                 185                 190

Thr Ala Asp Glu Leu Arg
        195
```

<210> SEQ ID NO 24
<211> LENGTH: 751
<212> TYPE: PRT
<213> ORGANISM: Saccharopolyspora spinosa

<400> SEQUENCE: 24

```
Val Leu Ser Val Glu Lys Gly Arg Glu Ser Ala Thr Trp Thr Ala Val
1               5                   10                  15

Leu Glu Gly Thr Leu Glu Arg Ile Thr Phe Ala Asn Glu Glu Ser Gly
            20                  25                  30

Tyr Thr Val Ala Arg Ile Asp Thr Gly Arg Gly Gly Asp Leu Val Thr
        35                  40                  45

Val Val Gly Ala Leu Leu Gly Ala Gln Pro Gly Glu Ala Leu Arg Met
    50                  55                  60
```

-continued

```
Arg Gly Arg Trp Gly Ser His Pro Gln Tyr Gly Arg Gln Phe His Val
 65                  70                  75                  80

Asp Asp Tyr Thr Thr Val Leu Pro Ala Thr Val Gln Gly Ile Arg Arg
                 85                  90                  95

Tyr Leu Gly Ser Gly Leu Ile Lys Gly Ile Gly Pro Lys Leu Ala Glu
            100                 105                 110

Lys Ile Val Asp His Phe Gly Val Ala Ala Leu Asp Val Ile Glu Gln
        115                 120                 125

Glu Pro Ala Arg Leu Ile Glu Val Pro Lys Leu Gly Pro Lys Arg Thr
    130                 135                 140

Lys Leu Ile Ala Asp Ala Trp Glu Glu Gln Lys Ala Ile Lys Glu Val
145                 150                 155                 160

Met Ile Phe Leu Gln Gly Val Gly Val Ser Thr Ser Leu Ala Val Lys
                165                 170                 175

Ile Tyr Lys Gln Tyr His Asp Asp Ala Ile Arg Thr Val Lys Glu Glu
            180                 185                 190

Pro Tyr Arg Leu Ala Gly Asp Val Trp Gly Ile Gly Phe Lys Thr Ala
        195                 200                 205

Asp Thr Ile Ala Lys Ala Val Gly Ile Pro His Asp Ser Pro Gln Arg
    210                 215                 220

Val Lys Ala Gly Leu Gln Phe Thr Leu Ser Glu Ser Thr Gly Asp Gly
225                 230                 235                 240

Asn Cys Tyr Leu Pro Glu Asn Glu Leu Ile Ala Glu Ala Val Lys Ile
                245                 250                 255

Leu Ala Val Asp Thr Gly Leu Val Ile Glu Cys Leu Ala Glu Leu Val
            260                 265                 270

Thr Glu Glu Gly Val Val Arg Glu Glu Ile Pro Thr Asp Asp Asp Glu
        275                 280                 285

Val Pro Thr Val Ala Ile Tyr Leu Val Pro Phe His Arg Ala Glu Val
    290                 295                 300

Ala Leu Ala Asn Gln Leu Ser Arg Leu Leu Asn Thr Ser Ala Asp Arg
305                 310                 315                 320

Met Pro Val Phe Ala Asp Val Asp Trp His Lys Ala Leu Asp Trp Leu
                325                 330                 335

Arg Arg Ala Thr Gly Ala Glu Leu Ala Glu Ala Gln Glu Arg Ala Val
            340                 345                 350

Lys Leu Ala Leu Thr Glu Lys Val Ala Val Leu Thr Gly Gly Pro Gly
        355                 360                 365

Cys Gly Lys Ser Phe Thr Val Arg Ser Ile Ile Ala Leu Ala Gln Ala
    370                 375                 380

Lys Lys Ala Lys Val Ile Leu Ala Ala Pro Thr Gly Arg Ala Ala Lys
385                 390                 395                 400

Arg Leu Thr Glu Leu Thr Gly His Asp Ala Ala Thr Val His Arg Leu
                405                 410                 415

Leu Gln Leu Gln Pro Gly Gly Asp Ala Ala Tyr Asp Arg Asp Asn Pro
            420                 425                 430

Leu Asp Ala Asp Leu Val Val Asp Glu Ala Ser Met Leu Asp Leu
        435                 440                 445

Leu Leu Ala Asn Lys Leu Ala Lys Ala Ile Ala Pro Gly Ala His Leu
    450                 455                 460

Leu Leu Val Gly Asp Val Asp Gln Leu Pro Ser Val Gly Ala Gly Glu
465                 470                 475                 480

Val Leu Arg Asp Leu Leu Ala Pro Gly Thr Pro Ile Pro His Val Arg
```

-continued

```
                        485                 490                 495
Leu Asn Glu Val Phe Arg Gln Ala Ala Glu Ser Gly Val Val Thr Asn
            500                 505                 510
Ala His Arg Ile Asn Ala Gly Asp Tyr Pro Leu Thr His Gly Leu Thr
        515                 520                 525
Asp Phe Phe Leu Phe His Val Glu Glu Ser Glu Pro Thr Ala Glu Leu
    530                 535                 540
Thr Val Asp Val Val Ala Arg Arg Ile Pro Arg Lys Phe Arg Phe Asn
545                 550                 555                 560
Pro Arg Thr Asp Val Gln Val Leu Ala Pro Met His Arg Gly Pro Ala
                565                 570                 575
Gly Ala Gly Ala Leu Asn Gln Leu Leu Gln Glu Ala Ile Thr Pro Ala
            580                 585                 590
Arg Glu Gly Leu Pro Glu Arg Arg Phe Gly Gly Arg Ile Phe Arg Val
        595                 600                 605
Gly Asp Lys Val Thr Gln Ile Arg Asn Asn Tyr Asp Lys Gly Ala Asn
    610                 615                 620
Gly Val Phe Asn Gly Thr Gln Gly Val Val Ser Ala Leu Asp Asn Glu
625                 630                 635                 640
Ala Gln Thr Met Thr Val Arg Thr Asp Glu Asp Glu Asp Ile Asp Tyr
                645                 650                 655
Asp Phe Thr Glu Leu Asp Glu Leu Val His Ala Tyr Ala Val Thr Ile
            660                 665                 670
His Arg Ser Gln Gly Ser Glu Tyr Pro Cys Val Val Ile Pro Leu Thr
        675                 680                 685
Thr Ser Ala Trp Met Met Leu Gln Arg Asn Leu Leu Tyr Thr Ala Val
    690                 695                 700
Thr Arg Ala Lys Lys Val Val Leu Val Gly Ser Lys Lys Ala Leu
705                 710                 715                 720
Gly Gln Ala Val Arg Thr Val Gly Ser Gly Arg His Thr Ala Leu
                725                 730                 735
Asp His Arg Leu Arg Arg Gly Gly Thr Gly Ser Arg Pro Ala Ala
            740                 745                 750
```

<210> SEQ ID NO 25
<211> LENGTH: 2310
<212> TYPE: DNA
<213> ORGANISM: Saccharopolyspora spinosa
<220> FEATURE:
<221> NAME/KEY: CDS
<222> LOCATION: (88)..(1077)
<220> FEATURE:
<221> NAME/KEY: CDS
<222> LOCATION: (1165)..(1992)

<400> SEQUENCE: 25

```
ggatcctgct tcgtagctcg gtgtgtcatg ccagactgcg cacgcggacc tgcagcgggc      60
cgcgaaatcc cggcgaggaa gggcgcg atg cgg att ctg gtc acc ggc gga gcc     114
                                Met Arg Ile Leu Val Thr Gly Gly Ala
                                  1               5 ggt ttc atc ggc tcg cac tac gtt cgg cag ttg ctc ggt ggt gcg tac       162
Gly Phe Ile Gly Ser His Tyr Val Arg Gln Leu Leu Gly Gly Ala Tyr
 10                  15                  20                  25 ccc gca ttc gcc gac gcc gac gtg gtc gtg ctc gac aag ctc acc tac       210
Pro Ala Phe Ala Asp Ala Asp Val Val Val Leu Asp Lys Leu Thr Tyr
                 30                  35                  40 gcc ggc aac gag gcg aac ctg gcg ccg gtc gcg gac aac ccc cgg ctg       258
```

-continued

|  |  |
|---|---|
| Ala Gly Asn Glu Ala Asn Leu Ala Pro Val Ala Asp Asn Pro Arg Leu<br>              45                     50                    55 |  |
| aag ttc gtc tgc ggc gac atc tgc gac cgc gaa ctg gtt ggc ggc ctg<br>Lys Phe Val Cys Gly Asp Ile Cys Asp Arg Glu Leu Val Gly Gly Leu<br>           60                     65                     70 | 306 |
| atg tcc ggc gtg gac gtg gtg gtg cac ttc gcc gcc gaa acc cac gtc<br>Met Ser Gly Val Asp Val Val Val His Phe Ala Ala Glu Thr His Val<br> 75                   80                     85 | 354 |
| gac cgc tcg atc acc ggc tcg gac gcc ttc gtg atc acc aac gtg gtc<br>Asp Arg Ser Ile Thr Gly Ser Asp Ala Phe Val Ile Thr Asn Val Val<br> 90                   95                 100             105 | 402 |
| ggc acc aac gtg ctg ctg cag gcc gcg ctc gac gcc gag atc ggc aag<br>Gly Thr Asn Val Leu Leu Gln Ala Ala Leu Asp Ala Glu Ile Gly Lys<br>              110                    115                   120 | 450 |
| ttc gtg cac gtt tcc acc gac gag gtc tac ggc tcc atc gag gac ggc<br>Phe Val His Val Ser Thr Asp Glu Val Tyr Gly Ser Ile Glu Asp Gly<br>                 125                    130                 135 | 498 |
| tcg tgg ccc gaa gac cac gcg ctg gag ccg aat tcc ccg tac tcg gcg<br>Ser Trp Pro Glu Asp His Ala Leu Glu Pro Asn Ser Pro Tyr Ser Ala<br>          140                    145                    150 | 546 |
| gcg aaa gcg ggc tcg gac ctg ctg gcc cgc gcc tac cac cgc acc cac<br>Ala Lys Ala Gly Ser Asp Leu Leu Ala Arg Ala Tyr His Arg Thr His<br> 155                   160                   165 | 594 |
| gga ctg ccg gtg tgc atc acc cgc tgc tcc aac aac tac ggg ccc tac<br>Gly Leu Pro Val Cys Ile Thr Arg Cys Ser Asn Asn Tyr Gly Pro Tyr<br>170                    175                   180               185 | 642 |
| cag ttc ccg gag aag gtg ctg ccg ctg ttc atc acg aac ctg atg gac<br>Gln Phe Pro Glu Lys Val Leu Pro Leu Phe Ile Thr Asn Leu Met Asp<br>              190                    195                   200 | 690 |
| ggc agc cag gtg ccg ctc tac ggc gac ggg ctc aac gtg cgg gac tgg<br>Gly Ser Gln Val Pro Leu Tyr Gly Asp Gly Leu Asn Val Arg Asp Trp<br>                 205                    210                 215 | 738 |
| ctg cac gtc agc gac cac tgc cgg ggc atc cag ctg gtg gcc gac tcc<br>Leu His Val Ser Asp His Cys Arg Gly Ile Gln Leu Val Ala Asp Ser<br>          220                    225                    230 | 786 |
| ggg cgc gcg ggc gag atc tac aac atc ggc ggc ggc acc gag ctg acc<br>Gly Arg Ala Gly Glu Ile Tyr Asn Ile Gly Gly Gly Thr Glu Leu Thr<br> 235                   240                   245 | 834 |
| aac aac gag ctg acc gag cgg ctg ctg gca gag ctg ggc ctc gac tgg<br>Asn Asn Glu Leu Thr Glu Arg Leu Leu Ala Glu Leu Gly Leu Asp Trp<br>250                    255                   260               265 | 882 |
| tcg gtg gtg cgg ccg gtc acc gac cgc aag ggc cac gac cgc gcc tac<br>Ser Val Val Arg Pro Val Thr Asp Arg Lys Gly His Asp Arg Arg Tyr<br>              270                    275                 280 | 930 |
| tcg gtg gac cac agc aag atc gtc gag gaa ctg ggg tac gcg ccg cag<br>Ser Val Asp His Ser Lys Ile Val Glu Glu Leu Gly Tyr Ala Pro Gln<br>                 285                    290                 295 | 978 |
| gtc gac ttc gag acc ggg ctg cgc gag aca atc cgc tgg tac cag gac<br>Val Asp Phe Glu Thr Gly Leu Arg Glu Thr Ile Arg Trp Tyr Gln Asp<br>          300                    305                    310 | 1026 |
| aac cgg gac tgg tgg gag ccg ctg aag gcc cga tcg gcg gtg gct cga<br>Asn Arg Asp Trp Trp Glu Pro Leu Lys Ala Arg Ser Ala Val Ala Arg<br> 315                    320                   325 | 1074 |
| tga gtcgcctcgc cgtgctggtt gcccggcggc cgcggccagc tgggctcgga | 1127 |
| gctggcccgg atcctcgccg cgcggacggg ggcgctg gtg cac cgg ccg ggt tcc<br>                                                                        Val His Arg Pro Gly Ser<br>                                                                           330                    335 | 1182 |
| ggg gaa ctg gac gtc acc gac gcc gag gag gtc gcc gac gcg ttg ggt<br>Gly Glu Leu Asp Val Thr Asp Ala Glu Glu Val Ala Asp Ala Leu Gly | 1230 |

-continued

```
                     340                 345                 350
tcc ttc gcg gag acg gcg aag gac gcg gag ctg cga ccg gtg gtg atc     1278
Ser Phe Ala Glu Thr Ala Lys Asp Ala Glu Leu Arg Pro Val Val Ile
                355                 360                 365 aac gcc gcg gcg tac acg gcg gtg gac gcg gcc gag tcc gac ccg gac     1326
Asn Ala Ala Ala Tyr Thr Ala Val Asp Ala Ala Glu Ser Asp Pro Asp
            370                 375                 380 cgc gcg gcc cgg atc aac gcc gaa ggc gcg gcc tcg ctg gcg aaa gcg     1374
Arg Ala Ala Arg Ile Asn Ala Glu Gly Ala Ala Ser Leu Ala Lys Ala
        385                 390                 395 tgc cgg agc agc ggt ctg ccc ctg gtg cac gtg tcg acg gat tac gtg     1422
Cys Arg Ser Ser Gly Leu Pro Leu Val His Val Ser Thr Asp Tyr Val
400                 405                 410                 415 ttc ccc cgt gat ggg gcc cgg ccg tac gag ccg acg gac ccg acc ggg     1470
Phe Pro Arg Asp Gly Ala Arg Pro Tyr Glu Pro Thr Asp Pro Thr Gly
                420                 425                 430 ccg cga tcg gtc tac ggg cgc acc aag ctc gaa ggc gaa cgg gcc gtg     1518
Pro Arg Ser Val Tyr Gly Arg Thr Lys Leu Glu Gly Glu Arg Ala Val
            435                 440                 445 ctg gag tcc ggc gcg cgg gcc tgg gtg gtg cgc acg gca tgg gtg tac     1566
Leu Glu Ser Gly Ala Arg Ala Trp Val Val Arg Thr Ala Trp Val Tyr
        450                 455                 460 ggc gcg agc ggc aag aac ttc ctg aaa acg atg atc cgc ctc tcg ggg     1614
Gly Ala Ser Gly Lys Asn Phe Leu Lys Thr Met Ile Arg Leu Ser Gly
465                 470                 475 gag cgc gac acg ctg tcc gtt gtg gac aat cag atc ggc tcg ccg act     1662
Glu Arg Asp Thr Leu Ser Val Val Asp Asn Gln Ile Gly Ser Pro Thr
480                 485                 490                 495 tgg gcg gcg gac ctg gcg agc ggc ctg ctg gag ctg gcc gaa cgg gtc     1710
Trp Ala Ala Asp Leu Ala Ser Gly Leu Leu Glu Leu Ala Glu Arg Val
                500                 505                 510 gcc gaa cgc cgt gga ccg gag cag aag gtg ctg cac tgc acc aat tcc     1758
Ala Glu Arg Arg Gly Pro Glu Gln Lys Val Leu His Cys Thr Asn Ser
            515                 520                 525 ggc cag gtg acc tgg tac gag ttc gcg cgg gcg atc ttc gcg gaa ttc     1806
Gly Gln Val Thr Trp Tyr Glu Phe Ala Arg Ala Ile Phe Ala Glu Phe
        530                 535                 540 ggc ctg gac gag aac cgc gtc cac ccg tgc acg acg gcg gac ttc ccc     1854
Gly Leu Asp Glu Asn Arg Val His Pro Cys Thr Thr Ala Asp Phe Pro
545                 550                 555 ctc ccg gcg cac cgc ccg gcc tac tcg gtc ctg tcc gac gtg gcg tgg     1902
Leu Pro Ala His Arg Pro Ala Tyr Ser Val Leu Ser Asp Val Ala Trp
560                 565                 570                 575 cga gag gcg ggc ctg acc ccg atg cgc acc tgg cgg gaa gcc ctg gcg     1950
Arg Glu Ala Gly Leu Thr Pro Met Arg Thr Trp Arg Glu Ala Leu Ala
                580                 585                 590 gcg gcc ttc gag aaa gac ggc gaa acc ctc cga acc cgc tga             1992
Ala Ala Phe Glu Lys Asp Gly Glu Thr Leu Arg Thr Arg
            595                 400 ccagtcaccc ggagggcgcg agtagccccg gcagggccgt ttcgacgcga tatcggctgg   2052
cgcggtgcgc acaatgggtg tcgccggggc gaggaaggaa ggccaggtgc ccgggggca    2112 tgactgggag cctggcctga tgcctgtccg gggcgttcag cctgcggcga ggcggtatgc   2172
gttcagggtt gcttcggcgc aggttcgcca ggtgaaggct ttagcttggg cacggccctt   2232
ttccgcgtct gggggactgg tcagggcttg gtgcaggggct tcgttgaggg ccgtcgggtc  2292
gccgtggggg aagcggat                                                 2310
```

```
<210> SEQ ID NO 26
<211> LENGTH: 329
<212> TYPE: PRT
<213> ORGANISM: Saccharopolyspora spinosa

<400> SEQUENCE: 26
```

| | | | | | | | | | | | | | | | |
|---|---|---|---|---|---|---|---|---|---|---|---|---|---|---|---|
| Met | Arg | Ile | Leu | Val | Thr | Gly | Gly | Ala | Gly | Phe | Ile | Gly | Ser | His | Tyr |
| 1 | | | | 5 | | | | | 10 | | | | | 15 | |
| Val | Arg | Gln | Leu | Leu | Gly | Gly | Ala | Tyr | Pro | Ala | Phe | Ala | Asp | Ala | Asp |
| | | | | 20 | | | | | 25 | | | | | 30 | |
| Val | Val | Val | Leu | Asp | Lys | Leu | Thr | Tyr | Ala | Gly | Asn | Glu | Ala | Asn | Leu |
| | | | 35 | | | | | 40 | | | | | 45 | | |
| Ala | Pro | Val | Ala | Asp | Asn | Pro | Arg | Leu | Lys | Phe | Val | Cys | Gly | Asp | Ile |
| | | 50 | | | | | 55 | | | | | 60 | | | |
| Cys | Asp | Arg | Glu | Leu | Val | Gly | Gly | Leu | Met | Ser | Gly | Val | Asp | Val | Val |
| 65 | | | | | 70 | | | | | 75 | | | | | 80 |
| Val | His | Phe | Ala | Ala | Glu | Thr | His | Val | Asp | Arg | Ser | Ile | Thr | Gly | Ser |
| | | | | 85 | | | | | 90 | | | | | 95 | |
| Asp | Ala | Phe | Val | Ile | Thr | Asn | Val | Val | Gly | Thr | Asn | Val | Leu | Leu | Gln |
| | | | | 100 | | | | | 105 | | | | | 110 | |
| Ala | Ala | Leu | Asp | Ala | Glu | Ile | Gly | Lys | Phe | Val | His | Val | Ser | Thr | Asp |
| | | | 115 | | | | | 120 | | | | | 125 | | |
| Glu | Val | Tyr | Gly | Ser | Ile | Glu | Asp | Gly | Ser | Trp | Pro | Glu | Asp | His | Ala |
| | | | 130 | | | | | 135 | | | | | 140 | | |
| Leu | Glu | Pro | Asn | Ser | Pro | Tyr | Ser | Ala | Ala | Lys | Ala | Gly | Ser | Asp | Leu |
| 145 | | | | | 150 | | | | | 155 | | | | | 160 |
| Leu | Ala | Arg | Ala | Tyr | His | Arg | Thr | His | Gly | Leu | Pro | Val | Cys | Ile | Thr |
| | | | | 165 | | | | | 170 | | | | | 175 | |
| Arg | Cys | Ser | Asn | Asn | Tyr | Gly | Pro | Tyr | Gln | Phe | Pro | Glu | Lys | Val | Leu |
| | | | | 180 | | | | | 185 | | | | | 190 | |
| Pro | Leu | Phe | Ile | Thr | Asn | Leu | Met | Asp | Gly | Ser | Gln | Val | Pro | Leu | Tyr |
| | | | 195 | | | | | 200 | | | | | 205 | | |
| Gly | Asp | Gly | Leu | Asn | Val | Arg | Asp | Trp | Leu | His | Val | Ser | Asp | His | Cys |
| | | | 210 | | | | | 215 | | | | | 220 | | |
| Arg | Gly | Ile | Gln | Leu | Val | Ala | Asp | Ser | Gly | Arg | Ala | Gly | Glu | Ile | Tyr |
| 225 | | | | | 230 | | | | | 235 | | | | | 240 |
| Asn | Ile | Gly | Gly | Gly | Thr | Glu | Leu | Thr | Asn | Asn | Glu | Leu | Thr | Glu | Arg |
| | | | | 245 | | | | | 250 | | | | | 255 | |
| Leu | Leu | Ala | Glu | Leu | Gly | Leu | Asp | Trp | Ser | Val | Val | Arg | Pro | Val | Thr |
| | | | | 260 | | | | | 265 | | | | | 270 | |
| Asp | Arg | Lys | Gly | His | Asp | Arg | Arg | Tyr | Ser | Val | Asp | His | Ser | Lys | Ile |
| | | | 275 | | | | | 280 | | | | | 285 | | |
| Val | Glu | Glu | Leu | Gly | Tyr | Ala | Pro | Gln | Val | Asp | Phe | Glu | Thr | Gly | Leu |
| | | | 290 | | | | | 295 | | | | | 300 | | |
| Arg | Glu | Thr | Ile | Arg | Trp | Tyr | Gln | Asp | Asn | Arg | Asp | Trp | Trp | Glu | Pro |
| 305 | | | | | 310 | | | | | 315 | | | | | 320 |
| Leu | Lys | Ala | Arg | Ser | Ala | Val | Ala | Arg | | | | | | | |
| | | | | 325 | | | | | | | | | | | |

```
<210> SEQ ID NO 27
<211> LENGTH: 275
<212> TYPE: PRT
<213> ORGANISM: Saccharopolyspora spinosa

<400> SEQUENCE: 27
```

| | | | | | | | | | | | | | | | |
|---|---|---|---|---|---|---|---|---|---|---|---|---|---|---|---|
| Val | His | Arg | Pro | Gly | Ser | Gly | Glu | Leu | Asp | Val | Thr | Asp | Ala | Glu | Glu |

```
                1               5              10              15
            Val Ala Asp Ala Leu Gly Ser Phe Ala Glu Thr Ala Lys Asp Ala Glu
                            20                  25                  30

Leu Arg Pro Val Val Ile Asn Ala Ala Tyr Thr Ala Val Asp Ala
                        35                  40                  45

Ala Glu Ser Asp Pro Asp Arg Ala Ala Arg Ile Asn Ala Glu Gly Ala
                            50                  55                  60

Ala Ser Leu Ala Lys Ala Cys Arg Ser Ser Gly Leu Pro Leu Val His
             65                 70                  75                  80

Val Ser Thr Asp Tyr Val Phe Pro Arg Asp Gly Ala Arg Pro Tyr Glu
                            85                  90                  95

Pro Thr Asp Pro Thr Gly Pro Arg Ser Val Tyr Gly Arg Thr Lys Leu
                            100                 105                 110

Glu Gly Glu Arg Ala Val Leu Glu Ser Gly Ala Arg Ala Trp Val Val
                        115                 120                 125

Arg Thr Ala Trp Val Tyr Gly Ala Ser Gly Lys Asn Phe Leu Lys Thr
                        130                 135                 140

Met Ile Arg Leu Ser Gly Glu Arg Asp Thr Leu Ser Val Val Asp Asn
            145                 150                 155                 160

Gln Ile Gly Ser Pro Thr Trp Ala Ala Asp Leu Ala Ser Gly Leu Leu
                            165                 170                 175

Glu Leu Ala Glu Arg Val Ala Glu Arg Arg Gly Pro Glu Gln Lys Val
                        180                 185                 190

Leu His Cys Thr Asn Ser Gly Gln Val Thr Trp Tyr Glu Phe Ala Arg
                        195                 200                 205

Ala Ile Phe Ala Glu Phe Gly Leu Asp Glu Asn Arg Val His Pro Cys
                        210                 215                 220

Thr Thr Ala Asp Phe Pro Leu Pro Ala His Arg Pro Ala Tyr Ser Val
            225                 230                 235                 240

Leu Ser Asp Val Ala Trp Arg Glu Ala Gly Leu Thr Pro Met Arg Thr
                            245                 250                 255

Trp Arg Glu Ala Leu Ala Ala Phe Glu Lys Asp Gly Glu Thr Leu
                        260                 265                 270

Arg Thr Arg
                    275

<210> SEQ ID NO 28
<211> LENGTH: 1272
<212> TYPE: DNA
<213> ORGANISM: Saccharopolyspora spinosa
<220> FEATURE:
<221> NAME/KEY: CDS
<222> LOCATION: (334)..(1119)

<400> SEQUENCE: 28
aaggccaccg gcaaggtcgt gcagggcatc tcgcaggacg tcgcgaagaa gatctccaag      60
aagatccgcg acgagggccc gaagggcgtt caggcccaga tccagggcga gcagctgcgg     120
gtgtccggca agaagaagga cgacctgcag gccgtgatcc agttgctgaa gtcgagcgac     180
ttcgacgtcg cgctccagtt cgagaatttc cggtaatcca ccgctggagg tatccgggtg     240
aaggggatct gctggcgggt ggcaacgggg accggctgca tccgctgac gcaggccgtg      300 tccaaacagc tacttccggt gtacgacaag ccg atg atc tac tac ccg ctg tcg     354
                                    Met Ile Tyr Tyr Pro Leu Ser
                                     1               5 gtg ctg atg ctg gcc ggc atc cgg gac gtg ctg ctg atc tcg acc ccg      402
```

```
                    Val Leu Met Leu Ala Gly Ile Arg Asp Val Leu Leu Ile Ser Thr Pro
                                10                  15                  20 gcc gac atg ccg ttg ttc cag cgg ctg ctc ggg aac ggg tcg cag ttc        450
Ala Asp Met Pro Leu Phe Gln Arg Leu Leu Gly Asn Gly Ser Gln Phe
         25                  30                  35 ggc att cgg atc gag tac gcc gag cag tcc cag ccc aac ggg cta gcc        498
Gly Ile Arg Ile Glu Tyr Ala Glu Gln Ser Gln Pro Asn Gly Leu Ala
 40                  45                  50                  55 gag gcg ttc gtg atc ggt gcc gac ttc gtc ggc gac gac tcg gtg gcg        546
Glu Ala Phe Val Ile Gly Ala Asp Phe Val Gly Asp Asp Ser Val Ala
                 60                  65                  70 ttg gtg ctc ggc gac aac atc ttt tac ggg cag ggc ttt tcc ggg atc        594
Leu Val Leu Gly Asp Asn Ile Phe Tyr Gly Gln Gly Phe Ser Gly Ile
             75                  80                  85 ctc cag cag tgc gtc cgg gag ctc gac ggc tgc acg ctg ttc ggc tac        642
Leu Gln Gln Cys Val Arg Glu Leu Asp Gly Cys Thr Leu Phe Gly Tyr
         90                  95                 100 ccg gtc cgc gac ccg cag cgc tac ggc gtc ggt gag gtg gac gac gac        690
Pro Val Arg Asp Pro Gln Arg Tyr Gly Val Gly Glu Val Asp Asp Asp
     105                 110                 115 ggt cgg ctg ttg tcc atc gtg gag aag ccg gag cgg ccg aag tcc aac        738
Gly Arg Leu Leu Ser Ile Val Glu Lys Pro Glu Arg Pro Lys Ser Asn
120                 125                 130                 135 atg gcc atc acc ggc ctg tac ttc tac gac aac gac gtg gtg cgc atc        786
Met Ala Ile Thr Gly Leu Tyr Phe Tyr Asp Asn Asp Val Val Arg Ile
                140                 145                 150 gcc aag ggg ctc acg ccg tcg gcc cgc ggc gag ctg gag atc acc gac        834
Ala Lys Gly Leu Thr Pro Ser Ala Arg Gly Glu Leu Glu Ile Thr Asp
            155                 160                 165 gtc aac ctg gcc tac ctg cag gag ggc cgg gcg cac ctg acc aag ctc        882
Val Asn Leu Ala Tyr Leu Gln Glu Gly Arg Ala His Leu Thr Lys Leu
        170                 175                 180 ggc cgc ggg ttc gcc tgg ctg gac acc ggg acc cac gac tcg cta gtg        930
Gly Arg Gly Phe Ala Trp Leu Asp Thr Gly Thr His Asp Ser Leu Val
    185                 190                 195 gag gcc tcg cag ttc gtg cag gtg ctg gag cac cgg cag ggc gtg cgg        978
Glu Ala Ser Gln Phe Val Gln Val Leu Glu His Arg Gln Gly Val Arg
200                 205                 210                 215 atc gcc tgc ctg gag gag atc ncc ctg cgc atg ggc tac atc tcg gcc       1026
Ile Ala Cys Leu Glu Glu Ile Xaa Leu Arg Met Gly Tyr Ile Ser Ala
                220                 225                 230 gac gac tgt ttc gcg ctg ggc gtg aag ctg gcc aag tcg ggc tac agc       1074
Asp Asp Cys Phe Ala Leu Gly Val Lys Leu Ala Lys Ser Gly Tyr Ser
            235                 240                 245 gag tac gtc atg gac gtc gcc cgc aac tcc ggc gcg cgg ggc tga           1119
Glu Tyr Val Met Asp Val Ala Arg Asn Ser Gly Ala Arg Gly
        250                 255                 260 cccgagctcg tccgatttcc attgaaatcg cggaccgtcg gcgtgtcgta gtccggtgcg    1179
ccgatattcc gggcggcgtc accaggccgg gggtagttgg tggccggcca tgccctccag    1239
gcggcgaaat gcggtcggcc atcggcgggt tgc                                  1272

<210> SEQ ID NO 29
<211> LENGTH: 261
<212> TYPE: PRT
<213> ORGANISM: Saccharopolyspora spinosa

<400> SEQUENCE: 29

Met Ile Tyr Tyr Pro Leu Ser Val Leu Met Leu Ala Gly Ile Arg Asp
  1               5                  10                  15
```

```
Val Leu Leu Ile Ser Thr Pro Ala Asp Met Pro Leu Phe Gln Arg Leu
             20                  25                  30

Leu Gly Asn Gly Ser Gln Phe Gly Ile Arg Ile Glu Tyr Ala Glu Gln
         35                  40                  45

Ser Gln Pro Asn Gly Leu Ala Glu Ala Phe Val Ile Gly Ala Asp Phe
     50                  55                  60

Val Gly Asp Asp Ser Val Ala Leu Val Leu Gly Asp Asn Ile Phe Tyr
 65                  70                  75                  80

Gly Gln Gly Phe Ser Gly Ile Leu Gln Gln Cys Val Arg Glu Leu Asp
                 85                  90                  95

Gly Cys Thr Leu Phe Gly Tyr Pro Val Arg Asp Pro Gln Arg Tyr Gly
            100                 105                 110

Val Gly Glu Val Asp Asp Gly Arg Leu Leu Ser Ile Val Glu Lys
        115                 120                 125

Pro Glu Arg Pro Lys Ser Asn Met Ala Ile Thr Gly Leu Tyr Phe Tyr
        130                 135                 140

Asp Asn Asp Val Val Arg Ile Ala Lys Gly Leu Thr Pro Ser Ala Arg
145                 150                 155                 160

Gly Glu Leu Glu Ile Thr Asp Val Asn Leu Ala Tyr Leu Gln Glu Gly
                165                 170                 175

Arg Ala His Leu Thr Lys Leu Gly Arg Gly Phe Ala Trp Leu Asp Thr
            180                 185                 190

Gly Thr His Asp Ser Leu Val Glu Ala Ser Gln Phe Val Gln Val Leu
        195                 200                 205

Glu His Arg Gln Gly Val Arg Ile Ala Cys Leu Glu Glu Ile Xaa Leu
    210                 215                 220

Arg Met Gly Tyr Ile Ser Ala Asp Asp Cys Phe Ala Leu Gly Val Lys
225                 230                 235                 240

Leu Ala Lys Ser Gly Tyr Ser Glu Tyr Val Met Asp Val Ala Arg Asn
                245                 250                 255

Ser Gly Ala Arg Gly
            260

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 30
ngsgtsggsn ssccaccttc cgg                                             23

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 31
catsangtcg tcytcsansg csacgaacgc gtg                                  33

<210> SEQ ID NO 32
<211> LENGTH: 1165
<212> TYPE: DNA
<213> ORGANISM: Artificial Sequence
<220> FEATURE:
```

<220> FEATURE:
<221> NAME/KEY: CDS
<222> LOCATION: (226)..(834)
<220> FEATURE:
<223> OTHER INFORMATION: Description of Artificial Sequence:pDAB1622

<400> SEQUENCE: 32

```
gggatcaaca acaacttcac cagcaggttc aacaatttgt caatcccact tggcagtacg      60
cgcgtccttt ttggatcggg attgcggcag tacgtgcacc cggtttcagt gccccatttc     120
gcagtacgta cgtccgtttt gaatatggcg atcaatggct cgcatgaccc atatcaactc     180
cgccccaccg aaccgcattc caaccaacgt cataggcttt cggcc gtg cag gta cgt    237
                                                  Val Gln Val Arg
                                                    1 cga ctt gac atc acg ggt gca tac gag ttc acc ccg aag gcc ttc ccc       285
Arg Leu Asp Ile Thr Gly Ala Tyr Glu Phe Thr Pro Lys Ala Phe Pro
  5                  10                  15                  20 gac cac cgg ggc ctg ttc gtg gcc ccg ttc cag gag gcg gcg ttc atc       333
Asp His Arg Gly Leu Phe Val Ala Pro Phe Gln Glu Ala Ala Phe Ile
                 25                  30                  35 gac gcc acg ggg cac ccg ctg cga gtc gcg cag acc aac cac agc gtc       381
Asp Ala Thr Gly His Pro Leu Arg Val Ala Gln Thr Asn His Ser Val
         40                  45                  50 tcg gcg cgc aac gtc atc cgc ggc gtg cac ttc tcg gac gtg ccg ccg       429
Ser Ala Arg Asn Val Ile Arg Gly Val His Phe Ser Asp Val Pro Pro
     55                  60                  65 ggc caa gcg aag tac gtg tac tgc ccg cag ggc gcg ctg ctc gac gtg       477
Gly Gln Ala Lys Tyr Val Tyr Cys Pro Gln Gly Ala Leu Leu Asp Val
 70                  75                  80 gtc atc gac atc cgg gtc ggt tcc ccg acc ttc ggc cgc tgg gag gcg       525
Val Ile Asp Ile Arg Val Gly Ser Pro Thr Phe Gly Arg Trp Glu Ala
 85                  90                  95                 100 gtc cgg ctc gac gac acc gag tac cgg gcc gtc tac cta gcc gaa gga       573
Val Arg Leu Asp Asp Thr Glu Tyr Arg Ala Val Tyr Leu Ala Glu Gly
                105                 110                 115 ctc ggg cac gcg ttc gcc gcg ctg acc gac gac acc gtg atg acc tac       621
Leu Gly His Ala Phe Ala Ala Leu Thr Asp Asp Thr Val Met Thr Tyr
            120                 125                 130 ctc tgc tcg acg ccc tac acc ccg ggc gcc gag cac ggc atc gac ccg       669
Leu Cys Ser Thr Pro Tyr Thr Pro Gly Ala Glu His Gly Ile Asp Pro
        135                 140                 145 ttc gac ccg gaa ctc gcg ttg ccg tgg tcc gac ctc gac ggt gaa ccg       717
Phe Asp Pro Glu Leu Ala Leu Pro Trp Ser Asp Leu Asp Gly Glu Pro
150                 155                 160 gtc ctg tcc gaa aag gac cgg acc gcc ccg agc ctc gcg gaa gcc gcc       765
Val Leu Ser Glu Lys Asp Arg Thr Ala Pro Ser Leu Ala Glu Ala Ala
165                 170                 175                 180 gac aac ggc ctg ctt ccg gac tac gaa aca tgc ctc gcc cac tac gaa       813
Asp Asn Gly Leu Leu Pro Asp Tyr Glu Thr Cys Leu Ala His Tyr Glu
                185                 190                 195 ggc ctg cgc agc ccc ggc tga acgtcaccg caagcggccc ggcttcggcc           864
Gly Leu Arg Ser Pro Gly
                200 agaggcgcca ccggataatg ccgagcacct cggccgggcc gagctcccgc gagtccgtcg     924 agccgaagtt gttgtcgccc tcgacgtacc agccatcgcc ctcgcggcgc agcgcgcgct     984 tcaccgacaa ctgccccggg cgctgggccc aacgcaccag cacgacgttt ccccggccgg    1044 gcggaacccc gaagccgcag cagcaccact tcgcgatccc gcagggtggg aaccataaac    1104 ggcccgcgca ccaccaaccg ccgccagggc cagcgcccga gggatttcac atccacctcc    1164
``` a                                                                        1165

<210> SEQ ID NO 33
<211> LENGTH: 202
<212> TYPE: PRT
<213> ORGANISM: Artificial Sequence
<220> FEATURE:
<223> OTHER INFORMATION: :

<400> SEQUENCE: 33

```
Val Gln Val Arg Arg Leu Asp Ile Thr Gly Ala Tyr Glu Phe Thr Pro
 1               5                  10                  15
Lys Ala Phe Pro Asp His Arg Gly Leu Phe Val Ala Pro Phe Gln Glu
                20                  25                  30
Ala Ala Phe Ile Asp Ala Thr Gly His Pro Leu Arg Val Ala Gln Thr
            35                  40                  45
Asn His Ser Val Ser Ala Arg Asn Val Ile Arg Gly Val His Phe Ser
        50                  55                  60
Asp Val Pro Pro Gly Gln Ala Lys Tyr Val Tyr Cys Pro Gln Gly Ala
65                  70                  75                  80
Leu Leu Asp Val Val Ile Asp Ile Arg Val Gly Ser Pro Thr Phe Gly
                85                  90                  95
Arg Trp Glu Ala Val Arg Leu Asp Asp Thr Glu Tyr Arg Ala Val Tyr
            100                 105                 110
Leu Ala Glu Gly Leu Gly His Ala Phe Ala Ala Leu Thr Asp Asp Thr
        115                 120                 125
Val Met Thr Tyr Leu Cys Ser Thr Pro Tyr Thr Pro Gly Ala Glu His
    130                 135                 140
Gly Ile Asp Pro Phe Asp Pro Glu Leu Ala Leu Pro Trp Ser Asp Leu
145                 150                 155                 160
Asp Gly Glu Pro Val Leu Ser Glu Lys Asp Arg Thr Ala Pro Ser Leu
                165                 170                 175
Ala Glu Ala Ala Asp Asn Gly Leu Leu Pro Asp Tyr Glu Thr Cys Leu
            180                 185                 190
Ala His Tyr Glu Gly Leu Arg Ser Pro Gly
        195                 200
```

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 34
cccgaattcg agctgctgtc aatcaact                                              28

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 35
gggaagcttg ttgaccgtgg cggtttcct                                             29

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence:mutagenic
      primer

<400> SEQUENCE: 36
ctggttcatt cggccgcctc accggtgggg atggccgcga tc                              42

<210> SEQ ID NO 37
<211> LENGTH: 42

```
<212> TYPE: DNA
<213> ORGANISM: Artificial Sequence
<220> FEATURE:
<223> OTHER INFORMATION: Description of Artificial Sequence:mutagenic
      primer

<400> SEQUENCE: 37
gatcgcggcc atccccaccg gtgaggcggc cgaatgaacc ag                42

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:flanking
      primer

<400> SEQUENCE: 38
gctgctcgaa atcgcacgtc                                         20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:flanking
      primer

<400> SEQUENCE: 39
gcatcgctgg gcagtgagg                                          19
```

DNA ENCODING SPNF OF THE SPINOSYN CLUSTER

This application is a divisional of application Ser. No. 09/603,207, filed Jun. 23, 2000, U.S. Pat. No. 6,521,406, which is is a divisional of application Ser. No. 09/370,700, filed Aug. 9, 1999, U.S. Pat. No. 6,274,350, which is a divisional of application Ser. No. 09/036,987, filed Mar. 9, 1998, U.S. Pat. No. 6,143,526.

SUMMARY OF THE INVENTION

The present invention provides novel biosynthetic genes, vectors incorporating the biosynthetic genes, *Saccharopolyspora spinosa* strains transformed with the biosynthetic genes, methods using these genes to increase production of spinosyn insecticidal macrolides, and methods using the genes or fragments thereof to change the products produced by spinosyn-producing strains of *Saccharopolyspora spinosa*.

BACKGROUND OF THE INVENTION

As disclosed in U.S. Pat. No. 5,362,634, fermentation product A83543 is a family of related compounds produced by *Saccharopolyspora spinosa*. The known members of this family have been referred to as factors or components, and each has been given an identifying letter designation. These compounds are hereinafter referred to as spinosyn A, B, etc. The spinosyn compounds are useful for the control of arachnids, nematodes and insects, in particular *Lepidoptera* and *Diptera* species, and they are quite environmentally friendly and have an appealing toxicological profile. Tables 1 and 2 identify the structures of a variety of known spinosyn compounds:

TABLE 1

[Structure of spinosyn core with positions labeled: $OR^{3'}$, $R^{2'}$, 16, 14, 13, H, H, $OR^{5'}$, $CH_3$, $4'$, $OR^{7'}$, $O$, $2'$, $OR^{6'}$, 21, $R^{4'}$, O, 1, O, H, 5, 6, H, $R^{1'}$]

| Factor | $R^{1'}$ | $R^{2'}$ | $R^{3'}$ | $R^{4'}$ | $R^{5'}$ | $R^{6'}$ | $R^{7'}$ |
|---|---|---|---|---|---|---|---|
| spinosyn A | H | $CH_3$ | $(CH_3)_2N$—[sugar]—O— with $CH_3$ (a) | $C_2H_5$ | $CH_3$ | $CH_3$ | $CH_3$ |
| spinosyn B | H | $CH_3$ | $(CH_3)NH$—[sugar]—O— with $CH_3$ (b) | $C_2H_5$ | $CH_3$ | $CH_3$ | $CH_3$ |
| spinosyn C | H | $CH_3$ | $H_2N$—[sugar]—O— with $CH_3$ (c) | $C_2H_5$ | $CH_3$ | $CH_3$ | $CH_3$ |
| spinosyn D | $CH_3$ | $CH_3$ | (a) | $C_2H_5$ | $CH_3$ | $CH_3$ | $CH_3$ |
| spinosyn E | H | $CH_3$ | (a) | $CH_3$ | $CH_3$ | $CH_3$ | $CH_3$ |
| spinosyn F | H | H | (a) | $C_2H_5$ | $CH_3$ | $CH_3$ | $CH_3$ |
| spinosyn G | H | $CH_3$ | $(CH_3)_2N$—[sugar]—O— with $CH_3$ (d) | $C_2H_5$ | $CH_3$ | $CH_3$ | $CH_3$ |
| spinosyn H | H | $CH_3$ | (a) | $C_2H_5$ | H | $CH_3$ | $CH_3$ |
| spinosyn J | H | $CH_3$ | (a) | $C_2H_5$ | $CH_3$ | H | $CH_3$ |
| spinosyn K | H | $CH_3$ | (a) | $C_2H_5$ | $CH_3$ | $CH_3$ | H |
| spinosyn L | $CH_3$ | $CH_3$ | (a) | $C_2H_5$ | $CH_3$ | H | $CH_3$ |
| spinosyn M | H | $CH_3$ | (b) | $C_2H_5$ | $CH_3$ | H | $CH_3$ |
| spinosyn N | $CH_3$ | $CH_3$ | (b) | $C_2H_5$ | $CH_3$ | H | $CH_3$ |

TABLE 1-continued

| Factor | $R^{1'}$ | $R^{2'}$ | $R^{3'}$ | $R^{4'}$ | $R^{5'}$ | $R^{6'}$ | $R^{7'}$ |
|---|---|---|---|---|---|---|---|
| spinosyn O | $CH_3$ | $CH_3$ | (a) | $C_2H_5$ | $CH_3$ | $CH_3$ | H |
| spinosyn P | H | $CH_3$ | (a) | $C_2H_5$ | $CH_3$ | H | H |
| spinosyn Q | $CH_3$ | $CH_3$ | (a) | $C_2H_5$ | H | $CH_3$ | $CH_3$ |
| spinosyn R | H | $CH_3$ | (b) | $C_2H_5$ | H | $CH_3$ | $CH_3$ |
| spinosyn S | H | $CH_3$ | (a) | $CH_3$ | H | $CH_3$ | $CH_3$ |
| spinosyn T | H | $CH_3$ | (a) | $C_2H_5$ | H | H | $CH_3$ |
| spinosyn U | H | $CH_3$ | (a) | $C_2H_5$ | H | $CH_3$ | H |
| spinosyn V | $CH_3$ | $CH_3$ | (a) | $C_2H_5$ | H | $CH_3$ | H |
| spinosyn W | $CH_3$ | $CH_3$ | (a) | $C_2H_5$ | $CH_3$ | H | H |
| spinosyn Y | H | $CH_3$ | (a) | $CH_3$ | $CH_3$ | $CH_3$ | H |
| spinosyn A 17-Psa | H | $CH_3$ | H | $C_2H_5$ | $CH_3$ | $CH_3$ | $CH_3$ |
| spinosyn D 17-Psa | $CH_3$ | $CH_3$ | H | $C_2H_5$ | $CH_3$ | $CH_3$ | $CH_3$ |
| spinosyn E 17-Psa | H | $CH_3$ | H | $CH_3$ | $CH_3$ | $CH_3$ | $CH_3$ |
| spinosyn F 17-Psa | H | H | H | $C_2H_5$ | $CH_3$ | $CH_3$ | $CH_3$ |
| spinosyn H 17-Psa | H | $CH_3$ | H | $C_2H_5$ | H | $CH_3$ | $CH_3$ |
| spinosyn J 17-Psa | H | $CH_3$ | H | $C_2H_5$ | $CH_3$ | H | $CH_3$ |
| spinosyn L 17-Psa | $CH_3$ | $CH_3$ | H | $C_2H_5$ | $CH_3$ | H | $CH_3$ |

TABLE 2

| Factor | $R^{1'}$ | $R^{2'}$ | $R^{3'}$ | $R^{4'}$ | $R^{5'}$ |
|---|---|---|---|---|---|
| spinosyn A 9-Psa | H | $CH_3$ | (a) | $C_2H_5$ | H |
| spinosyn D 9-Psa | $CH_3$ | $CH_3$ | (a) | $C_2H_5$ | H |
| spinosyn A Aglycone | H | $CH_3$ | H | $C_2H_5$ | H |
| spinosyn D Aglycone | $CH_3$ | $CH_3$ | H | $C_2H_5$ | H |

The naturally produced spinosyn compounds consist of a 5,6,5-tricylic ring system, fused to a 12-membered macrocyclic lactone, a neutral sugar (rhamnose) and an amino sugar (forosamine) (see Kirst et al. (1991). If the amino sugar is not present the compounds have been referred to as the pseudoaglycone of A, D, etc., and if the neutral sugar is not present then the compounds have been referred to as the reverse pseudoaglycone of A, D, etc. A more preferred nomenclature is to refer to the pseudoaglycones as spinosyn A 17-Psa, spinosyn D 17-Psa, etc., and to the reverse pseudoaglycones as spinosyn A 9-Psa, spinosyn D 9-Psa, etc.

The naturally produced spinosyn compounds may be produced via fermentation from cultures NRRL 18395, 18537, 18538, 18539, 18719, 18720, 18743 and 18823. These cultures have been deposited and made part of the stock culture collection of the Midwest Area Northern Regional Research Center, Agricultural Research Service, United States Department of Agriculture, 1815 North University Street, Peoria, Ill. 61604.

U.S. Pat. No. 5,362,634 and corresponding European Patent Application No. 375316 A1 disclose spinosyns A, B, C, D, E, F, G, H, and J. These compounds are disclosed as being produced by culturing a strain of the novel microorganism *Saccharopolyspora spinosa* selected from NRRL 18395, NRRL 18537, NRRL 18538, and NRRL 18539.

WO 93/09126 disclosed spinosyns L, M, N, Q, R, S, and T. Also disclosed therein are two spinosyn J producing strains: NRRL 18719 and NRRL 18720, and a strain that produces spinosyns Q, R, S, and T: NRRL 18823.

WO 94/20518 and U.S. Pat. No. 5,6704,486 disclose spinosyns K, O, P, U, V, W, and Y, and derivatives thereof. Also disclosed is spinosyn K-producing strain NRRL 18743.

A challenge in producing spinosyn compounds arises from the fact that a very large fermentation volume is required to produce a very small quantity of spinosyns. It is highly desired to increase spinosyn production efficiency and thereby increase availability of the spinosyns while reducing their cost. A cloned fragment of DNA containing genes for spinosyn biosynthetic enzymes would enable duplication of genes coding for rate limiting enzymes in the production of spinosyns. This could be used to increase yield in any circumstance when one of the encoded activities limited synthesis of the desired spinosyn. A yield increase of this type was achieved in fermentations of *Streptomyces fradiae* by duplicating the gene encoding a rate-limiting methyltransferase that converts macrocin to tylosin (Baltz et al., 1997).

Cloned biosynthetic genes would also provide a method for producing new derivatives of the spinosyns which may have a different spectrum of insecticidal activity. New derivatives are desirable because, although known spinosyns inhibit a broad spectrum of insects, they do not control all pests. Different patterns of control may be provided by biosynthetic intermediates of the spinosyns, or by their derivatives produced in vivo, or by derivatives resulting from their chemical modification in vitro. Specific intermediates (or their natural derivatives) could be synthesized by mutant strains of *S. spinosa* in which certain genes encoding enzymes for spinosyn biosynthesis have been disrupted. Such strains can be generated by integrating, via homologous recombination, a mutagenic plasmid containing an internal fragment of the target gene. Upon plasmid integration, two incomplete copies of the biosynthetic gene are formed, thereby eliminating the enzymatic function it encoded. The substrate for this enzyme, or some natural derivative thereof, should accumulate upon fermentation of the mutant strain. Such a strategy was used effectively to generate a strain of *Saccharopolyspora erythraea* producing novel 6-deoxyerythromycin derivatives (Weber & McAlpine, 1992).

Novel intermediates could also be synthesized by mutant strains of *S. spinosa* in which parts of certain genes encoding enzymes for spinosyn biosynthesis have been replaced with parts of the same gene which have been specifically mutated in vitro, or with corresponding parts of genes from other organisms. Such strains could be generated by swapping the target region, via double homologous recombination, with a mutagenic plasmid containing the new fragment between non-mutated sequences which flank the target region. The hybrid gene would produce protein with altered functions, either lacking an activity or performing a novel enzymatic transformation. A new derivative would accumulate upon fermentation of the mutant strain. Such a strategy was used to generate a strain of *Saccharopolyspora erythraea* producing a novel anhydroerythromycin derivative (Donadio et al., 1993).

Biosynthesis of spinosyns proceeds via stepwise condensation and modification of 2- and 3-carbon carboxylic acid precursors, generating a linear polyketide that is cyclized and bridged to produce the tetracyclic aglycone. Pseudoaglycone (containing tri-O-methylated rhamnose) is formed next, then di-N-methylated forosamine is added to complete the biosynthesis (Broughton et al., 1991). Other macrolides, such as the antibiotic erythromycin, the antiparasitic avermectin and the immunosuppressant rapamycin, are synthesized in a similar fashion. In the bacteria producing these compounds, most of the macrolide biosynthetic genes are clustered together in a 70–80 kb region of the genome (Donadio et al., 1991). At the centers of these clusters are 3–5 highly conserved genes coding for the very large, multifunctional proteins of a Type I polyketide synthase (PKS). Together the polypeptides form a complex consisting of an initiator module and several extender modules, each of which adds a specific acyl-CoA precursor to a growing polyketide chain, and modifies the β-keto group in a specific manner. The structure of a polyketide is therefore determined by the composition and order of the modules in the PKS. A module comprises several domains, each of which performs a specific function. The initiator module consists of an acyl transferase (AT) domain for addition of the acyl group from the precursor to an acyl carrier protein (ACP) domain. The extender modules contain these domains, along with a β-ketosynthase (KS) domain that adds the pre-existing polyketide chain to the new acyl-ACP by decarboxylative condensation. Additional domains may also be present in the extender modules to carry out specific β-keto modifications: a β-ketoreductase (KR) domain to reduce the β-keto group to a hydroxyl group, a dehydratase (DH) domain to remove the hydroxyl group and leave a double bond, and an enoyl reductase (ER) domain to reduce the double bond and leave a saturated carbon. The last extender module terminates with a thioesterase (TE) domain that liberates the polyketide from the PKS enzyme in the form of a macrocyclic lactone.

Macrolides are derived from macrocyclic lactones by additional modifications, such as methylation and changes in reductive state, and the addition of unusual sugars. Most of the genes required for these modifications, and for the synthesis and attachment of the sugars, are clustered around the PKS genes. The genes encoding deoxysugar biosynthetic enzymes are similar in producers of macrolide antibiotics, such as erythromycin and tylosin (Donadio et al., 1993), and producers of extracellular polysaccharides, such as the O-antigens of *Salmonella* and *Yersinia* (Jiang et al., 1991). All these syntheses involve activation of glucose by the addition of a nucleotide diphosphate, followed by dehydration, reduction and/or epimerization. The resultant sugar could undergo one or more modifications such as deoxygenation, transamination and methylation, depending upon the type of sugar moiety present in the macrolide. The sugars are incorporated into macrolides by the action of specific glycosyltransferases. Genes involved in the synthesis and attachment of a sugar may be tightly clustered—even transcribed as a single operon—or they may be dispersed. Spinosyn synthesis also involves bridging of the lactone nucleus, an activity that is rare in macrolide producers. Therefore, the spinosyn biosynthetic cluster may uniquely contain additional genes encoding enzymes for this function.

The following terms are used herein as defined below:

AmR—the apramycin resistance-conferring gene.

ApR—the ampicillin resistance-conferring gene.

ACP—acyl carrier protein.

AT—acyltransferase.

bp—base pairs.

Cloning—the process of incorporating a segment of DNA into a recombinant DNA cloning vector and transforming a host cell with the recombinant DNA.

CmR—the chloramphenicol resistance-conferring gene.

Codon bias—the propensity to use a particular codon to specify a specific amino acid. In the case of *S. spinosa,* the propensity is to use a codon having cytosine or guanine as the third base.

Complementation—the restoration of a mutant strain to its normal phenotype by a cloned gene.

Conjugation—a process in which genetic material is transferred from one bacterial cell to another.

cos—the lambda cohesive end sequence.

Cosmid—a recombinant DNA cloning vector which is a plasmid that not only can replicate in a host cell in the same manner as a plasmid but also can be packaged into phage heads.

DH—dehydratase.

ER—enoyl reductase.

Exconjugant—recombinant strain derived from a conjugal mating.

Gene—a DNA sequence that encodes a polypeptide.

Genomic Library—a set of recombinant DNA cloning vectors into which segments of DNA, representing substantially all DNA sequences in a particular organism have been cloned.

Homology—degree of similarity between sequences

Hybridization—the process of annealing two single stranded DNA molecules to form a double stranded DNA molecule, which may or may not be completely base paired.

In vitro packaging—the in vitro encapsulation of DNA in coat protein to produce a virus-like particle that can introduce DNA into a host cell by infection kb—kilo base pairs.

KR—β-keto reductase.

KS—ketosynthase.

Mutagenesis—creation of changes in DNA sequence. They can be random or targeted, generated in vivo or in vitro. Mutations can be silent, or can result in changes in the amino acid sequence of the translation product which alter the properties of the protein and produce a mutant phenotype.

NmR—the neomycin resistance-conferring gene.

ORF—open reading frame.

ori—a plasmid origin of replication (oriR) or transfer (oriT).

PKS—polyketide synthase.

Promoter—a DNA sequence that directs the initiation of transcription.

Recombinant DNA cloning vector—any autonomously replicating or integrating agent, including, but not limited to, plasmids, comprising a DNA molecule to which one or more additional DNA molecules can be or have been added.

Recombinant DNA methodology—technologies used for the creation, characterization, and modification of DNA segments cloned in recombinant DNA vectors.

Restriction fragment—any linear DNA molecule generated by the action of one or more restriction enzymes.

Spinosyn—a fermentation product typically characterized by a 5,6,5-tricylic ring system, fused to a 12-membered macrocyclic lactone, a neutral sugar (rhamnose) and an amino sugar (forosamine), or a similar macrocyclic lactone fermentation product produced by a microorganism utilizing all or most of the spinosyn genes.

Spinosyn genes—the DNA sequences that encode the products required for spinosyn biosynthesis, more specifically the genes spnA, spnB, spnC, spnD, spnE, spnF, spnG, spnH, spnI, spnJ, spnK, spnL, spnM, spnN, spnO, spnP, spnQ, spnR, spnS, *S. spinosa* gtt, *S. spinosa* gdh, *S. spinosa* epi, and *S. spinosa* kre, as described hereinafter, or functional equivalents thereof.

Subclone—a cloning vector with an insert DNA derived from another DNA of equal size or larger.

TE—thioesterase.

Transformation—the introduction of DNA (heterologous or homologous) into a recipient host cell that changes the genotype and results in a change in the recipient cell.

BRIEF DESCRIPTIONS OF THE INVENTION

Figure 1A:
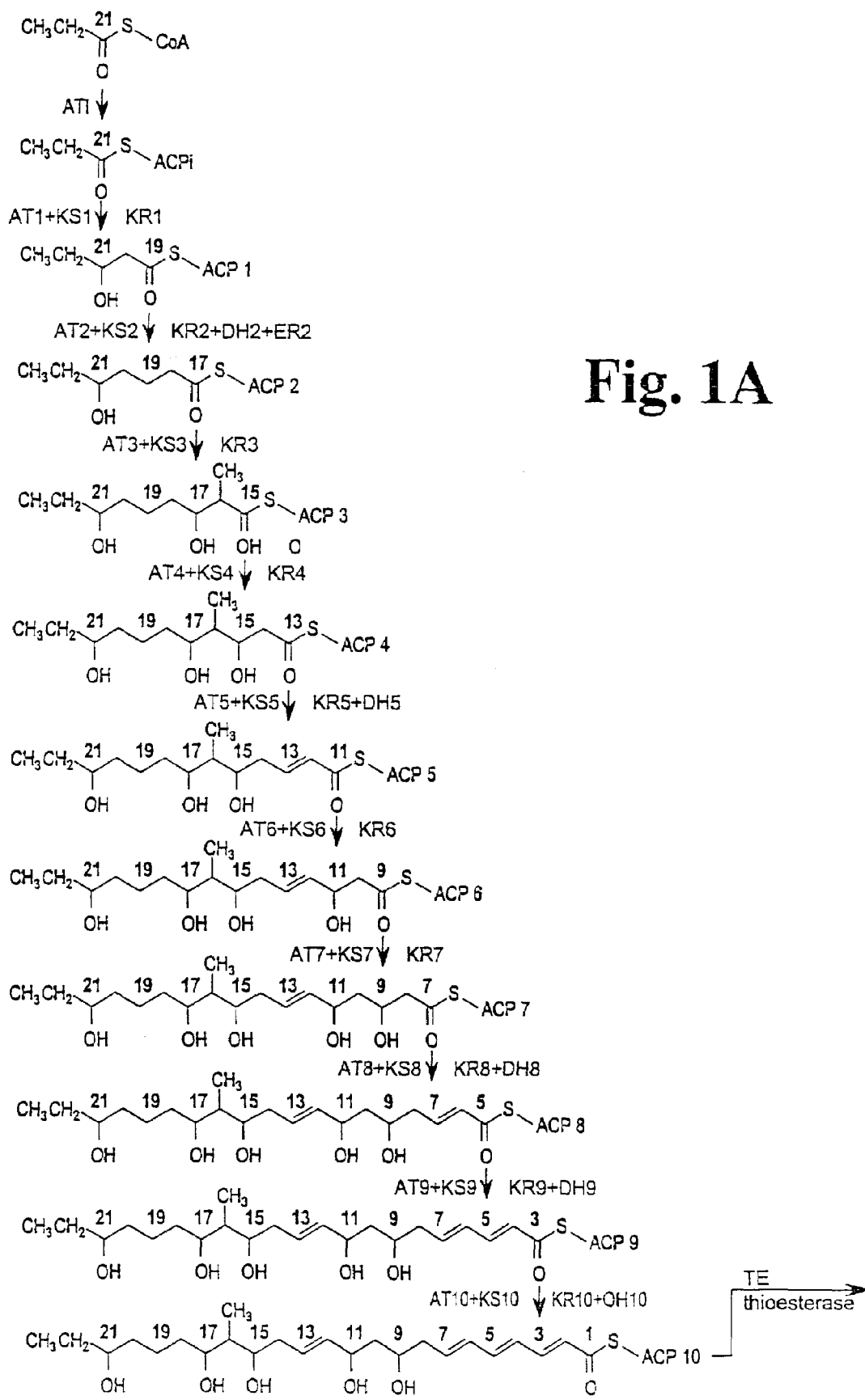
FIG. 1 is a diagram illustrating the spinosyn biosynthetic pathway.
Figure 1B:
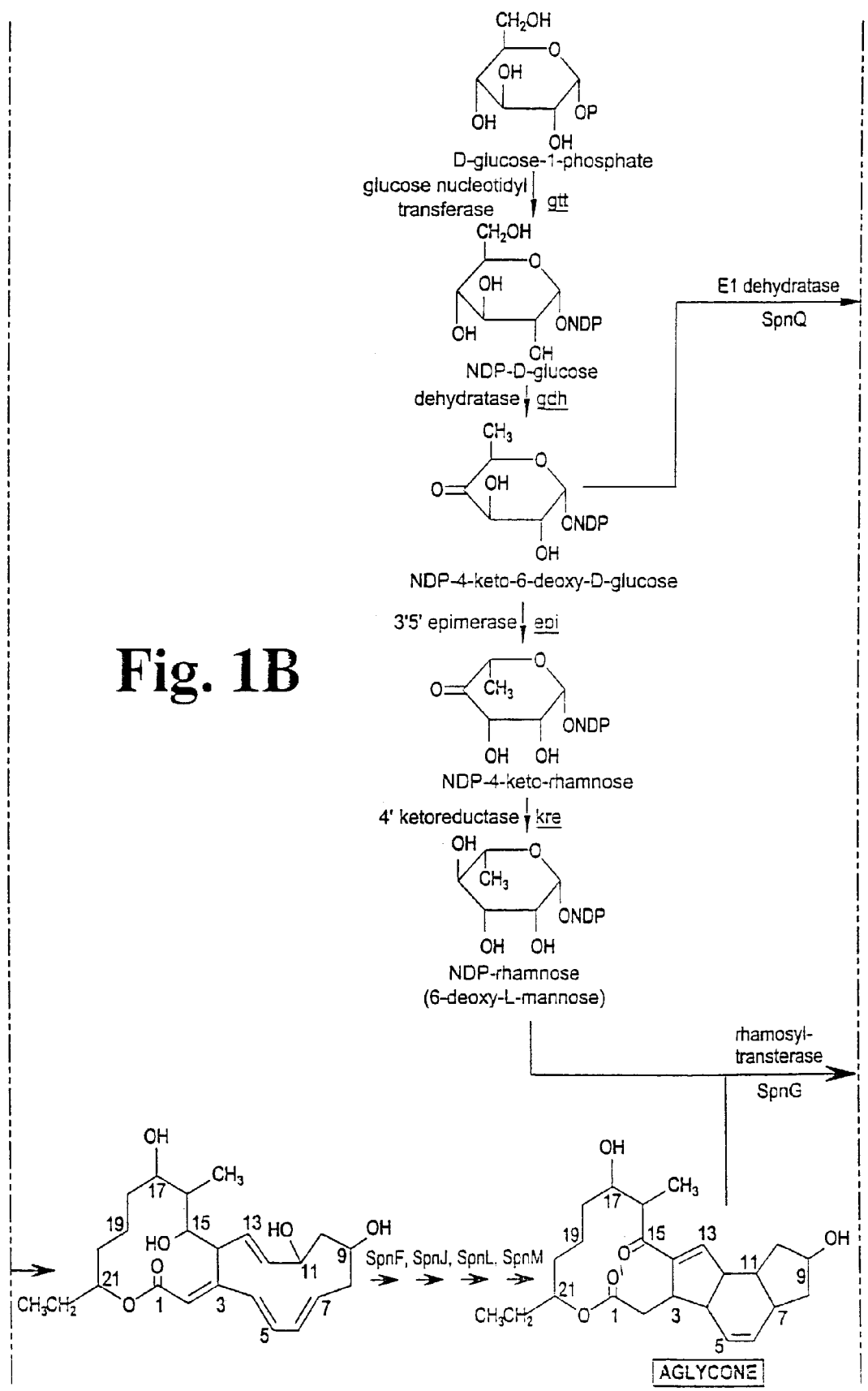
Figure 1C:
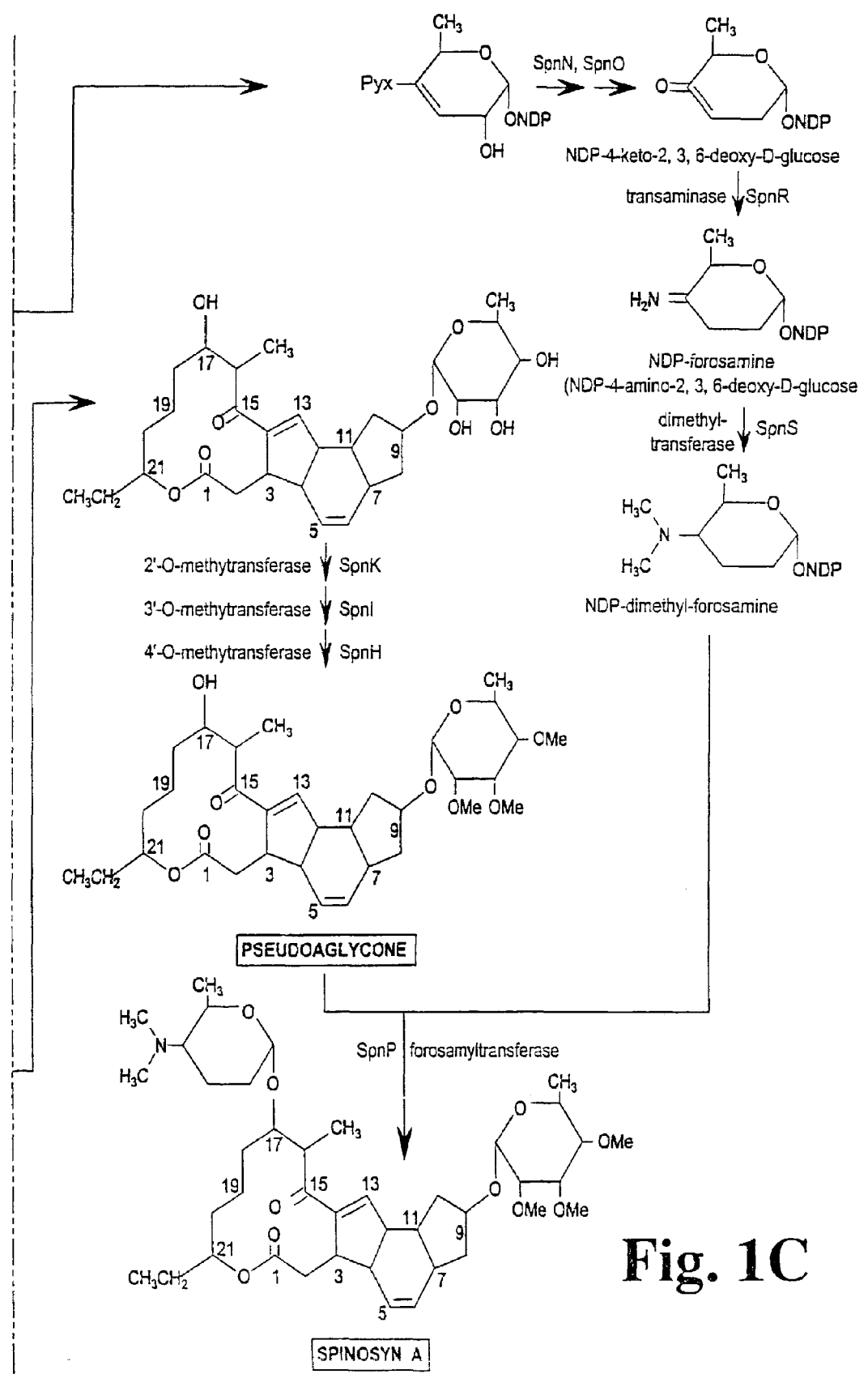

Spinosyn biosynthetic genes and related ORFs were cloned and the DNA sequence of each was determined. The cloned genes and ORFs are designated hereinafter as spnA, spnB, spnC, spnD, spnE, spnF, spnG, spnH, spnI, spnJ, spnK, spnL, spnM, spnN, spnO, spnP, spnQ, spnR, spnS, ORFL15, ORFL16, ORFR1, ORFR2, *S. spinosa* gtt, *S. spinosa* gdh, *S. spinosa* epi, and *S. spinosa* kre. The proposed functions of the cloned genes in spinosyn biosynthesis are identified FIG. 1 and in the discussion hereinafter.

In one of its aspects, the invention provides an isolated DNA molecule comprising a DNA sequence that encodes a spinosyn biosynthetic enzyme, wherein said enzyme is defined by an amino acid sequence selected from the group consisting of SEQ ID NOS 2–5, 7–24, 26, 27, 29, and 33, or said enzyme is defined by one of said amino acid sequences in which one or more amino acid substitutions have been made that do not affect the functional properties of the encoded enzyme. In a preferred embodiment, the DNA sequence is selected from the group of genes consisting of spnA, spnB, spnC, spnD, spnE, spnF, spnG, spnH, spnI, spnJ, spnK, spnL, spnM, spnN, spnO, spnP, spnQ, spnR, spnS, ORFL15, ORFL16, ORFR1, ORFR2, *S. spinosa* gtt, *S. spinosa* gdh, *S. spinosa* epi, and *S. spinosa* kre, said genes being described by, respectively, bases 21111–28898, 28916–35374, 35419–44931, 44966–59752, 59803–76569, 20168–20995, 18541–19713, 17749–18501, 16556–17743, 14799–16418, 13592–14785, 12696–13547, 11530–12492, 10436–11434, 8967–10427, 7083–8450, 5363–6751, 4168–5325, 3416–4165, 2024–2791, 1135–1971, 76932–77528 and 77729–79984 of SEQ ID NO:1, bases 334–1119 of SEQ ID NO:27, bases 88–1077 of SEQ ID NO 25, bases 226–834 of SEQ ID NO 32, and bases 1165–1992 of SEQ ID NO:25.

In another of its aspects, the invention provides an isolated DNA molecule comprising a DNA sequence that encodes a spinosyn PKS domain selected from KSi, ATi, ACPi, KS1, AT1, KR1, and ACP1, said domains being described by, respectively, amino acids 6–423, 528–853, 895–977, 998–1413, 1525–1858, 2158–2337, and 2432–2513 of SEQ ID NO:2. In a preferred embodiment, the DNA sequence is selected from the group consisting of bases 21126–22379, 22692–23669, 23793–24041, 24102–25349, 25683–26684, 27582–28121, and 28404–28649 of SEQ ID NO:1.

In another of its aspects, the invention provides an isolated DNA molecule comprising a DNA sequence that encodes a spinosyn PKS domain selected from KS2, AT2, DH2, ER2, KR2, and ACP2, said domains being described by, respectively, amino acids 1–424, 536–866, 892–1077, 1338–1683, 1687–1866, and 1955–2034 of SEQ ID NO:3. In a preferred embodiment the DNA sequence is selected from the group consisting of bases 29024–30295, 30629–31621, 31697–32254, 33035–34072, 34082–34621, 34886–35125 of SEQ ID NO:1.

Figure 4:
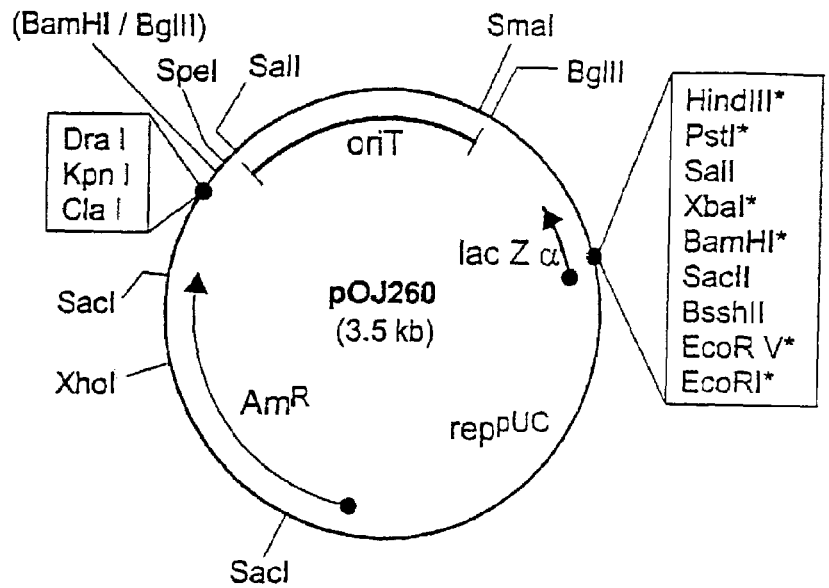
FIG. 4 is a restriction site and functional map of Cosmid pOJ260.

In another of its aspects, the invention provides an isolated DNA molecule comprising a DNA sequence that encodes a spinosyn PKS domain selected from KS3, AT3, KR3, ACP3, KS4, AT4, KR4, and ACP4, said domains being described by, respectively, amino acids 1–423, 531–280, 1159–1337, 1425–1506, 1529–1952, 2066–2396, 2700–2880, and 2972–3053 of SEQ ID NO:4. In a preferred embodiment the DNA sequence is selected from the group consisting of bases 35518–36786, 37108–38097, 38992–39528, 39790–40035, 40102–41373, 41713–42705, 43615–44157, and 44431–44676 of SEQ ID NO:1.

In another of its aspects the invention provides an isolated DNA molecule comprising a DNA sequence that encodes a spinosyn PKS domain selected from KS5, AT5, DH5, KR5, ACP5, KS6, AT6, KR6, ACP6, KS7, AT7, KR7, and ACP7, said domains being described by, respectively, amino acids 1–424, 539–866, 893–1078, 1384–1565, 1645–1726, 1748–2172, 2283–2613, 2916–3095, 3188–3269, 3291–3713, 3825–4153, 4344–4638, and 4725–4806 of SEQ ID NO:5. In a preferred embodiment the DNA sequence is selected from the group consisting of bases 45077–46348, 46691–47674, 47753–48310, 49226–49771, 50009–50254, 50318–51592, 51923–52915, 53822–54361, 54638–54883, 54947–56215, 56549–57535, 58106–58990, and 59249–59494 of SEQ ID NO:1.

In another of its aspects, the invention provides an isolated DNA molecule comprising a DNA sequence that encodes a spinosyn PKS domain selected from KS8, AT8, DH8, KR8, ACP8, KS9, AT9, DH9, KR9, ACP9, KS10, AT10, DH10, KR10, ACP 10, and TE10, said domains being described by, respectively, amino acids 1–424, 530–848, 883–1070, 1369–1552, 1648–1726, 1749–2173, 2287–2614, 2640–2800, 3157–3341, 3422–3500, 3534–3948, 4060–4390, 4413–4597, 4900–5078, 5172–5253, and 5302–5555 of SEQ ID NO:6. In a preferred embodiment, the DNA sequence is selected from the group consisting of bases 59902–61173, 61489–62445, 62548–63111, 64006–64557, 64843–65079, 65146–66420, 66760–67743, 67819–68301, 69370–69924, 70165–70401, 70471–71745, 72079–73071, 73138–73692, 74599–75135, 75415–75660, and 75805–76566 of SEQ ID NO:1.

In another of its aspects the invention provides an isolated DNA molecule comprising a DNA sequence that encodes a spinosyn PKS module, said module being selected from the group consisting of amino acids 6–1413 of SEQ ID NO:2, 1525–2513 of SEQ ID NO:2, 1–2034 of SEQ ID NO:3, 1–1506 of SEQ ID NO:4, 1529–3053 of SEQ ID NO:4, 1–1726 of SEQ ID NO:5, 1748–3269 of SEQ ID NO:5, 3291–4806 of SEQ ID NO:5, 1–1726 of SEQ ID NO:5, 1–1726 of SEQ ID NO:6, 1749–3500 of SEQ ID NO:6, and 35434–5555 of SEQ ID NO:6. In a preferred embodiment the DNA sequence is selected from the group consisting of bases 21126–24041, 24102–28649, 29024–35125, 35518–40035, 40102–44676, 45077–50254, 50318–54883, 54947–59494, 59902–65079, 65146–70401, and 70471–76566 of SEQ ID NO:1.

In another of its aspects, the invention provides a recombinant DNA vector which comprises a DNA sequence of the invention as described above.

In another of its aspects the invention provides a host cell transformed with a recombinant vector of the invention as described above.

In another of its aspects, the invention provides a method of increasing the spinosyn-producing ability of a spinosyn-producing microorganism comprising the steps of 1) transforming with a recombinant DNA vector or portion thereof a microorganism that produces spinosyn or a spinosyn precursor by means of a biosynthetic pathway, said vector or portion thereof comprising a DNA sequence of the invention, as described above, that codes for the expression of an activity that is rate limiting in said pathway, and 2) culturing said microorganism transformed with said vector under conditions suitable for cell growth and division, expression of said DNA sequence, and production of spinosyn.

In another of its aspects the invention provides a spinosyn-producing microorganism having operative spinosyn biosynthetic genes wherein at least one of the spinosyn biosynthetic genes spnA, spnB, spnC, spnD, spnE, spnF, spnG, spnH, spnI, spnJ, spnK, spnL, spnM, spnN, spnO, spnP, spnQ, spnR, spnS, *S. spinosa* gtt, *S. spinosa* gdh, *S. spinosa* epi, or *S. spinosa* kre has been duplicated.

In another of its aspects the invention provides a spinosyn-producing microorganism, said microorganism having spinosyn biosynthetic genes in its genome, wherein at least one of said genes has been disrupted by recombination with an internal fragment of that gene, the rest of said genes being operational to produce a spinosyn other than the one that would be produced if the disrupted gene were operational. Preferably the microorganism is an *S. spinosa* mutant.

The invention also provides a spinosyn-producing microorganism having operational spinosyn biosynthetic genes in its genome, wherein said genes a) include at least one operational PKS module more than or at least one less than is present in SEQ ID NO:1; or b) include a PKS module that differs from the corresponding module described in SEQ ID NO:1 by the deletion, inactivation, or addition of a KR, DH or ER domain, or by the substitution of an AT domain. Preferably the microorganism is an *S. spinosa* mutant.

The invention also provides spinosyns produced by cultivation of the novel microorganisms of the invention.

In another of its aspects the invention provides a process for isolating spinosyn biosynthetic genes which comprises creating a genomic library of a spinosyn producing microorganism, and using a labeled fragment of SEQ ID NO:1 that is at least 20 bases long as a hybridization probe.

DETAILED DESCRIPTION OF THE INVENTION

A cosmid library of *S. spinosa* (NRRL 18395) DNA was constructed from fragments generated by partial digestion with Sau3A I. They were cloned into the BamHI site of vector pOJ436 (See FIG. 3) (Bierman et al., 1992) and introduced into *E. coli* cells by in vitro packaging and transduction. The library of recombinant bacteria thus prepared was screened for homology to two radiolabelled DNA probes by hybridization using the methods of Solenberg & Burgett (1989). One probe was the 400 kb SpeI fragment which is often deleted in non-producing *S. spinosa* strains generated by transformation or mutagenesis with N-methyl-N'-nitro-N-nitrosoguanidine (Matsushima et al., 1994). The second probe was a 300 bp piece of *S. spinosa* DNA that codes for part of a ketosynthase not involved in spinosyn biosynthesis (B. E. Schoner, personal communication). It includes a region which is highly conserved in all polyketide and fatty acid synthase genes, and was therefore expected to cross-hybridize with the spinosyn PKS genes. Cosmids 9A6 and 2C10 were two of seven clones that hybridized to both probes. Cosmid 3E11 was selected from the genomic library by hybridization to a radiolabelled SgrA1-BamH1 fragment of cosmid 9A6 (bases 26757–26936 in SEQ ID NO: 1). To determine the nucleotide sequence of the insert in cosmid 9A6, BamHI fragments were subcloned into the BamHI site of plasmid pOJ260 (See FIG. 4) (Bierman et al., 1992). The sequences of the inserts in these plasmids were determined by either of two methods. In one method, subcloned fragments were partially digested with Sau3A I, and size-selected pieces were cloned into the BamHI site of DNA from the phage M13 mp19. Single-stranded DNA was prepared from randomly selected recombinants, and sequenced by fluorescent cycle sequencing using reagents and equipment from ABI (Applied Biosystems, Inc., Foster, Calif.), according to the methods of Burgett & Rosteck (1994). The sequences from phage subclones of each plasmid were assembled into one contiguous sequence. In the other sequencing method, double-stranded plasmid DNAs were primed reiteratively with single-stranded oligonucleotides, each designed to complement a region near the end of previously determined sequence. The complete sequence was thus compiled from a series of partially-overlapping sequences. Prism-Ready Sequencing Kits (ABI) were used according to the manufacturer's instructions, and analyzed on an ABI373A Sequencer. The same strategy was employed to sequence across the BamHI sites of double-stranded 9A6 DNA. These data allowed the subcloned sequences to be aligned and oriented relative to one another using the AssemblyLIGN module of the MacVector program (Oxford Molecular, Campbell, Ky.), and thereby allowed the entire nucleotide sequence of the *S. spinosa* DNA in cosmid 9A6 to be assembled. The complete sequences of cosmids 2C10 and 3E11 were determined by the method of fluorescent cycle sequencing of random DNA fragments cloned in phage M13 (SeqWright, Houston, Tex.). The inserts in cosmids 2C10 and 3E11 overlapped, and the insert in 3E11 overlapped the end of the insert in cosmid 9A6. See FIG. 2. Together, the three cosmid inserts spanned about 80 kb of unique sequence (SEQ ID NO: 1). The following Table 3 identifies the portions of SEQ ID NO:1 included in each of the three inserts.

TABLE 3

| insert | bases in SEQ ID NO:1 |
|---|---|
| cosmid 9A6 | 1–26941 |
| cosmid 3E11 | 23489–57287 |
| cosmid 2C10 (corrected) | 41429–80161 |

Figure 2:
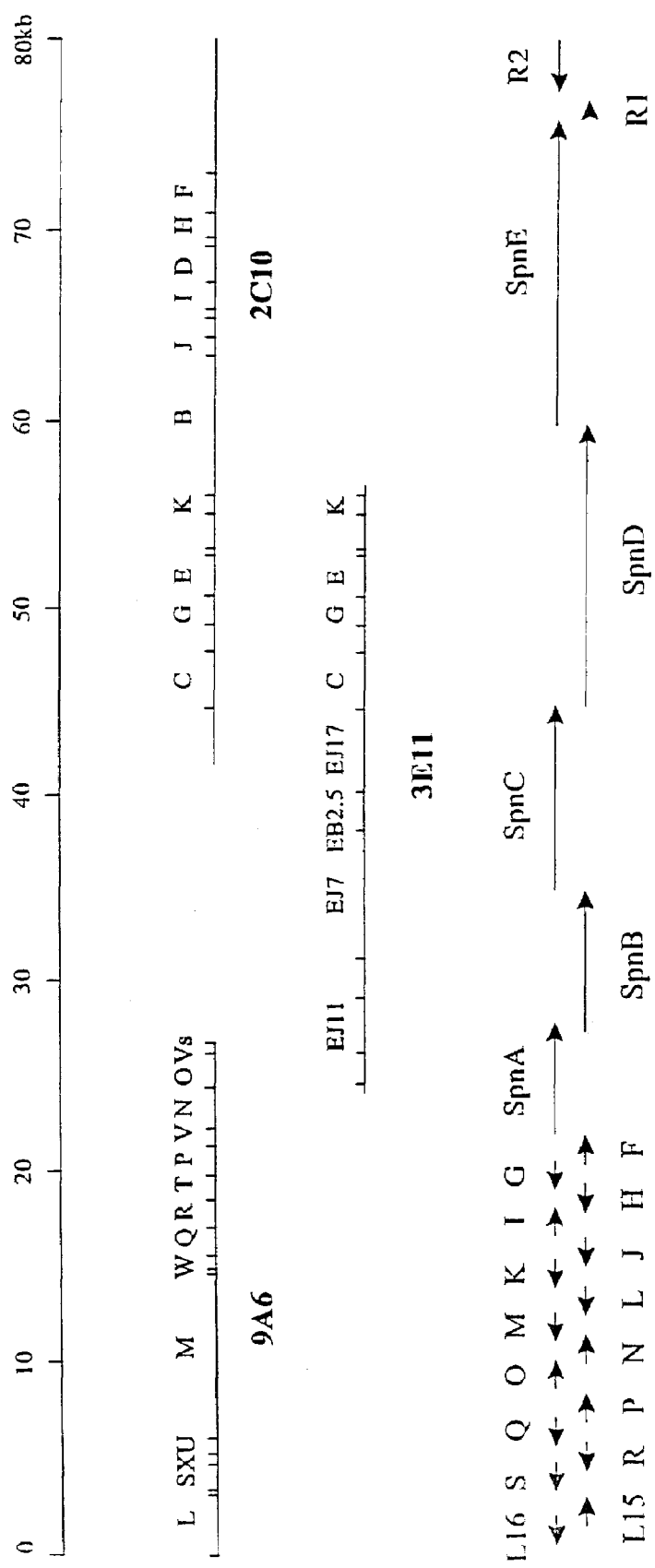
FIG. 2 is a map illustrating the arrangement of BamHI fragments and open reading frames in the cloned region of *S. spinosa* DNA.
Figure 3:
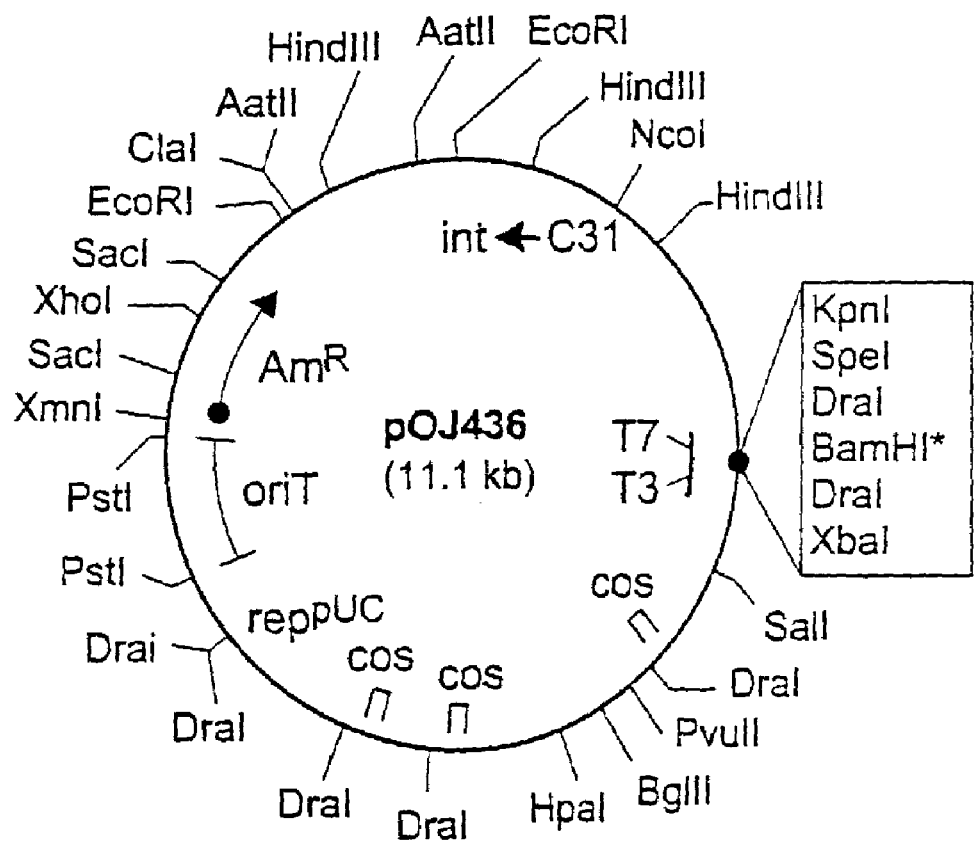
FIG. 3 is a restriction site and functional map of Cosmid pOJ436.

FIG. 2 gives a graphical representation of the relationship of the three inserts to the 80 kb of sequence.

It should be noted that cosmid 2C10 was missing bases G41877, C45570, C57845 and G73173 of SEQ ID NO:1. These deletions were determined to be cloning artifacts. The deletions generated in-frame stop codons that truncated PKS polypeptides. One of them occurred in a region also cloned in cosmid 3E11, but was not present in the region of 3E11 for which sequence was obtained. Uncloned DNA spanning all 8 stop codons in the PKS region was therefore sequenced directly from PCR-amplified regions of the genome of *S. spinosa* (NRRL 18395). The sequences from uncloned DNA confirmed the existence of the 4 stop codons at the end of ACP domains, and proved that the 4 frameshifts within other coding regions were cloning artifacts unique to cosmid 2C10.

PKS Genes

SEQ ID NO:1 includes a central region of about 55 kb with striking homology to the DNA encoding the polyketide synthases of known macrolide producers (Donadio et al., 1991; Dehoff et al., 1997). The spinosyn PKS DNA region consists of 5 ORFs with in-frame stop codons at the end of ACP domains, similar to the PKS ORFs in the other macrolide-producing bacteria. The five spinosyn PKS genes are arranged head-to-tail (see FIG. 2), without any intervening non-PKS functions such as the insertion element found between the erythromycin PKS genes AI and AII (Donadio et al., 1993). They are designated spnA, spnB, spnC, spnD, and spnE. The nucleotide sequence for each of the five spinosyn PKS genes, and the corresponding polypeptides, are identified in the following Table 4:

TABLE 4

| GENE | BASES IN SEQ ID NO:1 | CORRESPONDING POLYPEPTIDE |
|---|---|---|
| spnA | 21111–28898 | SEQ ID NO:2 |
| spnB | 28916–35374 | SEQ ID NO:3 |
| spnC | 35419–44931 | SEQ ID NO:4 |
| spnD | 44966–59752 | SEQ ID NO:5 |
| spnE | 59803–76569 | SEQ ID NO:6 | spnA encodes the initiator module (SEQ ID NO:1, bases 21126–24041) and extender module 1 (SEQ ID NO:1, bases 24102–28649). The nucleotide sequence and corresponding amino acid sequence for each of the functional domains within the initiator module and extender module 1 are identified in the following Table 5:

TABLE 5 spnA

| DOMAIN | BASES IN SEQ ID NO:1 | AMINO ACIDS IN SEQ ID NO:2 |
|---|---|---|
| KSi | 21126–22379 | 6–423 |
| ATi | 22692–23669 | 528–853 |
| ACPi | 23793–24041 | 895–977 |
| KS1 | 24102–25349 | 998–1413 |
| AT1 | 25683–26684 | 1525–1858 |
| KR1 | 27582–28121 | 2158–2337 |
| ACP1 | 28404–28649 | 2432–2513 | spnB encodes extender module 2 (SEQ ID NO:1, bases 29024–35125). The nucleotide sequence and corresponding amino acid sequence for each of the functional domains within extender module 2 are identified in the following Table 6:

TABLE 6 spnB

| DOMAIN | BASES IN SEQ ID NO:1 | AMINO ACIDS IN SEQUENCE ID NO.3 |
|---|---|---|
| KS2 | 29024–30295 | 1–424 |
| AT2 | 30629–31621 | 536–866 |
| DH2 | 31697–32254 | 892–1077 |
| ER2 | 33035–34072 | 1338–1683 |

TABLE 6-continued spnB

| DOMAIN | BASES IN SEQ ID NO:1 | AMINO ACIDS IN SEQUENCE ID NO.3 |
|---|---|---|
| KR2 | 34082–34621 | 1687–1866 |
| ACP2 | 34886–35125 | 1955–2034 | spnC encodes extender module 3 (SEQ ID NO:1, bases 35518–40035) and extender module 4 (SEQ ID NO:1, bases 40102–44676). The nucleotide sequence and corresponding amino acid sequence for each of the functional domains within extender modules 3 and 4 are identified in the following Table 7:

TABLE 7 spnC

| DOMAIN | BASES IN SEQ ID NO:1 | AMINO ACIDS IN SEQ ID NO:4 |
|---|---|---|
| KS3 | 35518–36786 | 1–423 |
| AT3 | 37108–38097 | 531–280 |
| KR3 | 38992–39528 | 1159–1337 |
| ACP3 | 39790–40035 | 1425–1506 |
| KS4 | 40102–41373 | 1529–1952 |
| AT4 | 41713–42705 | 2066–2396 |
| KR4 | 43615–44157 | 2700–2880 |
| ACP4 | 44431–44676 | 2972–3053 | spnD encodes extender module 5 (SEQ ID NO:1, bases 45077–50254), extender module 6 (SEQ ID NO:1, bases 50318–54883), and extender module 7 (SEQ ID NO:1, bases 54947–59494). The nucleotide sequence and corresponding amino acid sequence for each of the functional domains within extender modules 5, 6, and 7 is identified in the following Table 8:

TABLE 8 spnD

| DOMAIN | BASES IN SEQ ID NO:1 | AMINO ACIDS IN SEQ ID NO:5 |
|---|---|---|
| KS5 | 45077–46348 | 1–424 |
| AT5 | 46691–47674 | 539–866 |
| DH5 | 47753–48310 | 893–1078 |
| KR5 | 49226–49771 | 1384–1565 |
| ACP5 | 50009–50254 | 1645–1726 |
| KS6 | 50318–51592 | 1748–2172 |
| AT6 | 51923–52915 | 2283–2613 |
| KR6 | 53822–54361 | 2916–3095 |
| ACP6 | 54638–54883 | 3188–3269 |
| KS7 | 54947–56215 | 3291–3713 |
| AT7 | 56549–57535 | 3825–4153 |
| KR7 | 58106–58990 | 4344–4638 |
| ACP7 | 59249–59494 | 4725–4806 | spnE encodes extender module 8 (SEQ ID NO:1, bases 59902–65079), extender module 9 (SEQ ID NO:1, bases 65146–70401), and extender module 10 (SEQ ID NO:1, bases 70471–76566). The nucleotide sequence and corresponding amino acid sequence for each of the functional domains within extender modules 8, 9, and 10 is identified in the following Table 9:

TABLE 9 spnE

| DOMAIN | BASES IN SEQ ID NO:1 | AMINO ACIDS IN SEQ ID NO:6 |
|---|---|---|
| KS8 | 59902–61173 | 1–424 |
| AT8 | 61489–62445 | 530–848 |
| DH8 | 62548–63111 | 883–1070 |
| KR8 | 64006–64557 | 1369–1552 |
| ACP8 | 64843–65079 | 1648–1726 |
| KS9 | 65146–66420 | 1749–2173 |
| AT9 | 66760–67743 | 2287–2614 |
| DH9 | 67819–68301 | 2640–2800 |
| KR9 | 69370–69924 | 3157–3341 |
| ACP9 | 70165–70401 | 3422–3500 |
| KS10 | 70471–71745 | 3534–3948 |
| AT10 | 72079–73071 | 4060–4390 |
| DH10 | 73138–73692 | 4413–4597 |
| KR10 | 74599–75135 | 4900–5078 |
| ACP10 | 75415–75660 | 5172–5253 |
| TE10 | 75805–76566 | 5302–5555 |

The boundaries and functions of the 50 domains identified in the foregoing Tables 5–9 are predicted based on similarities to the conserved amino acid sequences of the domains in other polyketide synthases, particularly the erythromycin polyketide synthase (Donadio et al., 1992). The unexpected KSi domain at the amino terminus of the initiator module is presumed to be non-functional because it contains a glutamine residue at amino acid 172, in place of the cysteine required for β-ketosynthase activity (Siggard-Andersen, 1993). A similar non-functional KS domain has been discovered in the initiator module of the tylosin PKS (Dehoff et al., 1997). The other spinosyn PKS domains are functional. None of them has the sequence characteristics of the inactive domains found in the erythromycin and rapamycin PKS genes (Donadio et al., 1991; Aparicio et al., 1996). The cloned PKS genes were shown to be essential for spinosyn biosynthesis by the discovery that strains of S. spinosa in which these genes had been disrupted were unable to produce spinosyns by fermentation. Gene disruption was achieved by cloning an internal fragment of the gene into plasmid pOJ260 (FIG. 4), using procedures well-known to those skilled in the art. The recombinant plasmids were then introduced into S. spinosa by conjugation from E. coli using the procedures of Matsushima et al. (1994), and selecting for apramycin-resistant exconjugants. Plasmids based on pOJ260 do not replicate independently in S. spinosa, and are stably maintained by integrating the plasmid into the chromosome via recombination between the cloned DNA and its homologous sequence in the genome. Integration creates two incomplete versions of the targeted gene (one lacking 5' sequences and one lacking 3' sequences) in the chromosome, with the pOJ260 DNA between them. Spinosyn biosynthesis was blocked by disrupting the spnA ORF with the BamH1 fragments V, N, or K, corresponding respectively to the following segments of SEQ ID NO: 1: 21365–22052, 22052–24338, or 24338–26227. Spinosyn biosynthesis was also blocked by disrupting the spnD ORF with BamH1 fragments G, E, or K, corresponding respectively to the following segments of SEQ ID NO: 1: bases 48848–50578, 50578–52467, or 55207–55888. Spinosyn biosynthesis was also blocked by disrupting the spnE ORF with BamH1 fragments J, I, D, H, and F, corresponding respectively to the following segments of SEQ ID NO: 1: 63219–63989, 65406–66733, 66733–68997, 69369–70731, and 70731–72675. Spinosyn biosynthesis was not blocked by integration via BamH1 fragments C (bases 44612–47565 in SEQ ID NO: 1) or B (bases 55936–63219 in SEQ ID NO: 1) because they are not internal to any one gene; BamH1 fragment C spans the junction between spnC and spnD, and BamH1 fragment B spans the junction between spnD and spnE. In these cases, integration leaves one complete version of each gene.

Genes Adjacent to the PKS Responsible for Additional Modifications

In the DNA upstream of the PKS genes (cloned in cosmid 9A6) there were 16 open reading frames (ORFs), each consisting of at least 100 codons, beginning with ATG or GTG and ending with TAA, TAG or TGA, and having the codon bias expected of protein-coding regions in an organism whose DNA contains a high percentage of guanine and cytosine residues (Bibb et al, 1984). See the bottom right hand side of FIG. 2 for a graphical representation of the 16 ORFs in 9A6. Based on evidence that will be discussed hereinafter, 14 of the ORFs have been designated as spinosyn biosynthetic genes, namely: spnF, spnG, spnH, spnI, spnJ, spnK, spnL, spnM, spnN, spnO, spnP, spnQ, spnR, and spnS (they are labeled F through S in FIG. 2). In the following Table 10, the DNA sequence and the amino acid sequence for the corresponding polypeptide are identified for each of these genes, as well as for two ORFs (ORFL15 and ORFL16) found immediately upstream of spnS. Also identified in Table 10 are the nucleotide sequences for ORFR1 and ORFR2 downstream of the PKS genes (in cosmid 2C10), and the amino acid sequences corresponding to them.

TABLE 10

| GENE | BASES IN SEQUENCE ID NO: 1 | | POLYPEPTIDE |
| --- | --- | --- | --- |
| spnF | 20168–20995 | | SEQ ID NO: 7 |
| spnG | 18541–19713 | (C) | SEQ ID NO: 8 |
| spnH | 17749–18501 | (C) | SEQ ID NO: 9 |
| spnI | 16556–17743 | | SEQ ID NO: 10 |
| spnJ | 14799–16418 | (C) | SEQ ID NO: 11 |
| spnK | 13592–14785 | (C) | SEQ ID NO: 12 |
| spnL | 12696–13547 | (C) | SEQ ID NO: 13 |
| spnM | 11530–12492 | (C) | SEQ ID NO: 14 |
| spnN | 10436–11434 | | SEQ ID NO: 15 |
| spnO | 8967–10427 | | SEQ ID NO: 16 |
| spnP | 7083–8450 | | SEQ ID NO: 17 |
| spnQ | 5363–6751 | (C) | SEQ ID NO: 18 |
| spnR | 4168–5325 | (C) | SEQ ID NO: 19 |
| spnS | 3416–4165 | (C) | SEQ ID NO: 20 |
| ORFL 15 | 2024–2791 | | SEQ ID NO: 21 |
| ORFL 16 | 1135–1971 | (C) | SEQ ID NO: 22 |
| ORFR 1 | 76932–77528 | | SEQ ID NO: 23 |
| ORFR 2 | 77729–79984 | | SEQ ID NO: 24 |

(C) indicates complementary strand is given in the sequence listing

To assign functions to the polypeptides identified in Table 10, three lines of evidence were utilized: similarity to sequences of known function, results of targeted gene disruption experiments, and results of bioconversion experiments.

The amino acid sequences of the predicted polypeptides were compared to sequences deposited in the databases at the National Center for Biotechnology Information (NCBI), Washington, D.C.), using the BLAST algorithm to determine how well they are related to known proteins. The BLAST searches of the NCBI databases were also repeated periodically to obtain new insights from additional homologies. Table 11 gives the best matches from a basic BLAST search on Jan. 12, 1998:

TABLE 11

| Gene | Significant Protein Match | GenBank Accession | BLAST Score* | Reported function |
| --- | --- | --- | --- | --- |
| spnF | C-24 sterol methyl-transferase (Zea mays) | U79669 | 202 | C-methylation |
| spnG | Daunosamyl transferase dnrS (Streptomyces peucetius) | L47164 | 202 | sugar addition |
| spnH | Mycinamicin III O-methyltransferase (Micromonospora griseorubida) | D16097 | 408 | sugar methylation |
| spnI | ORFY (Streptomyces nogalater) | Z48262 | 192 | unknown |
| spnJ | Hexose oxidase (Chondrus crispus) | U89770 | 143 | oxido-reduction |
| spnK | ORFY (Streptomyces nogalater) | Z48262 | 137 | unknown |
| spnL | C-24 sterol methyl-transferase (Zea mays) | U79669 | 166 | C-methylation |
| spnM | Unknown (Mycobacterium tuberculosis) | Z95586 | 132 | unknown |
| spnN | RdmF (Streptomyces purpurascens) | U10405 | 409 | unknown |
| spnO | 2,3 dehydratase EryBV1 (Saccharopolyspora erythraea) | Y11199 | 595 | deoxysugar synthesis |
| spnP | Mycarosyl transferase EryBV (Saccharopolyspora erythraea) | U77459 | 336 | sugar addition |
| spnQ | CDP-4-keto-6-deoxy-D-glucose-3-dehydrase (Salmonella enterica) | P26398 | 784 | dideoxysugar synthesis |
| spnR | Spore coat polysaccharide biosynthesis protein (Bacillus subtilis) | P39623 | 286 | sugar transamination |
| spnS | TDP-N-dimethyldesosamine-N-methyltransferase EryCVI (Saccharopolyspora erythraea) | U77459 | 484 | aminosugar methylation |
| ORFL15 | Keto acyl reductase (Streptomyces cinnamonensis) | Z11511 | 132 | oxido-reduction |
| ORFL16 | Regulatory protein of the als operon, (Bacillus subtilis) | | | transcription control |
| ORFR1 | None | | | |
| ORFR2 | Conjugation transfer protein (Bacillus subtilis) | Z99117 | 328 | DNA replication |

*Greater similarity is associated with higher BLAST scores (Altschul et al., 1990).

In targeted gene disruptions, internal fragments were generated by PCR amplification from the cosmid DNAs, and cloned into plasmid pOJ260. The resulting plasmids were then conjugated into S. spinosa (NRRL 18395), and apramycin-resistant exconjugants were isolated and fermented. As stated earlier, the basis of disruption experiments is that when a plasmid bearing an internal gene fragment is integrated, two incomplete copies of the biosynthetic gene result, thereby eliminating the enzymatic function. Resulting fermentation products were analyzed to determine which spinosyns accumulated. The results of the targeted gene disruption experiments are summarized in Table 12.

In bioconversion studies, strains in which spinosyn synthesis was altered were tested for their ability to convert available spinosyn intermediates to other spinosyns. The intermediates used were spinosyn A Aglycone (AGL), spinosyn P(P), spinosyn K (K), and spinosyn A 9-Psa (PSA). The results of the bioconversion experiments are also summarized in Table 12

TABLE 12

| Disrupted Gene | Internal Fragment in SEQ ID NO: 1 | spinosyns accumu- lated | Bioconversion products | | | |
|---|---|---|---|---|---|---|
| | | | AGL→ | P→ | K→ | PSA→ |
| None | None | A + D | | | | |
| spnF | 20325–20924 | None | A | A | | A |
| spnG | 18818–19426 | None | AGL | K | | A |
| spnG–H | 18511–19559 | P | | | K | A |
| spnI | 16699–17400 | None | | J | A | A |
| spnJ | 14866–15470 | None | A | | A | |
| spnK | 13785–14574 | None | | | | |
| spnL | 12791–13428 | None | A | A | | A |
| spnM | 11705–12371 | 3% A | A | | | A |
| spnN | 10636–11369 | PSA | | | | |
| spnO | 9262–10226 | PSA | | | | |
| spnP | 7391–8159 | PSA | PSA | | | |
| ORFL15 | 2145–2719 | A + D | | | | |
| ORFL16 | 1226–1852 | A + D | | | | |
| ORFR2 | 79321–79855 | A + D | | | | |

The conclusions drawn from BLAST searches, the gene disruption experiments, and the bioconversion studies will now be discussed in greater detail on a gene by gene basis.

The 11 genes upstream of the PKS were shown to be involved in spinosyn biosynthesis because strains in which they were disrupted failed to accumulate the major spinosyns A and D (Table 12). The next 2 genes upstream (ORFL15, ORFL16), and the large gene downstream (ORFR2) of the PKS, do not contribute to spinosyn production because fermentation was not affected by their disruption (Table 12). Disruption of the ORF immediately downstream of the PKS genes (ORFR1) was not attempted because it was too small to yield an internal fragment that would recombine at an acceptable frequency. Disruptions of the spnQ, spnR, and spnS genes were not attempted because early BLAST searches showed that these genes had striking similarity to enzymes known to be involved in the biosynthesis of unusual deoxysugars. spnQ had 53% identity between its gene product and the CDP-4-keto-6-deoxy-D-glucose-3-dehydrase involved in synthesis of the abequose moiety of the *Salmonella enterica* cell surface lipopolysaccharide (Jiang et al., 1991); spnR had up to 40% identity between its product and a group of proteins proposed to function as deoxysugar transaminases (Thorson et al., 1993); and spnS had 42% identity between its product and the SrmX product of *Streptomyces ambofaciens,* an organism that synthesizes the forosamine-containing antibiotic spiramycin (Geistlich et al., 1992). Even stronger similarities have emerged from recent BLAST searches (Table 11). Based on these similarities, and the close linkage of the genes to other spinosyn biosynthetic genes, it is concluded that spnQ spnR, and spnS are involved in production of the forosamine moiety of spinosyns.

spnF, spnJ, spnL, spnM

Strains disrupted in genes spnF, spnJ, spnL or spnM did not accumulate any spinosyns to significant levels (the low level of spinosyn A in the spnM mutant presumably resulted from some residual activity in the gene product deleted at its carboxy terminus). However, they bioconverted exogenously-supplied aglycone to spinosyn A, and therefore contained all the enzymes necessary for the later steps in spinosyn biosynthesis. These particular genes must be involved in generation of the aglycone from the putative monocyclic lactone product of the PKS genes. Roles for spnF and spnL in the formation of carbon-carbon bridges are consistent with their similarities to enzymes that methylate carbon atoms (Table 11). The absence of partially modified intermediates in the blocked mutants may result from instability of the compounds, or from reduced biosynthesis due to lack of glycosylated molecules to act as positive regulators, analogous to those of the tylosin pathway (Fish & Cundliffe, 1997).

spnG, spnH, spnI, spnK

Disruption of spnG also prevented spinosyn production, but the mutant strain could not bioconvert aglycone so this gene is required for a later step in the pathway (Table 12). Its sequence similarity to known glycosyl transferase genes (Table 11) suggests that spnG encodes the rhamnosyl transferase required for addition of the first sugar to the aglycone. The mutant with a disrupted spnG also lacked a functional 4'-O-methyltransferase (OMT) because it converted the 3',4'-didesmethyl spinosyn (P) to the 4'-desmethyl spinosyn (K), but not to the fully methylated spinosyn A. The 4'-OMT activity was presumably not expressed in the mutant because the encoding gene (spnH) lies downstream of the disrupting integration in the same operon. The existence of this operon was confirmed by disrupting BamH1 fragment T, which spans the junction between spnG and spnH but is not internal to any open reading frame. Nevertheless, its disruption altered spinosyn synthesis, so this fragment must be internal to a single transcript that encompasses both genes. In addition to the expected loss of 4'-OMT activity encoded by spnH, this disruption also caused the unexpected loss of 3'-OMT function, leading to accumulation of spinosyn P (Table 12). The 3' OMT activity appears to be encoded by the convergent downstream gene, spnI. This gene has most sequence similarity to the ORF Y gene of *Streptomyces nogalator* (Table 11). The function of the ORF Y product is unknown, but the organism produces an unusual tetramethylated deoxysugar (nogalose) that is similar to the tri-methylated rhamnose of spinosyn A, so presumably both genes are involved in sugar methylation. Consistent with this hypothesis, disruption of spnI created a mutant that bioconverted spinosyn P only to the 3'-desmethyl spinosyn (J), not spinosyn A (Table 12). The disruption prevented any spinosyn accumulation in unsupplemented fermentations. spnK has a sequence similar to spnI and ORF Y, and presumably encodes the 2'-OMT. Its disruption also prevented accumulation of any spinosyns in unsupplemented fermentations (Table 12).

spnN, spnO, spnP

Disruption of genes spnN, spnO and spnP led to accumulation of the pseudoaglycone (Table 12). These genes are therefore involved in the biosynthesis or addition of the forosamine sugar. The similarity of spnP to glycosyl transferases (Table 11) indicates that it encodes the spinosyn forosamyl transferase. The high degree of similarity between spnO and a 2,3 dehydratase (Table 11) indicates that it is involved in the 2'-deoxygenation step of forosamine synthesis.

Rhamnose Genes

The overlapping inserts cloned in cosmids 9A6, 3E11 and 2C10 do not contain genes that encode the four enzymes required to produce rhamnose from glucose (Liu & Thorson, 1994). The first enzyme is a glucose thymidylate transferase (gtt), or equivalent enzyme, that activates glucose by addition of a nucleotidyl diphosphate (NDP). The second is a glucose dehydratase (gdh) to produce NDP-4-keto-6-deoxy-glucose, an intermediate common to many deoxysugar biosynthetic pathways. An epimerase (epi) and a ketoreductase (kre) specific for rhamnose synthesis are also required, to convert the NDP-4-keto-6-deoxy-glucose to NDP-L-rhamnose, the activated sugar that is the substrate of the glycosyltransferase adding rhamnose to the aglycone. Genes that code for these enzymes in *S. spinosa* were cloned from a separate library of 7–12 kb partial Sau3A I fragments in the λ vector ZAP Express™ (Stratagene, LaJolla, Calif.). Radiolabelled probes were prepared by random primer extension (Boehringer Mannheim, Indianapolis, Ind.) of fragments from plasmid pESC1 containing the *Saccharopolyspora erythraea* gdh (Linton et al., 1995) and gtt genes. Plaque hybridizations to screen the phage library were performed with a stringent wash of 0.5×SSC, 0.1%SDS at 65° C. for 1 h. The plasmid (pDAB1620 and pDAB1621) portions of the vector containing inserts were excised from two of the three hybridizing phage, and partially sequenced using Prism-Ready Sequencing Kits (ABI) and multiple primers. The sequenced part of the insert in pDAB1620 (SEQ ID NO: 25) includes an ORF that would encode a 329-amino acid polypeptide (SEQ ID NO:26) with 82% identity to the gdh product of *S. erythraea*. Adjacent to this gene is an ORF coding for a 275-amino acid polypeptide (SEQ ID NO:27) with 72% identity to the *S. erythraea* kre gene product. The sequenced part of the insert in pDAB1621 (SEQ ID NO: 28) contains an ORF encoding a 261-amino acid polypeptide (SEQ ID NO: 29) with 83% identity to the *S. erythraea* gtt gene product. A second probe for rhamnose genes was prepared by PCR amplification of *S. spinosa* genomic DNA using degenerate oligonucleotide primers (SEQ ID NO: 30 and SEQ ID NO: 31) based on conserved amino acid regions in known epi proteins (Jiang et al., 1991; Linton et al., 1995). PCR reactions were performed in a GeneAmp 9600 Thermocycler with AmpliTaq polymerase (Perkin-Elmer) using 30 cycles of 30 sec at 94° C., 30 sec at 60° C. and 45 sec at 72° C. The probe hybridized to one phage in the 7–12 kb library; the plasmid portion of the vector containing this insert (pDAB1622) was excised and partially sequenced (SEQ ID NO:32). It includes an ORF for a 202-amino acid polypeptide (SEQ ID NO:33) with 57% homology to the *S. erythraea* epi protein. The genes were disrupted by recombination with plasmids containing internal fragments (bases 382–941 in SEQ ID NO: 25, 1268–1867 in SEQ ID NO:25, 447–994 in SEQ ID NO:28 or 346–739 in SEQ ID NO:32). Apramycin-resistant exconjugants were obtained in all cases, but they were only capable of growth on osmotically-stabilized media such as CSM supplemented with sucrose at 200 g/L, or R6 (Matsushima et al., 1994). Even under these conditions, they grew much slower than the parent *S. spinosa* (NRRL 18395), and were morphologically distinct, with highly fragmented mycelia. These results could be due to the presence of rhamnose in the cell wall in *S. spinosa* and a requirement that these four genes be present for normal cell wall synthesis in this organism. Mutants disrupted in these genes grew too slowly to be fermented under conditions known to produce spinosyns. However, Southern hybridizations of *S. spinosa* genomic DNA with the *S. erythraea* gtt/gdh probe (washed in 2×SSC, 0.1%SDS at 65° C. for 1 h) or with the degenerate epi probe (washed in 0.1×SSC, 0.1% SDS at 65° C. for 1 h) indicated that there are no other homologues of these genes present in the *S. spinosa* genome. Therefore, the four cloned *S. spinosa* genes must be the sole source of rhamnose for both cell wall formation and spinosyn biosynthesis.

The nucleotide sequence and corresponding amino acid sequence for each of the four *S. spinosa* genes required to produce rhamnose are identified in the following Table 13:

TABLE 13

| gene | DNA sequence | amino acid sequence |
| --- | --- | --- |
| *S. spinosa* gtt | SEQ ID NO:28, bases 334–1119 | SEQ ID NO:29 |
| *S. spinosa* gdh | SEQ ID NO:25, bases 88–1077 | SEQ ID NO:26 |
| *S. spinosa* epi | SEQ ID NO:32, bases 226–834 | SEQ ID NO:33 |
| *S. spinosa* kre | SEQ ID NO:25, bases 1165–1992 | SEQ ID NO:27 |

Thus 23 genes from *S. spinosa* can be assigned roles in spinosyn biosynthesis: 5 PKS genes to produce a macrocyclic lactone, 4 genes to modify this to the aglycone, 5 genes to synthesize and add rhamnose, 3 genes to methylate the rhamnose, and 6 genes to synthesize and add forosamine. The hypothetical biosynthetic pathway is summarized in FIG. 1.

Utility

There are many uses for the cloned *Saccharopolyspora spinosa* DNA. The cloned genes can be used to improve yields of spinosyns and to produce new spinosyns. Improved yields can be obtained by integrating into the genome of a particular strain a duplicate copy of the gene for whatever enzyme is rate limiting in that strain. In the extreme case where the biosynthetic pathway is blocked in a particular mutant strain due to lack of a required enzyme, production of the desired spinosyns can be restored by integrating a copy of the required gene. Yield improvement obtained by integrating copies of spinosyn genes is illustrated hereinafter in Examples 1–3 and 6.

Novel spinosyns can be produced using fragments of the cloned DNA to disrupt steps in the biosynthesis of spinosyns. Such disruption may lead to the accumulation of precursors or "shunt" products (the naturally-processed derivatives of precursors). The fragments useful in carrying out disruptions are those internal to a gene with bases omitted from both the 5' and 3' ends of the gene. Homologous recombination events utilizing such fragments result in two partial copies of the gene: one that is missing the omitted bases from the 5' end and one that is missing the omitted bases from the 3' end. The number of bases omitted at each end of the fragment must be large enough so that neither of the partial copies of the gene retains activity. At least 50 bases will normally be omitted from each end, and more preferably at least 100 bases are omitted from each end. The length of the partial gene fragment should be large enough so that recombination frequency is high enough for a practical experiment. Useful fragments for disruptions are desirably at least 300 bases long, and more preferably at least about 600 bases long. Modified spinosyns produced by disrupting genes may be insect control agents themselves, or serve as substrates for further chemical modification, creating new semi-synthetic spinosyns with unique properties and spectra of activity. Example 4 hereinafter illustrates the use of disruption.

Novel spinosyns can also be produced by mutagenesis of the cloned genes, and substitution of the mutated genes for their unmutated counterparts in a spinosyn-producing organism. Mutagenesis may involve, for example: 1) deletion or inactivation of a KR, DH or ER domain so that one or more of these functions is blocked and the strain produces a spinosyn having a lactone nucleus with a double bond, a hydroxyl group, or a keto group that is not present in the nucleus of spinosyn A (see Donadio et al., 1993); 2) replacement of an AT domain so that a different carboxylic acid is incorporated in the lactone nucleus (see Ruan et al., 1997); 3) addition of a KR, DH, or ER domain to an existing PKS module so that the strain produces a spinosyn having a lactone nucleus with a saturated bond, hydroxyl group, or double bond that is not present in the nucleus of spinosyn A; or 4) addition or subtraction of a complete PKS module so that the cyclic lactone nucleus has a greater or lesser number of carbon atoms. Example 5 illustrates use of mutagenesis to produce a spinosyn with modified functionality.

The DNA from the spinosyn gene cluster region can be used as a hybridization probe to identify homologous sequences. Thus, the DNA cloned here could be used to locate additional plasmids from the *Saccharopolyspora spinosa* gene libraries which overlap the region described here but also contain previously uncloned DNA from adjacent regions in the genome of *Saccharopolyspora spinosa*. In addition, DNA from the region cloned here may be used to identify non-identical but similar sequences in other organisms. Hybridization probes are normally at least about 20 bases long and are labeled to permit detection.

The modified strains provided by the invention may be cultivated to provide spinosyns using conventional protocols such as those disclosed in U.S. Pat. No. 5,362,634.

The following examples are provided in order that the invention might be more completely understood. They should not be construed as limitations of the invention.

EXAMPLE 1

Improved Yield of Spinosyns A and D by Transformation with Cosmid 9A6

Vegetative cultures of *S. spinosa* strain NRRL18538 were grown in 50 ml CSM medium (trypticase soy broth 30 g/l, yeast extract 3 g/l, magnesium sulfate 2 g/l, glucose 5 g/l, maltose 4 g/l) in 250 ml Erlenmeyer flasks shaken at 300 rpm at 30° C. for 48 h. Fermentation cultures contained a 1 ml inoculum of this vegetative culture in 7 ml of INF202, a proprietary medium similar to that described in Strobel & Nakatsukasa (1993). The cultures were grown in 30 ml plastic bottles arranged in 10×10 modules, shaken at 300 rpm in a 30° C. room for 3, 5 or 7 days. Broths were extracted with 4 volumes of acetonitrile, then analyzed for spinosyns A+D by isocratic high pressure liquid chromatography (HPLC) through a C-18 reversed-phase column (Strobel and Nakatsukasa, 1993). The amount of spinosyns was determined from absorbance at 250 nm. For each time point, spinosyns A+D were determined from 10 fermentation bottles. Two representative samples from each set of replicates were also analyzed by a slightly modified HPLC system for pseudoaglycone (PSA), the spinosyn precursor which lacks forosamine. In this system the mobile phase is 35:35:30 acetonitrile/methanol/0.5% (w/v) aqueous ammonium acetate (R. Wijayaratne, unpublished).

The cultures contain not only the insect-active spinosyns A and D, but also pseudoaglycone (Table 14).

TABLE 14

Spinosyn production in strain NRRL 18538

| Time | A + D (µg/ml) | PSA (µg/ml) |
|---|---|---|
| 3 d | 101 ± 3 | 109 ± 11 |
| 5 d | 269 ± 14 | 155 ± 26 |
| 7 d | 334 ± 32 | 110 ± 53 |

The values are means ± 95% confidence levels.

The accumulation of the pseudoaglycone, a forosamine-deficient precursor of spinosyn A, suggests that, in this strain grown under these conditions, the yield of spinosyns A+D is limited by the supply and/or addition of forosamine Cosmid 9A6 was conjugated from *E. coli* strain S17-1 (Simon et al., 1983) into *S. spinosa* strain NRRL 18538 using the method of Matsushima et al. (1994). Six independent isolates transformed with Cosmid 9A6 were subsequently grown and analyzed for spinosyn factor production under the fermentation conditions described above. The average yield of spinosyns A+D from these strains was higher than from their parent, by 35 µg/ml after 3 days of fermentation, and by 37 µg/ml after 5 days. The amount of pseudoaglycone in the transformed cultures was lower than in the parent strain throughout the fermentation (Table 15)

TABLE 15

Spinosyn production in derivatives of NRRL 18538 transformed with Cosmid 9A6.

| Time | A + D (µg/ml) | PSA (µg/ml) |
|---|---|---|
| 3 d | 136 ± 4 | 31 ± 2 |
| 5 d | 306 ± 5 | 7 ± 2 |
| 7 d | 365 ± 7 | 7 ± 1 |

The values are means ± 95% confidence levels.

Strain NRRL 18538 and 6 independent isolates transformed with Cosmid 9A6 were analyzed for spinosyn content at different times during fermentation. For each strain, spinosyns A+D were determined from 10 fermentation bottles (Table 16). Two samples from each set of replicates were also analyzed for pseudoaglycone content (Table 17).

TABLE 16

Effect of Cosmid 9A6 on spinosyn A + D in NRRL 18538

| Time | −9A6 | +9A6 | Effect of 9A6 |
|---|---|---|---|
| 3 d | 101 ± 3 | 136 ± 4 | +35% |
| 5 d | 269 ± 14 | 306 ± 5 | +14% |
| 7 d | 334 ± 32 | 365 ± 7 | +9% |
| 9 d | 414 ± 17 | 411 ± 8 | −1% |

The values are means in µg/ml ± 95% confidence levels.

TABLE 17

Effect of Cosmid 9A6 on pseudoaglycone accumulation in NRRL 18538

| Time | −9A6 | +9A6 | Effect of 9A6 |
|---|---|---|---|
| 3 d | 109 ± 11 | 31 ± 2 | −72% |
| 5 d | 155 ± 26 | 7 ± 2 | −95% |
| 7 d | 110 ± 53 | 7 ± 1 | −94% |
| 9 d | 119 ± 11 | 5 ± 1 | −96% |

The values are means in µg/ml ± 95% confidence levels.

It has therefore been demonstrated that transformation with Cosmid 9A6 can improve the efficiency with which precursor pseudoaglycone is processed to spinosyns. In NRRL 18538, the yield improvements for spinosyn A+D were 35% after 3 days of fermentation, and 14% after 5 days (Table 15). The rate-limiting process appears be the supply and/or addition of forosamine because pseudoaglycone was present in the parent at about 120 µg/ml throughout the fermentation, but in the transconjugants it was reduced to about 30 µg/ml at 3 days, and essentially depleted thereafter (Table 15). Although the conversion was not quantitative, the data are consistent with an improved efficiency in the processing of pseudoaglycone to spinosyn A+D in strains transformed with Cosmid 9A6. The effect could be the result of duplicating a forosamine biosynthetic gene, a forosaminyltransferase gene, or a combination of improvements. There was no statistically significant difference between the spinosyn A+D yields from the NRRL 18358 strains with or without Cosmid 9A6 after 7 or 9 days fermentation. Pseudoaglycone was still reduced in the transconjugants, but the extra spinosyn A+D produced by its conversion may not have been detectable against the higher background of spinosyns accumulated by this stage of the fermentation.

EXAMPLE 2

Correction of Methylation Deficiencies in Strain NRRL 18823 by Cosmid 9A6

Although spinosyn synthesis is limited by forosamine supply/addition in strain NRRL 18358, other biosynthetic functions may be limiting in other strains. S. spinosa strain NRRL18823 accumulates spinosyn H (2'-desmethyl-spinosyn A; Kirst et al., 1992), rather than spinosyn A. Spinosyn H is not an intermediate in the spinosyn A biosynthetic pathway, but a "shunt" product synthesized naturally when 2'-O-methylation does not occur. Cosmid 9A6 was conjugated from E. coli strain S17-1 into strain NRRL 18823 using the method described above. Two of the resulting exconjugants, when fermented, produced predominantly spinosyn A, with little spinosyn H (Table 18).

TABLE 18

| Strain | H (µg/ml) | A + D (µg/ml) |
| --- | --- | --- |
| NRRL 18823 | 323 | 0 |
| NRRL 18823/9A6-2 | 36 | 551 |
| NRRL 18823/9A6-5 | 45 | 646 |

This shows that transformation with Cosmid 9A6 is able to overcome a second type of limitation to spinosyn production—the methylation deficiency in strain NRRL 18823.

EXAMPLE 3

Correction of 4'-O-methylation Deficiency in Strain NRRL 18743 by Cosmid 9A6

S. spinosa strain NRRL18743 accumulates spinosyn K (4'-desmethyl-spinosyn A), an intermediate in the spinosyn A biosynthetic pathway. Two of the exconjugants of strain NRRL 18743 containing Cosmid 9A6 produced predominantly spinosyn A, with little spinosyn K, while the third produced no detectable spinosyn K (Table 19).

TABLE 19

| Strain | K (µg/ml) | A + D (µg/ml) |
| --- | --- | --- |
| NRRL 18743 | 488 | 0 |
| NRRL 18743/9A6-1 | 38 | 829 |
| NRRL 18743/9A6-2 | 22 | 725 |
| NRRL 18743/9A6-3 | 0 | 706 |

This demonstrates that transformation with Cosmid 9A6 is able to overcome a third type of limitation to spinosyn A production—the methylation deficiency in strain NRRL 18743.

EXAMPLE 4

Accumulation of Spinosyn Precursor Caused by Disruption of spnP

An internal fragment of spnP (bases 7391–8159) was amplified in a polymerase chain reaction using primers given in SEQ ID NO:34 and SEQ ID NO:35. AmpliTaq polymerase (Perkin Elmer, Foster City, Calif.) was used according to the manufacturer's instructions, in a 100 µl reaction with 20 pmoles of each primer and 1 µg of 9A6 DNA. The mixture was subjected to 25 cycles of 60 sec at 94° C., 60 sec at 37° C. and 120 sec at 72° C. The amplification product was cloned as an EcoR1-HindIII fragment into the plasmid vector pOJ260 (Bierman et al., 1992), then conjugated from E. coli S17-1 into S. spinosa NRRL 18538. Stable exconjugants, resulting from a single homologous recombination event between the plasmid-born and chromosomal sequences, contain a copy of the vector DNA integrated into the chromosome between two incomplete copies of spnP. When fermented, these exconjugants accumulate the forosamine-deficient precursor pseudoaglycones, rather than the end products spinosyns A and D (Table 20).

TABLE 20

| Strain | PSA (µg/ml) | A + D (µg/ml) |
| --- | --- | --- |
| NRRL 18538 | 79 | 284 |
| NRRL 18538/1614-2 | 416 | 22 |
| NRRL 18538/1615-1 | 372 | 21 |
| NRRL 18538/1615-2 | 543 | 21 |
| NRRL 18538/1615-5 | 476 | 19 |
| NRRL 18538/1615-6 | 504 | 18 |

The pseudoaglycones are intermediates useful in the preparation of known insecticides (International Application WO 93/09126)

EXAMPLE 5

Accumulation of a Novel Spinosyn Following Modification of the PKS Domain ER2

Overlapping, complementary oligonucleotides SEQ ID NO: 36 and SEQ ID NO: 37 were designed to modify the gene encoding the enoyl reductase function in module 2 of the spinosyn PKS. These mutagenic primers provide for substitution of the sequence TCACC in place of GGTGG at bases 33563–33567 of SEQ ID NO:1, so that the sequence encodes a serine-proline dipeptide instead of a glycine-glycine dipeptide in the putative NAD(P)H-binding motif A similar substitution was successfully used to inactivate an erythromycin ER without affecting any other PKS functions (Donadio et al., 1993). The substitution simultaneously introduced a novel PinA1 restriction site, and eliminated a SgrA1 site, to facilitate detection of the engineered DNA in recombinant organisms.

Figure 5:
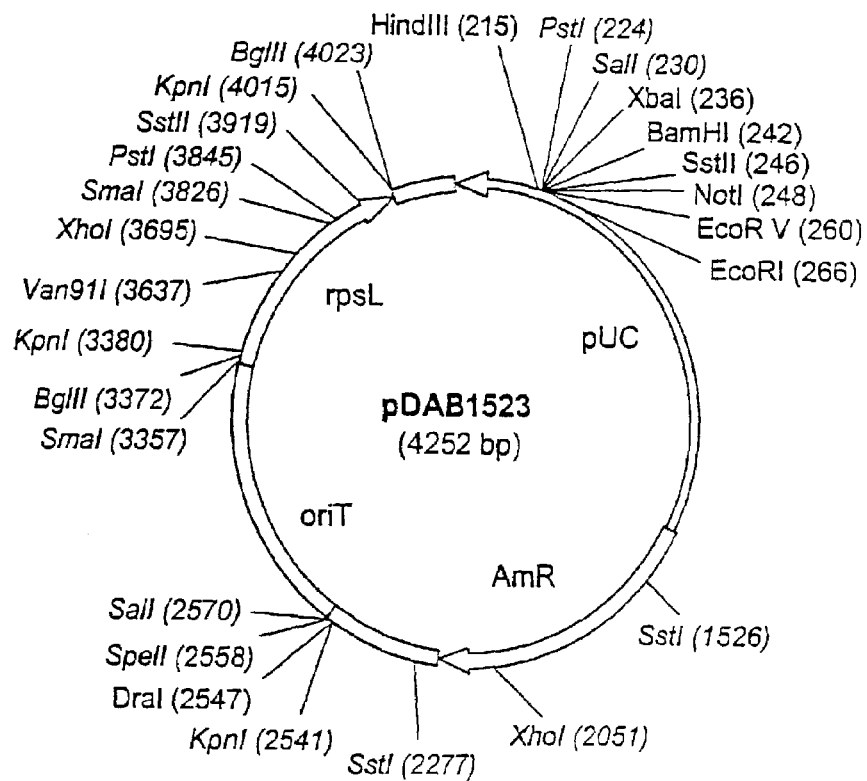
FIG. 5 is a restriction site and functional map of pDAB1523.

In the first step of the mutagenesis, two separate PCR amplifications were performed, one using the mutagenic primer SEQ ID NO: 36 and flanking primer SEQ ID NO: 38, the other using mutagenic primer SEQ ID NO: 37 and flanking primer SEQ ID NO: 39. In the second step, the products of the first reactions were diluted 100-fold, pooled and amplified with only the flanking primers SEQ ID NO: 38 and SEQ ID NO: 39. In the third step, the products of the second PCR reaction were cloned into the plasmid pCRII according to the manufacturer's instructions (InVitrogen, San Diego, Calif.). A portion of the mutated ER2 domain (spanning bases 33424–33626 in SEQ ID NO: 1) was excised as a Van911-NheI fragment, and inserted in place of the wild-type Van911-NheI fragment in a 3.5 kb EcoR1 fragment of cosmid 3E11 (bases 32162–35620 in SEQ ID NO: 1) cloned in the plasmid pBluescript SK-(Stratagene). The mutated EcoR1 fragment was then transferred into the conjugative plasmid pDAB1523 (FIG. 5), a derivative of pOJ260 containing the rpsL gene of *Streptomyces roseosporus* that confers a counter-selectable streptomycin-sensitive phenotype (Hosted & Baltz, 1997). The resultant plasmid containing the mutated EcoR1 fragment was conjugated from *E. coli* S17-1 (Simon et al., 1983) into SS15, a spontaneous streptomycin-resistant derivative of *S. spinosa* strain NRRL18538, using the method of Matsushima et al. (1994). (Spontaneous streptomycin-resistant derivatives of *S. spinosa* strain NRRL18538 can be readily isolated by those skilled in the art.) Apramycin-resistant exconjugants were shown to contain both wild-type and mutated versions of the ER2 domain by Southern hybridization with digoxygenin-labeled probes (Boehringer Mannheim). They also contained the *S. roseosporus* rpsL gene and consequently, on BHI agar (Difco, Detroit, Mich.) containing streptomycin at 150 mg/L, they grew poorly and failed to produce aerial mycelium. Spontaneous revertants to streptomycin-resistance were selected on the basis of their ability to grow and produce white, aerial mycelium on BHI agar containing streptomycin at 150 mg/L. Southern analysis indicated that these strains no longer contained the *S. roseosporus* rpsL gene or any other pDAB1523 sequences. Some strains had lost the entire cluster of spinosyn biosynthetic genes, including the ER2 domain, as well as pDAB1523. In other strains the pDAB1523 sequences had been excised along with the mutant ER2 domain, re-creating the parental gene structure. In a third type of streptomycin-resistant strain, the pDAB1523 had been excised with the wild-type ER2 domain, leaving the mutated version in its place. When fermented, a strain of this third type produced a novel metabolite, separable from spinosyn A by liquid chromatography on a C18 column (ODS-AQ, YMC, Wilmington, N.C.) using a mobile phase of acetonitrile: methanol: 2% ammonium acetate (44:44:12). The new entity was analyzed by electrospray ionization and tandem mass spectroscopy (Balcer et al., 1996) using a triple quadrupole mass spectrometer (TSQ700, Finnigan MAT, San Jose, Calif.). It had the properties expected of the C18:C19-anhydrospinosyn A, with a mass of 729.5 daltons and produced the 142 dalton forosamine fragment. We conclude that modification of DNA encoding PKS domains results in the production of novel fermentation products.

EXAMPLE 6

Improved Yield of Spinosyns A and D by Transformation of NRRL 18538 with Rhamnose Biosynthetic Genes Fragments containing the rhamnose biosynthetic genes were cloned independently into the conjugative vector pOJ260 (Bierman et al., 1992). The resulting plasmids are listed in Table 21.

TABLE 21

| Plasmid | Genes |
| --- | --- |
| pDAB1632 | gtt |
| pDAB1634 | gdh + kre |
| pDAB1633 | epi |

Each plasmid was conjugated from *E. coli* S17-1 (Simon et al., 1983) into *S. spinosa* NRRL 18538 by the method of Matsushima et al. (1994). Apramycin-resistant exconjugants, presumably containing a plasmid integrated into the chromosome by homologous recombination, were selected and fermented (Table 22).

TABLE 22

Spinosyn production in derivatives of NRRL 15328 transformed with rhamnose genes

| | Duplicated | A + D ($\mu$g/ml) | |
| --- | --- | --- | --- |
| Strain | Genes | Experiment 1 | Experiment 2 |
| NRRL 18538 | None | 344 ± 39 | 405 ± 25 |
| NRRL 18538/1632-1 | gtt | 410 ± 21 | 418 ± 38 |
| NRRL 18538/1634-1 | gdh + kre | 351 ± 27 | 360 ± 21 |
| NRRL 18538/1633-1 | epi | 318 ± 29 | 315 ± 18 |

The values are means ± 95% confidence limits.

In derivatives of NRRL 15328 transformed with gtt or epi, or the combination of gdh and kre, there was no consistent increase in the yield of spinosyns.

The fragments containing the gtt and gdh+kre genes were combined in a single plasmid. Two plasmids containing the combined gtt, gdh and kre genes (pDAB1654 and pDAB1655) were isolated, and conjugated from *E. coli* S17-1 (Simon et al., 1983) into *S. spinosa* NRRL 18538 by the method of Matsushima et al. (1994). Apramycin-resistant exconjugants were selected and fermented (Table 23).

TABLE 23

Spinosyn production in derivatives of NRRL 15328 transformed with rhamnose genes

| | Duplicated | A + D ($\mu$g/ml) | |
| --- | --- | --- | --- |
| Strain | Genes | Experiment 1 | Experiment 2 |
| NRRL 18538 | None | 109 ± 9 | 133 ± 36 |
| NRRL 18538/1654-2 | gtt, gdh and kre | 323 ± 19 | 244 ± 34 |
| NRRL 18538/1654-5 | gtt, gdh and kre | 571 ± 23 | 412 ± 61 |
| NRRL 18538/1654-6 | gtt, gdh and kre | 577 ± 17 | 425 ± 51 |
| NRRL 18538/1654-11 | gtt, gdh and kre | 587 ± 23 | 426 ± 55 |
| NRRL 18538/1655-1 | gtt, gdh and kre | 501 ± 20 | 395 ± 59 |
| NRRL 18538/1655-3 | gtt, gdh and kre | 537 ± 27 | 421 ± 63 |
| NRRL 18538/1655-5 | gtt, gdh and kre | 529 ± 21 | 428 ± 47 |
| NRRL 18538/1655-12 | gtt, gdh and kre | 526 ± 26 | 401 ± 60 |

The values are means ± 95% confidence limits.

In derivatives of NRRL 15328 transformed with the gtt, gdh and kre genes, significant increases in spinosyn yields were observed. This probably results from overcoming a rate-limiting supply of NDP-4-keto-6-deoxy-glucose by simultaneously increasing the amounts of both gtt and gdh gene products, the enzymes necessary for its biosynthesis (see FIG. 1). A greater supply of the NDP-4-keto-6-deoxy-glucose intermediate would lead to increased production of both rhamnose and forosamine, and therefore greater ability to convert aglycone to spinosyns A+D. Consistent with the hypothesis that deoxysugar supply is limiting spinosyn production in NRRL 18538, many mutants blocked in forosamine synthesis or addition accumulate PSA to very high levels. More of this intermediate can be made because it requires only one deoxysugar, compared with the two required for spinosyns A or D.

The present invention is not limited to a particular vector comprising spinosyn genes of the invention, but rather encompasses the biosynthetic genes in whatever vector is used to introduce the genes into a recombinant host cell.

In addition, due to the degeneracy of the genetic code, those skilled in the art are familiar with synthetic methods of preparing DNA sequences which may code for the same or functionally the same activity as that of the natural gene sequence. Likewise, those skilled in the art are familiar with techniques for modifying or mutating the gene sequence to prepare new sequences which encode the same or substantially the same polypeptide activity as the natural sequences. Consequently, these synthetic mutant and modified forms of the genes and expression products of these genes are also meant to be encompassed by the present invention.

All patents and publications referred to above are incorporated by reference herein.

REFERENCES

1. Altschul, S. F., W. Gish, W. Miller, E. W. Myers, and David J. Lipman (1990). Basic local alignment search tool. *J. Molec. Biol.* 215:403–10.
2. Aparicio, J. F., I. Molnar, T. Schwecke, A. Konig, S. F. Haydock, L. E. Khaw, J. Staunton & J. F. Leadlay (1996). "Organization of the biosynthetic gene cluster for rapamycin in *Streptomyces hygroscopicus*: analysis of the enzymatic domains in the modular polyketide synthase," *Gene* 169: 9–16.
3. Balcer, J. L., S. M. Brown & D. F. Berard (1996). "A rapid screening technique for identification of Spinosad photolysis products using ESI/MS/MS," *Proc. 44$^{th}$ Conf. Amer. Soc. Mass Spec.*
4. Baltz, R. H., M. A. McHenney, C. A. Cantwell, S. W. Queener & P. J. Solenberg (1997). "Applications of transposition mutagenesis in antibiotic producing streptomycetes," *Ant. van Leeuw.* 71:179–187.
5. Bibb, M. J., P. R. Findlay & M. W. Johnson (1984). "The relationship between base composition and codon usage in bacterial genes and its use for the simple and reliable identification of protein-coding sequences," *Gene* 30: 157–166.
6. Bierman, M., R. Logan, K. O'Brien, E. T. Seno, R. N. Rao & B. E. Schoner (1992). "Plasmid cloning vectors for the conjugal transfer of DNA from *Escherichia coli* to *Streptomyces* spp," *Gene* 116: 43–49.
7. Broughton, M. C., M. L. B. Huber, L. C. Creemer, H. A. Kirst & J. A. Turner (1991). "Biosynthesis of the macrolide insecticidal compound A83543 by *Saccharopolyspora spinosa,*" *Ann. Mtg. Amer. Soc. Microbiol.*
8. Burgett, S. G. & P. R. J. Rosteck (1994). "Use of dimethyl sulfoxide to improve fluorescent, Taq cycle sequencing. in *Automated DNA sequencing and analysis,*". M. Adams, C. Fields & J. C. Venter, eds. NY, Academic Press: pp. 211–215.
9. Dehoff, B. S., S. A. Kuhstoss, P. R. Rosteck & K. L. Sutton (1997). "Polyketide synthase genes." EPA 0791655.
10. Don, R. H., P. T. Cox, B. J. Wainwright, K. Baker & J. S. Mattick (1991). "'Touchdown' PCR to circumvent spurious priming during gene amplification," *Nucl. Acid Res.* 19: 4008.
11. Donadio, S., J. B. McAlpine, P. S. Sheldon, M. Jackson & L. Katz (1993). "An erythromycin analog produced by reprogramming of polyketide synthesis," *Proc. Natn. Acad. Sci. USA* 90: 7119–7123.
12. Donadio, S. & L. Katz (1992). "Organization of the enzymatic domains in the multifunctional polyketide synthase involved in erythromycin formation in *Saccharopolyspora erythrae,*" *Gene* 111: 51–60.
13. Donadio, S., M. J. Staver, J. B. McAlpine, S. J. Swanson & L. Katz (1991). "Modular organization of genes required for complex polyketide biosynthesis," *Science* 252: 675–679.
14. Fish, S. A. & E. Cundliffe (1997). "Stimulation of polyketide metabolism in *Streptomyces fradiae* by tylosin and its glycosylated precursors," *Microbiology* 143: 3871–3876.
15. Geistlich, M., R. Losick, J. R. Turner & R. N. Rao (1992). "Characterization of a novel regulatory gene governing the expression of a polyketide synthase gene in *Streptomyces ambofaciens,*" *Mol. Microbiol.* 6: 2019–2029.
16. Hosted, T. J. & R. H. Baltz (1997). "Use of rpsL for dominance selection and gene replacement in *Streptomyces roseosporus*", *J. Bacteriol.* 179: 180–186.
17. Inouye, M., H. Suzuki, Y. Takada, N. Muto, S. Horinouchi & T. Beppu (1994). "A gene encoding mycinamicin III O-methyltransferase from *Micromonospora griseorubida,*" *Gene* 141: 121–124.
18. Jiang, X. M., B. Neal, F. Santiago, S. J. Lee, L. K. Romana & P. R. Reeves (1991). "Structure and sequence of the rfb (O antigen) gene cluster of *Salmonella* serovar typhimurium (strain LT2)," *Mol. Microbiol.* 5: 695–713.
20. Kirst, H. A., K. H. Michel, J. S. Mynderse, E. H. Chio, R. C. Yao, W. M. Nakatsukasa, L. D. Boeck, J. L. Occlowitz, J. W. Paschal, J. B. Deeter & G. D. Thompson (1992). "Discovery, isolation and structure elucidation of a family of structurally unique, fermentation-derived tetracyclic macrolides. in *Synthesis and Chemistry of Agrochemicals III,*" D. R. Baker, J. G. Fenyes & J. J. Steffens, eds. Washington, D.C., American Chemical Society: pp. 214–225.
21. Linton, K. J., B. W. Jarvis & C. R. Hutchinson (1995). "Cloning the genes encoding thymidine diphosphoglucose 4,6-dehydratase and thymidine diphospho-4-keto-6-deoxyglucose 3,5-epimerase from the erythromycin-producing *Saccharopolyspora erythraea*." Gene 153(1): 33–40.
22. Liu, H. W. & J. S. Thorson (1994). "Pathways and mechanisms in the biogenesis of novel deoxysugars by bacteria," *Ann Rev Microbiol* 48: 223–256.

23. Matsushima, P., M. C. Broughton, J. R. Turner & R. H. Baltz (1994). "Conjugal transfer of cosmid DNA from *Escherichia coli* to *Saccharopolyspora spinosa*: effects of chromosomal insertion on macrolide A83543 production," *Gene* 146: 39–45.
24. Ruan, X., et al.(1997). "Acyltransferase Domain Substitutions in Erythromycin Polyketide Synthase Yield Novel Erythromycin Derivatives," *J. Bacteriology* 179, 6416.
25. Siggard-Andersen, M. (1993). "Conserved residues in condensing enzyme domains of fatty acid synthases and related sequences," *Protein Seq. Data Anal.* 5: 325–335.
26. Simon, R., U. Preifer & A. Puhler (1983). "A broad host range mobilization system for in vivo genetic engineering: transposon mutagenesis in Gram negative bacteria," *Bio/Technology* 1: 784–791.
27. Solenberg, P. J. & S. G. Burgett (1989). "Method for selection of transposable DNA and characterization of a new insertion sequence, IS493, from *Streptomyces lividans*," *J Bacteriol.* 171: 4807–4813.
28. Strobel, R. J. & W. M. Nakatsukasa (1993). "Response surface methods for optimizing *Saccharopolyspora spinosa*, a novel macrolide producer," *J. Ind. Microbiol.* 11: 121–127.
29. Thorson, J. S., S. F. Lo & H. Liu (1993). "Biosynthesis of 3,6-dideoxyhexoses: new mechanistic reflections upon 2,6-dideoxy, 4,6-dideoxy, and amino sugar construction," *J. Am. Chem. Soc.* 115: 6993–6994.
30. Weber, J. M. & J. B. McAlpine (1992). "Erythromycin derivatives," U.S. Pat. No. 5,141,926.

We claim:

1. An isolated DNA molecule comprising a DNA sequence that encodes the spinosyn biosynthetic enzyme spnF, wherein said enzyme is defined by the amino acid sequence SEQ ID NO: 7.

2. An isolated DNA molecule of claim 1 wherein said DNA sequence is bases 20168–20995 of SEQ ID NO:1.

3. A recombinant DNA vector which comprises a DNA sequence as defined in claim 1.

4. A host cell transformed with a recombinant vector as claimed in claim 3.

5. A process for isolating a macrolide biosynthetic gene which comprises
   a) creating a genomic library of a macrolide producing microorganism, and
   b) using a labeled DNA molecule according to claim 1 as a hybridization probe.

6. A process of claim 5 wherein the microorganism is a spinosyn producing microorganism.

* * * * *